US006376655B1

(12) United States Patent
Berg et al.

(10) Patent No.: US 6,376,655 B1
(45) Date of Patent: Apr. 23, 2002

(54) PHYSICALLY FUNCTIONAL MATERIALS

(75) Inventors: Rolf Henrik Berg, Rungsted Kyst; Søren Hvilsted, Hørsholm; P. S. Ramanujam, Roskilde, all of (DK)

(73) Assignee: Riso National Laboratory, Roskilde (DK)

( * ) Notice: Subject to any disclaimer, the term of this patent is extended or adjusted under 35 U.S.C. 154(b) by 0 days.

(21) Appl. No.: 08/973,179

(22) PCT Filed: Jun. 3, 1996

(86) PCT No.: PCT/DK96/00237

§ 371 Date: Dec. 2, 1997

§ 102(e) Date: Dec. 2, 1997

(87) PCT Pub. No.: WO96/38410

PCT Pub. Date: Dec. 5, 1996

(30) Foreign Application Priority Data

Jun. 2, 1995  (DK) .............................. 0628/95

(51) Int. Cl.⁷ ............... C07C 245/08; C07C 255/65; G11B 7/24
(52) U.S. Cl. ............... 534/573; 534/829; 534/854; 534/DIG. 3; 524/190; 527/207; 430/1; 430/2
(58) Field of Search ............... 534/573, DIG. 3, 534/854, 829; 524/190; 527/207; 430/1, 2

(56) References Cited

U.S. PATENT DOCUMENTS

| 4,619,990 A | * | 10/1986 | Elmasry | 534/573 |
|---|---|---|---|---|
| 5,019,476 A | * | 5/1991 | Kanno et al. | 430/20 |
| 5,275,924 A | * | 1/1994 | Devonald et al. | 430/495 |
| 5,496,670 A | * | 3/1996 | Hvilsted et al. | 430/56 |
| 5,525,265 A | * | 6/1996 | Wit et al. | 252/587 |

FOREIGN PATENT DOCUMENTS

| DE | 19500228 | 7/1995 |
|---|---|---|
| EP | 0369432 | 5/1990 |
| EP | 0474431 | 3/1992 |
| EP | 0550105 | 7/1993 |
| EP | 0597826 | 5/1994 |
| EP | 0615234 | 9/1994 |
| GB | 2201155 | 8/1988 |
| WO | 8605505 | 9/1986 |

OTHER PUBLICATIONS

Natansohn, et al., Azo Polymers for Reversible Optical Storage. 4. Cooperative Motion of Rigid Groups in Semicrystalline Polymers, Macromolecules, vol. 27, No. 9, pp. 2580–2585, 1994.

* cited by examiner

Primary Examiner—Fiona T. Powers
(74) Attorney, Agent, or Firm—Iver P. Cooper

(57) ABSTRACT

The invention relates to novel monodisperse or polydisperse compounds, in general named DNO (diamino acid Nα-substituted oligopeptides), preferably low molecular weight polypeptides, e.g., based on ornithine, lysine, diaminobutyric acid, diaminopropionic acid, aminoethylglycine or other amino acids or peptides having azobenzenes or other physicially functional groups, e.g., photoresponsive groups, as side chains. These compounds may be synthesized using solid phase peptide synthesis techniques. Materials, e.g., thin films, comprising such compounds may be used for optical storage of information (holographic data storage), nonlinear optics (NLO), as photoconductors, photonic band-gap materials, electrically conducting materials, electroluminescent materials, piezo-electric materials, pyroelectric materials, magnetic materials, ferromagnetic materials, ferroelectric materials, photorefractive materials, or materials in which light-induced conformational changes can be produced. Optical anisotropy may reversibly be generated with polarized laser light whereby a hologram is formed. First order diffraction efficiencies of up to around 80% have been obtained.

84 Claims, 58 Drawing Sheets

FIG. 4
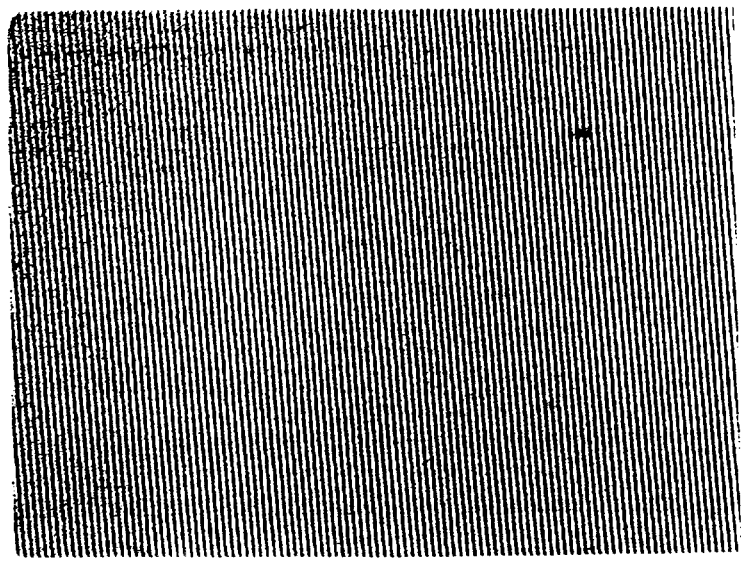
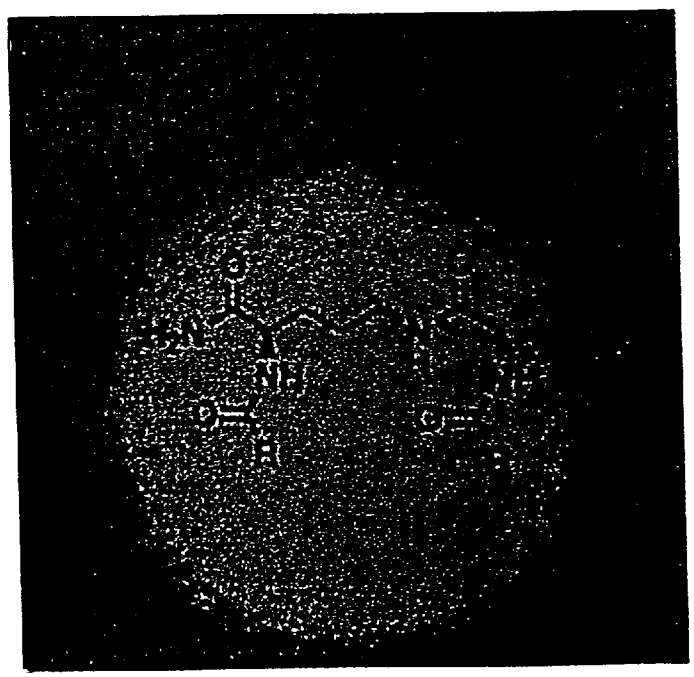

FIG. 5
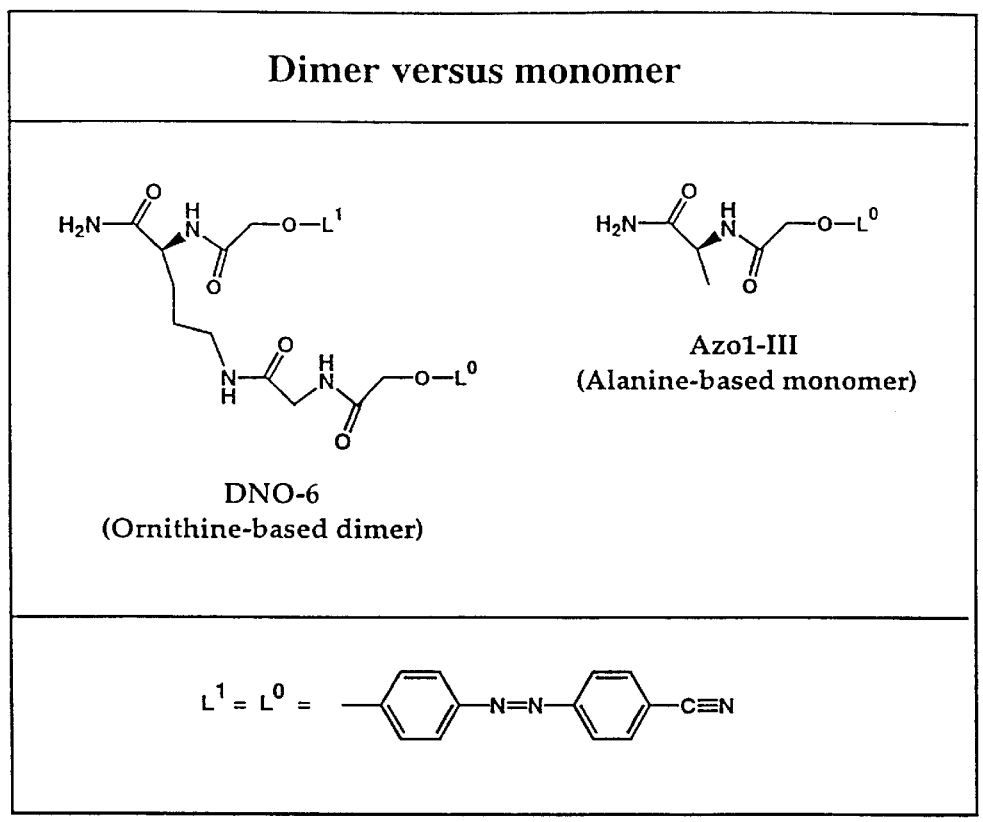
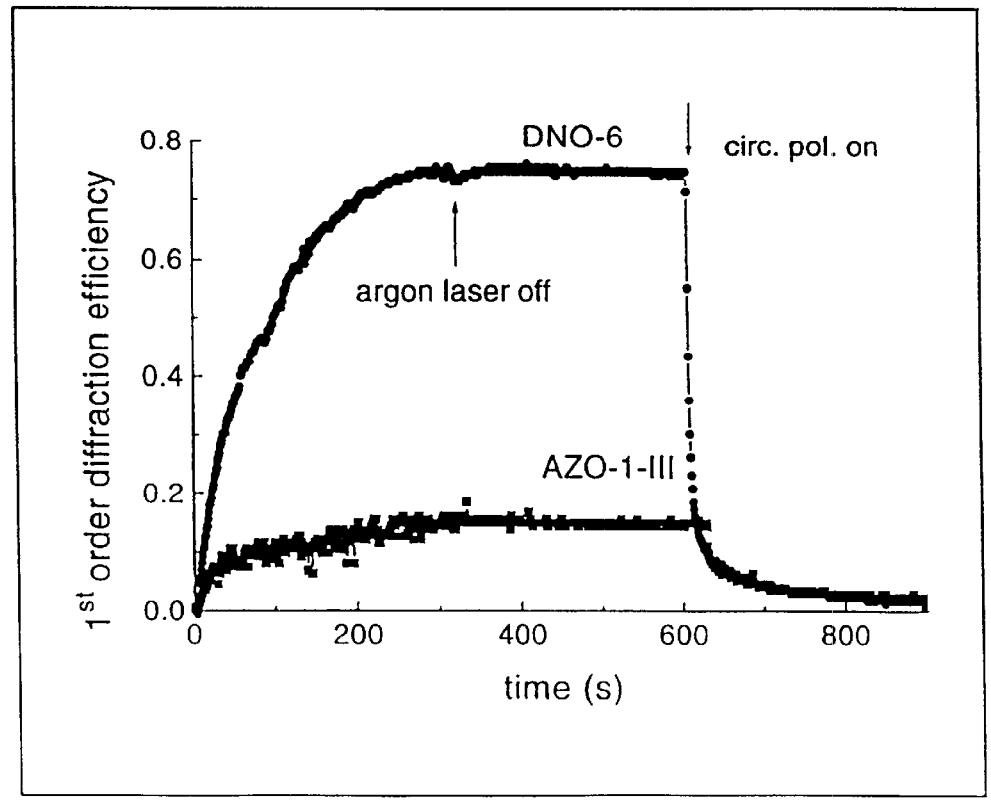

FIG. 9
Effect of number of bonds in the backbone
DNO-19: $p = 0$ (4 bonds: diaminopropionic acid)
DNO-18: $p = 1$ (5 bonds: diaminobutyric acid)
DNO-6:  $p = 2$ (6 bonds: ornithine)
DNO-14: $p = 3$ (7 bonds: lysine)
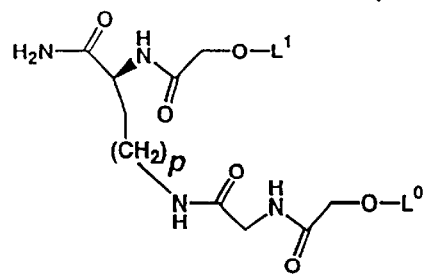
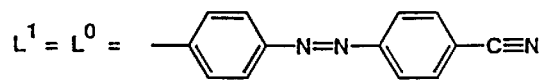
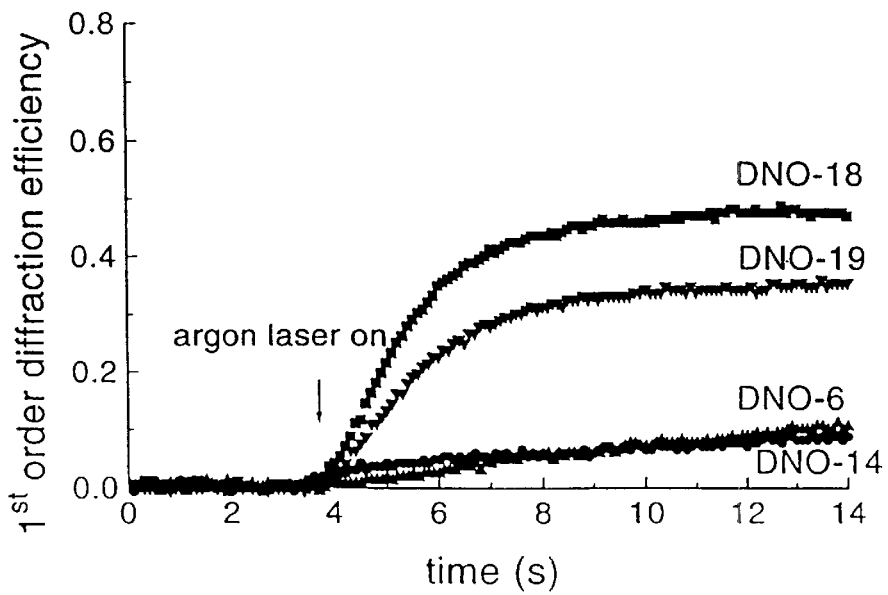

FIG. 10
Effect of oligomer size (diaminobutyric acid)
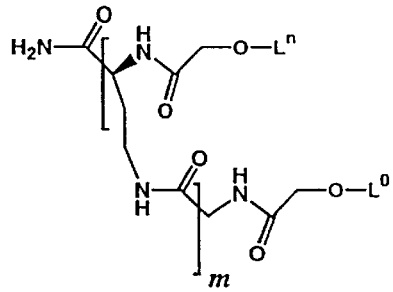
DNO-18: $m = 1$ (2-mer)
DNO-109: $m = 3$ (4-mer)
DNO-112: $m = 6$ (7-mer)
DNO-115: $m = 9$ (10-mer)
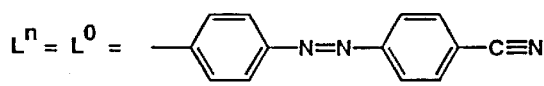
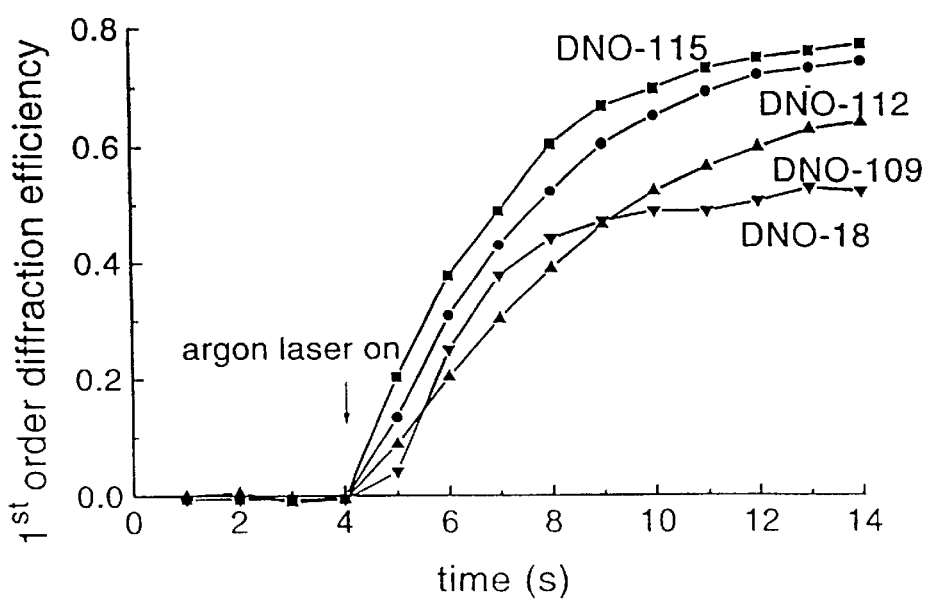

FIG. 11
DNO-6 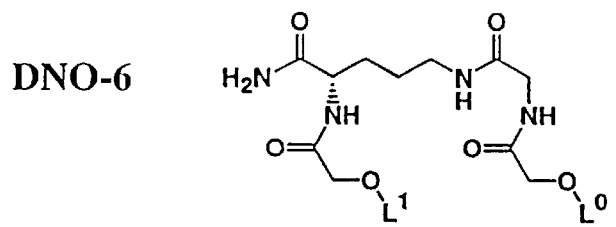
Azo1-V 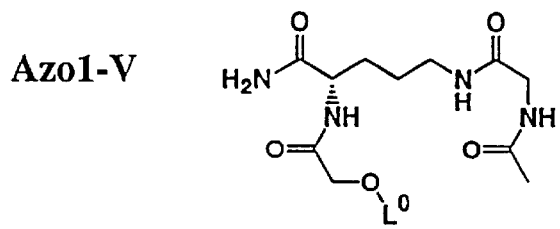
Azo1-IV 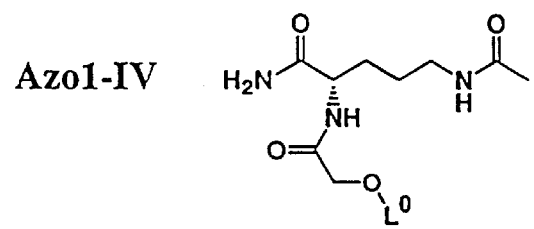
Azo1-III 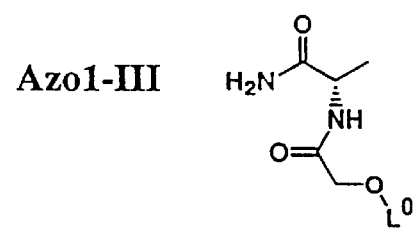
$L^1 = L^0 =$ 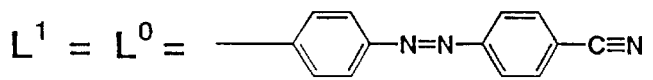

FIG. 12
DNO-19-n 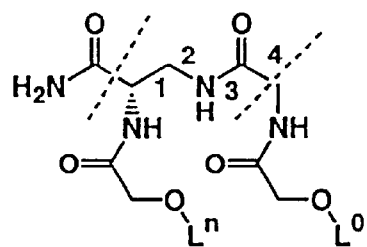
DNO-18-n 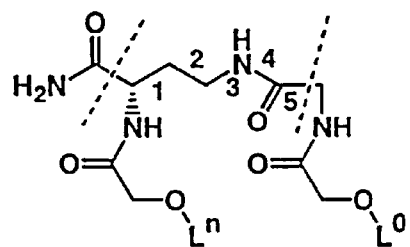
DNO-6-n 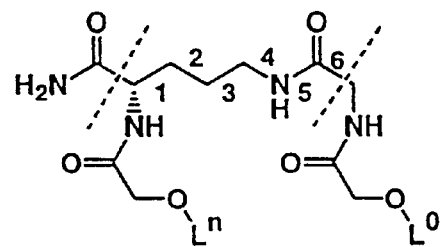
DNO-14-n 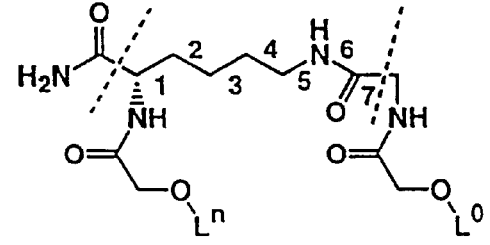

FIG. 13
DNO-98-n 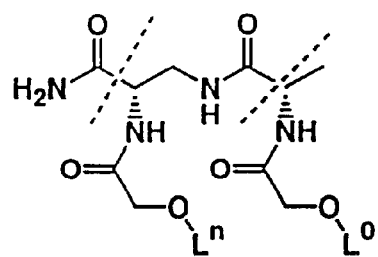
DNO-97-n 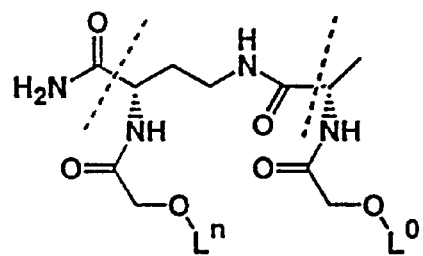
DNO-12-n 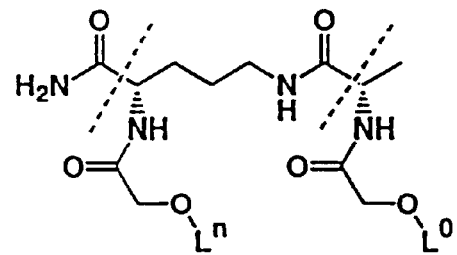
DNO-239-n 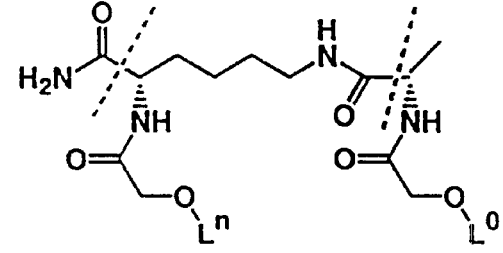

FIG. 14
DNO-53-n 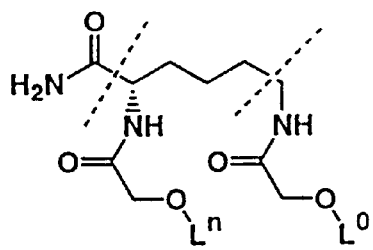
DNO-54-n 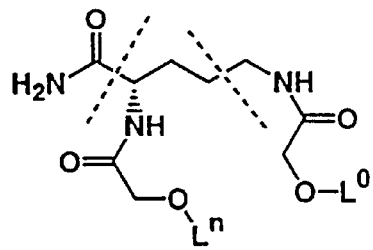
DNO-55-n 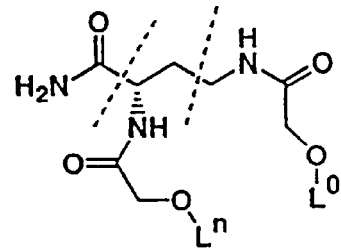
DNO-56-n 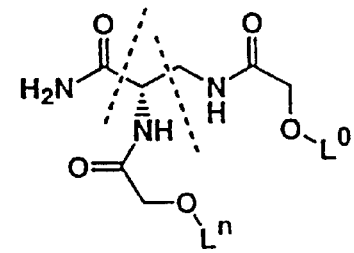

FIG. 15
DNO-56-n 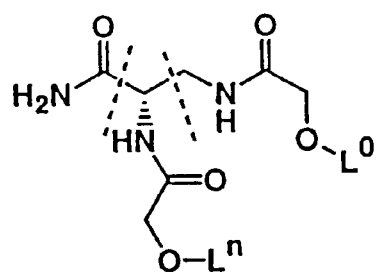
DNO-22-n 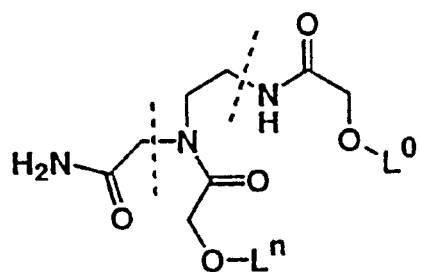

FIG. 16
DNO-22-n 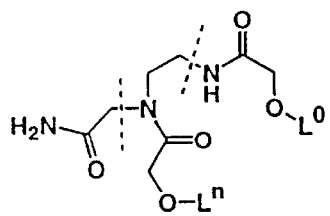
DNO-400-n 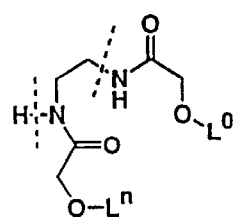
DNO-401-n 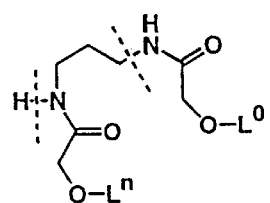
DNO-402-n 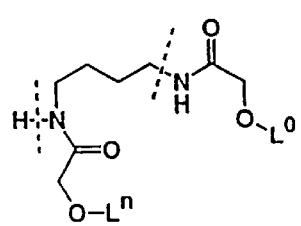
DNO-403-n 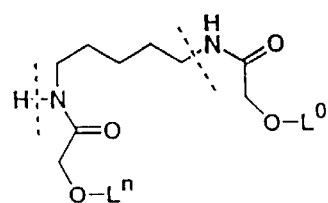

FIG. 17
DNO-6-n 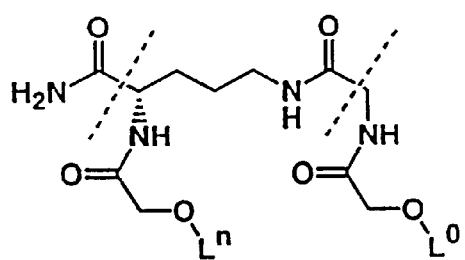
DNO-104-n 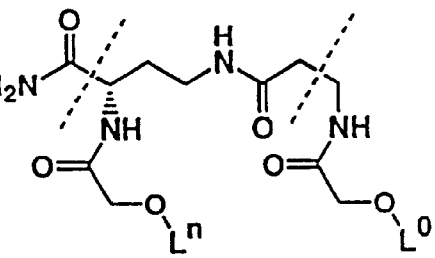

FIG. 20
DNO-6-n 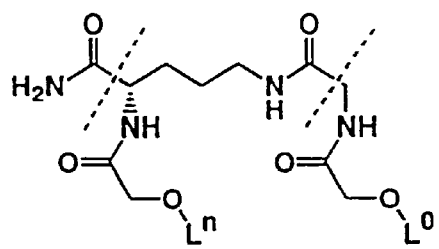
DNO-33-n 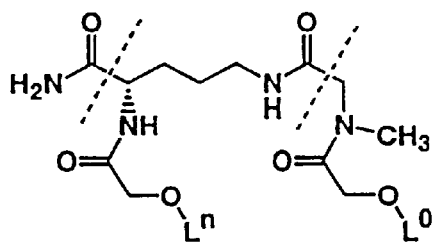
DNO-12-n 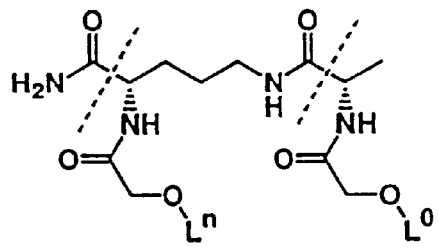
DNO-38-n 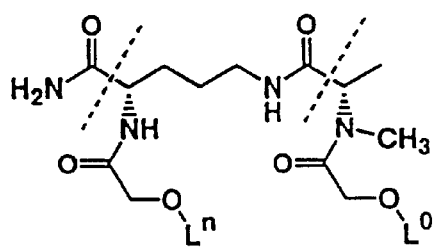

FIG. 21
DNO-411-n
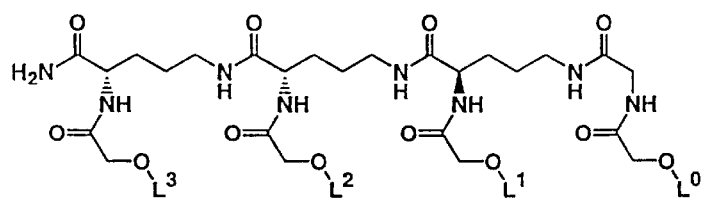
DNO-412-n
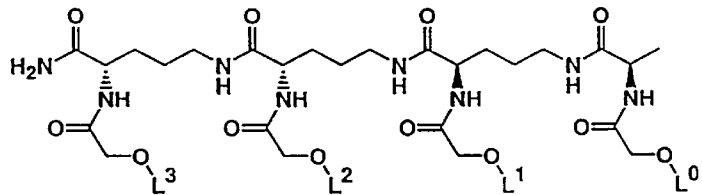
DNO-413-n
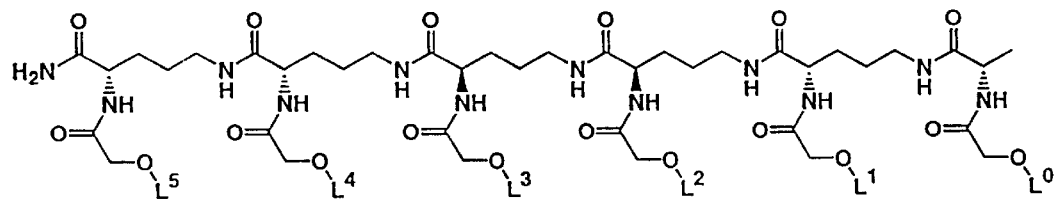

FIG. 22
DNO-414-n 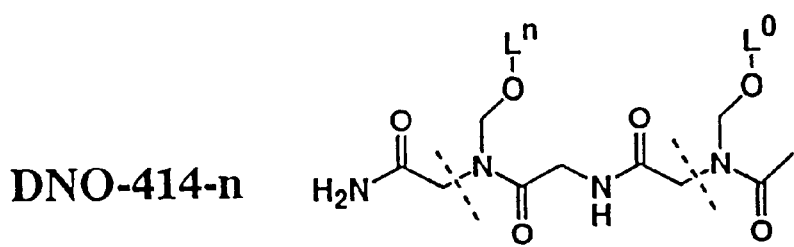
DNO-415-n 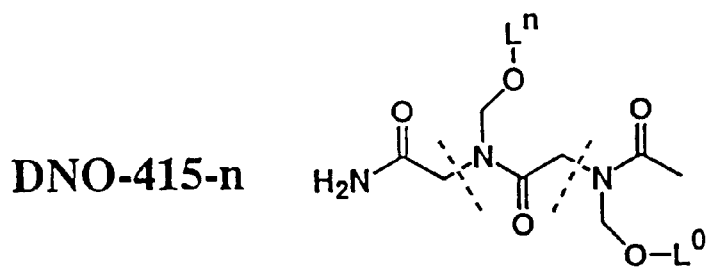

FIG. 23
DNO-6-n 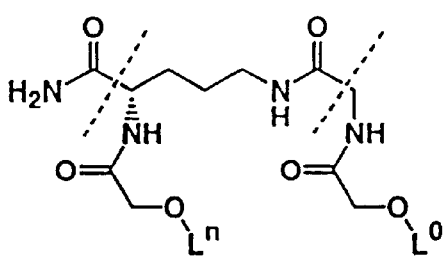
DNO-51-n 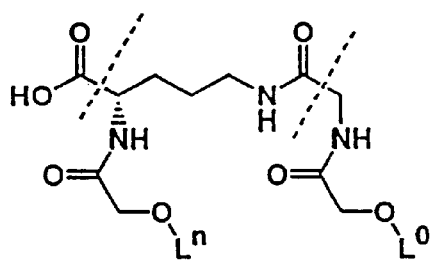
DNO-52-n 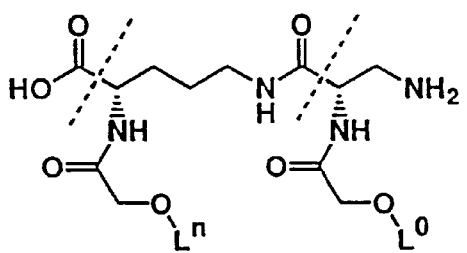

FIG. 29
MnTPP
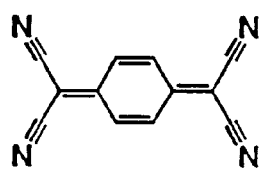
TCNQ
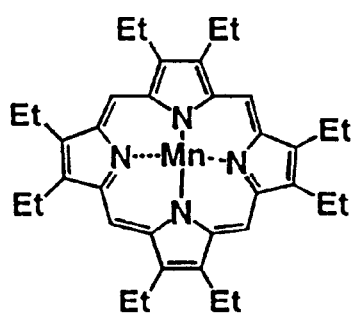
MnOEP
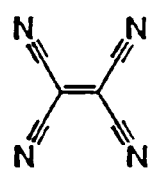
TCNE

FIG. 30
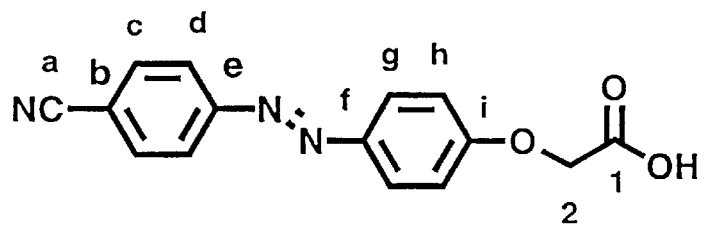
a) 2-[4-(4-Cyanophenylazo)phenoxy]-ethanoic acid
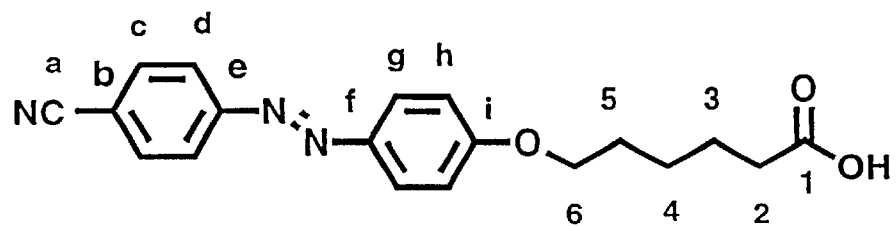
b) 6-[4-(4-Cyanophenylazo)phenoxy]-hexanoic acid
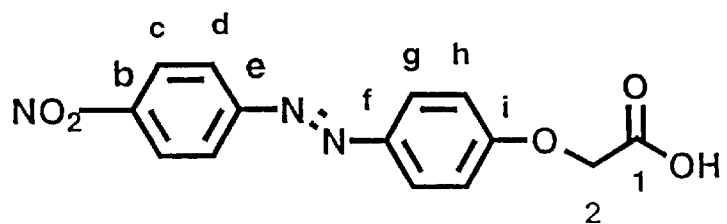
c) 2-[4-(4-Nitrophenylazo)phenoxy]-ethanoic acid

FIG. 35
A)
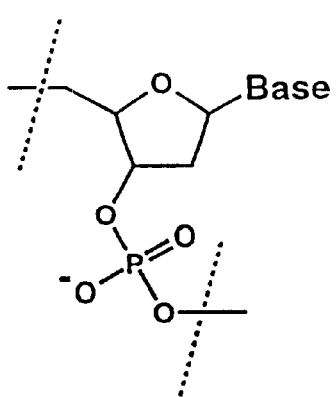
B)
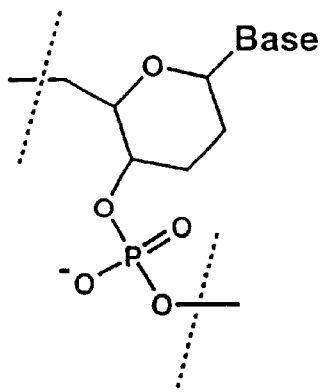
C)
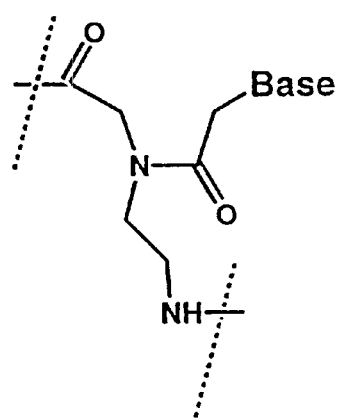
D)
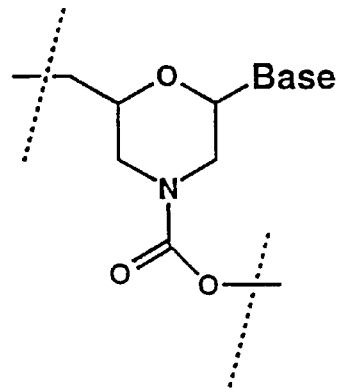

FIG. 42
A)
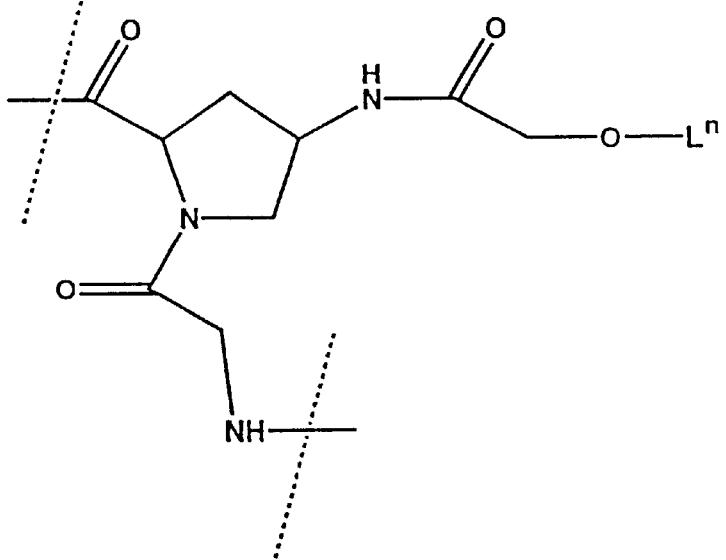
B)
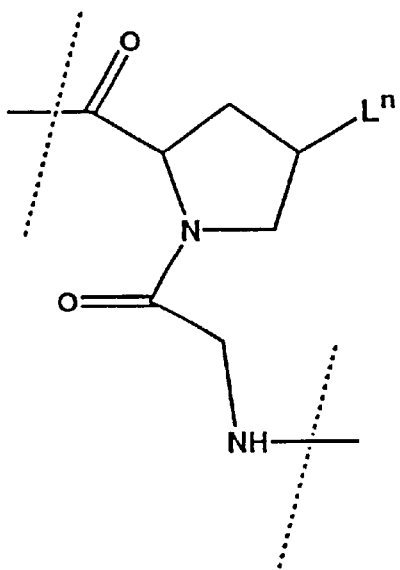

FIG. 46
DNO-206
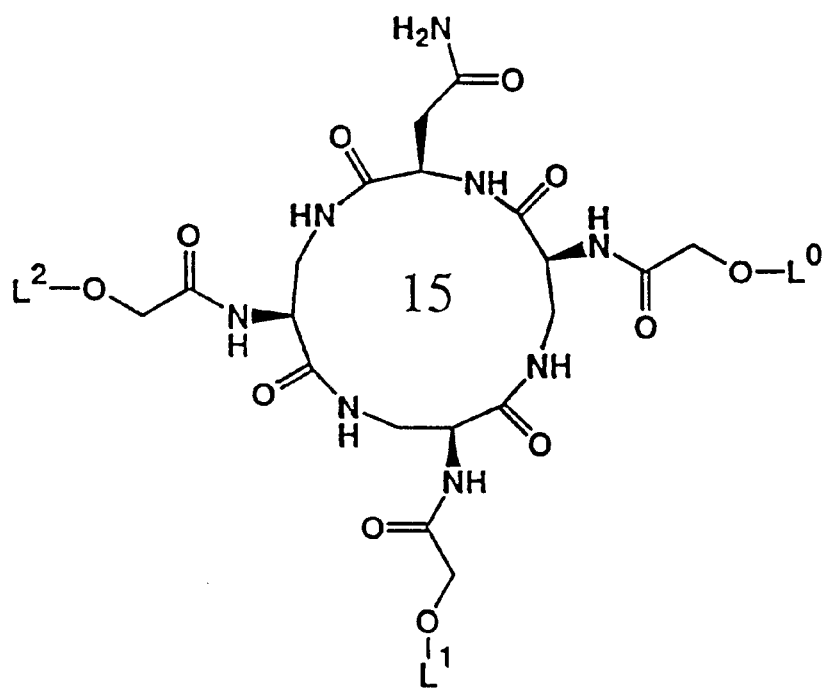
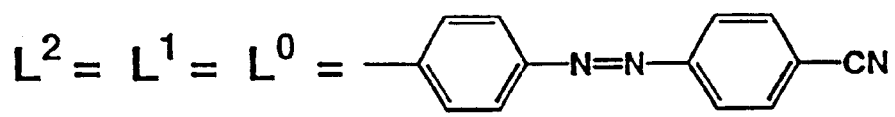

FIG. 47
DNO-6
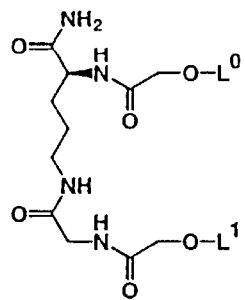
DNO-127
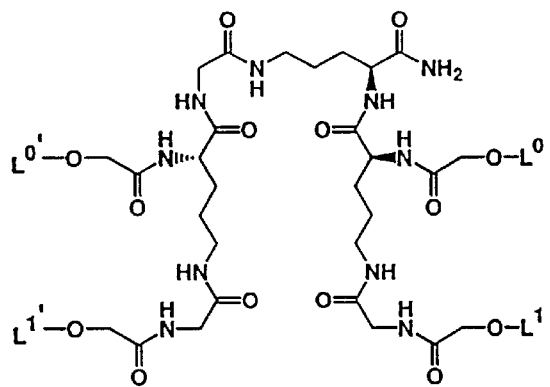
DNO-214
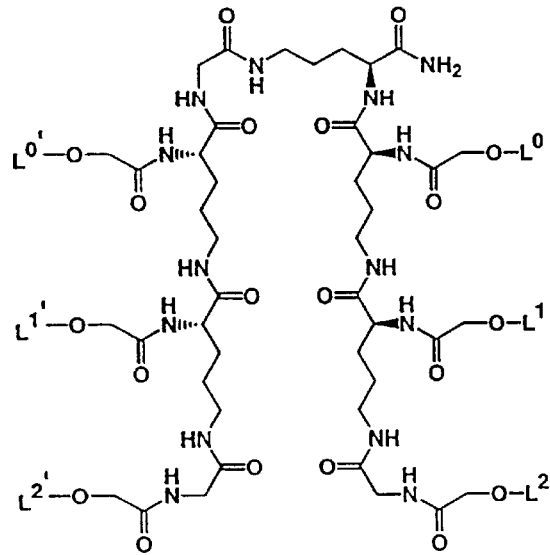

FIG. 50
DNO-500-n 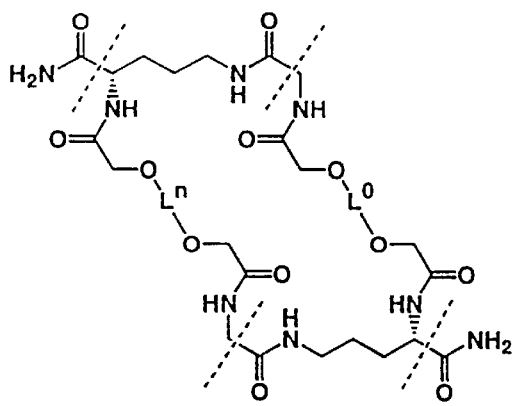
DNO-501-n 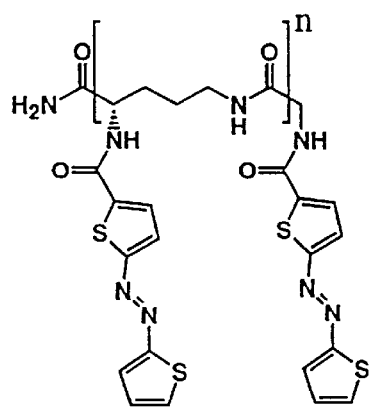
DNO-502-n 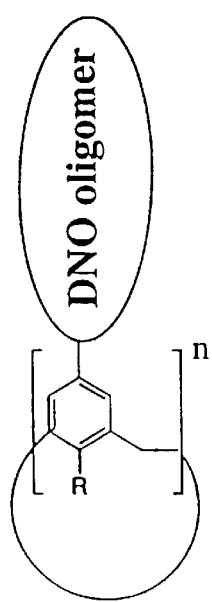

FIG. 52
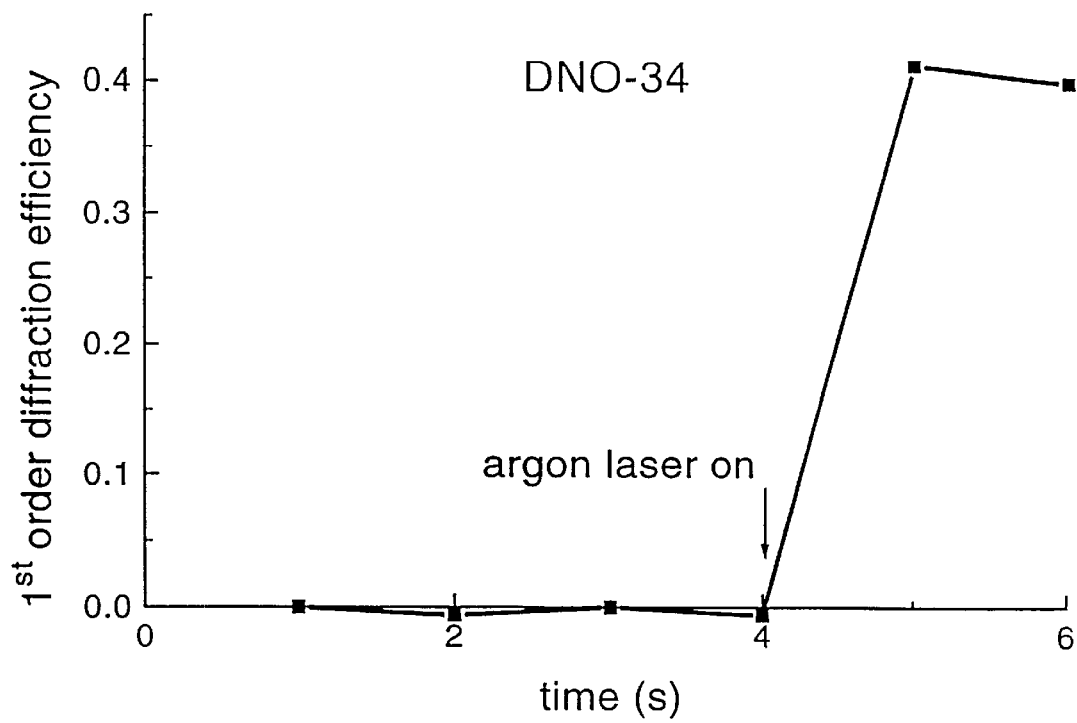
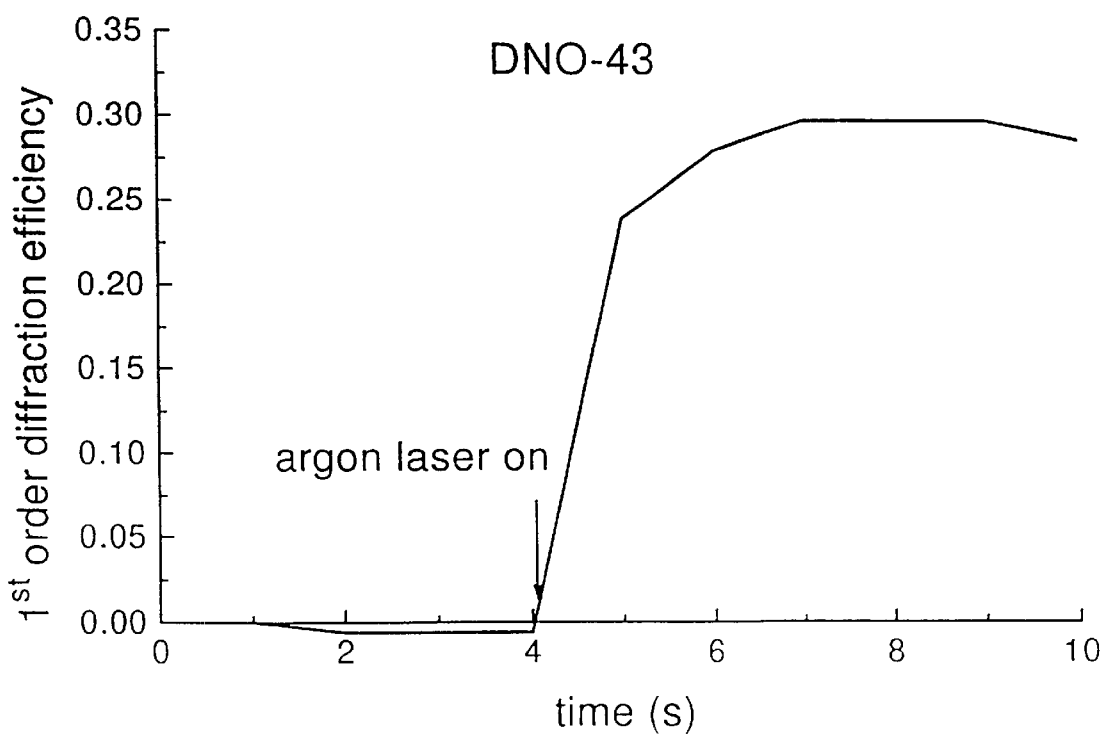

FIG. 53
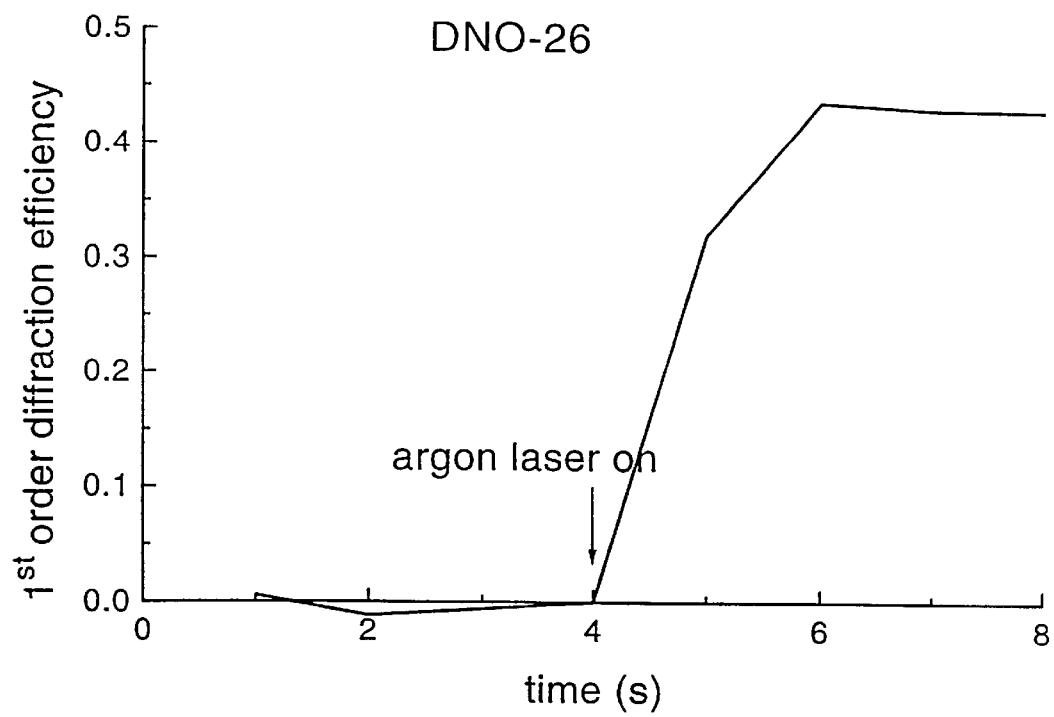
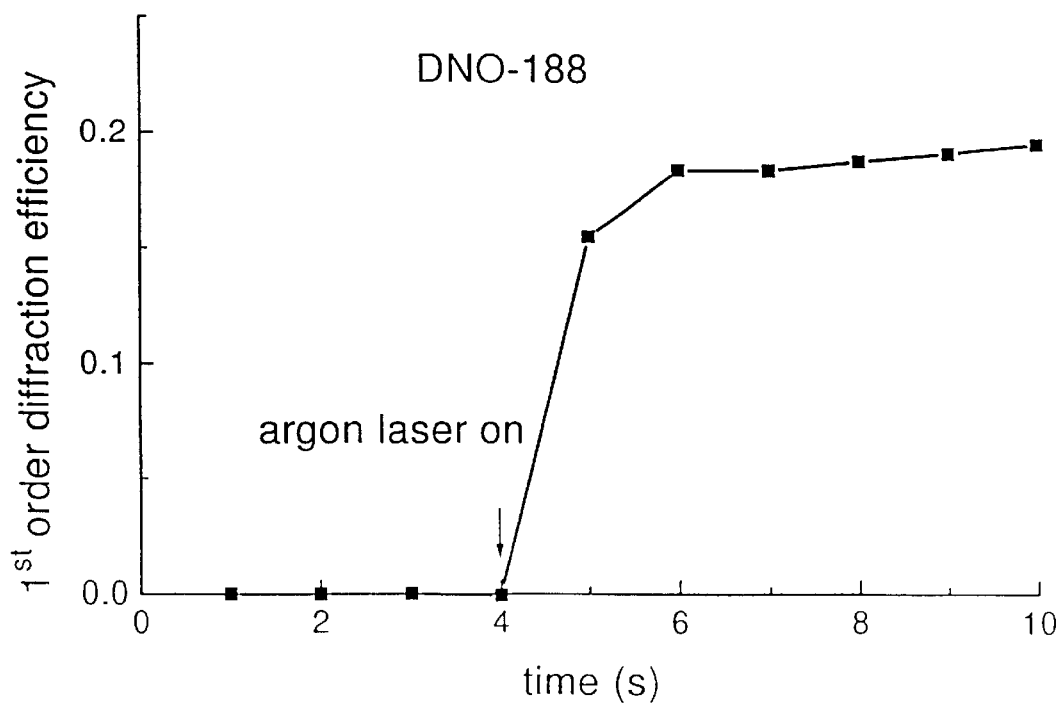

FIG. 54
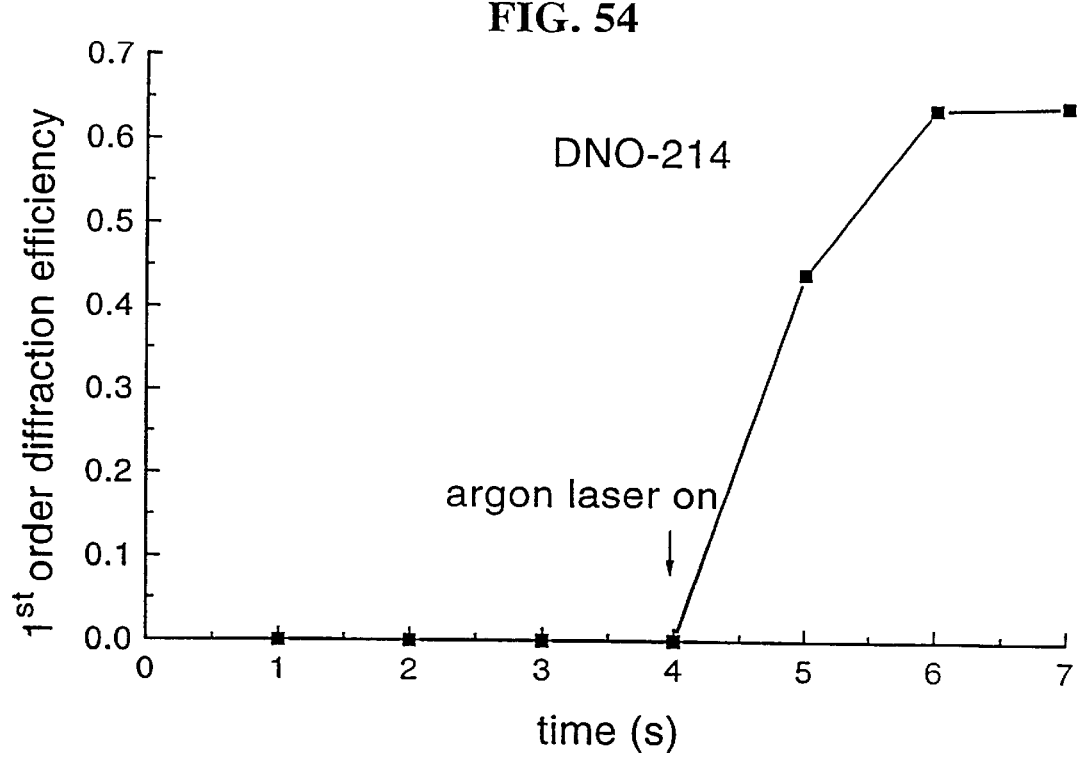
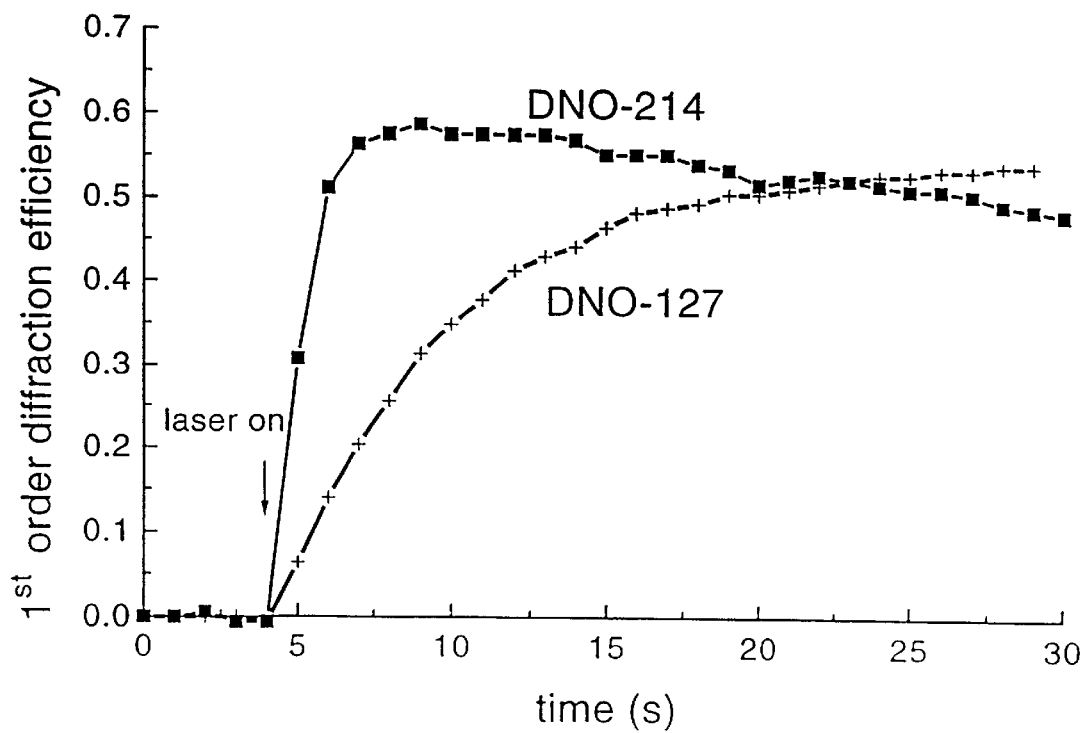

FIG. 57
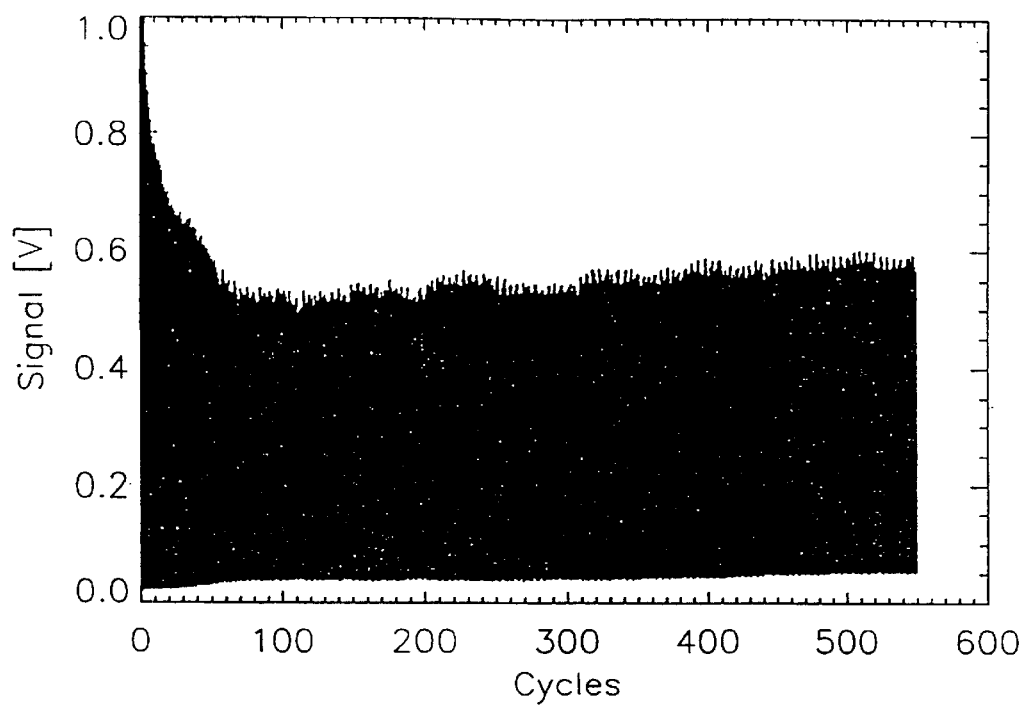
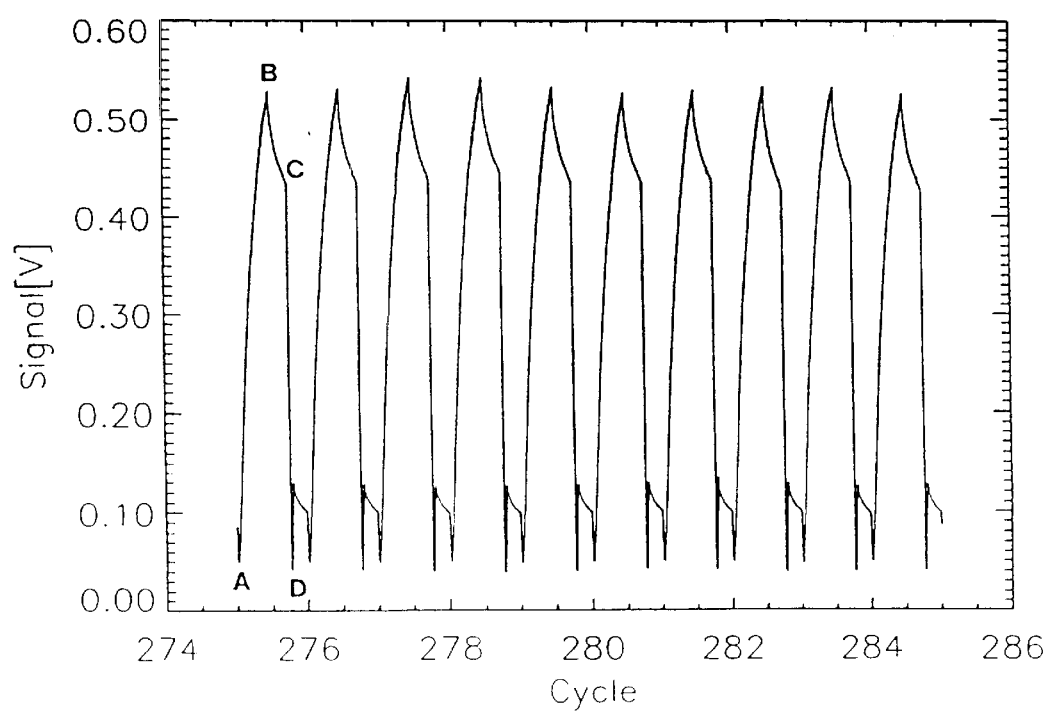

DNO-6

PHYSICALLY FUNCTIONAL MATERIALS

FIELD OF THE INVENTION

This invention concerns novel monodisperse or polydisperse compounds, which can be monomeric or oligomeric, and which, e.g., are based on ornithine, lysine, diaminobutyric acid, diaminopropionic acid, aminoethylglycine or other amino acids or peptides and analogues thereof, and which contain substituted or unsubstituted azobenzenes or other physically functional groups, e.g., photoresponsive groups, as side chains and, if desired, in combination with other functional ligands or side chains. In particular, the invention is directed to materials comprising such compounds used for optical storage and processing applications.

BACKGROUND OF THE INVENTION

Polymers containing photoresponsive functionalities appear promising as future materials for optical storage of information. In particular, liquid-Mrystalline polymers (Eich, M., Wendorff, J. H., Reck, B. & Ringsdorf, H. *Makromol. Chem. Rapid Commun.* 8, 59–63 (1987); Eich, M. & Wendorff. J. H., *Makromol. Chem. Rapid Commun.* 8, 467–471 (1987); Wiesner, U., Antonietti, M., Boeffel, C. & Spiess, H. W. *Makromol. Chem.* 191, 2133–2149 (1990); Gibbons, W. M., Shannon, P. J., Sun, S.-T. & Swetlin, B. J. *Nature* 351, 49–50 (1991); Stumpe, J., Muller, L., Kreysig, D. *Makromol. Chem. Rapid Commun.* 12, 81–87 (1991); Hvilsted, S., Andruzzi, F. & Ramanujam, P. S. *Opt. Lett.* 17, 1234–1236 (1992); Xie, S., Natansohn, A & Rochon, P. *Chem. Mater.* 5, 403–411 (1993); Hvilsted, S., Andruzzi, F., Kulinna, C., Siesler, H. W. & Ramanujam, P. S. *Macromolecules* 28, 2172–2183 (1995)) and photorefractive polymers (Ducharme, S., Scott, J. C., Twieg, R. J. & Moerner, W. E. *Phys. Rev. Lett.* 66, 1846–1849 (1991); Liphardt, M., Goonesekera, A, Jones, B. E., Ducharme, S., Takacs, J. M. & Zhang, L. *Science* 263, 367–369 (1994); Meerholz, K., Volodin, B. L., Sandalphon, Kippelen, B. & Peyghambarian, N. *Nature* 371, 497–500 (1994)) have been the focus of considerable attention.

The known art in the area of optical storage has been concentrated on polymers either doped with dyes or with dyes covalently attached to them. Previous work in this area has been described in several articles; Eich, M. & Wendorff, J. H., *J. Opt. Soc. Am.* B 7, 1428–1436 (1990); Xie, S., Natansohn, A & Rochon, P., *Chem. Mater.* 6, 403–411, (1993), Hvilsted, S., Andruzzi, F., Kulinna, C., Siesler, H. W. & Ramanujam, P. S., *Macromolecules*, 28, 2172–2183 (1995). Most earlier work has been centred around molecules that need to be aligned either by rubbing or poling with electric fields. As discussed by Xie et al. and Hvilsted et al. it is also possible to store on thin films of organic materials which need no prealignment of the molecules. Erasure of information can be performed either by means of light or heat. Diffraction efficiencies in these films have been of the order of 50–60%. Recently, nearly 100% diffraction efficiency has been achieved in a photorefractive composite polymer film (Meerholz, K, Vblodin, B. L., Sandalphon, Kippeln, B. & Peyghambarian, N., *Nature,* 371, 497–500 (1994)). The composite film used in that application was made up of the following compounds: 2,5-dimethyl-4-(p-nitiophenylazo)anisole, poly(N-vinylcarbazole), 2,4,7-trinitro-9-fluorenone, N-ethylcarbazole. The maximum diffraction efficiency of 86% was achieved when an electric field of 90 V/mm was applied over the film. However the grating efficiency dropped to 15% of the maximum value within 24 hours after all the light beams and the electric field were switched off. Bieringer et al. have obtained a diffraction efficiency on the order of 90% in thick films of liquid crystalline side chain polymers with azochromophores. (Th. Bieringer, R. Wuttke, D. Haarer, U. Geoner and J. Rüibner, *Macromolecular Chemistry and Physics,* 196, 1375–1390 (1995)). As far as we are aware, the only instance of optical storage in peptides is the work of Cooper et al (Cooper, T. M., Tondiglia, V., Natarajan, L. V., Shapiro, M., Obermeier, K. & Crane, R. L., *Appl. Opt.* 82, 674–677 (1993)) on holographic grating in poly(spiropyran-L-glutamate). A diffraction efficiency of 0.02% was achieved at an incident energy at 488 nm of about 100 J/cm$^2$, dropping to 0.015% 40 minutes after the recording.

EP 0474431 relates to amphiphilic compounds having a polyamide backbone carrying, e.g., molecular moieties made hydrophobic by attachment of a group containing from 8 to 40 carbon atoms. These compounds are used for forming optical elements for use in optical devices with non-linear optical (NLO) properties. These compounds may be organised into ordered arrays using the Langmuir-Blodgett technique. It is clear from the present description and claims that the organic compounds of the present invention does not include compounds having ligands carrying such hydrophobic moieties, in particular not $C_{8-40}$ moieties.

SUMMARY OF THE INVENTION

The present invention in particular relates to organic compounds having a physical functionality which can be influenced by external stimulation, said compounds comprising one or more segments of the following formula G

G wherein Y is a linking group or a single bond; L is a physically functional group comprising one or more physically functiona ligand(s); and —A—B— designates a backbone moiety. The segment G is preferably included in a domain comprising a total of 2–25 segments where some of the segments may be segments of the following formula G'

G' wherein the groups A', B', and Y' have the same meaning as defined for the groups A, B, and Y, respectively, and where the group L' designates a physically non-functional group comprising one or more physically non-functional ligand(s).

The present invention further relates to materials comprising or consisting of such compounds. These materials have excellent properties with respect to diffraction efficiency in relatively thin films and with respect to stability of the material even at temperatures as high as at around 150° C.

The present invention also relates to the use of a material comprising an ensemble of the compounds, preferably monodisperse, for optical storage of information.

The invention further relates to the use of a material comprising an ensemble of compounds, preferably monodisperse, in nonlinear optics, as a photoconductor, as a photonic band-gap material, as an electrically conducting material, as an electroluminescent material, as a piezo-electric material, as a pyroelectric material, as a magnetic material, as a ferromagnetic material, as a ferroelectric material, as a photorefractive material, or as a material in which light-induced conformational changes can be produced.

The invention further relates to a process for optically storing information comprising irradiaton of an optically isotropic area of a material of monodisperse or substantially monodisperse compounds with polarised light, thereby forming an optically anisotropic phase in the irradiated area of the film.

BRIEF DESCRIPTION OF THE DRAWINGS

FIG. 4.a A photograph of the diffraction gratings recorded in a film of DNO-6. The photograph was obtained in a polarisation microscope between crossed polarisers at a magnification of 400×. The resolution of the gratings is about 500 lines/mm.

FIG. 4.b Reconstruction of holographic display, wherein the structure of DNO-6 is stored in a film of DNO-6. The hologram fills an area of about 1 mm$^2$ in the film.

FIGS. 5–10 First-order diffraction efficiencies as a function of time, measured during the grating formation in ~5 μm thick films of different DNO oligomers.

FIG. 5 Ornithine-based dimer (DNO-6) versus alanine-based monomer (Azo1-III). For a film of DNO-6, the diffracted power in the first order increases in about 300 s to 3.2 mW representing a first-order diffraction efficiency of 76%. Diffracted power in other orders accounted for 10% (0.4 mW) and absorption losses in the film and reflection losses from the glass accounted for approximately 14%. Thus, a total diffraction efficiency of near 100% of the maximum achievable was obtained. The diffraction efficiency remains stable after the argon laser is switched off.

FIG. 6 Diffraction efficiency of films of ornithine-based dimer versus films of longer analogues.

FIG. 7 Diffraction efficiency of a film of ornithine-based dimers with increasing number of methylene groups between the backbone and the azobenzene chromophore.

FIG. 8 Diffraction efficiency of films of ornithine-based dimers where one backbone unit (L-ornithine) is combined with a second backbone unit which is either achiral (Gly) or has the same (L-Ala) or the opposite (D-Ala) chirality.

FIG. 9 Diffraction efficiency of films of dimers with increasing number of methylene groups in the backbone.

FIG. 10 Diffraction efficiency of films of diamino-butyric acid-based dimer versus longer analogues.

FIG. 11 Chemical structure of DNO-6 and shortened fragments or analogs.

FIGS. 12–27 Examples of structures of compounds according to the invention with particular emphasis on the variability with respect to the backbone chain —A$^n$—B$^n$— . . . A$^0$ and on the types of such chain structures that can readily be prepared from commercially available reagents.

FIGS. 28–29 Examples of electron donors and acceptors which can provide organometallic molecular magnetic materials in the form of electron-transfer salts.

FIG. 30 The chemical structures with relevant letters and numbers referring to the $^{13}$C chemical shift assignments of a) 2-[4-(4-cyanophenylazo)phenoxy]-ethanoic acid (Example 1), b) 6-[4-(4-cyanophenylazo)phenoxy]-hexanoic acid (Example 4), and c) 2-[4-(4-nitrophenylazo) phenoxy]-ethanoic acid (Example 6).

FIG. 6).

FIG. 35 The chemical structure of the repeating units in A) natural DNA and B) homo-DNA are shown (between the dotted lines) for comparison; the chemical structures of the repeating units in two drastically altered DNA analogs, PNA and morphohino-carbamates, are shown in C) and D), respectively.

FIG. 42 Chemical structure of proline-glycine backbone unit with L$^n$ substituted in the 4-position of the ring. a) L$^n$ is attached via a —NH—C(=O)—CH$_2$— linker to the ring and b) L$^n$ is attached directly to the ring.

FIG. 48). The film was irradiated at 488 nm at 400 mW for 600 s with linearly polarised light.

FIG. 46 Two-dimensional representation of the chemical structure of the 15-membered cyclic compound, DNO-206, with three azobenzenes.

FIG. 47 Chemical structures of DNO-6, DNO-127, and DNO-214. DNO-127 is a bis-dimer connected via an ornithine-glycine linker. DNO-214 is a bis-trimer similarly connected.

FIG. 48 Chemical structures of DNO-26 and DNO-188 (cf. FIG. 53), DNO-34 and DNO-43 (cf FIG. 52), DNO-9 (cf. FIGS. 44 and 45).

FIG. 50 Examples of double-stranded DNO compounds, a DNO oligdmers with both electron conducting and photoresponsive properties, and DNO oligomers attached to a cyclic template based on a calixarene.

FIG. 52 Diffraction efficiency of films of DNO-34 and DNO-43 (cf. FIG. 48) as a function of time. This is an example of how architectural changes of DNQ enabling shorter exposures.

FIG. 53 Diffraction efficiency of films of DNO-26 and DNO-188 (cf. FIG. 48) as a function of time. These DNO structures incorporating non-active side-groups also enable the use of shorter exposures to obtain high diffraction efficiency.

FIG. 54 Diffraction efficiency of films of DNO-214 and DNO-127 (cf. FIG. 47) as a function of time. Dendritic structures can also result in large diffraction efficiency with short exposures.

FIG. 56 Erasure of hologram with circularly polarised light. A circularly polarised beam was turned on at the indicated time, resulting in a rapid erasure of the hologram. A new hologram can be recorded in the same space.

FIG. 57 Erasure of recorded anisotropy using UV light. 560 write-read-erase cycles have been performed in DNO-6. The X-axis indicates the number of cycles and Y-axis, the induced anisotropy at 633 nm. An Expanded region between cycles 275–285. At A, the argon laser beam at 488 nm was turned on inducing the anisotropy; At B, the argon laser beam was switched off allowing a readout of the anisotropy; At C, a krypton laser beam at 351 nm was turned on resulting in an erasure; At D, the krypton laser was turned off. The cycle was repeated 560 times.

DETAILED DESCRIPTION OF THE INVENTION

Figure 1:
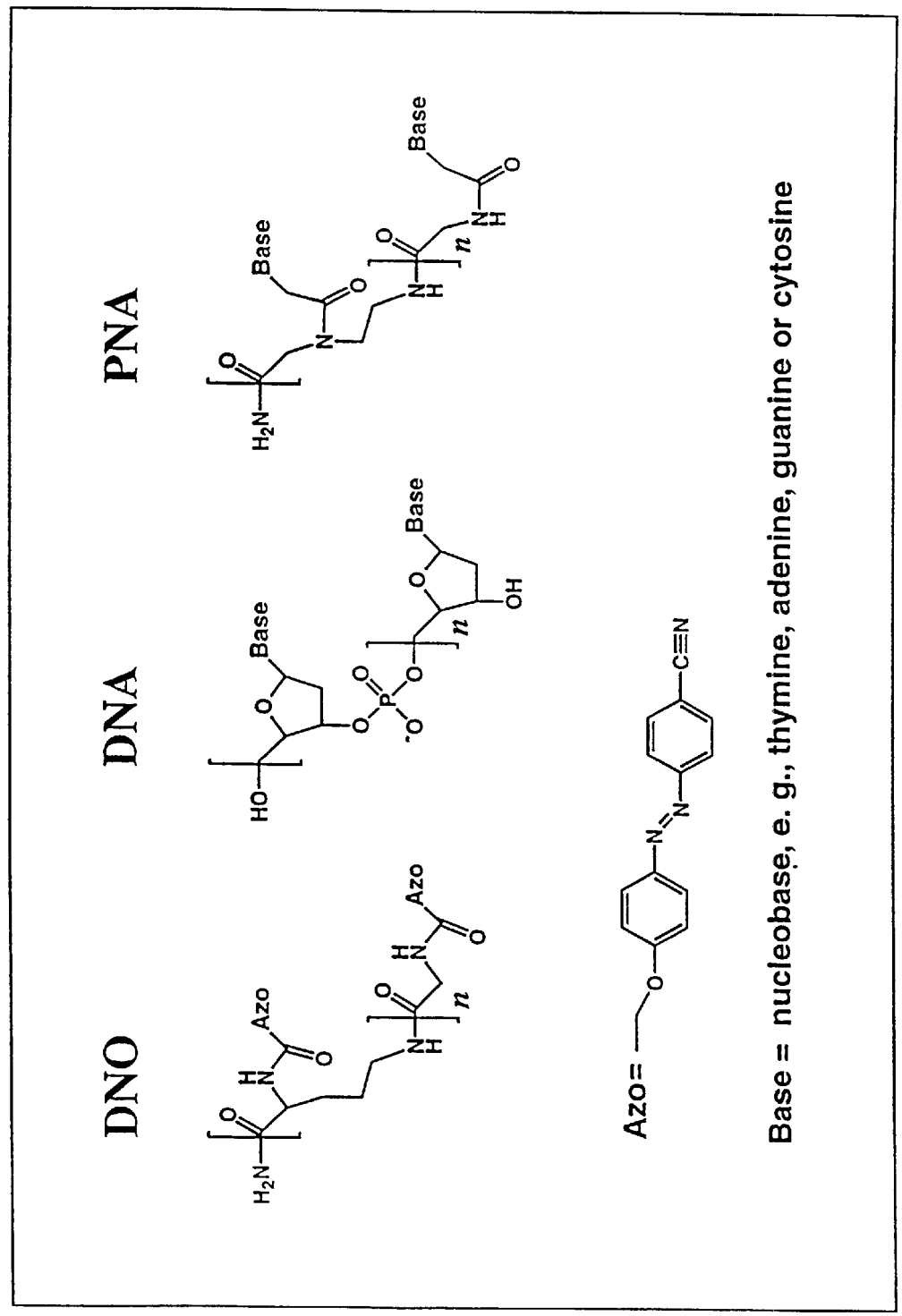
FIG. 1 Chemical structure of DNO oligomer versus the structures of DNA and PNA The name DNO is chosen as a general acronym for diamino acid $\underline{N}^\alpha$-substituted Qligopeptides. The length of the tras-azobenzene chromophore shown is in the same order as that of a hydrogen-bonded base pair in DNA (~10 Å).

This invention relates to the use of peptide oligomers, preferably monodisperse, for a new class of materials for holographic optical storage and for nonlinear optical applications. The results, which will be illustrated and described herein, show that first order diffraction efficiencies of approximately 80% can be obtained from polarisation holographic gratings formed in approximately 5 $\mu$m thick films of short oligomers. The values measured are, by far, the largest found in a thin photoanisotropic material Holograms formed in the oligomers are exceptionally stable and were not erased after exposure to 180° C. for one month. The origin of the large diffraction efficiencies is rationalised on the basis of the molecular design, and by systematically varying the oligomer structure it is shown how the holographic properties correlate with the chemical structure. The peptide strategy used permits efficient solid-phase assembly of large numbers of diverse molecular structures by Merrifield synthesis [Merrifield, R. B. *J. Am. Chem. Soc.* 85, 2149–2154 (1963); Merrifield, B. *Science* 232, 341–347 (1986)] and thus could expand considerably the framework for designing materials with new properties.

In the present context the terms "physically functional group" and "physically functional ligand" are intended to mean a group or a ligand, respectively, which is influenced by or responds to stimuli selected from heat, electromagnetic radiation, electricity, magnetism, pressure, mechanical stress, and sound in such a way that a material made of a compound comprising such a group or ligand becomes anisotropic with respect to at least one of said stimuli. As an example can be mentioned irradiation of a material with polarised light, which causes a reorientation of the molecules, thereby inducing a photodichorism or birefringence or both in the material, making the material optically anisotropic.

As examples of types of physically functional groups may be mentioned photochromic (or chromophore) groups; groups with nonlinear optical (NLO) properties; electron-conducting groups, including groups capable of providing superconducting properties; groups with photoconducting properties; groups with electroluminescence properties; groups or complexes of groups providing magnetic properties; and groups with ion-conducting properties.

In the present context, the term "photochromic" or "chromophore" is intended to mean that the group in question absorbs light at wavelengths between 100 nm and 1600 nm, in particular between 300 nm and 700 nm, and that the group as a result of light absorption is able to undergo a reversible conformational change. A common conformational change in this category is photochemical trans-cis isomerization. Examples of such groups include azobenzenes, diazobenzenes, benzylidene anilines, and stilbenes. Another useful conformational change is the photochemically induced zwitter ion formation of spiropyrans and spirobenzopyrans to the corresponding merocyanines. Yet another advantageous photochemically initiated reversible conformational change is accomplished by ionic dissociation as in triphenylnethane leucoderivatives. Other useful conformational changes are radical formation, ring-formation and ring-cleavage (Irie, M., *Adv. Polym. Sci.* 94, 27–67 (1990)). Other examples of photochromic groups are ketene dithioacetals and nitrophenylprohinols.

As examples of electron-conducting groups may be mentioned acetylenes, oligoacetylenes, pyrroles, oligopyrroles, thiophenes, oligothiophenes, phenylenes, oligo(p-phenylenes), p-phenylene sulphides, oligo(p-phenylene sulphides), oligo(p-phenylene-vinylene), anilines, oligoanilines, triphenylenes, and 2,3,6,7,10,11-hexakis-(hexyloxy)triphenylenes HalT6), 2,3,7,8,12,13-hexakis (hexylthio)tricycloquinazolines (HHTQ); electron-donor groups such as the following, either in their neutral form or in their radical cationic form: perylenes (Per), oligoperylenes, tetrathiafulvalenes (TTF), hexamethyltetraselenafulvalenes (HMTSF), tetramethyltetraselenafulvalenes (TMTSF), bis(ethylenedithio)tetrathiafulvalenes (BEDT-TTF), methylenedithiotetrathiafulvalenes (MDT-TTF), bis(methylenedithio)tetrathiafulvalenes (BMDT-TTF), bis(propylenedithio)tetrathiafulvalenes (BPDT-TTF), dimethyl(ethylenedithio)diselenadithiafulvalenes (DMET), bis(TTF) groups, bis(TTF)telluride groups, 1,3-dithiole-2-ylidene groups, chalcogenaarenes, oligochalcogenaarenes, tetraoxafulvalenes, tetraphospafulvalenes, fulvathianes, oligofulvathianes, and 1,4-phenylene-bis(dithiazolyl) groups; electron-acceptor groups such as the following, either in their neutral form or in their radical anionic form: 7,7,8,8-tetracyano-p-quinodimethanes (TCNQ), 11,11,12,12-tetracyanonaptho-2,6-quinodimethanes (TNAP).

As examples of electroluminescence properties may be mentioned radicals of oligo(p-phenylenevinylenes) and oligo(p-phenylenes). Compounds incorporating such groups may conceivably be used in light-emitting diode (LED) devices.

With respect to groups or complexes of groups providing magnetic properties, these may comprise electron-transfer salts. Such salts typically comprise pairs of electron donors and acceptors. Examples of electron donors are metallocenium moieties of Fe(III), Mn(III) or Cr(III), vanadium complexes, and metalloporphyrins comprising Mn(III). Examples of electron acceptors are of the cyanocarbon type such as tetracyanoethylene TCNE) and 7,7,8,8-tetracyano-p-quinodimethanes (TCNQ).

Examples of groups with ion-conducting properties comprise radicals of crown ethers, e.g. 18-crown-6, 15-crown-5, 12-crown-4, or crown-ether type compounds such as cryptands, cryptates, coronands, sperands, speleands, speleates, or ponands, as well as cyclic peptides.

With respect to nonlinear optical groups, a number of photochromic groups as discussed above exhibit nonlinear optical properties, provided that there is a change in the dipole moment of the group between the excited and the ground stte. Examples of such groups include azobenzenes (Formula I), diazobenzenes (Formula II), benzylidene anilines (Formula III and IV), and stilbenes (Formula V). However, other examples of NLO groups include radicals of 2,4-nitrophenyl-L-alanine methyl ester, 3-methyl4-nitro-pyridine-N-oxide, 3-nitroaniline, 2-methyl-4-nitroaniline, (−)-2-(α-methylbenzylamino)-5-nitropyridine, 4-(N,N-dimethyl-amino)-3-acetamidonitrobenzene, and N-(4-nitrophenyl)-(L)-prolinol.

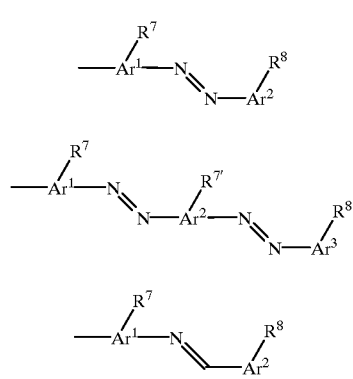

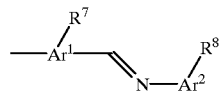

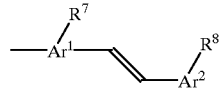

In a preferred embodiment, the physically functional group comprises one or more ligand(s) of the formulae I, II, IV, IV, or V, wherein each of $Ar^1$, $Ar^2$, and $Ar^3$ independently is selected from benzene, naphthalene, acridine, anthracene, pyrene, fluorene, pyrrol, furan, thiophene, thiene, imidazole, oxazole, thiazole, pyrazole, pyridine, piperidine, pyrimidine, purine, quinoline, isoquinoline, indole, pyridazine, sym-triazine, sym-tetrazine, phtyridine, pteridine, isoindole, 2,3,2',3'-pyrrolopyrrole, 1,2,4-triazole, 1,2,3-triazole, tetrazole, benzimidazole, indazole, benzofuran, isobenzofuran, benzothiophene, thienothiophene, isoxazole, 1,2,5-oxadiazole, isothiazole, 1,3,4-thiadiazole, benzoxazole, and benzothiazole.

Thus, each of $R^7$, $R^{7'}$, and $R^8$ independently designates one or more substituent(s) each independently selected from hydrogen, deuterium, hydroxy, halogen such as fluorine, chlorine, bromine. and iodine, linear or branched optionally substituted $C_{1-6}$-alkyl, optionally substituted $C_{1-6}$-alkoxy, optionally substituted heterocyclyl, (optionally substituted heterocyclyl)-$C_{1-6}$-alkyl, optionally substituted axyl, (optionally substituted aryl)-$C_{1-6}$-alkyl, optionally substituted aryloxy, (optionally substituted aryloxy)-$C_{1-6}$-alkyl, ketene, thioketene, keteninmine, halogen, cyano, nitro, nitroso, amino, mono- or di(optionally substituted $C_{1-6}$-alkyl)amino, mono- or di(optionally substituted $C_{1-6}$-alkyl)amino-$C_{1-6}$-alkyl, (optionally substituted $C_{1-6}$-alkyl) carbonylamino, (optionally substituted $C_{1-6}$-alkyl) carbonylamino-$C_{1-6}$-alkyl, aminocarbonyl, aminocarbonyl-$C_{1-6}$-alkyl, mono- or di(optionally substituted $C_{1-6}$alkyl) aminocarbonyl, mono- or di(optionally substituted $C_{1-6}$-alkyl)aminocarbonyl-$C_{1-6}$-alkyl, optionally substituted $C_{1-6}$-acyl, optionally substituted $C_{1-6}$-acyloxy, carboxy, —COSH, (optionally substituted $C_{1-6}$-alkoxy)carbonyl, thiolo, $C_{1-6}$-alkylthio, optionally substituted $C_{1-6}$-alkylthio-$C_{1-6}$-alkyl, (optionally substituted aryl)thio, guanidino, guanidino-$C_{1-6}$-alkyl, optionally substituted $C_{1-6}$-alkylsulphonyl, (optionally substituted aryl)sulphonyl, mono- or di(optionally substituted $C_{1-6}$-alkyl) aminosulphonyl, sulphono (—$SO_3H$), sulphino (—$SO_2H$), halosulphonyl, isocyano, isothiocyano, thiocyano, ($R^9$)$_3$Si—, ($R^9$)$_3$Si—$C_{1-6}$-alkyl, ($R^9$)$_3$Si-phenyl, wherein each of $R^9$ is independently selected from $C_{1-6}$-alkyl, $C_{1-6}$-alkoxy, phenyl, $C_{1-6}$-alkyl-phenyl, phenyl-$C_{1-6}$-alkyl, chloro, and vinyl; or where two substituents $R^7$ or $R^8$ together form a substituent selected from biradicals corresponding to the above-mentioned radicals and —W—$CH_2CH_2$—W—$CH_2$—(—$CH_2$—W—$CH_2$—)$_w$—$CH_2$—W— where W is selected from —O— and —NH— and w is 1–3.

Substituents on the aromatic or heteroaromatic rings which may increase stacking interactions between the individual physically functional groups and and any physically non-functional groups include electron-withdrawing or electron-donating groups and atoms.

Furthermore, in an especially preferred embodiment, each of $Ar^1$, $Ar^2$, and $Ar^3$ independently designates benzene, naphthalene, acridine, thiophene, imidazole, pyridine, piperidine, pyrimidine, purine, and indole; and each of $R^7$, $R^{7'}$, and $R^8$ independently designates one or more substituent(s) each independently selected from hydrogen, deuterium, hydroxy, halogen such as fluorine, chlorine, bromine, and iodine, linear or branched optionally substituted $C_{1-6}$-alkyl, optionally substituted $C_{1-6}$-alkoxy, cyano, nitro, amino, mono- or di(optionally substituted $C_{1-6}$-alkyl)amino, mono- or di(optionally substituted $C_{1-6}$-alkyl)amino-$C_{1-6}$-alkyl, (optionally substituted $C_{1-6}$-alkyl)carbonylamino, (optionally substituted $C_{1-6}$-alkyl)carbonylamino-$C_{1-6}$-alkyl, aminocarbonyl, aminocarbonyl-$C_{1-6}$-alkyl, mono- or di(optionally substituted $C_{1-6}$-alkyl)aminocarbonyl, mono- or di(optionally substituted $C_{1-6}$-alkyl)aminocarbonyl-$C_{1-6}$-alkyl, optionally substituted $C_{1-6}$-acyl, optionally substituted $C_{1-6}$-acyloxy, carboxy, —COSH, (optionally substituted $C_{1-6}$-alkoxy)carbonyl, thiolo, $C_{1-6}$-alkylthio, optionally substituted $C_{1-6}$-alkylthio-$C_{1-6}$-alkyl, guanidino, isocyano, isothiocyano, and thiocyano.

Examples of substitutents on the aromatic rings $Ar^1$, $Ar^2$, and $Ar^3$ are, —$CH_2$—*$CH(CH_3)$—$CH_2$—$CH_3$, —$OR^{10}$, —$SR^{10}$, phenyl, benzyl, —F, —Cl, —Br, —I, —$CF_3$, —$CF_2CF_3$, —$OCF_3$, —$OCF_2CF_3$, —$NHR^{10}$, —$NR^{10}R^{10'}$, —$NH(CH_2)_{2-10}OH$, —$N((CH_2)_{2-10}OH)_2$, —$N<$(—$CH_2CH_2)_2)$>$CH$—$O$—$(CH_2)_{0-10}CH_3$, —COOH, —COSH, —$COOR^{10}$, —$COSR^{10}$, —$OC(=O)R^{10}$, —$OC(=O)$—$CH=CH_2$, —$SC(=O)R^{10}$, —COCl, —COBr, —CHO, —$COR^{10}$, —$SO_2OH$, —$SO_2OR^{10}$, —$SO_2R^{10}$, —$SO_2(CF_2)_{0-10}CF_3$, —$SO_2(CH_2)_{2-10}OH$, —$SO_2(CH_2)_{2-10}SH$, —$SO_2(CH_2)_{2-10}OC(=O)C(CH_3)=CH_2$, —$SO_2(CH_2)_{2-10}OC(=O)CH=CH_2$, —$CONH_2$, —$CONHR^{10}$, —$CONR^{10}R^{10'}$, —NCO, —NCS, —$CH=CH_2$, —$CR^{10}=CR^{10'}R^{10''}$, —$CH=C(CN)_2$, —$CH=C(CN)(NO_2)$, —$C(CN)=(CN)_2$, —$CH=C(SO_2R^{10})_2$, —$CH_2CH=CH_2$, —$CH_2CR^{10}=CR^{10'}R^{10''}$, —$N_2^+PF_6^-$, —$N_2^+PAs_6^-$, —$N_2^+BF_4^-$, —$OC(=O)C_6H_3<$(—$O(CH_2CH_2$—$O)_{4-6}$—), —$OC(=O)C_6H_3<$(—$O(CH_2CH_2$—$O)_y$—$CH_2CH_2$—NH—$(CH_2CH_2$—$O)_z$—), where y and z each are 0–5 and the sum y+z is 3–5, tert-butyldiphenylsilyl, ethylmethyldichlorosilyl, ethyltrichlorosilyl, 2-ethylmethyldichlorosilyl, 2-ethyltrichlorosilyl, 2-ethyltriethoxysilyl, 1-ethyltrimethylsilyl, methyldimethylchlorosilyl, methyldimethylethoxysilyl, methyldimethylphenylsilyl, methyldimethylsilyl, methyldimethylvinylsilyl, methylmethyldichlorosilyl, methylmethyldiethoxysilyl, p-(methyl)phenyltrichlorosilyl, p-(methyl)phenyltrimethoxysilyl, methyltrichlorosilyl, methyltriethoxysilyl methyltrimethylsilyl, 2-methyl-3-trimethylsilyl-1-propene, (phenylethyl)methyldichlorosilyl, phenyltrichlorosilyl, phenyltriethoxysilyl, p-phenyltrimethylsilyl, 3-propyldimethylchlorosilyl, 3-propyldimethylchlorosilyl, 3-propyldimethylvinylsilyl, 3-propylmethyldichlorosilyl, 3-propylmethyldimethoxysilyl 3-propyltrichlorosilyl, 3-propyltriethoxysilyl, 3-propyltrimethoxysilyl, 3-propyltrimethylsilyl, 3-propyltris(trimethylsiloxy)silyl, 2-(4-sulfonylphenyl)ethyltrichlorosilyl, 2-(4-sulfonylphenyl)ethyltrimethoxysilyl, and oxirane; where $R^{10}$, $R^{10'}$, and $R^{10''}$ each independently is selected from optionally substituted $C_{1-6}$-alkyl, —$CH_2$—*$CH(CH_3)$—$CH_2$—$CH_3$, —*CH(Cl)—*$CH(CH_3)$—$C_2H_5$, —*CH(Br)—*$CH(CH_3)$—$C_2H_5$, —*CH(CN)—$C_4H_9$, 13 *CH(Cl)—$CH_3$, —*CH($CF_3$)—$CH_2$—$CH(CH_3)_2$, —*$CH(CH_3)$—$COOC_2H_5$, —$CH_2$—*CH(F)—*$CH(CH_3)$—$C_2H_5$, optionally substituted phenyl, and optionally substituted benzyl.

It is clear that any of the physically functional ligands I–V according to the invention fulfils the requirements of being susceptible to photochemical transcis isomerization. Therefore, reference to "azobenzene(s)", where not explicitly directed to a $C_6H_5$—N=N—$C_6H_4$— moiety, should includes any of the the ligands I–V defined herein.

It should be understood that the physically functional groups may comprise two or more physically functional ligands and in these cases, the individual ligands are linked together with linking groups as defined for the linking groups defined for Y herein or they are linked together directly, i.e. through a single or double bond. For most of the applications described herein L preferably consist of one ligand.

Complementary to the physically functional groups and ligand are the physically non-functional groups and ligands.

In the present context, the terms "physically non-functional group" and "physically non-functional ligand" are intended to mean a group or a ligand, respectively, containing one or more cyclic moieties comprising π-electrons (cyclic π-electron system(s)), where said group or ligand is not influenced by or respond to the stimuli in question. However, the group or ligand can participate in stacking interactions with the physically functional groups.

In the present context, "cyclic π-electron systems" is intended to mean aromatic, heteroaromatic or non-aromatic rings containing π-electrons.

In the present context, the term "stacking" is intended to mean interactions stabilized through the combined effects of π-electron interactions, dipole interactions and dipole-induced dipole moments. Such interactions are well known in the literature (Wolfgang Saenger, "Principles of Nucleic Acid Structure", Springer-Verlag, New York 1988).

One aim of introducing physically non-functional groups would be e.g., intramolecular dissolution, in order to avoid extensive absorption. Physically non-functional groups which can stack with azobenzenes include groups containing one or more cyclic moieties which contain π-electrons, and which may be substituted or not. Examples of such groups are: benzenes, thiophenes, imidazoles, pyrans, furans, pyrroles, pyrimidines, napthalenes, indenes, indoles, purines, quinolines, pentalines, azulenes, heptalenes, flourenes, carbazoles, xanthenes, acridines, pyrenes, anthracenes, anthraquinones, phenanthrenes, phenalenes, benzo[e]perimidines, and steroids.

In the present context, the term "anisotropic" means that the response of the material with respect to the stimulus in question is different in different spatial directions.

In the present context the term "photoresponsive" is intended to mean that the group in question responds to light of wavelengths between 100 nm and 1600 nm, either through direct absorption of light or through changes in refractive index.

In the present context the term, "diffraction efficiency" is intended to denote the ratio between (A) the intensity of light of a specific wavelength between 100 nm and 1600 nm, such as at 488 nm and 515 nm from an argon ion laser, 532 nm from a frequency-doubled YAG laser, 633 nm from a He—Ne laser or 780 nm from a diode laser, diffracted into various orders from a material and (B) the intensity of light of the said wavelength incident on the material.

It is an aspect of the present invention to provide an optically anisotropic material comprising the compounds defined herein, wherein the diffraction efficiency, when tested at a wavelength in the range of 100 nm to 1600 nm, e.g. at 488 nm, 515 nm, 532 nm, 633 nm, or 780 nm, is at least 50%, preferably at least 60%, in particular at least 70%, such as at least 80%, without application of an electrical field over the material.

Diffraction gratings generated in materials according to the invention have proved to be stable for more than one month, and even more than one year, even at increased temperatures, such as temperatures at around 150° C.

It is believed that materials of oligomeric compounds, e.g. comprising 2–20 segments, having 10 such a high diffraction efficiency in them selves are novel irrespective the structure of A, B, and Y. Thus, materials having either a high diffraction efficiency or good thermal stability are special aspects of the present invention.

In the present context the term "monodisperse" as used about a compound is intended to mean that the molecules of the compound in question are identical It is understood that "monodisperse" is a theoretical term which in reality, and within in the present context, means that the compounds are as pure as it is possible within the technologi used, e.g. the solid phase peptide chemistry technology, thus, monodisperse compounds may comprise small traces of impurities so that the purity of the compounds are at least 98% pure, preferably 99% pure, in particular 99.9% pure.

In the present context the term "photoanisotropic" is intended to mean that an optical anisotropy, such as a variation in the refractive index in different directions in the compound, is created by incident polarised light, between the wavelengths 100 nm and 1600 nm, e.g. the wavelengths mentioned above.

For holographic storage purposes, it is preferred that the compound is irradiated with polarised light. The conversion into.the optically anisotropic phase is accomplished by the rotation of the chromophores away from the isotropic distribution of the directions of the chromophores towards a state in which the axes of the chromophores are substantially aligned at a certain angle to the polarisation of the incident light.

This is preferred as it is possible to affect the chromophores with the electric field of light. The direction of the electric field defines the direction of the polarisation of light. The probability of the dipole moment of the chromophore interacting with the light is proportional to the square of the cosine to the angle between the dipole moment and the electric field of the incident light.

It is contemplated that the degree of anisotropy of the chromophores containing an azo-group is a function of the intensity of the incident light and the period during which the light is incident.

The chromophore which is normally in the trans state, after absorption of light is isomerized to the cis state and will eventually return to the trans state. The chromophore may end up at a different angle than the one it originally had after such a transmis isomerization. As long as there is a component of the dipole moment in the direction of the electric field, the chromophore will continue to absorb light. Eventually it will end up at right angles to the electric field of the incident light, and will not be able to absorb any light. When a significant number of the chromophores are aligned in this direction, an anisotropic phase is obtained. The alignment of the chromophores is preserved even after the incident polarised light is removed.

Figure 51:
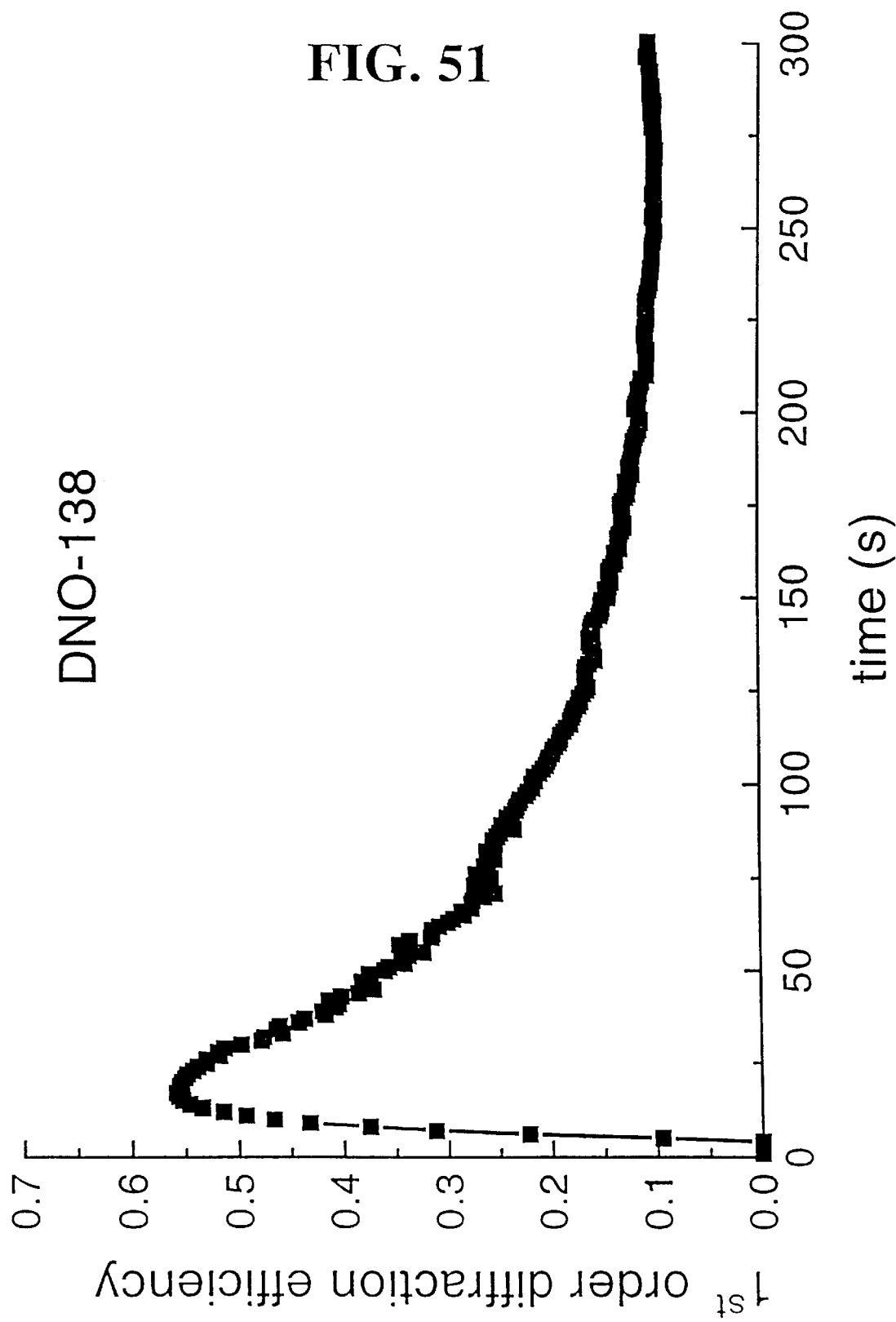
FIG. 51 Diffraction efficiency of a film of DNO-138 (cf FIG. 48) as a function of time. The intensity of the 488 nm line of the argon laser is about 2 W/cm$^2$. The fall in the diffraction efficiency is due to the sin$^2$(Δn) dependence of the diffraction efficiency, where An is the change in the refractive index due to irradiation.
Figure 55:
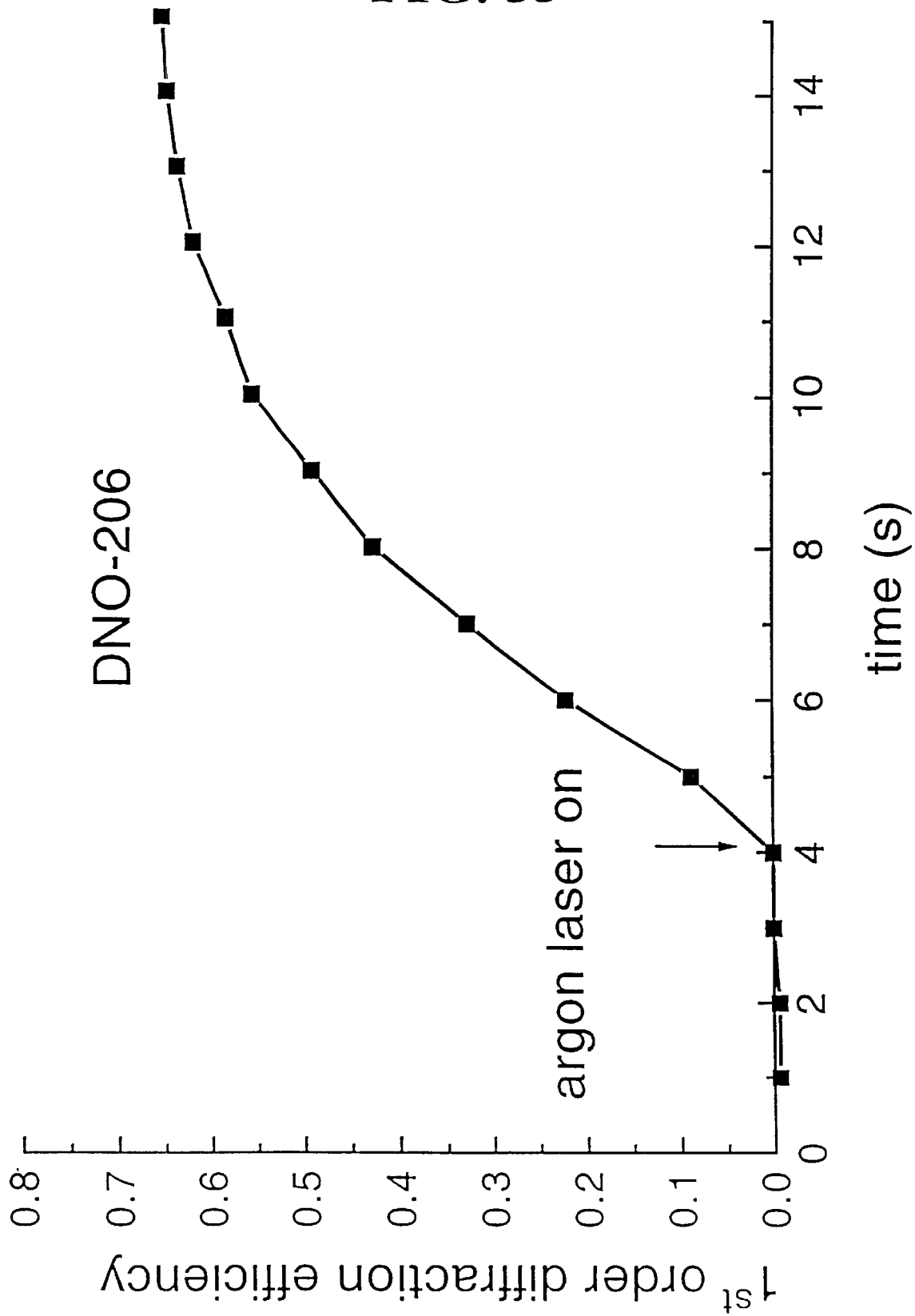
FIG. 55 Diffraction efficiency of a film of DNO-206 as a function of time. This is an example of a cyclic peptide with three azobenzene side chains.

It is believed that the compounds according to the present invention are helical in structure with the physically functional groups, preferably azobenzene groups, stacking perpendicular to the helical axis. It is further believed that when one azobenzene chromophore is aligned perpendicular to the polarisation of light, due to the stacking properties, all the azobenzenes are aligned perpendicular to the polarisation of the incident light as well. In other words, the helical axis of the molecule is aligned approximately parallel to the polarisation of the incident light. Thus, the alignment effect is amplified greatly because of stacking. This results in different amounts of absorption of light in directions parallel and perpendicular to the polarisation of the incident light, as well as different refractive indices. This process is more familiarly known as optical anisotropy. The amount of change in the refractive index is responsible for the varying diffraction efficiency. The diffraction efficiency of a thick holographic grating is proportional to the square of the sine to the change in the refractive index. Thus, initially the diffraction efficiency increases, reaches a maximum and begins to fall as the optical birefringence increases. The diffraction efficiency oscillates as a function of the change in refractive index. In the present invention, the change in the refractive index is proportional to the irradiation time. Hence the diffraction efficiency can be seen to vary as a function of time (FIG. 51).

In the present context, "birefringence" is intended to mean the presence of two or three refractive indices in the material upon irradiation with a polarised laser beam.

In the present context, "dichroism" is intended to mean different absorbance of a material, e.g. a film, for different polarisations of the incident light.

Polarised light may be obtained by either using a laser light source or by transmitting light from, e.g., a lamp through a polariser.

To be able to form, e.g., a hologram in a compound, it is preferred that the thickness of the film correspond to an absorbance between 0.001 and 10 at the wavelength used to irradiate the compound, so as to on the one hand give a sufficiently strong signal and on the other hand be able to transmit a sufficient amount of light through the compound. It is particularly preferred that the thickness of the film be such that the absorbance be between 0.01 and 5, such as between 0.1 and 3, or even more preferred between 0.5 and 2, such as about 1 at the wavelength used to irradiate the compound.

Since the optical storage medium is suited for almost all types of information, it will be preferred to be able to use less power-consuming and compact light emitters such as light diodes, laser diodes, lamps, or low power gas lasers. The wavelength of these light emitters is at present between 100 and 1600 nm having a power of several milliwatts to watts.

The compound is preferably one which is capable of being permanently or substantially permanently converted into an optically anisotropic phase by irradiation with light of a single wavelength in the range 100–1600 nm.

In the present context the term "optically anisotropic phase" is intended to have the same meaning as "photo-anisotropic" phase defined above.

In order to obtain convenient writing of information, it is preferred that the irradiation is performed with light between 300 and 700 nm with an energy between 1 mJ/cm$^2$ and 10 J/cm$^2$ for a period of time of at the most 1000 s, more specifically the irradiation is performed with light at 350–550 nm with an energy between 50 mJ/cm$^2$ and 5 J/cm$^2$ for a period of at the most 800 s, or more specifically that the irradiation is performed with light at 350–515 nm, such as 488 or 514 nm, as emitted by an argon-ion laser with an energy of 2 J/cm$^2$ for a period of time at the most 400 s, such as at the most 300 s. By a the compound according to the present invention, storage of information can be facilitated within even shorter irradiation-periods, e.g., at the most 100 s, such as at the most 30 s, or at the most 10 s, or even less than 5 s, such as less than 1 s. By varying the backbone length or by including two or more domains of a successive chain of segment(s) of the formula G and, optionally, segment(s) of the formula G' in the molecule, it may be possible to record information with even shorter exposures, such as less than 100 ms or even less than 1 ms. Examples of shorter exposure times obtainable with such architectural changes are outlined in FIG. 9 (shorter backbones) or FIG. 54 (dendritic structures).

In one embodiment, for ease of writing with the available laser sources, it is preferred that the compound be capable of being permanently or substantially permanently converted into an optically anisotropic phase by irradiation with light of a single wavelength in the range of 100–1600 nm, such as in the range of 300–700 nm, preferably in the range of 330–515 nm, such as in the range of 350–515 nm, e.g. 488 nm or 514 nm, as emitted by an argon ion laser.

Naturally, all of the types of light sources emitting light in the above range, such as excimer lasers, frequency doubled YAG lasers, Kr lasers, diode lasers and synchrotron sources may be used for the purpose of writing information in the compound. Well-known examples of laser wavelengths are 360, 488, and 515 nm from argon ion lasers, 350, 403, 407, 578, and 647 nm from krypton lasers, 1064, 532, and 266 nm from YAG lasers, 633 nm from He—Ne lasers, 780, 850, 1320, and 1550 nm from diode lasers.

This type of information is typically stored as a hologram stored over at least a large part of the surface of a material according to the invention, e.g. in the form of a film. The area used to store the hologram may be reduced by, e.g., using an aperture or optical components to define this area. Furthermore, binary information may be stored, e.g., as bits by a focused laser.

In order to facilitate storage of information using low energy light sources, which is desirable if the storage is to be performed by domestic users, it is preferred that storage of information is obtained by applying light to the compound at an energy between 1 mJ/cm$^2$ and 10 J/cm$^2$, when the compound is in the form of or incorporated into a thin film of a thickness in a range between 0.5 $\mu$m and 1000 $\mu$m. It is specifically preferred that the light is applied to the compound at an energy between 50 mJ/cm$^2$ and 5 J/cm$^2$ when the compound is in the form of or incorporated into a film of a thickness in a range between 0.5 $\mu$m and 100 $\mu$m.

To enable storage of information using safe light sources, it is preferred that the light is applied to the film at an energy between 100 mJ/cm$^2$ and 5 J/cm$^2$ when the compound is in the form of a film of thickness in a range between 1 and 10 $\mu$m, such as light at an energy of about 2 J/cm$^2$ when the compound is in the form of a film with thickness of about 5 $\mu$m.

Generally, it is preferred that the anisotropic phase is formed by a change in the refractive index. In this case, the major part of the incident light is transmitted through the medium increasing the signal-to-noise ratio of the detection of information.

Typically, the change in refractive index is at least 0.1%, such as at least 0.5%, preferably at least 1%, such as at least 5%, preferably at least 10%, such as at least 30% of the refractive index of the compound in the isotropic state. Large modulations of the refractive index, in general, lead to higher diffraction efficiencies and, thus, a better signal-to-noise ratio in the detection of information.

One way of erasing the information in the material is to apply a beam of light with a polarisation having a different polarisation than the polarisation of the light carrying out the conversion of the isotropic phase to the anisotropic phase to the spot to be erased. It is preferred to use circularly polarised light for erasure of information. The light can either be left or right circularly polarised. As the polarisation of the circularly polarised light rotates in time, the resulting directions of the individual chromophores will be random in the plane of the film.

A material according to the invention is able to store information at a density (expressed in lines per unit of length) of up to 5000 lines per mm and even up to 6000 lines per mm when a grating is formed in the compound by two counter-propagating coherent beams. It has been suggested that 1500 lines are sufficient to reproduce a page of information legibly ("Holographic ultrafiche", D. H. McMahon, *Appl. Opt.* 11, 798–806 (1972)). It is believed that because of the high resolution of the material according the present invention, that one page could be stored in a spot size of 0.25 mm diameter and can be retrieved to produce a legible image. Thus 2000 pages of information can be stored in one cm$^2$ of the material It is contemplated that another way of storing a large amount of information is through storage in thick films of the material. It is well known (G. T. Sincerbox, *Opt. Mater.* 4, 370–375 (1995)) that using angular or phase multiplexing techniques, that several holograms can be recorded in the same volume of the film. In the present invention, the material has been incorporated in 65 $\mu$m thick films of polyethylene-polystyrene (PEPS) film, giving a diffraction efficiency of 20%. It is contemplated that this can be extended to store several holograms in the same volume of the film.

Typically, it is preferred to irradiate the compound with two circularly or linearly polarised beams of light, in particular, two circularly polarised beams of light.

It is convenient and preferred to irradiate the compound with monochromatic light, such as coherent light, especially laser light, especially for holographic storage.

In some aspects of the present invention it is believed to be particularly advantageous if the material in question has been prealigned prior to exposure to the laser beam and/or other external stimulations. One example of preignment would be to cast the compound on a smooth glass substrate coated with a layer of an orienting material Such orienting materials include a whole range of polymeric materials and, in particular, polyimides [Eich, M & Wendorff, J. *J. Opt. Soc. Am.* B 7, 1428–1436 (1990)] or poly(tetra fluoroethylenes) [Wittmann, J. C. & Smith, P. *Nature* 352, 414–417 (1991)] are known to induce a remarkable degree of prealignment. In a second example the compound in question may be prealigned using the Langmuir-Blodgett (LB) film technique [Yokoyama, S., Kakimoto, M. & Imai, Y. *Thin Solid Films* 242, 183–186 (1994)].

An advantage of the present invention is that the compounds, which can be used for holographic optical storage of information, can be synthesised by using conventional peptide chemistry techniques. An advantage of the peptide strategy is that it permits stepwise assembly of monodisperse and chemically unambiguous oligomers by Merrifield solid-phase synthesis.

Moreover, it permits the specific replacement of particular backbone or side-chain residues by other residues and thus could expand considerably the framework for designing materials with new properties.

Oligomer or polymer backbones used to align the physically functional side chain groups in question, e.g., azobenzene-containing side chains, should preferably fulfill a number of requirements. First, the backbones should provide a proper geometry in terms of the number of bonds between the side chains to allow for stacking of the π-electron systems of the physically functional groups in question. Second, the backbones should preferably be conformationally constrained to a degree that limits the number of possible conformational states. Third, the backbones should have enough flexibility to allow for the stacking of a whole variety of different π-electron systems.

It appears from naturally occuring biological oligomers and polymers such as peptides, proteins and DNA that amide bonds and sugar moieties are ideal candidates possessing such properties. Therefore, in large part, the backbones constructed according to the present invention, are constructed by combining the unique features of naturally occurring oligomers and polymers.

Oligomers were designed, in which physically functional groups, e.g., azobenzenes, were linked to a peptide-like backbone in a manner that was expected to maximize stacking interactions between the π-electron systems of the azobenzenes. Azobenzenes were chosen as the side chains as they have been shown to induce changes in the orientational order of polymer films upon trans-to-cis photochemical isomerization (Eich, M., Wendorff, J. H., Reck, B. & Ringsdorf, H. *Makromol. Chem. Rapid Commun.* 8, 59–63 (1987); Eich, M. & Wendorff. *Makromol. Chem. Rapid Commun.* 8, 467–471 (1987); Wiesner, U., Antonietti, M., Boeffel, C. & Spiess, H. W. *Makromol. Chem.* 191, 2133–2149 (1990); Gibbons, W. M., Shannon, P. J., Sun, S.-T. & Swetlin, B. J. *Nature* 351, 49–50 (1991); Stumpe, J., Muller, L., Kreysig, D. *Makromol. Chem. Rapid Commun.* 12, 81–87 (1991); Hvilsted, S., Andruzzi, F. & Ramanujam, P. S. *Opt. Lett.* 17, 1234–1236 (1992); Xie, S., Natansohn, A & Rochon, P. *Chem. Mater.* 5, 403–411 (1993); Hvilsted, S., Andruzzi, F., Kulinna, C., Siesler, H. W. & Ramanujam, P. S. *Macromolecules* 28, 2172–2183 (1995)).

A proper distance in the backbone between the individual azobenzenes was estimated by a simple molecular model. In this model, the stacking distance between the individual azobenzene rings in the direction perpendicular to the ring planes is about 3.5 Å. The optimal number of bonds between the azobenzene side chains was found to be six, which corresponds to the number of bonds that allows for stacking between nucleobases attached to the deoxyribose phosphate backbone of DNA or for stacking between nucleobases attached to the (2-amino)ethylglycine backbone of peptide nucleic acids (PNA) (Niles, P. E., Egholm, M., Berg, R. H. & Buchardt, O. *Science* 254, 1497–1500 (1991); Egholm, M., Buchardt, O., Niles, P. E. & Berg, R. H. *J. Am. Chem. Soc.* 114, 1895–1897 (1992); Egholm, M., Nielson, P. E., Buchardt, O. & Berg, R. H. *J. Am. Chem. Soc.* 114, 9677–9678 (1992)). This indicated that a backbone consisting of all-L or all-D ornithine units oligomerized through the δ-amino group and with the side chains attached to the α-groups via methylenecarbonyl linkers could be used. According to the model, such a backbone consisting of a highly flexible trimethylene group in combination with two conformationally constrained amide groups per unit would allow the azobenzenes to stack in a helical arrangement. Examination of the model further suggested that a specific hydrogen bond between the side-chain carbonyl oxygen (=O) and the nearest backbone amide (>NH) could play a structural role in predefining the stacking of the azobenzene side chains.

In view of the fundamental principles and the entire rationale for the design of DNO compounds, it is highly conceivable that the properties of DNO oligomers reported according to the present invention may also be obtained using similar oligomers constructed from the sugar-phosphate backbones of DNA or RNA or the backbones of analogous compounds which contains six consecutive covalent bonds per backbone unit, Thus, oligonucleotides and analogs thereof equipped with suitable physically functional ligand(s), either incorporated in replacement for the nucleobases or in another specific position, should be useful within the context of the present invention. Likewise, it is predicted that such oligomers should contain preferably two or more residues. The analogous compounds in question include a wide variety of oligonucleotides modified either in the phosphate moiety or the sugar moiety, or both, and include monothiophosphates [Stech, W. J. et al. *J. Am. Chem. Soc.* 106, 6077–6079 (1984) and Connolly, B. A. et al. *Biochemistry* 23, 3443–3453 (1984)], dithiophosphates [Nielsen, J. et al. *Tetrahedron Lett.* 29, 2911 (1988)], methylphosphonates [Lesschner, T. & Engels, J. W. *Nucleosides Nucleotides* 7, 729–732 (1988)], borano phosphates [Sood, A. et al. *J. Am. Chem. Soc.* 112, 9000–9001 (1990)], etc. [Uhlmann, E. & Peyman, A. *Chem. Rev.* 90, 544–584 (1990)], as well as formacetal [Matteucci, M. *Tetrahedron Lett.* 31, 2385–2388 (1990)], carbamate [Coull, J. M. et al. *Tetrahedron Lett.* 28, 745–748 (1987) and Stirchak et al. *J. Org. Chem.* 52, 4202–4206 (1987)], and siloxane [Cormier, J. F. & Ogilvie, K. K. *Nucleic Acids Res.* 16, 4583–4594 (1988)], or dimethylenethio-, sulfoxido-, and -sulfono-linked species [Huang, Z. et al. *J. Org. Chem.* 56, 3869–3882 (1991) and Schneider, K. C. & Benner, S. A. *Tetrahedron Lett.* 31, 335–338 (1990)] as well as morpholno-type of oligonucleotides [Stirchak, E. P. et al. *Nucl. Acids Res.*, 15, 6129 (1989)], oxyamide-linked oligonucleotides [Burgess, K. et al. *J. Chem. Soc., Chem. Commun.* 915–916 (1994)], amide-types of oligonucleotides [De Mesmaeker, A. et al. *Angew. Chem. Int Ed. Engl.* 33, 226–229 (1994)], and methylhydroxylamine-linked oligonucleotides [Vasseur, J.-J. et al. *J. Am. Chem. Soc.* 114, 4006–4007 (1992)]. For the chemical synthesis of standard oligonucleotides as well as several analogs, a number of standard procedures, and the phosphoramidite method in particular [Caruthers, M. H. *Science* 230, 281–285 (1985) and *Acc. Chem. Res.* 24, 278–284 (1991), and references cited herein] can be used ["Nucleic Acids in Chemistry and Biology", Blackburn and Gait, eds., Oxford University Press, Oxford, 1990, and references cited herein].

Thus, numerous types of modifications of DNA and RNA and their smaller versions (oligonucleotides) are well-known. Within the context of the present invention it may be particularly desirable to attach the physical functionality, e.g., an azobenzene, through an amino group present in the oligonucleotide in question. One preferred position of such an amino group (e.g., in the form of a aminomethyl group) would be the 1' position in the sugar moiety, that is, the position where the nucleobase is normally attached However, the 2' position and even the 3', 4', and 5' positions should be useful, as well. A relatively simple and very appealing possibility would be to attach the physically functional group, e.g., an azobenzene, directly through the exocyclic amino groups of either of the three naturally occuring nucleobases (DNA bases) adenine, guanine or cytosine. In other embodiments of the present invention, the physically functional groups should be attached directly to, e.g., the sugar moities, and not via amino groups. The chemical structure of the repeating unit in natural DNA as well as examples of how the physically functional group (illustrated by $L^1$ in Azo1-III (see FIG. 5)) may be positioned are shown in FIG. 33.

Figure 33:
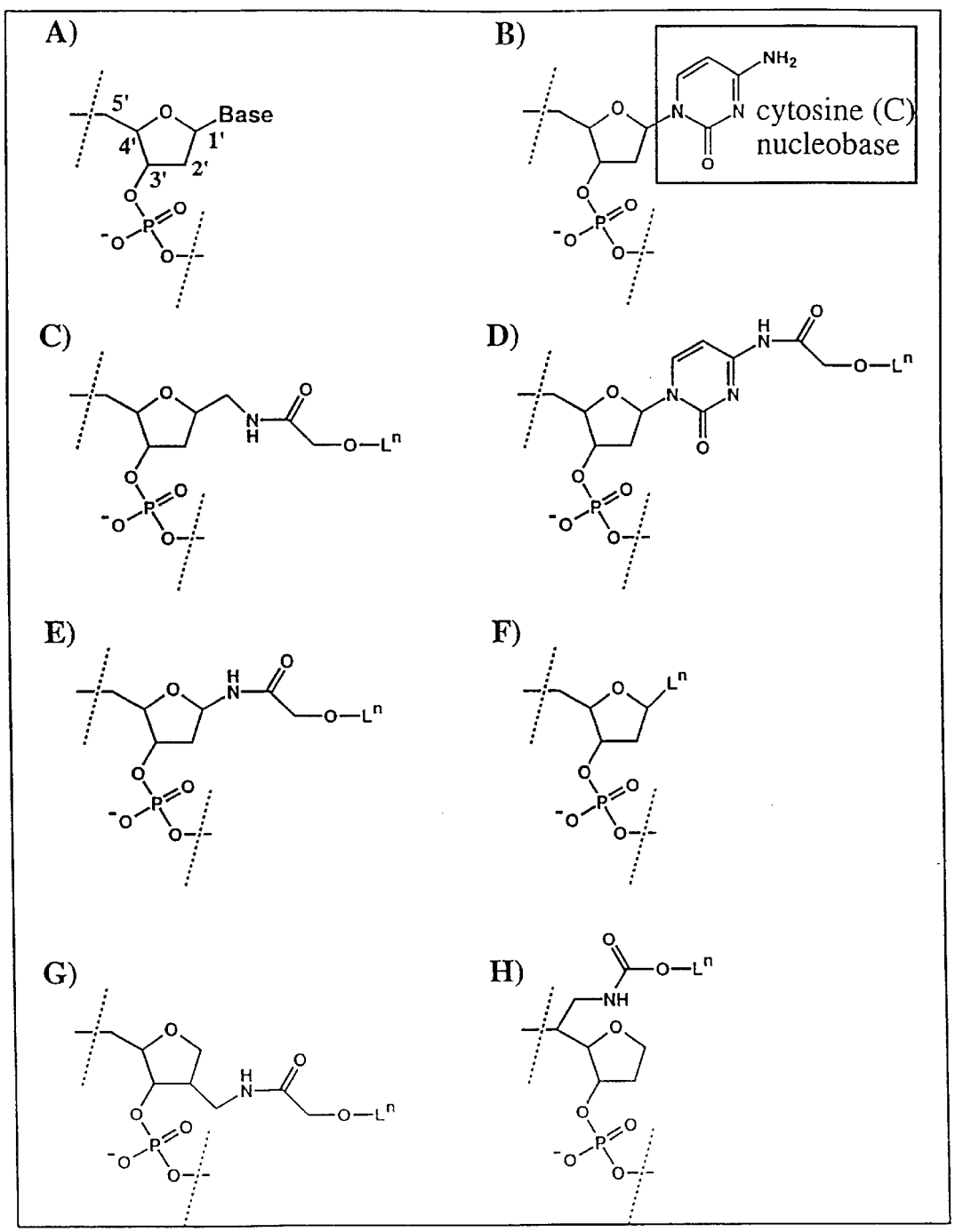
FIG. 33 Different structures based on the DNA backbone.

In FIG. 33 the chemical structure of the repeating unit in natural DNA is shown in A; also the 1', 2', 3', 4', and 5' positions as well as the position in which the naturally occuring nucleobase B is attached are shown. B) shows the repeating unit of natural DNA in which the naturally occuring nucleobase B is cytosine, that is one of the three naturally occuring nucleobases which contains an exocyclic amino group. C) shows the repeating unit of natural DNA in which a physically functional group $L''$ is attached via a —O—CH$_2$—C(=O)— moiety linked through an amide bond to an aminomethyl-substituted 1' carbon atom in the sugar ring. D) shows the repeating unit of natural DNA in which a physically functional group $L''$ is attached via a —O—CH$_2$—C(=O)— moiety linked through an amide bond to the exocyclic amino group in the naturally occuringnucleobase cytosine. E) shows the repeating unit of natural DNA in which a physically functional group $L''$ is attached via a —O—CH$_2$—C(=O)— moiety linked through an amide bond to an amino-substituted 1' carbon atom in the sugar ring. F) shows the repeating unit of natural DNA in which a physically functional group $L''$ is substituted directly onto 1' carbon atom in the sugar ring. G) shows the repeating unit of natural DNA in which a physically functional group $L''$ is attached via a —O—CH$_2$—C(=O)— moiety linked through an amide bond to an aminomethyl-substituted 2' carbon atom in the sugar ring. H) shows the repeating unit of natural DNA in which a physically functional group $L''$ is attached via a —O—CH$_2$—C(=O)— moiety linked through an amide bond to an aminomethyl-substituted 5'-carbon atom in the sugar moiety.

Figure 34:
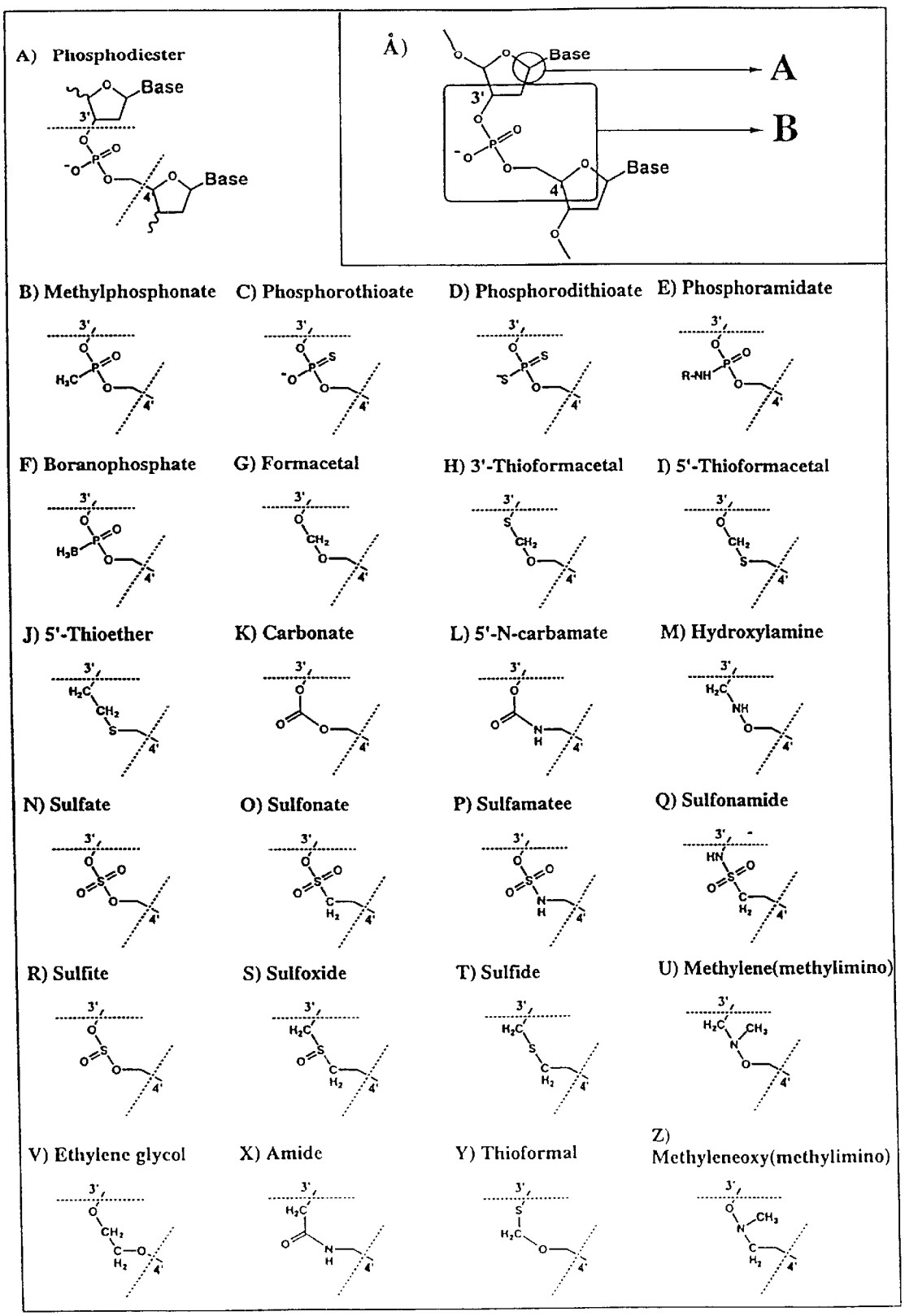
FIG. 34 The natural phosphordiester linkage of DNA shown between the dotted lines in A); a number of well-known alternative linkages for oligonucleotide analogs shown in structures B) to Z).

Some examples of well-known modified internucleoside linkages as well as modified sugar moieties are shown in FIG. 34 and FIG. 35. The sugar-phosphate backbone of the so-called homo-DNA analog [Eschenmoser, A. & Loewenthal, E. Chem. Soc. Rev. 21, 1–16 (1992)] (shown in FIG. 35 B), which contains one additional methylene group in the sugar moiety (gives a six-membered ring), may be of particular interest in some aspects of the present invention because homo-DNA compounds are known to stack and form duplexes in a linear fashion rather than the helical fashion of natural DNA and most other analogs.

Thus, the present invention also relates to organic compounds having a peptide-like or DNA. based backbone which, dependent on the selected physically functional groups, can be used for one, or in some cases more, of the fields: holographic materials, material for nonlinear optics, electric and ionic conductors, light emitting materials, photonic band gap materials, photoconducting materials.

In particular, the present invention relates to organic compounds having a physical functionality which can be influenced by external stimulation, e.g., by irradiation with light through application of electric and magnetic fields, heat or mechanical stress.

An important object of the present invention is to provide novel organic compounds having a physical functionality which can be influenced by external stimulation, where the compounds comprising one or more segments of the following formula G

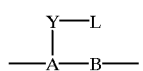

G wherein Y is a linking group or a single bond; L is a physically functional group comprising one or more physically functional ligand(s);

where A is a moiety selected from a nitrogen atom; a group C—R in which R is selected from hydrogen and optionally substituted $C_{1-4}$-alkyl, or the group C—R is part of a carbocyclic or heterocyclic ringin which case R is selected from optionally substituted $C_{1-4}$-alkylene, optionally substituted $C_{1-4}$-alkyleneoxy, oxy-(optionally substituted $C_{1-4}$-alkylene), and optionally substituted $C_{1-4}$-alkyleneoxy-$C_{1-4}$-alkylene; and a group Si—R' where R' is selected from hydrogen, optionally substituted $C_{1-4}$-alkyl, optionally substituted $C_{1-4}$-alkoxy, optionally substituted aryl, optionally substituted aryloxy, optionally substituted aryl-$C_{1-4}$-alkyl, and optionally substituted aryl-$C_{1-4}$-alkoxy; and B is a chain consisting of one or more groups selected from $CR^1R^2$, $SiR^1R^2$, and C=X where X is selected from —O—, —S—, —Se—, —Te—, and —NH—, wherein $R^1$ is hydrogen, and $R^2$ is selected from side chains of α-amino acids, or $R^1$ and $R^2$ each independently is selected from hydrogen, optionally substituted $C_{1-6}$-alkyl, hydroxy, optionally substituted $C_{1-6}$-alkoxy, optionally substituted heterocyclyl, (optionally substituted heterocyclyl)-$C_{1-6}$-alkyl, optionally substituted aryl, (optionally substituted aryl)-$C_{1-6}$alkyl, optionally substituted aryloxy, (optionally substituted aryloxy)-$C_{1-6}$-alkyl, halogen, cyano, amino, mono- or di(optionally substituted $C_{1-6}$-alkyl)amino, mono- or di(optionally substituted $C_{1-6}$-alkyl)amino-$C_{1-6}$-alkyl, (optionally substituted $C_{1-6}$-alkyl)carbonylamino, (optionally substituted $C_{1-6}$-alkyl)carbonylamino-$C_{1-6}$-alkyl, aminocarbonyl, aminocarbonyl-$C_{1-6}$-alkyl, mono- or di(optionally substituted $C_{1-6}$-alkyl)aminocarbonyl, mono- or di(optionally substituted $C_{1-6}$-alkyl)aminocarbonyl-$C_{1-6}$-alkyl, optionally substituted $C_{1-6}$-acyl, optionally substituted $C_{1-6}$-acyloxy, carboxy, (optionally substituted $C_{1-6}$-alkoxy) carbonyl, thiolo, $C_{1-6}$-alkylthio, optionally substituted $C_{1-6}$-alkylthio-$C_{1-6}$-alkyl, (optionally substituted aryl)thio, guanidino, guanidino-$C_{1-6}$-alkyl, optionally substituted $C_{1-6}$-alkylsulphonyl, (optionally substituted aryl)sulphonyl, mono- or di(optionally substituted $C_{1-6}$-alkyl) aminosulphonyl, sulphono (—SO$_3$H), sulphino (—SO$_2$H), halosulphonyl, isocyano, isothiocyano, and thiocyano;

said chain B optionally being interrupted, initiated, or terminated by one or more groups selected from —O—, —S—, —SO—, —S(O)$_2$—, —O—SO—O—, —O—S(O)$_2$—O—, —O—S(O)$_2$—NH—, —O—S(O)$_2$—, —O—P(O)$_2$—O—, —O—P(O,S)—O—, —O—P(S)$_2$—O—, —O—PO(CH$_3$)—O—, —O—PO(BH$_3$)—O—, —O—PO(NHR$^3$)—O—, —Se—, Nr$^3$, and —NR$^3$—O—, wherein R$^3$ is selected from hydrogen, optionally substituted $C_{1-6}$-alkyl, hydroxy, optionally substituted $C_{1-6}$-alkoxy, optionally substituted heterocyclyl, (optionally substituted heterocyclyl)-$C_{1-6}$-alkyl, optionally substituted aryl, (optionally substituted aryl)-$C_{1-6}$-alkyl, optionally substituted aryloxy, (optionally substituted aryloxy)-$C_{1-6}$-alkyl, mono- or di(optionally substituted $C_{1-6}$-alkyl)amino-$C_{1-6}$-alkyl, (optionally substituted $C_{1-6}$-alkyl)carbonylamino-$C_{1-6}$-alkyl, aminocarbonyl, aminocarbonyl-$C_{1-6}$-alkyl, mono- or di(optionally substituted $C_{1-6}$-alkyl)aminocarbonyl, mono- or di(optionally substituted $C_{1-6}$-alkyl)aminocarbonyl-$C_{1-6}$-alkyl, optionally substituted $C_{1-6}$-acyl, optionally substituted $C_{1-6}$-acyloxy, optionally substituted aryloxycarbonyl, optionally substituted $C_{1-6}$-alkoxycarbonyl, (optionally substituted aryl)-$C_{1-6}$-alkoxycarbonyl, optionally substituted $C_{1-6}$-alkylthio-$C_{1-6}$-alkyl, optionally substituted $C_{1-6}$-alkylsulphonyl, (optionally substituted aryl)sulphonyl, and mono- or di(optionally substituted $C_{1-6}$-alkyl) aminosulphonyl; B optionally being part of one or more carbocyclic or heterocyclic ring(s); and wherein 1) the backbone chain —A—B— has a total of at least 3 consecutive covalent bonds between the radical positions; and 2)
a) when the linking group Y has a total of at least 3 consecutive covalent bonds,
  (i) the linking group Y contains an amide function bound directly to the moiety A, or
  (ii) the moiety A constitutes the nitrogen atom of an amide function, i.e the moiety A in combination with an adjacent carbonyl group in Y or in combination with an adjacent carbonyl group in B or in combination with a carbonyl group contained in an adjacent group from any neighbouring segment form an amide function; or
b) the moiety A—B includes a carbocyclic or heterocyclic ring or includes a part of a carbocyclic or heterocyclic ring, the remainder of which is contained in adjacent group(s) from any neighbouring segment.

The backbone moiety —A—B— may in principle be any of the possible moieties within the definition of the groups A and B, however, it will be understood that backbone moieties derived from amino acids, or in certain cases DNA backbone monomers, are preferred due to the commercial availability of the starting material and the ease of synthesis. Furthermore, it shall be understood that the backbone moiety —A—B— in itself only very rarely corresponds exactly to, e.g., an amino acid.

In the present context, the term "$C_{1-4}$-alkyl" designates a radical of a linear or branched or, although in contrast to custom use, cyclic aliphatic chain having from 1 to 4 carbon atoms, such as methyl, ethyl, 1-propyl, 2-propyl, 1-butyl, 2-butyl, tert-butyl and cyclobutyl. Similarly, the term "$C_{1-6}$-alkyl" designates a radical of a linear or branched or cyclic aliphatic chain having from 1 to 6 carbon atom, such as the radicals mentioned for $C_{1-4}$-alkyl and pentyl, isopentyl, neopentyl, hexyl, and cyclohexyl In the present context, the term "$C_{1-6}$-alkylene" designates a biradical of a linear or branched aliphatic chain having from 1 to 4 carbon atoms, such as methylene, 1,1-ethylene, 1,2-ethylene, 1,3-propylene, 1,2-propylene, 2,2-propylene, 1,1-propylene, and the possible butylenes.

In the present context, the terms "$C_{1-4}$-alkoxy" and "$C_{1-6}$-alkoxy" are intended to mean $C_{1-4}$-alkyl-oxy and $C_{1-6}$-alkyl-oxy, respectively.

In the present context, the term "$C_{1-6}$-acyl" designates alkanoyl, such as formyl, acetyl, propionyl, butyryl, isobutyryl, valeryl, isovaleryl, pivaloyl and hexanoyl In the present context, the term "aryl" is intended to mean a carbocyclic aromatic ring or ring system, such as phenyl, naphthyl, fluorenyl, and tetralinyl.

In the present context, the term "heterocyclyl" is intended to mean radicals of heterocyclic and heteroaromatic ring or ring systems such as 5-, 6-, or 7-membered monocychc or 8-, 9-, 10-, 11-, or 12-membered bicyclic, aromatic or partially or fully hydrogenated, radicals containing one or more, preferably 1–3, heteroatoms selected from oxygen, nitrogen and sulphur. Examples of the heterocyclic groups are pyrrolyl, furanyl, 2,3-dihydrofuranyl, tetrahydrofuranyl, thienyl, 2,3-dihydrothienyl, tetrahydrothienyl, imidazolyl, oxazolyl, thiazolyl, pyrazolyl, pyrrolinyl, pyrrolidinyl, pyridinyl, piperidinyl, pyrimidinyl, purinyl, quinolinyl, 1,2-dihydroquinolinyl, isoquinolinyl, indolyl, piperazinyl, pyrazinyl, dioxolanyl, dioxanyl, 1,3,5-trioxanyl, tetrahydrothiapyranyl, dithiolanyl, pyrazolidinyl, iminazolidinyl, pyridazinyl, sym-triazinyl, sym-tetrazinyl, quinazolinyl, 1,5-naphtyridinyl, pteridinyl, isoindolyl, 2,3 2',3'-pyrrolopyrrolyl, 1,2,4-triazolyl, 1,2,3-triazolyl, tetrazolyl, benzimidazolyl, indazolyl, benzofuranyl, isobenzofuranyl, benzothiophenyl, thienothiophenyl, isoxazolyl, 1,2,5-oxadiazolyl, isothiazolyl, 1,3,4-thiadiazolyl, diazepine, benzodiazepine, benzoxazolyl, and benzothiazolyl.

In the present context, the term "optionally substituted" in connection with "aryl" and "heterocyclyl" is intended to mean aryl and heterocyclyl, respectively, as defined above which may be substituted with one or more, preferably 1–3, substituents selected from hydroxy; $C_{1-4}$-alkyl and $C_{1-4}$-alkoxy optionally substituted one or more times with halogen, such as fluorine, chlorine, bromine, and iodine, hydroxy, amino, cyano, and carboxy; halogen such as fluorine, chlorine, bromine, and iodine; nitro; nitroso; cyano; amino; mono- or di($C_{1-4}$-alkyl)amino; aminocarbonyl; mono- or di($C_{1-4}$-alkyl)aminocarbonyl; $C_{1-6}$-acyl; $C_{1-6}$-acyloxy; carboxy; $C_{1-4}$-alkoxycarbonyl; thiolo; $C_{1-4}$-alkylthio; arylthio; $C_{1-4}$-alkylsulphonyl; arylsulphonyl; mono- or di($C_{1-4}$-alkyl)aminosulphonyl; sulphono ($SO_3H$); sulphino ($SO_2H$); halosulphonyl; isocyano; isothiocyano; and thiocyano.

In the present context, the term "optionally substituted" in connection with "alkyl", "alkylene", "alkoxy", and "acyl" is intended to mean that the group in question may be substituted one or more times with hydroxy; $C_{1-4}$-alkoxy optionally substituted one or more times with halogen, such as fluorine, chlorine, bromine, and iodine, hydroxy, amino, cyano, and carboxy; halogen such as fluorine, chlorine, bromine, iodine; nitro; nitroso; cyano; carboxy; thiolo; $C_{1-4}$-alkylthio; aylthio; $C_{1-4}$-alkylsulphonyl; arylsulphonyl; sulphono ($SO_3H$); sulphino ($SO_2H$); halosulphonyl; isocyano; isothiocyano; and thiocyano.

In interesting variants of the present invention, all or substantially all C—H moieties are replaced with C—D or C—F moieties in order to avoid C—H absorption in the wavelength range 0.8–1.6 µm which is a relevant wavelength range for optical communication. Thus, it should be understood that the definition of molecules comprising C—H moieties should also cover the corresponding fully or partially deuterated and fluorinated compounds.

In a preferred embodiment, A is selected from a nitrogen atom and a group C—R in which R is selected from hydrogen and optionally substituted $C_{1-4}$-alkyl; and B is a chain consisting of groups selected from $CR^1R^2$, and C=X where X is selected from —O—, —S—, and —NH—, wherein $R^1$ is hydrogen and $R^2$ is selected from side chains of α-amino acids, or $R^1$ and $R^2$ each independently is selected from hydrogen, optionally substituted $C_{1-6}$-alkyl, hydroxy, optionally substituted $C_{1-6}$-alkoxy, halogen, cyano, amino, mono- or di(optionally substituted $C_{1-6}$-alkyl)amino, mono- or di(optionally substituted $C_{1-6}$-alkyl)amino-$C_{1-6}$-alkyl, (optionally substituted $C_{1-6}$-alkyl)carbonylamino, (optionally substituted $C_{1-6}$-alkyl)carbonylamino-$C_{1-6}$-alkyl, aminocarbonyl, aminocarbonyl-$C_{1-6}$-alkyl, mono- or di(optionally substituted $C_{1-6}$-alkyl)aminocarbonyl, mono- or di(optionally substituted $C_{1-6}$-alkyl)aminocarbony-$C_{1-6}$-alkyl, optionally substituted $C_{1-6}$-acyl, optionally substituted $C_{1-6}$-acyloxy, carboxy, (optionally substituted $C_{1-6}$-alkoxy)carbonyl, thiolo, $C_{1-6}$-alkylthio, optionally substituted $C_{1-6}$-alkylthio-$C_{1-6}$-alkyl, guanidino, guanidino-$C_{1-6}$-alkyl, optionally substituted $C_{1-6}$-alkylsulphonyl, mono- or di(optionally substituted $C_{1-6}$-alkyl)aminosulphonyl, sulphono (—$SO_3H$), sulphino (—$SO_2H$), halosulphonyl, isocyano, isothiocyano, and thiocyano; preferably B is a chain consisting of groups selected from $CR^1R^2$ and C=O, wherein $R^1$ is hydrogen and $R^2$ is selected from side chains of α-amino acids, $C_{1-6}$-alkyl, hydroxy, optionally substituted $C_{1-6}$-alkoxy, halogen, cyano, amino, mono- or di(optionally substituted $C_{1-6}$-alkyl)amino, mono- or di(optionally substituted $C_{1-6}$-alkyl)amino-$C_{1-6}$-alkyl, (optionally substituted $C_{1-6}$-alkyl)carbonylamino, (optionally substituted $C_{1-6}$-alkyl)carbonylamino-$C_{1-6}$-alkyl, aminocarbonyl, aminocarbonyl-$C_{1-6}$-alkyl, mono- or di(optionally substituted $C_{1-6}$-alkyl)aminocarbonyl, mono- or di(optionally substituted $C_{1-6}$-alkyl)aminocarbonyl-$C_{1-6}$-alkyl, optionally substituted $C_{1-6}$-acyl, optionally substituted $C_{1-6}$-acyloxy, carboxy, and (optionally substituted $C_{1-6}$-alkoxy)carbonyl; said chain B optionally being interrupted, initiated, or terminated by one or more groups selected from —O—, —S—, —SO—, and $NR^3$, wherein $R^3$ is selected from hydrogen, optionally substituted $C_{1-6}$-alkyl, mono- or di(optionally substituted $C_{1-6}$-alkyl)amino-$C_{1-6}$-alkyl, (optionally substituted $C_{1-6}$-alkyl)carbonylamino-$C_{1-6}$-alkyl, aminocarbonyl, aminocarbonyl-$C_{1-6}$-alkyl, mono- or di(optionally substituted $C_{1-6}$-alkyl)aminocarlonyl, mono- or di(optionally substituted $C_{1-6}$-alkyl)aminocarbonyl-$C_{1-6}$-alkyl, (optionally substituted aryl)-$C_{1-6}$-alkoxycarbonyl, optionally substituted $C_{1-6}$-acyl, and optionally substituted $C_{1-6}$-alkoxycarbonyl; preferably said chain B optionally being interrupted, initiated, or terminated by one or more groups selected from —O—, and $NR^3$, wherein $R^3$ is selected from hydrogen, $C_{1-6}$-alkyl, mono- or di(optionally substituted $C_{1-6}$-alkyl)amino-$C_{1-6}$-alkyl, (optionally substituted $C_{1-6}$-alkyl)carbonylamino-$C_{1-6}$-alkyl, aminocarbonyl-$C_{1-6}$-alkyl, mono- or di(optionally substituted $C_{1-6}$-alkyl) aminocarbonyl, mono- or di(optionally substituted $C_{1-6}$-alkyl)aminocarbonyl-$C_{1-6}$-alkyl, (optionally substituted aryl)-$C_{1-6}$-alkoxycarbonyl, optionally substituted $C_{1-6}$-acyl, and optionally substituted $C_{1-6}$-alkoxycarbonyl.

In an especially preferred embodiment of the present invention, A is selected from a nitrogen atom and a group C—H; and B is a chain consisting of groups selected from $CR^1R^2$ and C=O, wherein $R^1$ is hydrogen and $R^2$ is selected from hydrogen and side chains of α-amino acids; and said chain B optionally being interrupted, initiated, or terminated by one or more groups selected from —O—, and $NR^3$, wherein $R^3$ is selected from hydrogen, $C_{1-6}$-alkyl, $C_{1-6}$-acyl, and amino protecting groups such as tert-butoxycarbonyl (Boc) or 9-fluorenylmethyloxycarbonyl (Fmoc).

Alternatively, e.g. in the case where the segment G is derived from a DNA backbone monomer, the backbone moiety —A—B— either includes a carbocyclic or heterocyclic ring; or the backbone group(s) —A— and/or —B— together with adjacent group(s) from neighbouring segments form(s) a carbocyclic or heterocyclic ring. Thus, it is in this case preferred that the linking group Y is selected from the groups defined below and a single bond, in particular a single bond; A is C—H: and B is —$CH_2$—C(-)H—Px—$CH_2$—C(-)H—O— where Px is selected from —O—$CH_2$—O—, —O—$CH_2$—$CH_2$—, —O—$CH_2$—S—, —S—$CH_2$—O—, —$CH_2$—$CH_2$—S—, —O—CO—O—, —$CH_2$—CO—NH—, —O—CO—NH—, —$CH_2$—$NR^3$—O—, —O—$NR^3$—$CH_2$—, —$CH_2$—S—$CH_2$—, —$CH_2$—SO—$CH_2$—, —O—SO—O—, —O—S(O)$_2$—O—, —O—S(O)$_2$—NH—, —NH—S(O)$_2$—$CH_2$—, —O—S(O)$_2$—$CH_2$—, —O—P(O)$_2$—O—, —O—P(O,S)—O—, —O—P(S)$_2$—O—, —O—PO($BH_3$)—O—, and —O—PO($NHR^3$)—O—; and where $R^3$ is as defined above.

With respect to the linking group Y, which is incorporated in the segment G in order to facilitate the desired orientation of the physically functional group L, this is preferably a biradical composed of a chain part which preferably has the definition as the moiety B and, optionally, a cyclic part selected from biradicals of carbocyclic, heterocyclic, aromatic, and heteroaromatic rings.

The optional cyclic part of Y comprises cyclic, heterocyclic, aromatic, and heteroaromatic rings which may be selected from benzene, naphthalene, fluorene, tetraline, morpholine, piperidinylpyrrol, furan, 2,3-dihydrofuran, tetrahydrofuran, thiene, 2,3-dihydrothiene, tetrahydrothiene, imidazole, oxazole, thiazole, pyrazole, pyrroline, pyrrolidine, pyridine, piperidine, pyrimidine, purine, quinoline, 1,2-dihydroquinoline, isoquinoline, indole, piperazine, pyrazine, dioxolane, dioxane, 1,3,5-trioxane, tetrahydrothiapyrane, dithiolane, pyrazolidine, iminazolidine, pyridazine, sym-trazine, sym-tetrazine, quinazoline, 1,5-naphtyridine, pteridine, isoindole, 2,3,2',3'-pyrrolopyrrole, 1,2,4-triazole, 1,2,3-triazole, tetrazole, benzimidazole, indazole, benzofurane, isobenzofurane, benzothiophene, thienothiophene, isoxazole, 1,2,5-oxadiazole, isothiazole, 1,3,4-thiadiazole, diazepine, benzodiazepine, benzoxazole, and benzothiazol.

The chain part of the linking group Y is preferably selected from —D—$(CR^4R^5)_p$—E—F—, —D—$(CR^4R^5)$$_p$—F—E—, —D—$[(CR^4R^5)$—E—F$]_t$—$(CR^4R^5)_p$—E—F—, —D—$[(CR^4R^5)$—E—F$]_t$—$(CR^4R^5)_p$—F—E—, —D—$[(CR^4R^5)$—F—E$]_t$—$(CR^4R^5)_p$—E—F—, and —D—$[(CR^4R^5)$—F—E$]_t$—$(CR^4R^5)_p$—F—E—, the left end of the chain part being bound to the physically functional group L, optionally through any cyclic part of Y, and the right end being bound to the moiety A; p is 0–10, preferably 0–8, t is 0–5, preferably 0–1; each of the groups $R^4$ and $R^5$ are independently selected from the same groups as defined for $R^1$ and $R^2$ in claim 1; D is selected from a single bond, —O—, —O—C(=O)—, —S—, —S(O)$_2$—, —Se—, —Te—, —NH—, and —N($C_{1-6}$-alkyl)-; each E independently is selected from a single bond, —C(=O)—, —C(=S)—, —C(=Se)—, —C(=Te)—, —C(=NH)—, —C(=N—$C_{1-6}$-alkyl)-, —S(O)—, —S(O$_2$)—, and —P(O$_2$)—; and each F is independently selected from a single bond and $NR^6$, where $R^6$ is selected from the same groups as defined for $R^3$.

In a preferred embodiment, the the chain part of the linking group Y is selected from —O—$(CH_2)_p$—C(=O)—NH—, —O—$(CH_2)_p$—NH—C(=O)—, —O—$(CH_2)_p$—C(=O)—, —O—$(CH_2)_p$—NH—, —$(CH_2)_p$—C(=O)—NH—, —$(CH_2)_p$—NH—C(=O)—, —$(CH_2)_p$—C(=O)—, —$(CH_2)_p$—NH—, —S—$(CH_2)_p$—C(=O)—NH—, —S—$(CH_2)_p$—NH—C(=O)—, —S—$(CH_2)_p$—C(=O)—, —S—$(CH_2)_p$—NH—, —OOC—$(CH_2)_p$—C(=O)—NH—, —OOC—$(CH_2)_p$—NH—C(=O)—, —OOC—$(CH_2)_p$—C(=O)—, —OOC—$(CH_2)_p$—NH—, —NH—$(CH_2)_p$—C(=O)—NH—, —N($C_{1-6}$-alkyl)-$(CH_2)_p$—C(=O)—NH—, —NH—$(CH_2)_p$—NH— C(=O)—, —N($C_{1-6}$-alkyl)-$(CH_2)_p$—NH—C(=O)—, —NH—$(CH_2)_p$—C(=O)—, —N($C_{1-6}$-alkyl)-$(CH_2)_p$—C(=O)—, —NH—$(CH_2)_p$—NH—, —N($C_{1-6}$-alkyl)-$(CH_2)_p$—NH—, —NH—C(=O)—$(CH_2)_p$—C(=O)—NH—, —N($C_{1-6}$-alkyl)-C(=O)—$(CH_2)_p$—C(=O)—NH—, —NH—C(=O)—$(CH_2)_p$—NH—C(=O)—, —N($C_{1-6}$-alkyl)-C(=O)—$(CH_2)_p$—NH—C(=O)—, —NH—C(=O)—$(CH_2)_p$—C(=O)—, —N($C_{1-6}$-alkyl)-C(=O)—$(CH_2)_p$—C(=O)—, —NH—C(=O)—$(CH_2)_p$—NH—, —N($C_{1-6}$-alkyl)-C(=O)—$(CH_2)_p$—NH—, —SO$_2$—$(CH_2)_p$—C(=O)—NH—, —SO$_2$—$(CH_2)$$_p$—NH—C(=O), —SO$_2$—$(CH_2)_p$—C(=O)—, and —SO$_2$—$(CH_2)_p$—NH—. Preferably p is 0–5, in particular 0–2.

In an especially preferred embodiment, the linking group Y is selected from —O—$(CH_2)_p$—C(=O)—NH—, —O—$(CH_2)_p$—NH—C(=O)—, —O—$(CH_2)_p$—C(=O)—, —O—$(CH_2)_p$—NH—, —$(CH_2)_p$—C(=O)—NH—, —$(CH_2)_p$—NH—C(=O)—, —$(CH_2)_p$—C(=O)—, —(CH$_2$)$_p$—NH—, —OOC—(CH$_2$)$_p$—C(=O)—NH—, —OOC—(CH$_2$)$_p$—NH—C(=O)—, —OOC—(CH$_2$)$_p$—C(=O)—, —OOC—(CH$_2$)$_p$—NH—, —NH—(CH$_2$)$_p$—C(=O)—NH—, —N(C$_{1-6}$-alkyl)-(CH$_2$)$_p$—C(=O)—NH—, —NH—(CH$_2$)$_p$—NH—C(=O)—, —N(C$_{1-6}$alkyl)-(CH$_2$)$_p$—NH—C(=O)—, —NH—(CH$_2$)$_p$—C(=O)—, —N(C$_{1-6}$-alkyl)-(CH$_2$)$_p$—C(=O)—, —NH—(CH$_2$)$_p$—NH—, —N(C$_{1-6}$-alkyl)-(CH$_2$)$_p$—NH—, —NH—C(=O)—(CH$_2$)$_p$—C(=O)—NH—, —N(C$_{1-6}$-alkyl)-C(=O)—(CH$_2$)$_p$—C(=O)—NH—, —NH—C(=O)—(CH$_2$)$_p$—NH—C(=O)—, —N(C$_{1-6}$alkyl)-C(=O)—(CH$_2$)$_p$—NH—C(=O)—, —NH—C(=O)—(CH$_2$)$_p$—C(=O)—, —N(C$_{1-6}$-alkyl)-C(=O)—(CH$_2$)$_p$—C(=O)—, —NH—C(=O)—(CH$_2$)$_p$—NH—, and —N(C$_{1-6}$-alkyl)-C(=O)—(CH$_2$)$_p$—NH—; which implies that no cyclic part is present in the linking group Y.

It is preferred that a certain rigidity of the backbone moiety —A—B— in combination with the linking group Y is introduced in order for the organic compound to orient the physically functional ligand in a limited number of ways. Thus, in a preferred embodiment of the present invention, the backbone chain —A—B— has a total of at least 3 consecutive covalent bonds between the radical positions, e.g., from 3 to 16, such as from 3 to 12, preferably from 3 to 8, in particular from 4 to 7, such as 4 or 5 or 6 or 7 consecutive covalent bonds. By "consecutive covalent bonds between the radical positions" is meant the lowest count of covalent bonds between the atoms having the free valences. As an example, the chain —NH—CH$_2$—S—CO—O— has a total of 4 consecutive covalent bonds between —NH and O—.

With respect to the linking group Y, this group has at the most 15 consecutive covalent bonds between the radical positions, such as at the most 12, preferably from 2 to 10, more preferably from 2 to 8, in particular 3 to 7, especially from 3 to 6, such as 3 consecutive covalent bonds. In some cases of interest falling within the scope of this invention, in particular in the cases where the backbone is derived from DNA backbone monomers, the group L may be linked directly to the backbone moiety A, i.e. Y is a single bond.

Preferably, the consecutive covalent bonds of the chain —A—B— do not comprise double or triple bonds or aromatic moieties, but in order to introduce conformational constraints, one or more amide bonds, or bonds with similarly restricted rotation, e.g. thioamides, or carbocyclic or heterocyclic rings are preferably introduced for each segment. Conformational constraints can also be introduced in the form of carbocyclic or heterocyclic ring(s) or by formation of a macrocyclic structure, e.g., by direct linking of the groups Q and Z. Typically, for each 4–8 consecutive covalent bonds between one physically functional group L and the group L or L' of the neighbouring segment, a constraining moiety is incorporated. It should be understood that the term "amide function" is intended. to mean amides, —NH—CO—, as well as thioamides, —NH—CS—.

Thus, when the backbone moiety —A—B— has a total of at least 4 consecutive covalent bonds between the radical positions, the moiety —A—B— (i) contains an amide function, or (ii) contains a part of an amide function, the remainder of which is contained in the corresponding linking group Y or in adjacent group(s) from any neighbouring segment.

In the present context, the term "carbocyclic or heterocyclic ring(s)" is intended to mean a ring or ring system comprising carbon atoms only or carbon atoms in combination with heteroatoms as ring atoms, e.g. 5-, 6-, or 7-membered rings or 8-, 9-, 10-, 11-, or 12-membered ring systems containing no or one or more, preferably 0–3, heteroatoms selected from oxygen, nitrogen and sulphur. Examples are cyclopentane, cyclohexane, cycloheptane, decaline, tetrahydrofuran, tetrahydrothiene, pyrrolidine, piperidine, piperazine, dioxane, and diazepine.

In the preferred embodiments where the compounds consist of a peptide-like structure bearing physically functional moieties, it is obvious to incorporate any readily available α-amino acid(s) in the structure. Therefore, the methylene group of any glycine units incorporated in the peptide-like structure can easily be substituted with side chains of α-amino acids simply by using the corresponding α-amino acid. This may, for α-amino acids having functional groups which are reactive under the reaction conditions prevailing during synthesis of the peptide-like structure, e.g., glutamic acid and lysine, imply one or more protection and/or deprotection step(s).

In the present context, the term "side chains of α-amino acids" is intended to mean a group bound to the α-atom of an α-amino acids, i.e. the α-amino acid in question without the glycine moiety, preferably an either naturally occuring or a readily available α-amino acid. Most interesting are the side chains of commercially available α-amino acids, e.g., the naturally occuring α-amino acids such as alanine, valine, norvaline, isovaline, leucine, norleucine, isoleucine, methionine, phenylalanine, tryptophan, serine, threonine, cysteine, penicillamine, tyrosine, asparagine, glutamine, aspartic acid, glutamic acid, ornithine, lysine, arginine, histidine, proline, 4-hydroxy-proline, and pipecolic acid Examples of such side chains are hydrogen(glycine itself), deuterium(deuterated glycine), methyl(alanine), cyanomethyl(β-cyano-alanin), ethyl, 1-propyl(norvaline), 2-propyl (valine), 2 -methyl-1-propyl(leucine), 2-hydroxy-2-methyl-1-propyl(β-hydroxy-leucine), 1-butyl (norleucine), 2-butyl (isoleucine), methylthioethyl (methionine), benzyl (phenylalanine), p-amino-benzyl (p-amino-phenylalanine), p-iodo-benzyl (p-iodo-phenylalanine), p-fluoro-benzyl (p-fluoro-phenylalanine), p-bromo-benzyl(p-bromophenylalanine), p-chloro-benzyl (p-chloro-phenylalanine), p-nitro-benzyl(p-nitro-phenylalanine), 3-pyridylmethyl(β-(3-pyridyl)-alanine), 3,5-diiodo-4-hydroxy-benzyl(3,5-diiodo-tyrosine), 3,5-dibromo-4-hydroxy-benzyl(3,5-dibromo-tyrosine), 3,5-dichloro-4-hydroxy-benzyl(3,5-dichloro-tyrosine), 3,5-difluoro-4-hydroxy-benzyl(3,5-difluorotyrosine), 4-methoxy-benzyl(O-methyl-tyrosin), 2-naphtylmethyl(β-(2-naphtyl)-alanin), 1-naphtylmethyl(β-(1-naphtyl)-alanin), 3-indolylmethyl(tryptophan), hydroxymethyl(serine), 1-hydroxyethyl(threonine), mercaptomethyl(cysteine), 2-mercapto-2-propyl(penicillamine), 4-hydroxybenzyl (tyrosine), aminocarbonylmethyl(asparagine), 2-aminocarbonylethyl(glutamine), carboxymethyl(aspartic acid), 2-carboxyethyl(glutamic acid), aminomethyl (α,β-diaminopropionic acid), 2-aminoethyl(α,γ-diaminobutyric acid), 3-amino-propyl(ornithine), 4-amino-1-butyl(lysine), 3-guanidino-1-propyl(arginine), and 4-imidazolylmethyl (histidine), and 1,3-propylene, 2-hydroxy-1,3-propylene, or 1,4-butylene forming a pyrrolidine ring, a 3-hydroxypyrrolidine ring, or a piperidine ring, respectively, involving the neighbouring carbon atom and a nitrogen atom (proline, 4-hydroxy-proline, and pipecolic acid, respectively). It is clear that other methylene groups being derived from the α-carbon of a glycine unit can be substituted with side chains of α-amino acids in a similar way.

In a preferred embodiment of the present invention, the novel organic compounds comprise a successive chain of segments of the formula G, such as 2–25 segments, preferably 2–20 segments, in particular 2–10 segments. Thus, the present invention provides novel compounds having the formula $G^h$

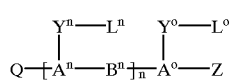

wherein n is a positive integer, preferably in the range of 1–19, in particular in the range of 1–9; each of $Y^0, \ldots, Y^n$ independently is a linking group as defined for Y; each of $L^0, \ldots, L^n$ independently is a physically functional group comprising one or more physically functional ligand(s) as defined for L; each of $A^0, \ldots, A^n$ independently is a group as defined for A; each of $B^1, \ldots, B^n$ independently is a chain as defined for B; and Q and Z are terminating groups. Furthermore, the same requirement to the rigidity of individual segments as defined above also applies in the case of an oligomeric compound, thus, 1) each of the chains from $A^m$—$B^m$—$A^{m-1}$ has a total of at least 4 consecutive covalent bonds; and
2)
   a) when the biradical $Y^m$ has a total of at least 3 consecutive covalent bonds, each of the moieties $Y^0$—$L^0, \ldots, Y^n$—$L^n$ independently
      (i) contains an amide function bound directly to the corresponding moiety A; or
      (ii) contains a part of an amide function, the remainder of which is contained in the corresponding moiety A, or
      (iii) is bound directly to the nitrogen atom of an amide function which comprises the A moiety corresponding to the Y—L moiety; or
   b) each of the moieties $B^1$—$A^0$—$Z, \ldots, B^{m+1}$—$A^m$—$B^m, \ldots, B^n$—$A^n$—$Q$ includes a carbocyclic or heterocyclic ring;

and, when one or more of $A^0, \ldots, A^n$ is/are C—R, the group(s) C—R may form a carbocyclic or heterocyclic ring involving one or two of the adjacent groups B and Y; and $1 \leq m \leq n$.

In one embodiment of the present invention, the segments of the general formula $G^h$ are identical throughout the chain of segments are identical, thus, the physically functional groups $L^0, \ldots, L^n$ as well as and the groups in each set $A^0, \ldots, A^n; B^1, \ldots, B^n; Y^0, \ldots, Y^n$; and $L^0, \ldots, L^n$, respectively, are the same. Alternatively, the physically functional groups $L^0, \ldots, L^n$ may comprise at least two different types of groups, e.g. groups which are different with respect to chemical structure and groups which are different with respect to chemical structure and physical functionality. Interesting variants of the above are the cases where the segments the general formula $G^h$ are identical throughout the chain, or they are derived from identical amino acids.

With respect to the terminating groups Q and Z, which also may terminate any other chain of segments described herein, these are preferably selected from the same groups as defined for the substituents $R^1$, $R^2$, and $R^3$, optionally substituted or interrupted by a chain consisting of, e.g., 1 to 5 amino acids or DNA-backbone monomers, or extended by a chain as defined for B. Furthermore, when one or both of the group(s) Q and Z are part of a carbocyclic or heterocyclic ring or a macrocycle, Q and/or Z is/are selected from the biradicals of the before-mentioned groups or one or both are simply a single bond. The latter possibility implies that the first segment and the last segment of the "chain" of segments are linked directly together to form a macrocycle.

From the above discussion of the feasibility of the synthesis of the amino acid derived structures, it is clear that the backbone structure of the novel organic compounds according to the invention may be extended by any number of amino acids or other backbone units not carrying any physially functional groups L, e.g., by repeating one or more of the reaction cycles (see the detailed discussion below) using, e.g, amino acids having side chains without functional groups within the meaning of the present application. Therefore, any of the terminating groups Z and Q and any spacer groups (see below) present in the organic compound $G^h$, or any other compound where applicable, may further comprise a chain of one or more amino acid(s), such as 1 to 5 amino acids.

In the present context the term "a chain of amino acid(s)" is intended to mean the radical of a chain of amino acids, e.g. α- and β-amino acid(s), preferably naturally occuring or commercially available amino acids. The chain is preferably linked to the backbone structure through one or, in special cases, both of the groups Q and Z The linkage is preferably an amide or peptide bond. "N—" and "C—", as a prefix, is indicating at which end of the chain of amino acid(s) the radical is present, i.e. at which end the chain or amino acid(s) is linked to the other part of the molecule.

Similarly, in the case where the structure of the novel organic compound according to the invention is a DNA-oligomer-like structure, the groups Q and Z may be extended by a chain of one or more DNA-backbone monomers.

In the present context the term "DNA-backbone monomer" is intended to mean a structure consisting of a deoxyribose-phosphate moiety, a ribose-phosphate moiety, or a similar structure. Similar structures and structure fragments are shown in FIGS. 33–35.

In a preferred embodiment of the present invention, Z is selected from amino, carboxy, C-(a chain of 1–5 amino acid(s))-amino, N-(a chain of 1–5 amino acid(s))-carbonyl, side chains of α-amino acids, hydrogen, deuterium, methyl, cyanomethyl, ethyl, 1-propyl, 2-propyl, 2-methyl-1-propyl, 2-hydroxy-2-methyl-1-propyl, 1-butyl, 2-butyl, methylthioethyl, benzyl, p-amino-benzyl, p-iodo-benzyl, p-fluoro-benzyl, p-bromo-benzyl, p-chloro-benzyl, p-nitro-benzyl, 3-pyridylmethyl, 3,5-diiodo-4-hydroxy-benzyl, 3,5-dibromo-4-hydroxy-benzyl, 3,5-dichloro-4-hydroxy-benzyl, 3,5-difluoro-4-hydroxy-benzyl, 4-methoxy-benzyl, 2-naphtylmethyl, 1-naphtylmethyl, 3-indolylmethyl, hydroxymethyl, 1-hydroxyethyl, mercaptomethyl, 2-mercapto-2-propyl, 4-hydroxybenzyl, aminocarbonylmethyl, 2-aminocarbonylethyl, carboxymethyl, 2-carboxyethyl, aminomethyl, 2-aminoethyl, 3-amino-propyl, 4-amino-1-butyl, 3-guanidino-1-propyl, and 4-imidazolylmethyl, and 1,3-propylene, 2-hydroxy-1,3-propylene, or 1,4-butylene forming a pyrrolidine ring, a 3-hydroxypyrrolidine ring, or a piperidine ring, respectively, involving A and a nitrogen atom of Y adjacent to A when A is C—R; and, when A is N, Z is selected from $C_{1-4}$-alkyl, $C_{1-4}$-acyl, $C_{1-4}$alkyl-carbonylamino-$C_{1-4}$-alkyl, and a chain of 1–5 amino acid(s); and Q is selected from hydrogen, carboxy, aminocarbonyl, mono- or di($C_{1-6}$-alkyl)aminocarbonyl, N-(a chain of 1–3 amino acid(s))-carboxy, carboxy-$C_{1-3}$-alk)yl aminocarbonyl-$C_{1-3}$-alkyl, mono- di($C_{1-6}$-alkyl) aminocarbonyl-$C_{1-3}$-alkyl, and N-(a chain of 1–3 amino acid(s))-carbonyl-$C_{1-3}$alkyl, where any methylene unit(s) of the alkyl group(s) is/are optionally substituted with groups selected from side chains of α-amino acids.

Several of the interesting compounds of the present invention fall within the definition of the novel organic compound $G^h$; among these the following examples serve to illustrate the meaning of A, B, and Y.

In an embodiment, the compounds have the formula

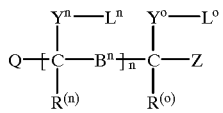

wherein each of $Y^o, \ldots, Y^n$ independently is selected from —O—$(CH_2)_p$—C(=O)—NH—, —$(CH_2)_p$—C(=O)—NH—, —O—$(CH_2)_p$—NH—C(=O)—, —$(CH_2)_p$—NH—C(=O)—, —$(CH_2)_p$—, where p is 0–5; each of $B^1, \ldots, B^n$ independently is selected from —$(CH_2)_q$—NH—C(=O)—$(CH_2)_r$—, —$(CH_2)_q$—C(=O)—NH—$(CH_2)_r$—, where q and r each independently are 0–6, preferably 0–4, and the sum q+r is 0–6, preferably 2–4; each of $R^{(o)}, \ldots, R^{(n)}$ independently is selected from hydrogen and optionally substituted $C_{1-4}$-alkyl; Q is selected from hydrogen, carboxy, aminocarbonyl, mono or di($C_{1-6}$-alkyl) aminocarbonyl, and (a chain of 1–3 amino acids)-carbonyl; and Z is selected from side chains of the α-amino acids.

In a more specific embodiment, the compounds have the formula

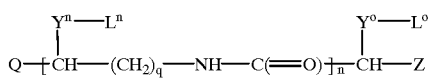

wherein Q is selected from hydrogen and aminocarbonyl ($H_2N$—C(=O)—), preferably aminocarbonyl; $Y^o, \ldots, Y^n$ are selected from —O—$CH_2$—C(=O)—NH— and —$CH_2$—C(=O)—NH—, preferably —O—$CH_2$—C(=O)—NH—; Z is selected from hydrogen and methyl; and q is 1–4, and n is 1–9, preferably 1–4.

In another specific embodiment, the compounds have the formula

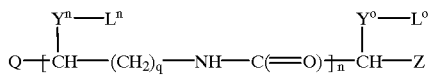

wherein n is 1; Q is aminocarbonyl ($H_2N$—C(=O)); $Y^o$ is —O—$CH_2C$(=O)—N<; $Y^1$ is —O—$CH_2$—C(=O)—NH—; Z is 1,3-propylene forming a pyrrolidine ring involving the adjacent carbon atom ($A^0$) and the nitrogen atom of $Y^0$.

In a further embodiment, the compounds have the formula

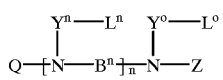

wherein each of $Y^o$—$Y^n$ independently is selected from —O—$(CH_2)_p$—C(=O)—, —$(CH_2)_p$—C(=O)—, —$(CH_2)_p$—NH—C(=O)—, and —O—$(CH_2)_p$—NH—C(=O)—, where p is 0–5; each of $B^1$—$B^n$ independently is selected from —$(CH_2)_q$—NH—C(=O)—$(CH_2)_r$—, —$(CH_2)_q$—C(=O)—NH—$(CH_2)_r$, where q and r each are 0–4, and the sum q+r is 2–4, and where one of the hydrogens of one or more of the methylene groups is/are optionally substituted with a group selected from side chains of α-amino acids; Q is selected from hydrogen, carboxy-$C_{1-3}$-alkyl, aminocarbonyl-$C_{1-3}$-allkyl, mono- or di($C_{1-6}$-alkyl) aminocarbonyl-$C_{1-3}$-alkyl; and Z is selected from hydrogen, and $C_{1-4}$alkylcarbonylamino-$C_{1-4}$-alkyl.

In a more specific embodiment, the compounds have the formula

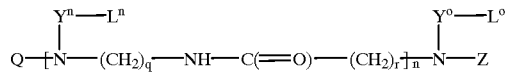

wherein q and r each are 1–3, and the sum q+r is 2–4.

In a still further embodiment, the compounds have the formula

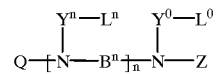

wherein each of $Y^o$—$Y^n$ independently is selected from —O—$(CH_2)_p$—C(=O)—, —$(CH_2)_p$—C(=O)—, —$(CH_2)_p$—NH—C(=O)—, —O—$(CH_2)_p$—NH—C(=O)—, where p is 0–5; each of $B^1$—$B^n$ independently is selected from —C(=O)—$(CH_2)_q$—NH—C(=O)—$(CH_2)_r$, —C(=O)—$(CH_2)_q$—C(=O)—NH—$(CH_2)_r$—, —$(CH_2)_s$—, preferably —C(=O)—$CH_2$—NH—C(=O)—$CH_2$— or —$(CH_2)_s$— where s is 1–4, such as 2 or 3, where q and r each are 0–3, and the sum q+r is 1–3, s is 2–6, and where one of the hydrogens of one or more of the methylene groups is/are optionally substituted with a group selected from side chains of α-amino acids; Q is selected from hydrogen, carboxy-$C_{1-3}$-alkyl, aminocarbonyl-$C_{1-3}$-alkyl, mono- or di($C_{1-6}$-alkyl)-aminocarbonyl-$C_{1-3}$-alkyl, and Z is selected from hydrogen, $C_{1-4}$-alkyl, $C_{1-4}$-alkyl-carbonylamino-$C_{1-4}$-alkyl.

In a special embodiment of the present invention, the compounds comprise only one segment of the formula G, thus, the compounds have the general formula $G^0$

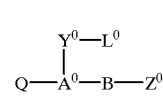

$G^0$ wherein —B—$Z^O$ designates a group as defined above for Z, and Q, $A^0$, $Y^0$, and $L^0$ have the same meanings as defined herein, for Q, A, Y, and L, respectively. In order for the "monomeric" compound $G^0$ to be, e.g., optically active, at least one of the groups $A^0$ and $Y^0$ must involve a chiral center.

A further object of the present invention is to provide novel organic compounds which comprise at least one segment of the formula G, and one or more segments of the following formula G'

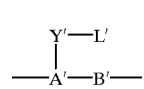

G' wherein the groups A', B', and Y' have the same meaning as defined for the groups A, B, and Y, respectively, and where the group L' designates a physically non-functional group comprising one or more physically non-functional ligand(s).

It should be understood that the physically non-functional groups have some of the same characteristics as the physically functional groups which make them able to interact, e.g. makes it reasonable to believe that the physically functional groups and physically non-functional groups may be able to stack in a regular manner. Thus, it is believed that an essential feature of the physically functional ligand(s) of L' is the presence of at least one cyclic p-electron system, in that it is believed that the physically non-functional groups will be oriented in accordance with the orientation of the physically functional groups when an external stimulation is applied.

It is believed that as few as one or two physically functional ligands in a domain of the size of, e.g., 10 segments will be sufficient for stacking and orientation of all the remaining ligands. Thus, it is envisaged that a compound having a domain comprising b segments of the general formula G and c segment of the general formula G', where b>0 and the sum b+c is at the least 2, preferably 2–20, will be able to exhibit interesting physically functional characteristics as described herein, irrespective that the domain may comprise as few as one segment G.

In an interesting embodiment of the present invention, the organic compounds comprise at least two domains each independently composed of b segments of the general formula G and c segment of the general formula G', where b>0 and the sum b+c is at least 2, preferably 2–20.

Such domains maybe separated by a spacer group SP, which in the simplest embodiment is a divalent group having the same chemical structure as defined for the linking group Y. In this case the domains and spacers form a chain of alternating blocks, ie. -Domain-SP-Domain- etc. In more elaborate embodiments, SP may be a tri- or polyvalent group, e.g. SP may form a dendritic structure, such as illustrated in FIG. 47. In order for SP to separate two adjacent domains so that no undesired interaction is possible, the spacer group has at least 3 consecutive covalent bonds, preferably between 3 and 15 consecutive covalent bonds.

Figure 49:
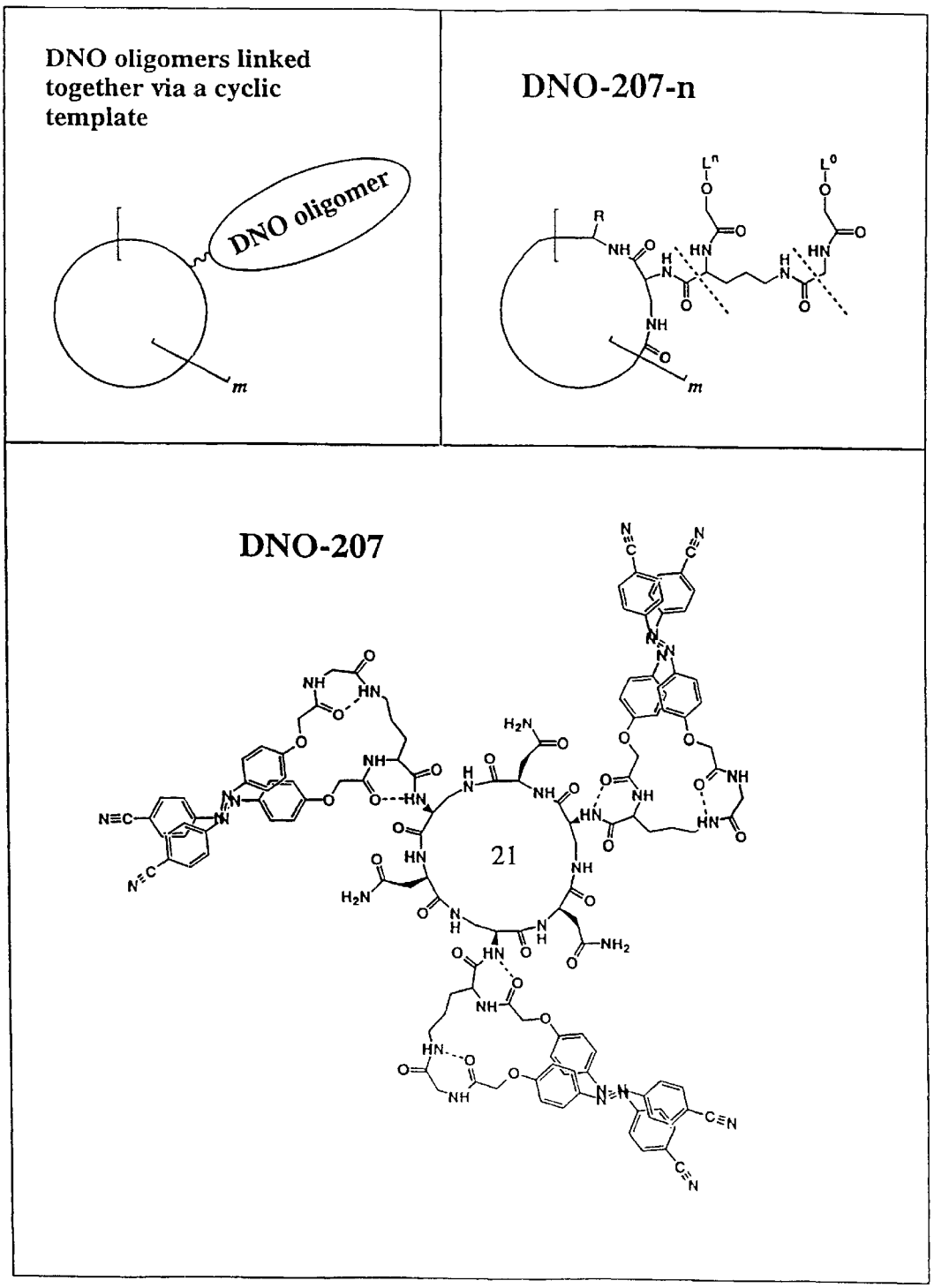
FIG. 49 DNO oligomers linked to cyclic templates.

In a interesting embodiment within the concept of "physically non-functional groups", "domains" and "spacer groups", the domain(s) and spacer(s) form a macrocyclic structure as illustrated in FIGS. 46, 49 and 50. More generally, the present invention also relates to compounds wherein the chain of segments of the general formula G, and, optionally, segments of the general formula G' and any spacer groups, form a macrocyclic structure.

It is clear from the present description that compounds comprising segments G as well as either segments G' or spacer groups SP, or both, provide the possibility of adjusting and improving the excellent physical, in particular optical, properties of the compounds comprising segments G exclusively.

Thus, a preferred embodiment of the present invention relates to the novel organic compound having a physical functionality which can be. influenced by external stimulation and comprising one or more segments of the formula G as defined herein and one or more segments of the formula G' as defined herein and/or one or more spacer groups as defined herein. In a further interesting embodiment of the present invention, the domains comprising segments G and, optionally, segments G' and spacer groups SP, are attached covalently to a template. Such templates may be selected from a number of sources and may have various forms and chemical structures. Obviously, in order to facilitate attachment of the domains comprising segments G, the outer surface of the template should preferably carry functional groups, e.g, amino or carboxyl groups, for the easy attachment of the domains.

With respect to the form of the template, it is envisaged that materials having a dendritic structure may have interesting properties with respect to inducing a physical anisotropy in a material thereof. Thus, it is envisaged that a dendritic structure having the chains or domains attached to substantially all of the branches may be especially interesting. Furthermore, novel organic compounds wherein the template is the polymeric matrix structure used for synthesizing the chains or domains may also be interesting alternatives.

In FIGS. 12–27several examples of the backbone structure are illustrated.

In FIG. 12, a number of structures are shown in which chains $A^m$—$B^m$—$A^{m-1}$ have from 4 to 7 consecutive covalent bonds in that a varying number of consecutive methylene groups are present. The formulas each represent several structures in that the two dotted lines represent the segment which in accordance with the formula $G^h$ is present n times. Thus, for example, the structure DNO-6-n represents a generalised form of the compound DNO-6 in that the two dotted lines represent a segment in accordance with the general formula G, and a similar significance is represented by the dotted lines in the other formulas DNO-19-n, DNO-18-n, and DNO-14-n, and the formulas should be considered to comprise and represent as well as specifically disclose each and every one of the structures formed when n assumes the possible values.

Furthermore, in the structures, the linking group $Y^n$ is specifically exemplified by a group $NHC(O)CH_2O$, but it is to be understood that the linking group may be any of those described in the above or the following, and the formulas should be considered to comprise and represent as well as specifically disclose each and every one of the structures formed when $Y^n$ assumes its possible meanings. Likewise, in the structures shown, the terminating groups Q and Z are shown as $H_2NC(O)$ and H, respectively, but it is to be understood that the terminating groups Q and Z may be any of those described in the above or the following. and the formulas should be considered to comprise and represent as well as specifically disclose each and every one of the structures formed when Q and Z assume their possible meanings. Also, asymmetric carbon atoms are shown in one particular chiral form, but it is to be understood that the atoms in question may each be in any of the possible two chiral forms.

Also, in the formulas the physically functional group $L^n$ may be any of those described in the above or the following, and the formulas should be considered to comprise and represent as well as specifically disclose each and every one of the structures formed when Ln assumes its possible meanings. A suitable example of the physically functional group may be the photochromic azo group used in the compound DNO-6.

As it will be seen, the structures DNO-6-n, DNO-19-n, DNO-18-n, and DNO-14-n, where the linking group is as shown, may be constructed using ornithine, 2,3-diaminopropionic acid, 2,4-diamino-butyric acid, and lysine, respectively, in combination with glycine.

In FIG. 13, the same general relationships apply as in FIG. 12 with respect to the significance of the dotted lines, the nature of the linking groups, the nature of the terminating groups, the chirality of any asymmetric carbon atom, and the nature of the physically functional groups. However, it is noted that each of the specific structures differs from the corresponding one in FIG. 12 by the nature of the terminating group Z in that Z is a methyl group in FIG. 13 instead of a hydrogen atom as in FIG. 12. Thus, in the specific structures shown, the part of the molecule formed using glycine in FIG. 12 are formed using alanine in FIG. 13.

In FIG. 14, the same general relationships apply as in FIG. 12 with respect to the significance of the dotted lines, the nature of the linking groups, the nature of the terminating groups, the chirality do any asymmetric carbon atom, and the nature of the physically functional groups. The structure DNO-53-n differs from DNO-19-n in that the amide function between the dotted lines has been replaced by a dimethylene group. Furthermore, the structures DNO-54-n, DNO-55-n, and DNO-56-n differ from DNO-53-n in that the tetramethylene group has been shortened by 1, 2, and 3 methylene groups, respectively. Thus, the structures DNQ-53-n, DNO-54-n, DNO-55-n, and DNO-56-n having the linking groups shown may be constructed from lysine, ornithine, 2,4-diamino-butyric acid, and 2,3-diamino-propionic acid, respectively.

In FIG. 15, the same general relationships apply as in FIG. 12 with respect to the significance of the dotted lines, the nature of the linking groups, the nature of the terminating groups, the chirality of any asymmetric carbon atom, and the nature of the physically functional groups, with the exception that in the structure DNO-22-n, the linking group shown is $C(O)CH_2O$ instead of $NHC(O)CH_2O$. This structure differs from DNO-56-n in that there is no chirality in the backbone because the side chain is attached through a nitrogen atom instead of a carbon atom. The specific structure can be constructed using (2-aminoethyl)glycine.

In FIG. 16, the same general relationships apply as in FIG. 15 (structure DNO-22-n) with respect to the significance of the dotted lines, the nature of the linking groups, the nature of the terminating group Z, and the nature of the physically functional groups. The structure DNO-400-n differs from DNO-22-n in that the terminating group Q is hydrogen instead of —$H_2NC(O)CH_2$—. The structures DNO-401-n, DNO-402-n, and DNO-403-n differ from DNO-400-n in that instead of a dimethylene group between the dotted lines as in DNO-400-n, they have a trimethylene, tetramethylene, and pentamethylene group, respectively. The structures DNO-400-n, DNO-401-n, DNO-402-n, and DNO-403-n may be constructed using 1,2-diamino-ethane, 1,3-diaminopropane, 1,4-diamino-butane, and 1,5-diamino-pentane, respectively.

In FIG. 17, the same general relationships apply as in FIG. 12 with respect to the significance of the dotted lines, the nature of the linking groups, the nature of the terminating groups, the chirality of any asymmetric carbon atom, and the nature of the physically functional groups. The structure DNO-104-n differs from DNO-6-n in that the amide function present between the dotted lines is located 1 atom further towards the left Thus, where the structure DNO-6-n can be constructed using ornithine and glycine, the structure DNO-104-n can be constructed using 2,4-diamino-butyric acid and beta-alanine (3-amino-propionic acid).

Figure 18:
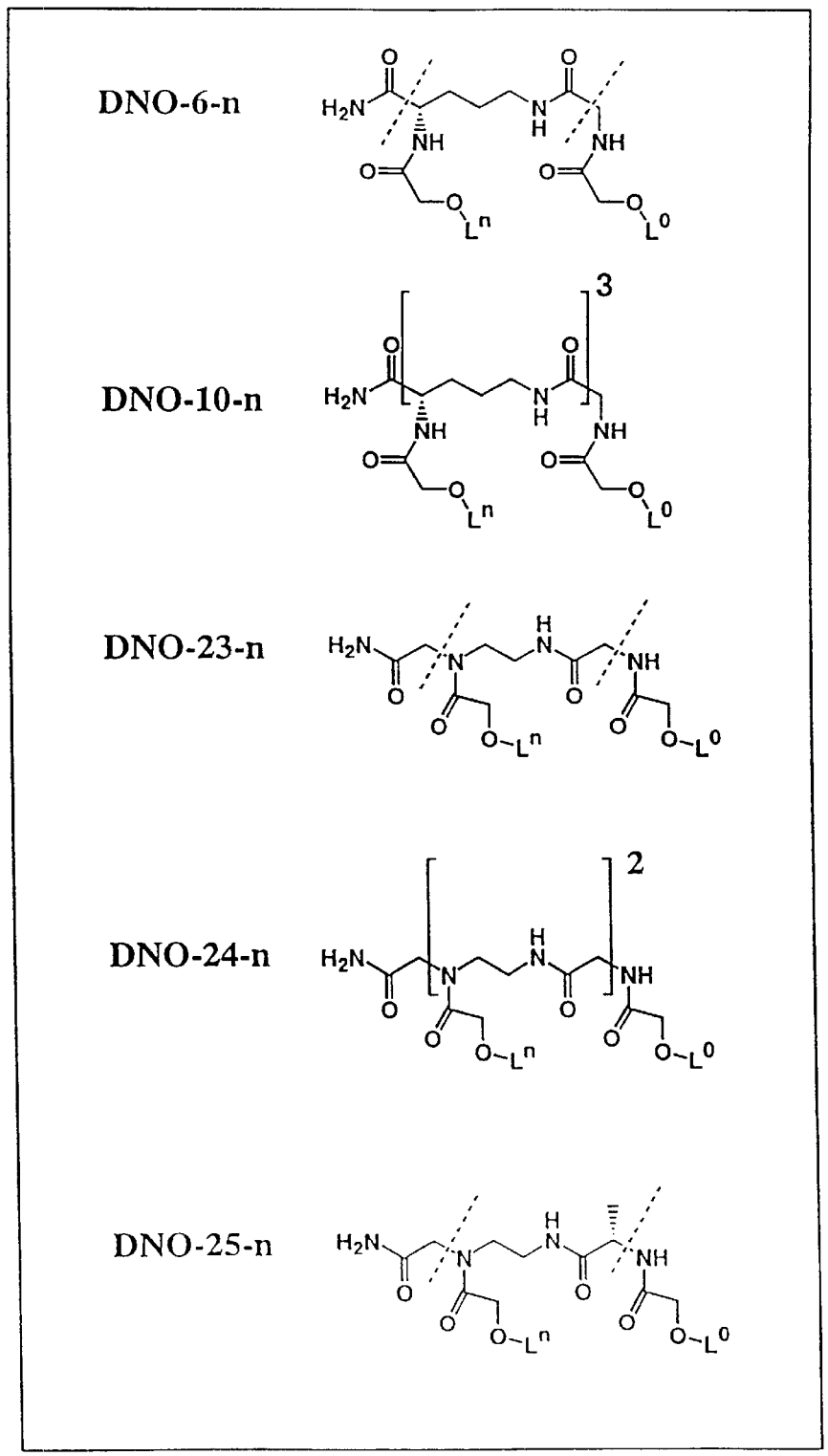

In FIG. 18, the same general relationships apply as in FIGS. 12 and 15 with respect-to the significance of the dotted lines, the nature of the linking groups, the nature of the terminating groups, the chirality of any asymmetric carbon atom, and the nature of the physically functional groups. The structure DNO-23-n differs from the structure DNO-22-n shown in FIG. 15 in that a moiety $NHC(O)CH_2$ has been inserted between the dotted lines, and the structure DNO-25-n differs from the structure DNO-22-n in that a moiety $NHC(O)CH(CH_3)$ has been inserted between the dotted lines. The specific structure DNO-24 represents a case in which two of the moieties shown between the dotted lines in structure DNO-23-n are present. The structures DNO-23-n and DNO-24 can both be constructed using (2-aminoethyl)glycine and glycine, and the structure DNO-25-n can be constructed using (2-aminoethyl)glycine and alanine.

Figure 19:
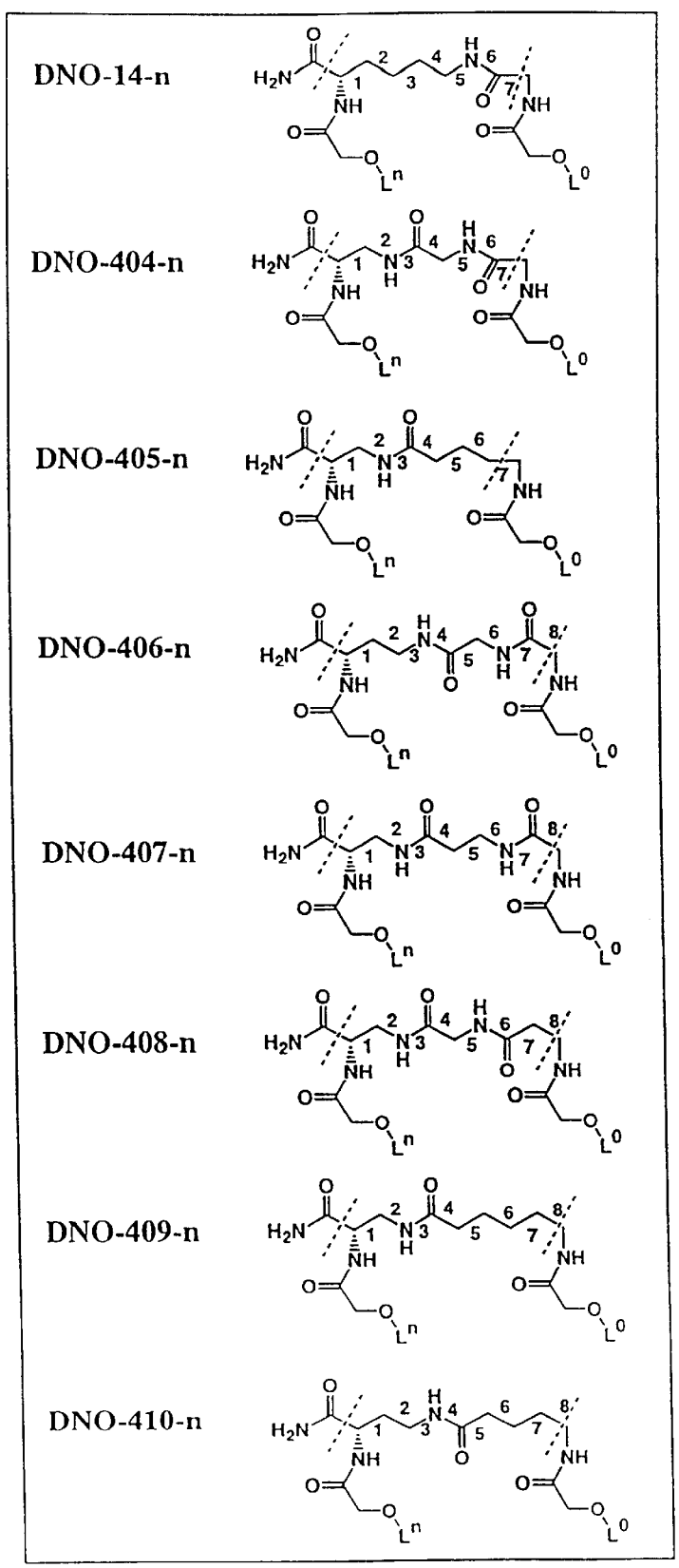
Figure 24:
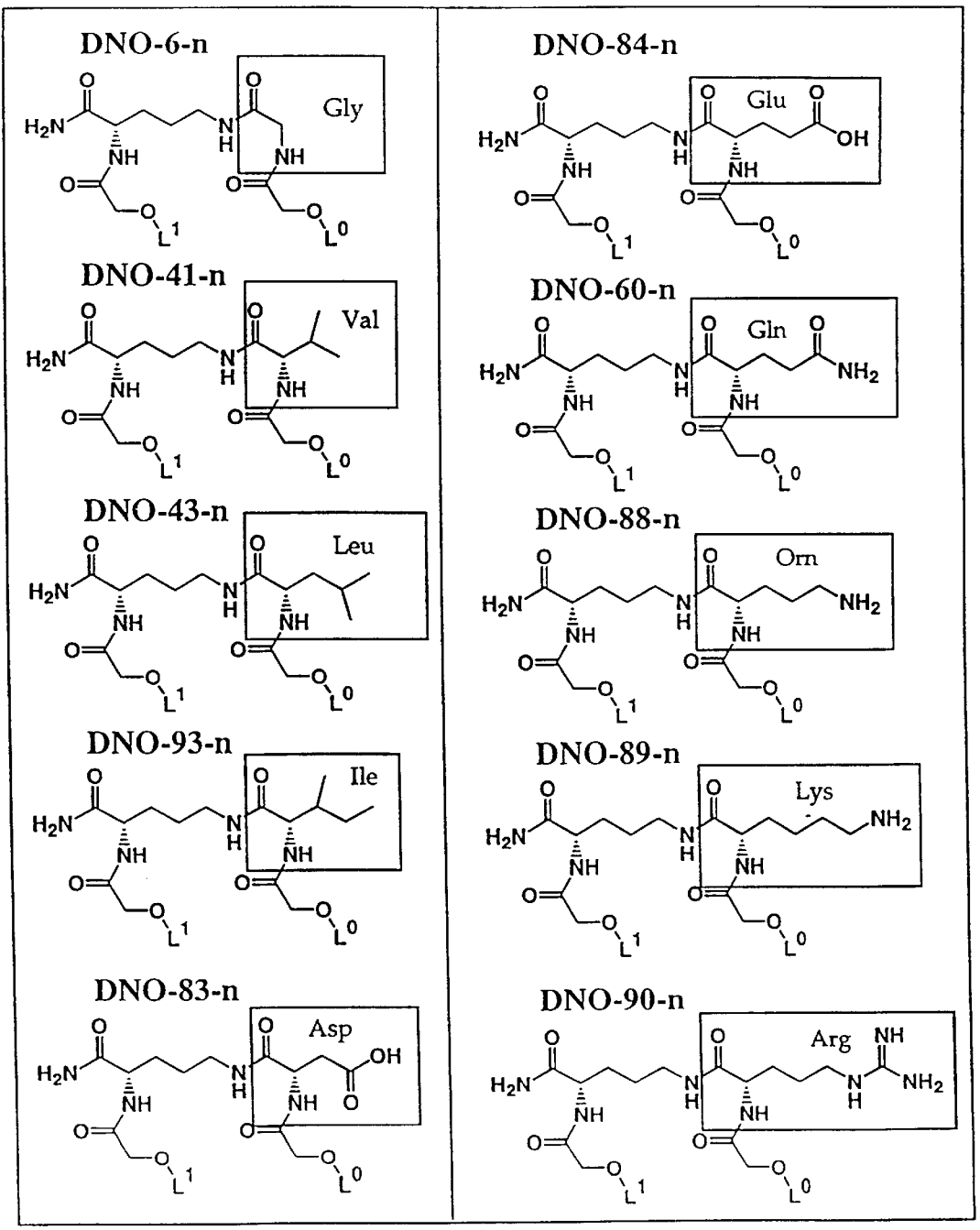
Figure 25:
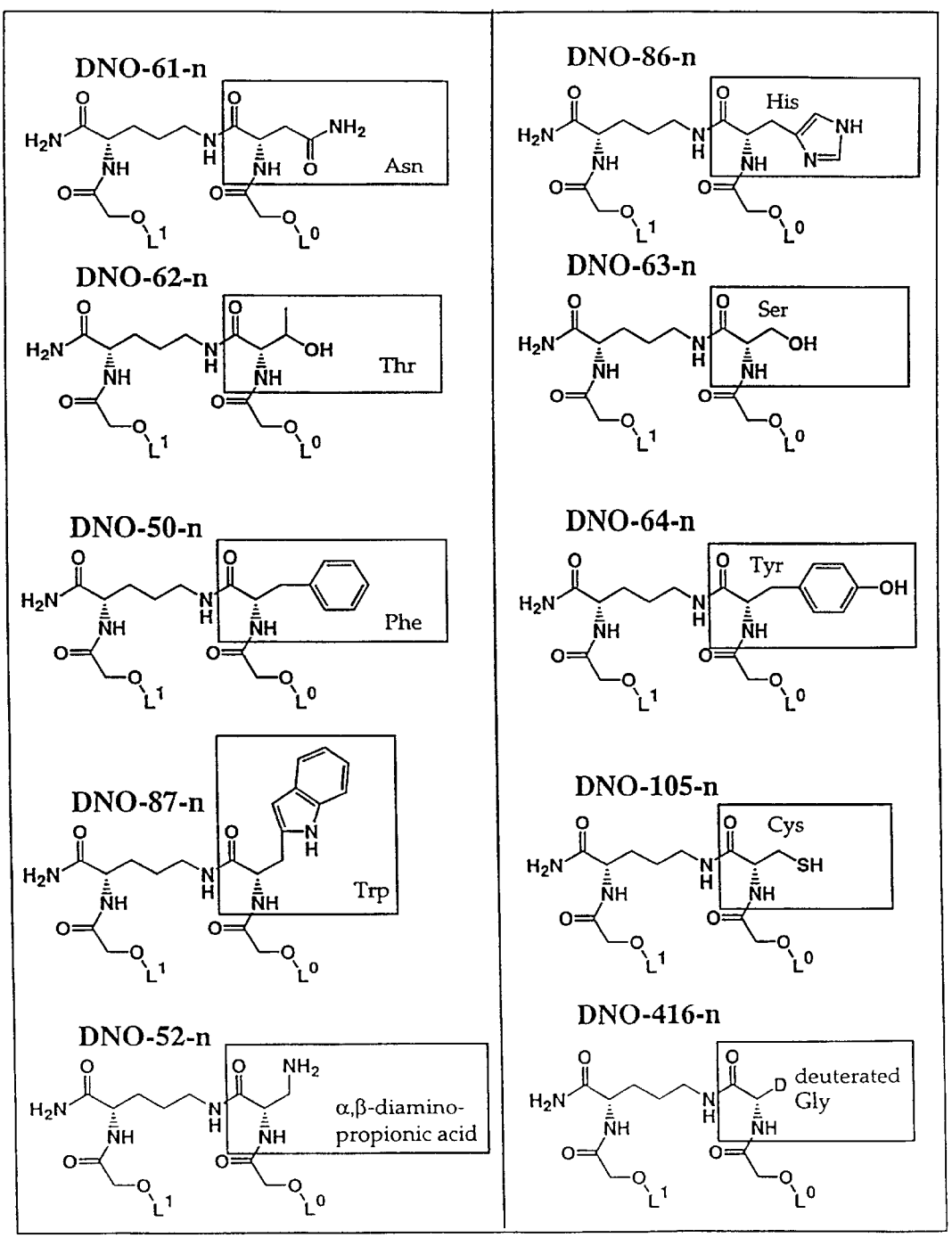
Figure 26:
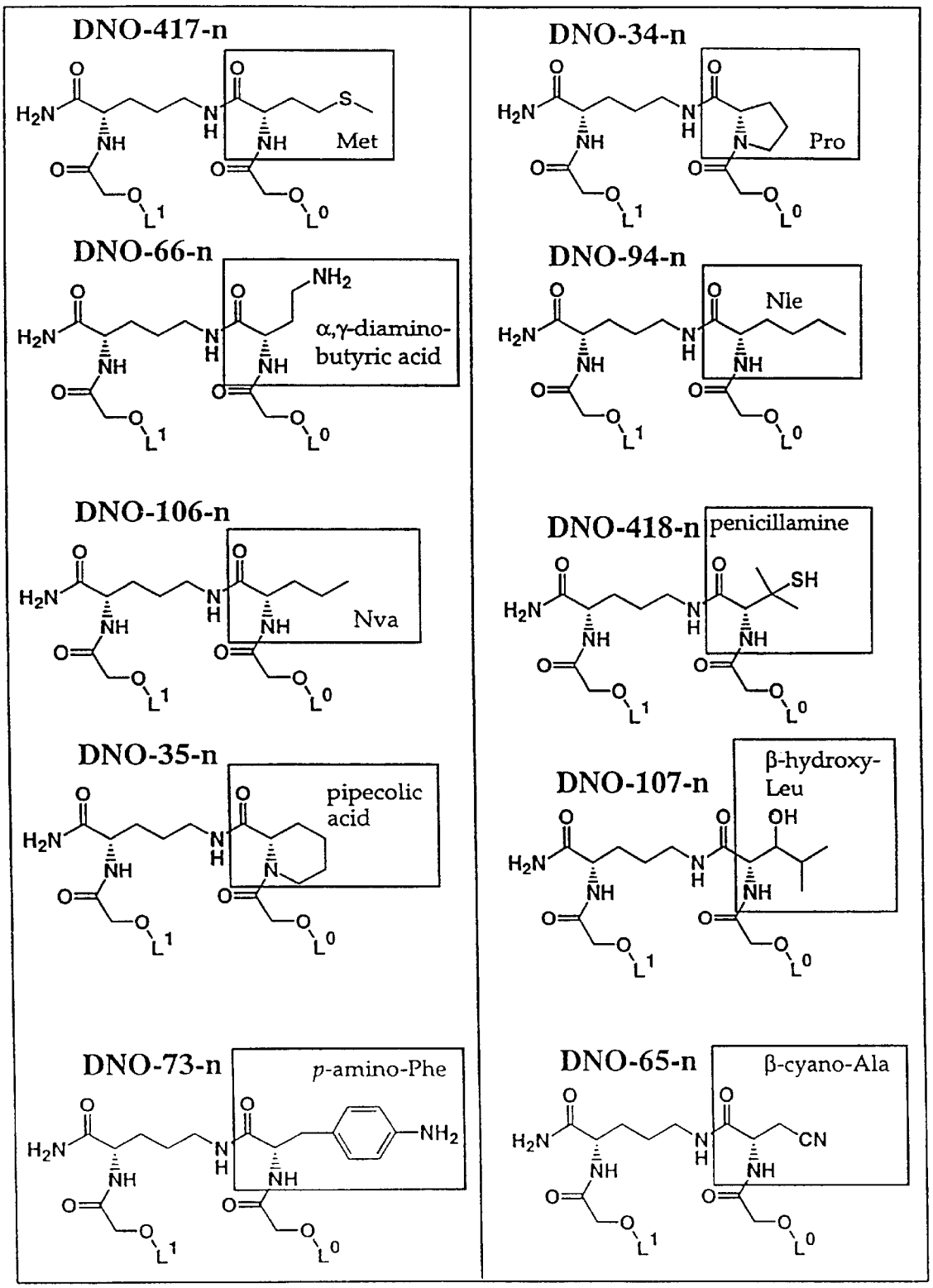
Figure 27:
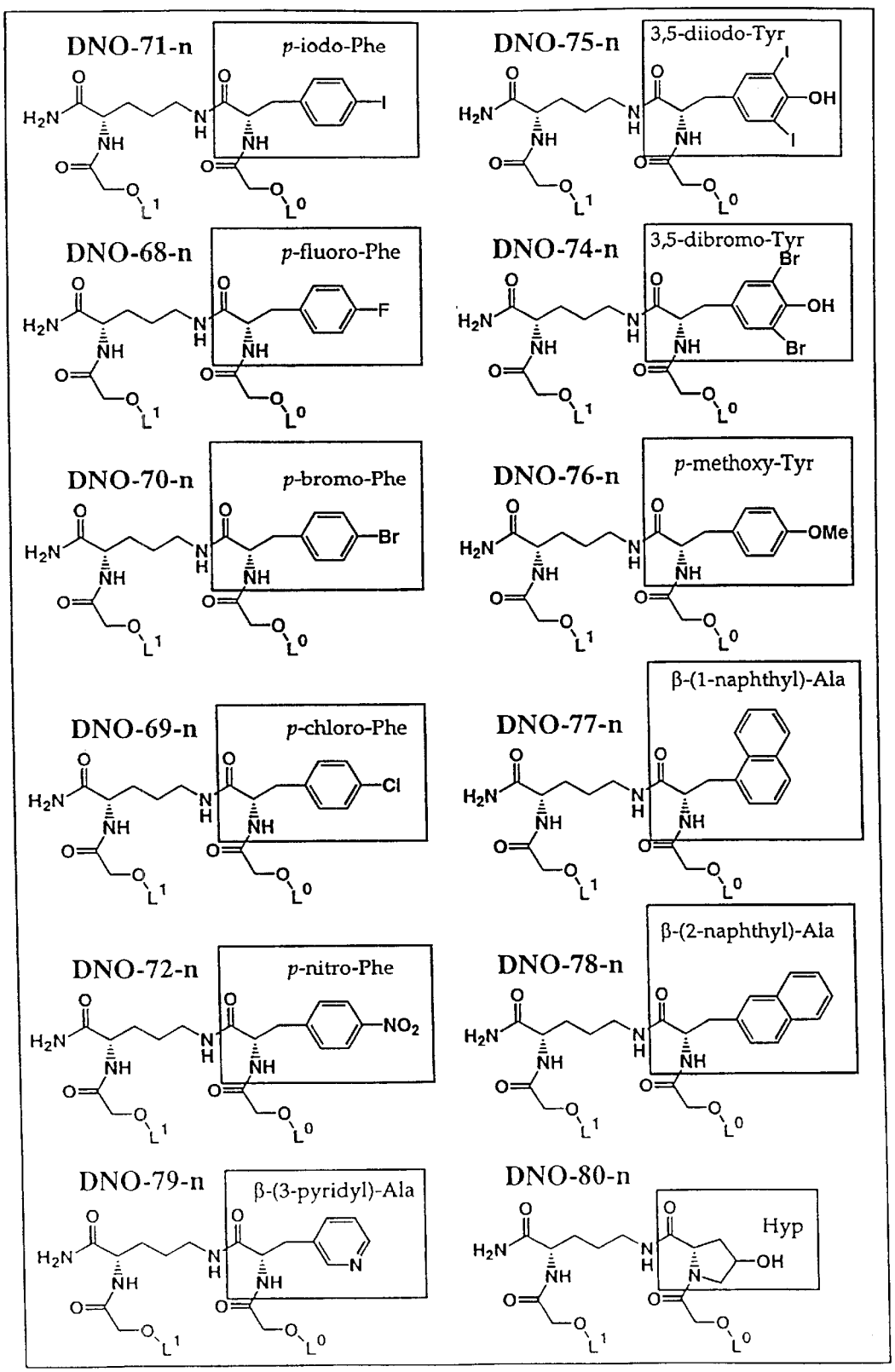

In FIG. 19, the same general relationships apply as in FIG. 12 with respect to the significance of the dotted lines, the nature of the linking groups, the nature of the terminating groups, the chirality of any asymmetric carbon atom, and the nature of the physically functional groups. In the figure, various structures are shown having either 7 or 8 consecutive bonds in the chain $A^m$—$B^m$—$A^{m-1}$ and having either one or two amide functions in the backbone. The structure DNO-404-n may be constructed using 2,3-diamino-propionic acid and two glycine moieties; the structure DNO-405-n may be constructed using 2,3-diamino-propionic acid and 5-amino-pentanoic acid; the structure DNO-406-n may be constructed using 2,4-diamino-butyric acid and two glycine moieties; the structure DNO-407-n may be constructed using 2,3-diamino-propionic acid and beta-alanine and glycine; the structure DNO-408-n may be constructed using 2,3-diamino-propionic acid and glycine and beta-alanine, the structureDNO-409-n may be constructed using 2,3-diamino-propionic acid and 6-amino-hexanoic acid; the structure DNO-410-n may be constructed using 2,4-diamino-butyric acid and 5-amino-pentanoic acid.

In FIG. 20, the same general relationships apply as in FIG. 12 with respect to the significance of the dotted lines, the nature of the linking groups, the nature of the terminating groups, the chirality of any asymmetric carbon atom, and the nature of the physically functional groups. The structures DNO-33-n and DNO-38-n resemble structures DNO-6-n and DNO-12-n, respectively, with the exception that DNO-33-n and DNO-38-n both contain a methyl group on the righthand nitrogen atom instead of a hydrogen atom. DNO-33-n can be constructed using ornithine and sarcosine (N-methyl-glycine), and DNO-38-n can be constructed using ornithine and N-methylalanine.

FIG. 21 shows three specific oligomer structures in which the chirality pattern is varied in several ways. Thus, DNO-411-n shows a tetramer having a L,L,D,achiral-pattern (the achiral element appearing through the use of a glycine moiety); DNO-412-n shows a tetramer having L,L,D,D-pattern; and DNO-413-n shows a hexamer having a L,L,D, D,L,L-pattern. The structure may be constructed in a manner analogous to that of DNO-6 or DNO-12 or DNO-13.

FIG. 22 shows some structures which are essentially N-substituted oligoglycine derivatives (also known as peptoids). Thus, DNO-414-n can be constructed using glycine and suitably N-substituted glycines, whereas DNO-415-n can be constructed using exclusively the suitably N-substituted glycines.

FIG. 23 shows some structures derived from DNO-6-n. Thus, the structure DNO-51-n is a compound where the terminating group Q is $HOC(O)$ rather than $H_2NC(O)$ in DNO-6-n. DNO-51-n may be constructed using ornithine and glycine. DNO-52-n is an analogue of DNO-51-n where the terminating group Z is $CH_2N_2$ instead of H. It may be constructed using ornithine and 2,3-diamino-propionic acid.

FIGS. 24–27 show a number of dimeric structures DNO-34-n; DNO-35-n; DNO-41-n; DNO-43-n; DNO-50-n; DNO-52-n; DNO-60-n to DNO-66-n; DNO-68-n to DNO-80-n; DNO-83-n; DNO-84-n; DNO-86-n to DNO-90-n; DNO-93-n; DNO-94-n; DNO-105-n to DNO-107-n which differ from DNO-6-n in that instead of the glycine moiety in DNO-6-n contained within the box marked Gly, the structures DNO-34-n; DNO-35-n; DNO-41-n; DNO-43-n; DNO-50-n; DNO-52-n; DNO-60-n to DNO-66-n; DNO-68-n to DNO-80-n; DNO-83-n; DNO-84-n, DNO-86-n to DNO-90-n: DNO-93-n; DNO-94-n; DNO-105-n to DNO-107-n each have another amino acid, some of which are naturally occurring. They may be constructed using ornithine and the relevant amino acid as marked in the individual boxes.

Figure 28:
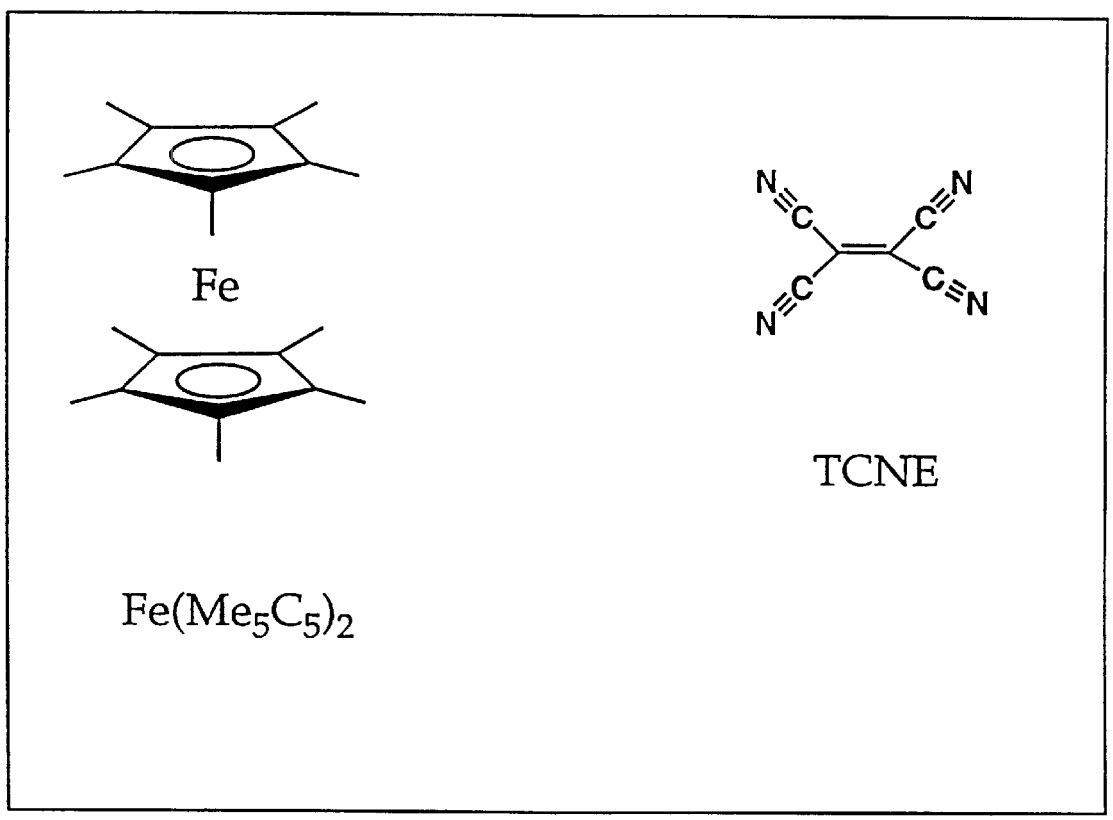

FIGS. 28–29 show examples of electron donors and acceptors which can provide organometallic molecular magnetic materials in the form of electron-transfer salts.

Figure 31:
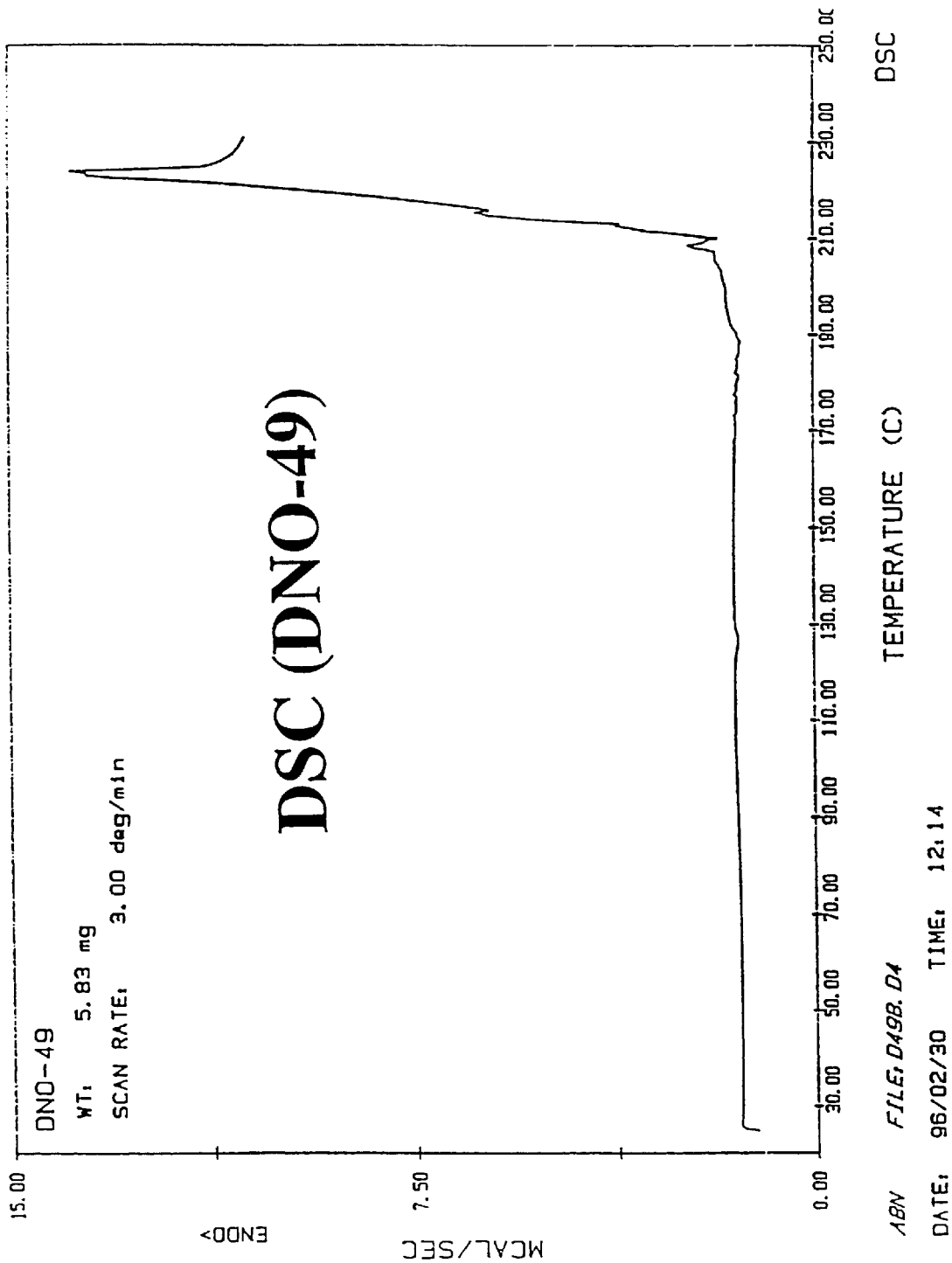
FIG. 31 A differential scanning calorimetry (DSC) trace of DNO-49 (cf.
Figure 32:
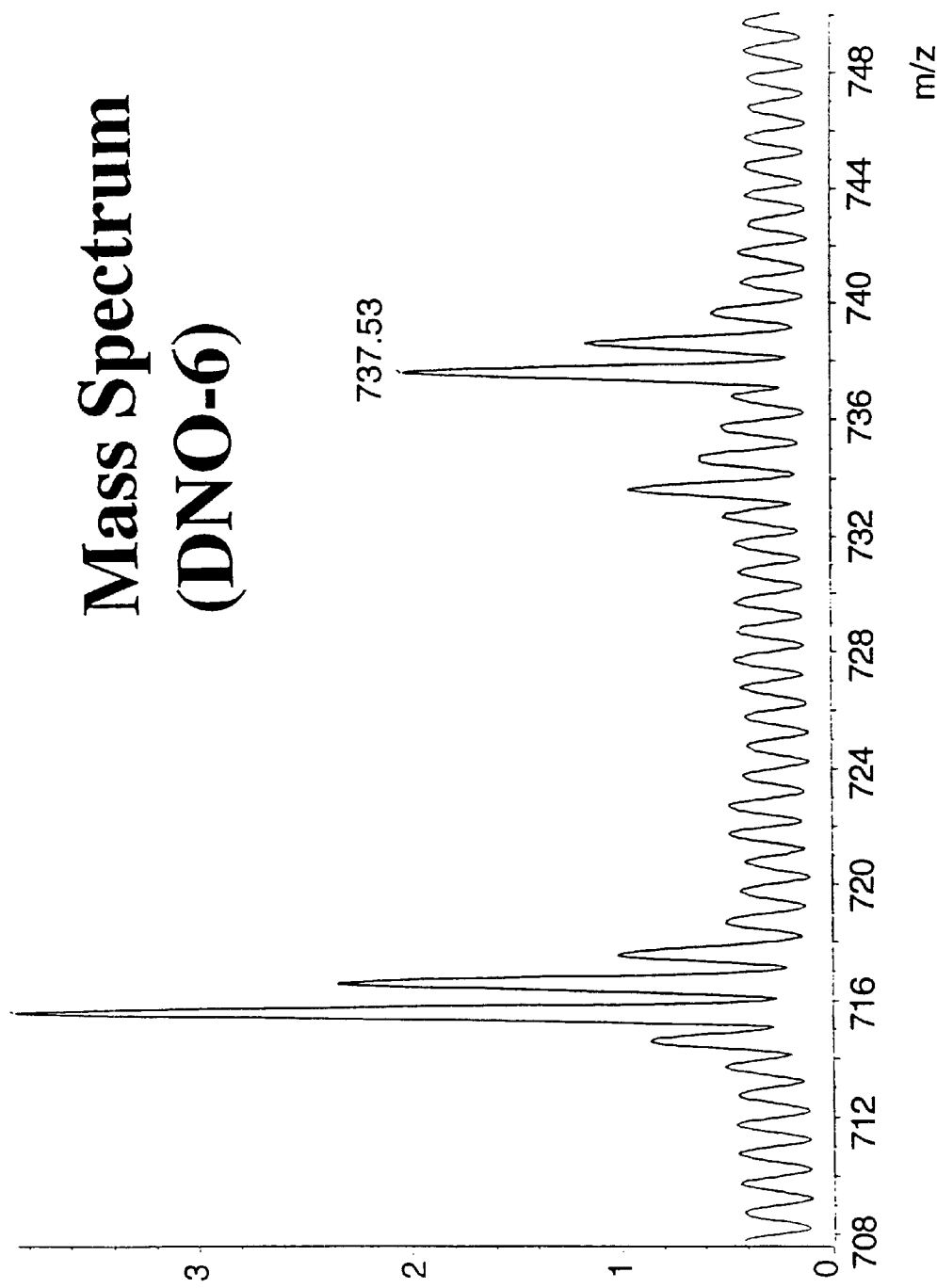
FIG. 32 Fast Atom Bombardment (FAB) mass spectrum of DNO-6 obtained from a four sector mass spectrometer.

FIGS. 30–32 display results of chemical and structural analyses performed on DNO compounds.

FIGS. 33–35 show the similarity of DNO with DNA.

Figure 36:
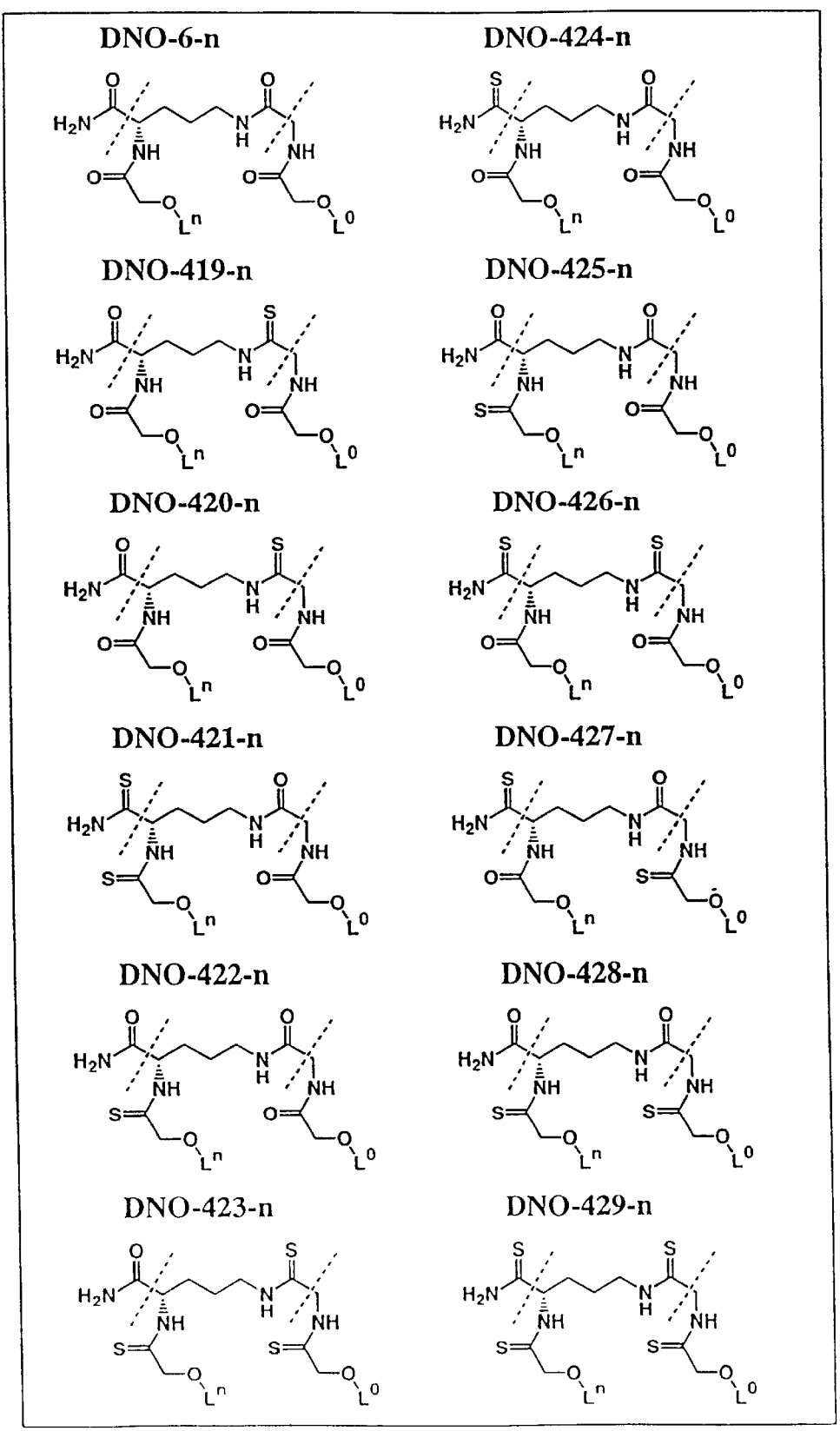
FIG. 36 Chemical structure of DNO-6-n and a number of thioamide-substituted analogs (DNO-419-n to DNO-429-n).

FIG. 36 shows the chemical structure of a number of thioamide-substituted analogs of DNO.

Figure 37:
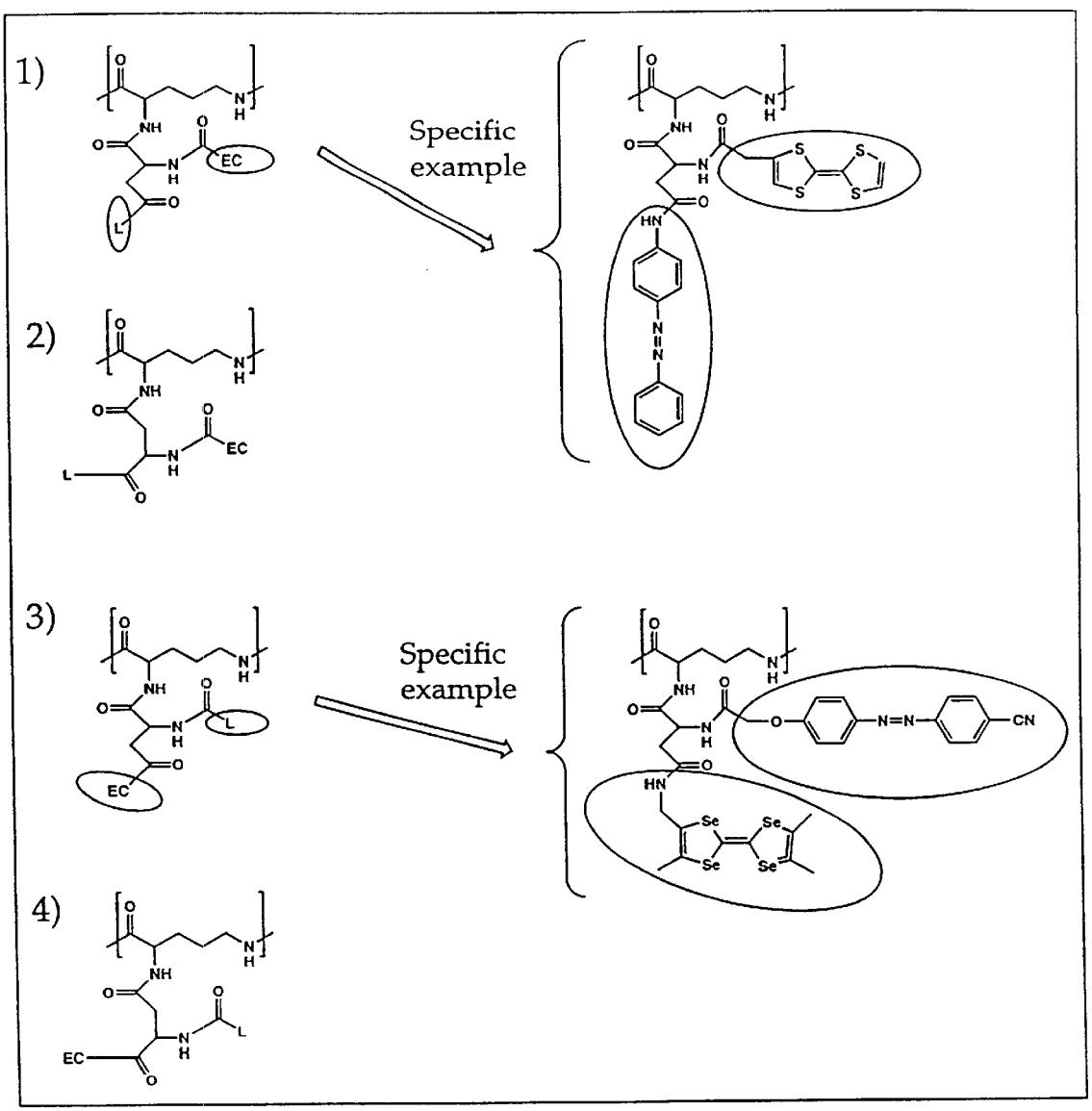
FIGS. 37 and 38 Two ways of attaching a photoresponsive ligand and one additional functional ligand to the backbone structure.
Figure 38:
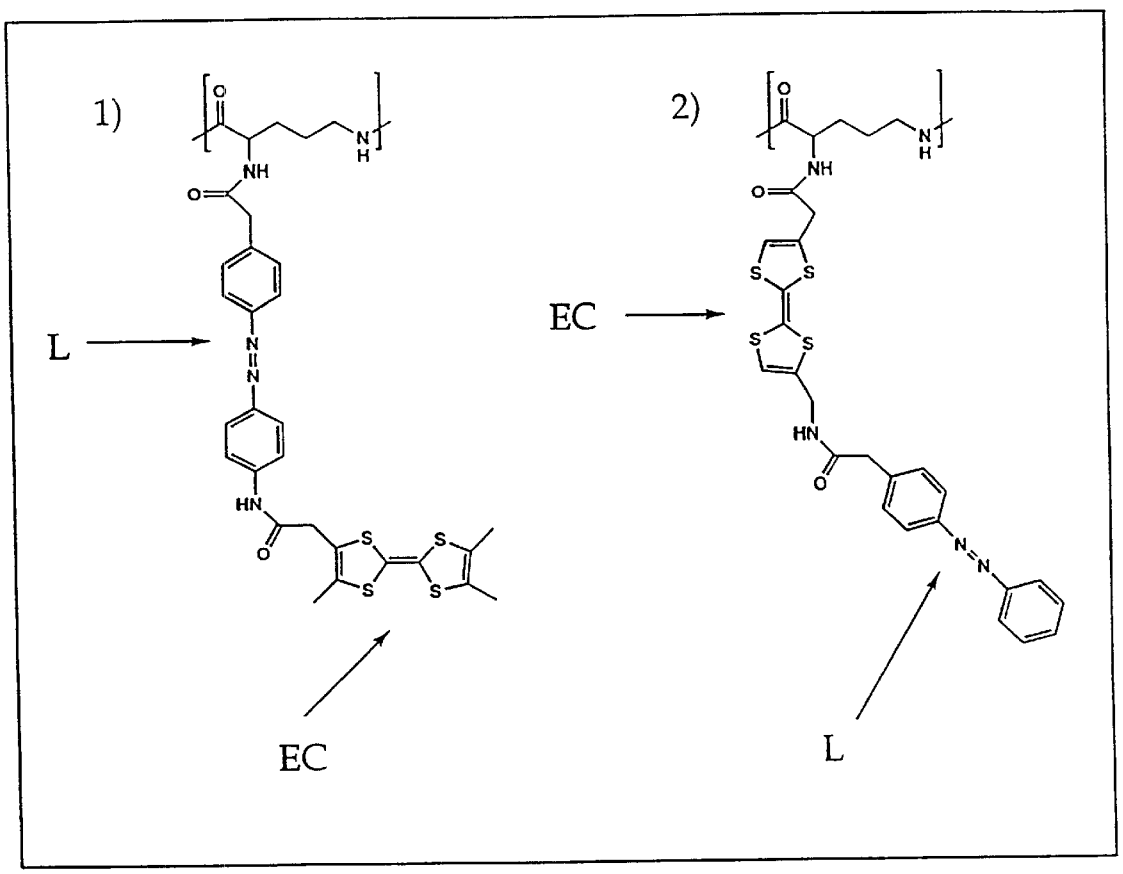

As outlined in FIGS. 37 and 38, preferred embodiments of the present invention may, in addition to the photoresponsive ligand (illustrated by the azobenzene ligand), include one additional functional ligand The rationale is that, upon irradiation, photoresponsive ligands, such as azobenzenes, are presumably aligned in a highly ordered manner; if the other functional ligands are specifically bound nearby, they are likely to be aligned (stacked) in a highly ordered manner, too. Thus, it is envisaged that materials made up of such compounds can be used for optical control of electron-conducting (and/or superconducting) properties [Bechgaard, K. et al. *J. Am. Chem. Soc.* 103, 2440–2442 (1981); Bryce, M. R. & Petty, M. C. *Nature* 374, 771–776 (1995)], ion-conducting properties [Tokuhisa, H., Yokoyama, M. & Kumura, K. *Chem. Mater.* 5, 989–993 (1993)] or magnetic properties [Miller, J. S. & Epstein, A. *J. Angew. Chem. Int. Ed. Engl.* 33, 385–415 (1994)], depending on the functional ligand in question.

In FIG. 37 the attachment of a photoresponsive ligand and one additional functional ligand via an Asp or Glu moiety is shown. The below-mentioned examples illustrate four general ways in which both a photoresponsive ligand in the group L, e.g., an azobenzene derivative, and another functional ligand, e.g., a ligand as defined below with electron-conducting (EC) behaviour, can be linked by amide bonds to an Asp residue which itself is linked via an amide bond to the α-amino group of an ornithine unit in an oligomer made up of ornithine units through the δ-amino groups. For the purpose of obtaining a single methylene group extension in any of the four examples, Asp can be replaced with Glu. Furthermore, the ligands in question can be linked in a similar fashion to other backbones, e.g., the previously mentioned backbones consisting of lysine units (oligomerized through the ε-amino group) or (2-aminoethyl) glycine units. The general methodology outlined here applies to other functional ligands than EC ligands. Other functional ligands include ligands as defined below with ion-conducting (IC) behaviour.

EC is a moiety selected from the group consisting of orgailiccompounds with electron-conducting behaviour, such as tetrathiafulvalenes, tetraselenafulvalenes, tetratellurofulvalenes, and derivatives thereof or salts thereof, such as TCNQ salts.

IC is a moiety selected from the group consisting of organic compounds with ion-conducting behaviour, such as crown ethers, cryptands, cryptates, cryptophanes, coronands, sperands, speleands, speleates, podands, and cyclic peptides.

Figure 2:
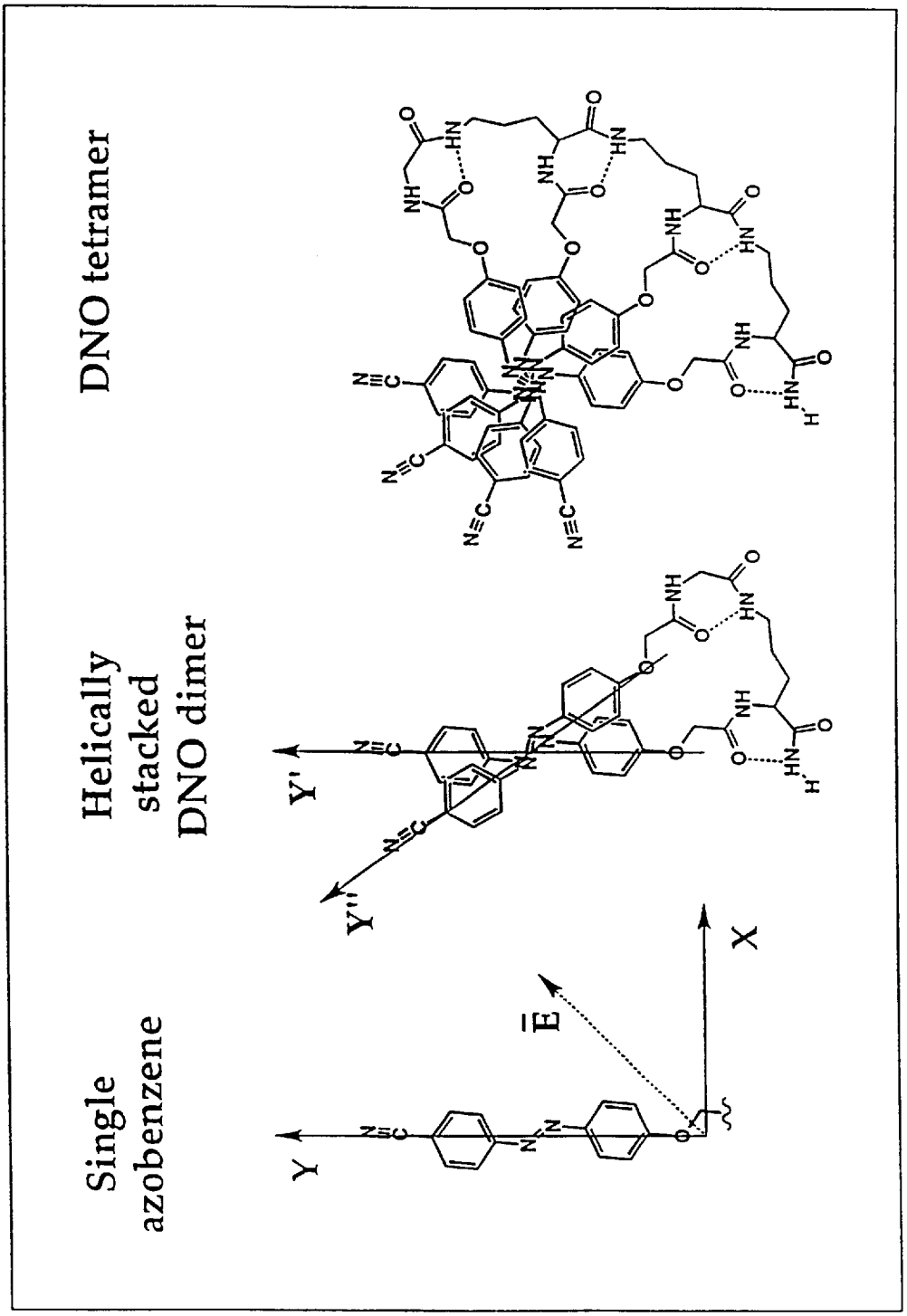
FIG. 2 Diagram illustrating that helically stacked azobenzenes, in contrast to single ones (or azobenzenes stacked in a parallel manner), cannot be rotated freely around their transition moment axis, e.g. Y, while still retaining the DNO molecule in a stationary orientation. The DNO dimer and tetramer models are viewed from the top and are drawn with the normal DNA (B-DNA) helical twist of 36° between neighbouring azobenzenes. Examination of a DNO model suggest that specific hydrogen bonds, e.g., the ones shown here, could play a structural role in predefining the stacking of the azobenzene side chains.

In FIG. 38 the attachment of a photoresponsive ligand and one additional functional ligand in a linear fashion is shown. The below-mentioned examples illustrates two ways in which both a photoresponsive ligand L and another functional ligand as described in FIG. 37 can be linked by amide bonds in a linear fashion via an amide bond to the α-amino group of an ornithine in an oligomer made up of ornithine units oligomerized through the δ-amino groups. In FIG. 38 2), the order of the ligands is reversed in comparison with that in FIG. 38 1). The ligands in question can be linked in a similar fashion to the other backbones mentioned in FIG. 37.

In a further aspect of the invention, it is preferred that the terminating groups Q and Z of the DNO compound in question are linked together molecularly, e.g., through an amide bond, so as to obtain a cyclic DNO compound. It is known that suitably designed cyclic peptides, e.g., those consisting of eight or more alternating L and D amino acid residues, may be triggered (by acidifying an alkaline solution of the peptide) to stack by spontaneous self-assembly through a network of intermolecular hydrogen bonds and, thus, form tubular structures, the so-called "peptide nanotubes" [M. R. Ghadiri et al. *Nature* 366, 324 (1993) and *Nature* 369, 301–304 (1994)]. Such peptide nanotubes are predicted to have a number of attractive applications, e.g., in molecular electronics, because the internal diameter of the tubes can be varied in a controlled manner by varying the number of amino acid residues in the cyclic peptides, and because the interior of the tubes can be equipped with almost any desirable functional group(s), e.g., groups that are relevant for electron-conductivity, by equipping the cyclic peptides with the functional group(s) in a manner where it (they) are pointing inwards the cyclic ring of the peptide. Likewise, the exterior (the surface) of such peptide nanotubes can be equipped with almost any desirable functional group(s).

Figure 39:
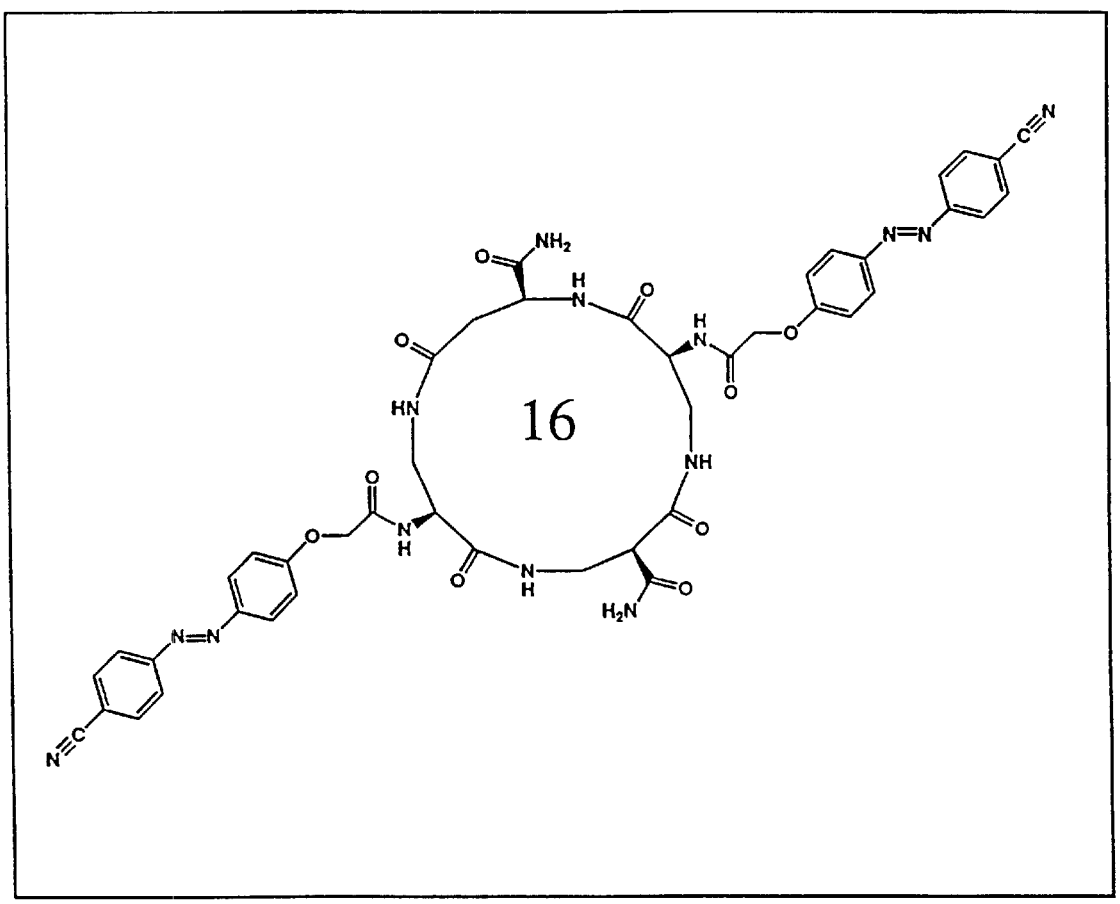
FIG. 39 Two-dimensional representation of the chemical structure of a cyclic DNO compound.
Figure 40:
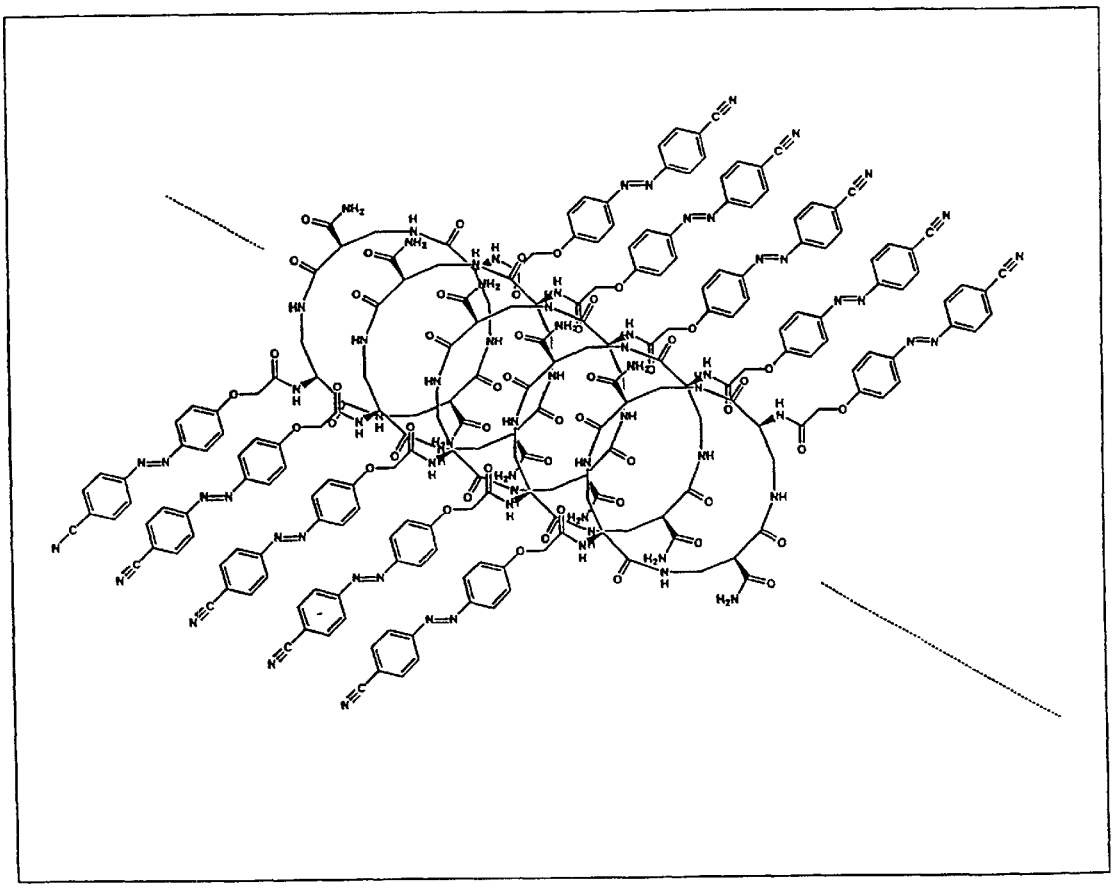
FIG. 40 DNO subunits, corresponding to those of FIG. 39, in a self-assembled tubular configuration emphasizing an intermolecular parallel stacking of the azobenzene-containing side chains obtained, e.g., in an optically controlled manner.

Within the context of the present invention, it is very likely that similar "DNO nanotubes" constructed from cyclic DNO compounds may be even more attractive for a number of applications. The internal diameter of a cyclic DNO compound may thus be regulated more intimately as the number of bonds may be varied at the level of a single covalent bond, in contrast with the cyclic peptides where the number of bonds can only be varied by three covalent bonds at a time corresponding to a single amino acid residue. Moreover, the conformational freedom, that is, the interplay between the flexibility and the rigidity of the DNO backbone, can be regulated much more delicately as it is not limited to the normal backbone pattern of peptides. Furthermore, the inwardly or outwardly pointing functional groups may be attached readily in a manner where they are located very close to the backbone of the cyclic DNO backbone, namely by attaching the functional groups in question to the α-amino groups, e.g., through an amide linkage, or, depending on the DNO compound in question, to nitrogen atoms (secondary amino groups) located in the backbone chain. Finally, and perhaps most importantly, it is very likely that cyclic DNO compounds, if equipped with appropriate physically functional groups such as, e.g., Azo1, can be stacked into tubular structures ("DNO nanotubes") in an optically controlled manner; to achieve such an intermolecular stacking, the cyclic DNO compounds should preferably be constructed in a manner where the backbone has enough stiffness to suppress the intramolecular stacking of, e.g., the Azo1 groups. An example of a cyclic DNO compound and a schematic representation of how it might be aligned in a tubular structure, are shown in FIGS. 39 and 40, respectively. The synthesis of cyclic DNO compounds can be performed in a manner completelyanalogous to the synthesis of cyclic peptides. To this end the solid-phase approach is absolutely superior to any other synthetic procedure because the cyclization (which is an intramolecular reaction) can be done while the DNO compound (or peptide) is still attached to the solid support, thereby preventing intermolecular coupling reactions.

FIG. 39 shows a 2-dimensional representation of the chemical structure of a cyclic DNO compound made up of alternating α,β-diaminopropionic acid units (with an azobenzene-containing side chain attached through the α-amino group) and isoasparagine units. The resulting DNO "ring" contains 16 bonds. The solid-phase synthesis of the structure shown is carried out by initially coupling the α-carboxylic acid group of aspartic acid (with protected α-amino and β-carboxylic acid groups) onto a benzhydrylamine type of solid support. After an assembly of all four units, the protected C-terminal carboxylic acid group is deprotected and coupled to the free N-terminal amino group. Final cleavage from the resin converts the initially coupled α-carboxylic acid group into its amide form.

FIG. 40 shows DNO subunits in a self assembled configuration forming a "DNO-nanotube".

Figure 41:
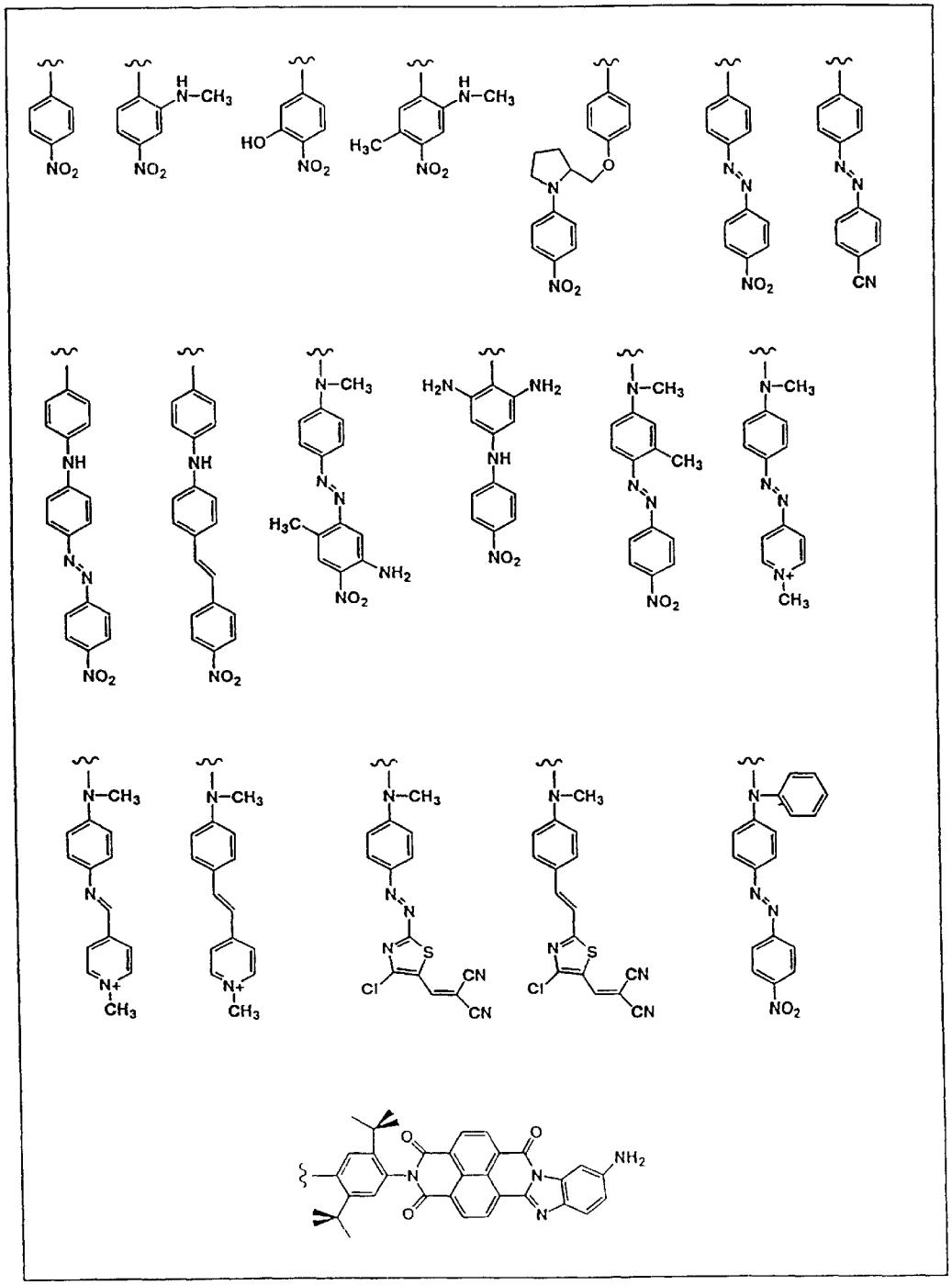
FIG. 41 Structures of some nonlinear chromophores which have been or may be used in the compounds according to the invention.

FIG. 41 shows a long range of common nonlinear optical chromophores. The chromophores all contain a pair of strong donors and acceptors which induce strong permanent dipoles in the moieties.

FIG. 42 This shows two common amino acids, proline and glycine linked together to form a backbone unit with the same molecular geometry as that of the backbone unit in DNA. The ligand $L^n$ is linked through the 4-position in the proline ring, which is equivalent to the linking position of the nucleobase to the sugar ring in DNA. The substituted proline moiety is generated from hydroxyproline which has the hydroxy group in the 4-position enabling functionalization; for example, substitution of a hydroxy group with an amino group.

Figure 43:
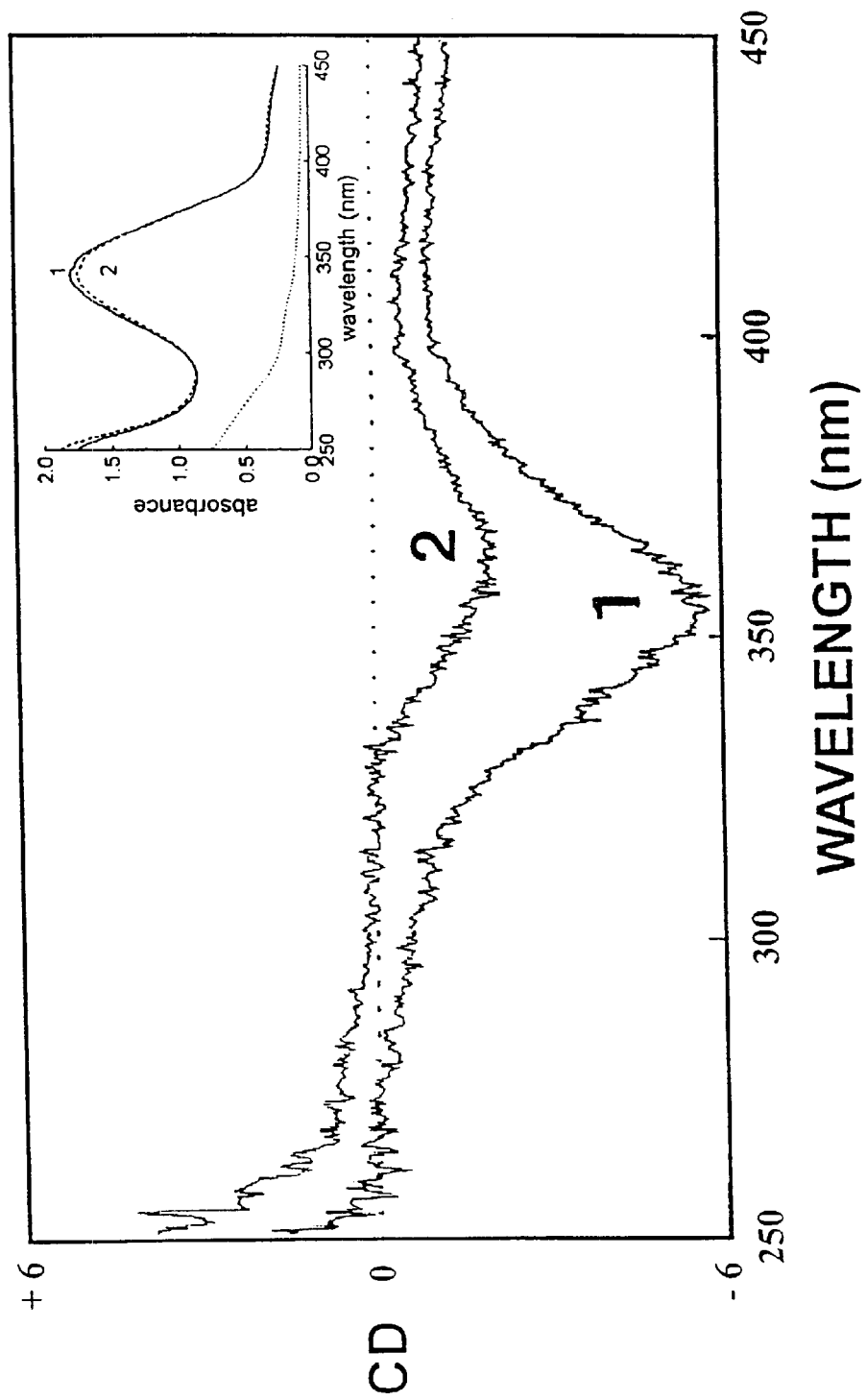
FIG. 43 Circular dichroism spectra of an ornithine-based DNO decamer (1) and an alanine-based monomer (2) in hexafluoroisopropanol solutions. In the insert, absorption spectra of the same solutions as well as that of hexafluoropropanol ( . . . ) are shown.

FIG. 43 The circular dichroism (CD) spectrum of an ornithine based decamer. The structure of DNO in the film should bear some resemblance to the structure of the oligomers dissolved in hexafluoroisopropanol and hence the CD spectrum of the solution should be similar to that of the film. The pronounced circular dichroism observed suggests the existence of close interactions between neighbouring chromophores oriented in a helical manner relative to each other (Cantor, C. R. & Schimmel, P. R. "Biophysical Chemistry. Part II: Techniques for the study of biological structure and function", W. H. Freeman and Company, 1980].

Figure 44:
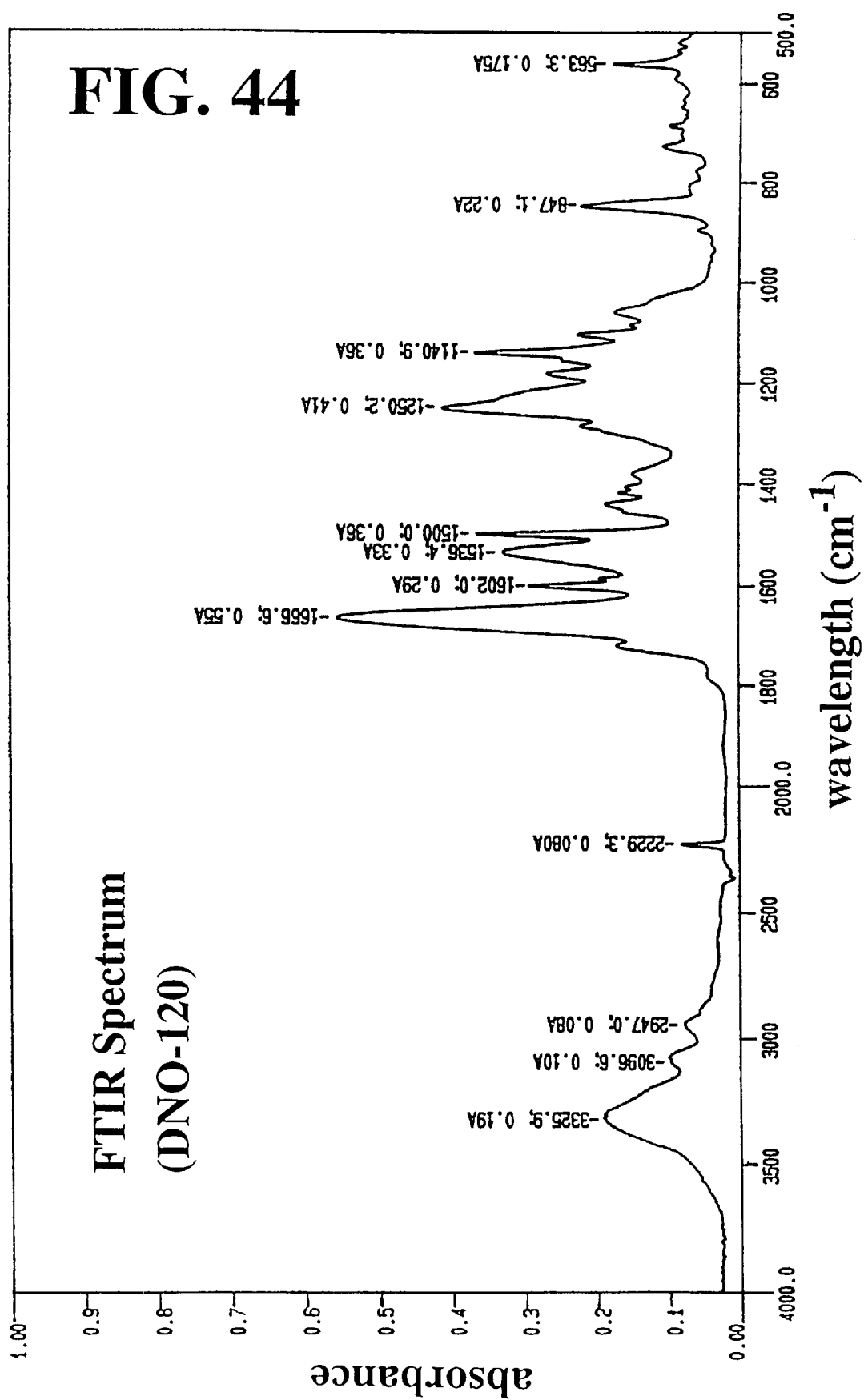
FIG. 44 Fourier-Transform infraed spectrum of DNO-120 (cf.
Figure 45:
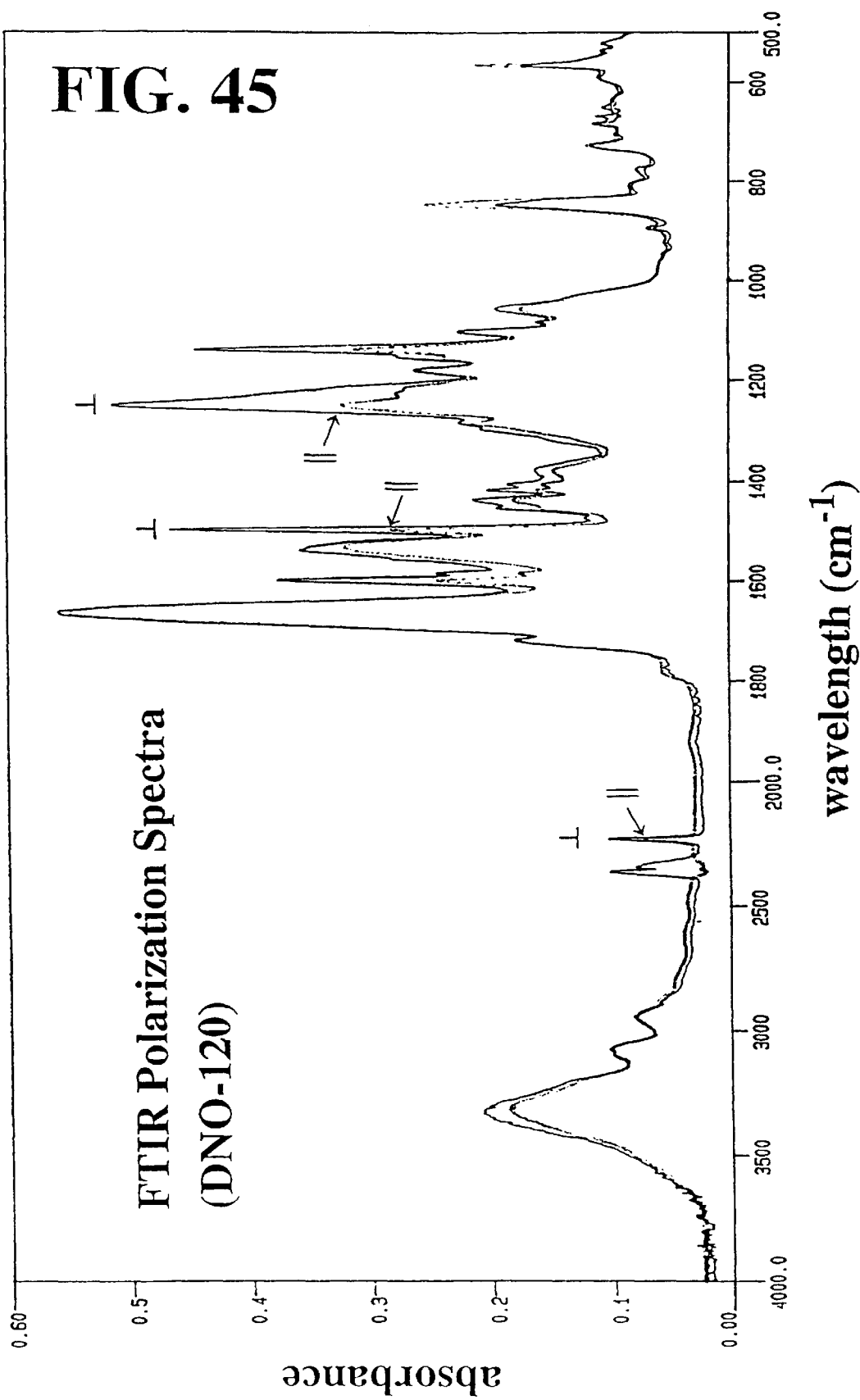
FIG. 45 Polarised Fourier-Transform infrared spectrum of DNO-120 (cf.

FIGS. 44 and 45 show the Fourier transform infrared spectra (FTIR) of the compound DNO-120. FIG. 44 is the spectrum before irradiation. The compound is then irradiated with linearly polarised laser light at 488 nm and the FITM spectra are recorded parallel and perpendicular to the polaristion of the laser light. The FTIM polarisation spectra shown in FIG. 45 demonstrate that the cyanoazobenzene chromophore (represented by the $\nu(C\equiv N)$, 2229 cm$^{-1}$; $\nu(C=C)_{arom.\,ring}$, 1500 cm$^{-1}$; $\nu(Ar-O-C)_{aryl.alkyl.ether}$, 1250 cm$^{-1}$ vibrations) orient preferably perpendicular ($\perp$) to the laser light polarisation.

FIGS. 5–10 show that very large diffraction efficiencies are obtainable with DNO oligomers. As to the origin of the extraordinarily large diffraction efficiencies observed with DNO-6 and longer oligomers, they may be rationalized in the following way: A conceptual model that illustrates the rationale behind the DNO design is shown in FIG. 2. It is seen that a single azobenzene, in which the transition moment of the chromophore lies along the Y axis, can be rotated in the entire XY plane and in any position around the Y axis while still retaining its transition moment oriented perpendicular to the polarisation Ê of the laser beam. In the case of the ornithine based DNO dimer it is assumed that the two neighbouring azobenzenes are stacked and, thus, any rotation around the Y' or the Y" axis will rotate both of them resulting in a rotation of the entire molecule. Assuming that the two azobenzenes are stacked in a helical manner, any such rotation, other than 180°, would lead to a situation where the transition moment of the neighbouring azobenzene is no longer oriented perpendicular to Ê. Accordingly, the molecule would still be able to undergo photoisomerization cycles. In other words, with the DNO dimer, or longer oligomers, a stationary orientation will not be obtained until the planes of the azobenzenes are oriented perpendicular, or roughly perpendicular, to Ê or in other words, the helical axis is roughly aligned parallel to the direction of the electric field of the incident light. As a result, there are considerably fewer stationary orientations possible than in cases where the azobenzenes are either not stacked or stacked parallel to one another. These stationary orientations include all possible rotations in the X-Y plane. In order to reduce still further the number of different stationary orieintations, the azobenzenes can be attached to a template that increases the rotational symmetry (cf. FIGS. 47 and 49).

FIG. 47 DNO-127 and DNO-214 are "dendrimer-like" examples demonstrating how the writing time can be accelerated dramatically if DNO oligomers are linked together via a "template" in an appropriate manner, i.e., in a manner that allows the individual oligomer moities to be oriented in a parallel (or anti-paralle) fashion. Thus, the effect of using an ornithine-glycine linker as a template shows that a much faster writing time is obtained with DNO-127 (cf. FIG. 54: approximately 45% 1st order diffraction efficiency in 10 s) than with DNO-10 (cf FIG. 6: approximately 10% 1st order diffraction efficiency in 10 s) even if they both contain four Azo1 side chains linked in the same manner to the same type of backbone units. Likewise, a much faster writing time is obtained with DNO-214 (cf. FIG. 54: approximately 65% 1st order diffraction efficiency in 2 s) than with DNO-46 (cf FIG. 6: approximately 10% 1st order diffraction efficiency in 2 s) even DNO-214 contains one Azo1 side chain less than DNO-46 (six and seven Azo1 side chains, respectively),and with the Azo1 side chains linked in the same manner to the same type of backbone units. A wide variety of other templates may be used, some of which are shown in FIG. 49.

FIG. 49 DNO oligomers linked via one particular type of template, namely cyclic templates. DNO-207-n is an example of a particular type of cyclic template, viz., a peptide-based cycle, to which DNO oligomers are attached DNO-207, which is a specific example of DNO-207-n consists of a 21 bond cycle made up of alternating aspartimide and diaminopropionic acid residues and with three DNO-6 dimers (cf. FIG. 6) bound covalently through the C-terminal to the α-amino groups of the diaminopropionic residues. The three dimers are shown in a stacked conformation similar to that shown in FIG. 40. It is seen that DNO-207 has rotational symmetry with respect to rotations around the centre of the macrocycle.

Other cyclic or macrocyclic templates include cyclophanes, such as calixarenes (cf FIG. 50). Besides cyclic and dendritic (cf FIG. 47) templates, the template can be cylindrical (e.g., cyclodextrins and carbon nanotubes) as well as other geometries. In order to attach a DNO oligomer covalently to the template in question, the template should comprise a chemical functionality, e.g., amino groups, carboxylic acid groups or both.

FIG. 50 DNO-502-n is an example of DNO oligomers attached to cyclic templates (cf. FIG. 49) based on calixarenes. DNO-501-n is an example of DNO oligomers in which the photoresponsive side-chain itself possesses electron-conducting properties, here exemplified by an azothiophene.

DNO-500-n is an example of a "double-stranded" DNO compound. In the particular type shown, the physically functional groups $L^n$ and $L^o$ are shown as divalent groups corresponding to the monovalent physically functional groups defined herein. As an example $L^n$ may be the divalent —C$_6$H$_4$—N=N—C$_6$H$_4$— attached via the 4 and 4' position. More generally a segment corresponding to this interesting situation is, where the situation outlined in the figure corresonds to a compound having two segments of the general formula G$^d$,

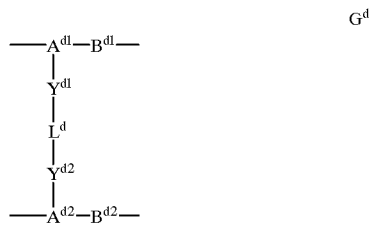

wherein L designate a divalent physically functional group corresponding to the monovalent physically functional groups L defined herein. As an example, physically functional ligands having the Formula I, would in the this case be the biradical of an azobenzene-like compound, in particular L$^d$ could designate the 4,4'-biradical of a ligand of Formula I where Ar$^1$ and Ar$^2$ both designate benzene.

FIGS. 51–55 show the diffraction efficiency of various DNO-compounds. As discussed in Example 27, the gratings are recorded using polarisation holography and the diffraction efficiency is followed as a function of time. These figures show how the diffraction efficiency falls due to an increase in the refractive index change due to laser irradiation, how changes in the molecular architecture result in shorter exposure times. For example, it is seen that a much faster writing time is obtained with the cyclic oligomer DNO-206 (cf. FIGS. 46 and 55) than with the linear oligomer DNO-9 (FIGS. 48 and 56) even though they both contain the same three azobenzene side chains attached to the same type of backbone structures.

Figure 56:
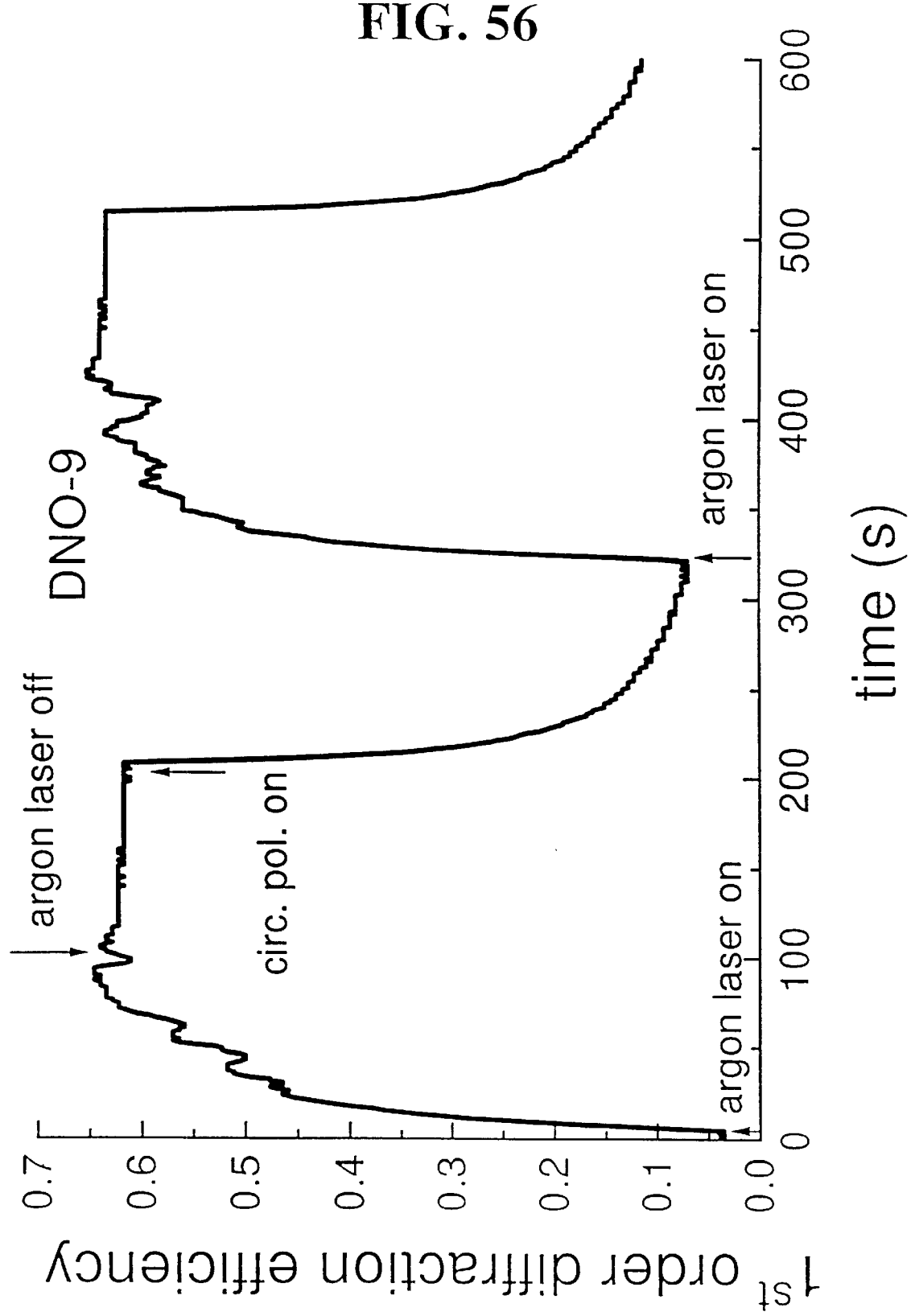
FIG. 56), DNO-138 (cf FIG. 51), and DNO-120 (cf.

FIGS. 56 and 57 show aspects of erasure of stored information. In FIG. 56, the stored information in the form of a grating is erased through the use of circularly polarised light at the same wavelength as the writing wavelength and in FIG. 57, the stored information in the form of optical anisotropy is erased through irradiation with UV-light.

Figure 58:
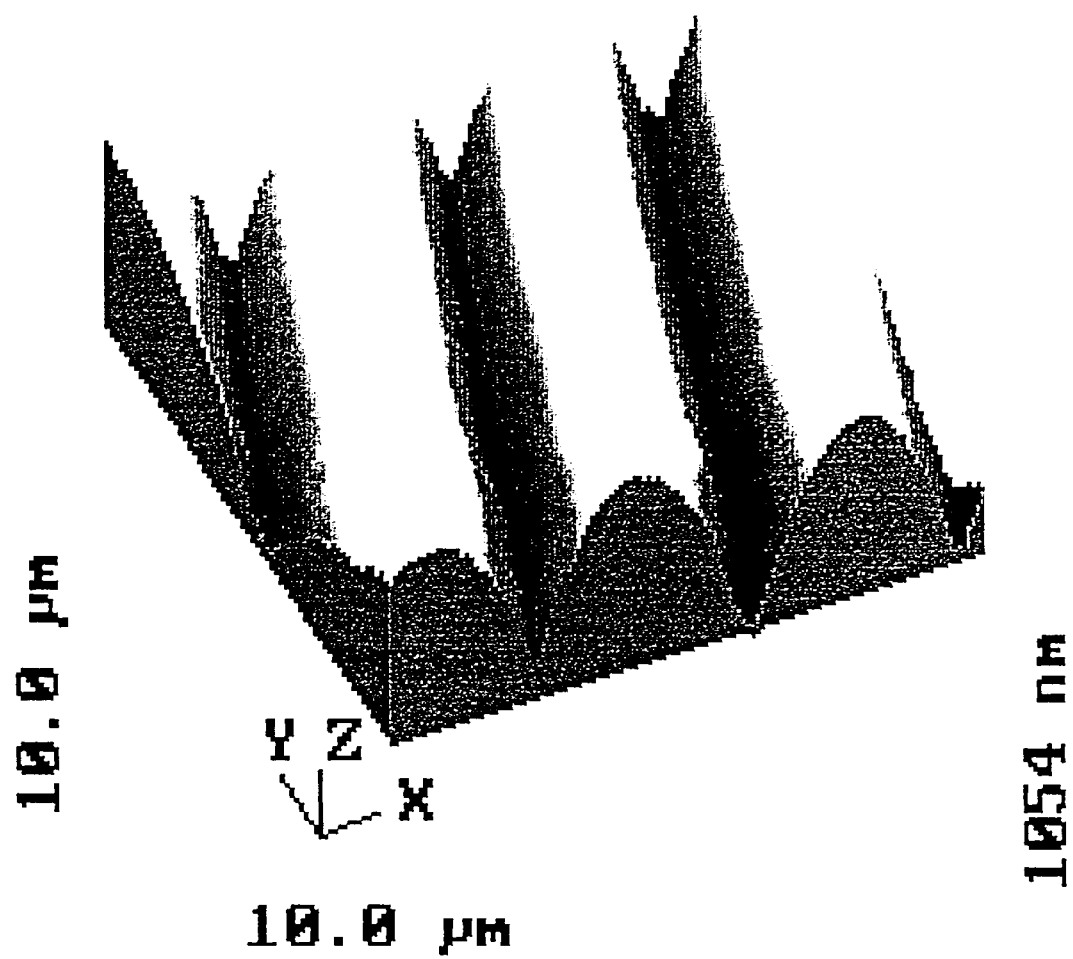
FIG. 58 Atomic Force Microscopic scan of a grating obtained in a polarisation holographic setup. The scan area is 10 $\mu$m×10 $\mu$m; the maximum roughness is indicated in the figure to be 1054 nm.

FIG. 58 shows an Atomic Force Microscopic (AFM) scan of a grating produced using polarisation holography. The grating was written with two orthogonally circularly polarised beams, which result in a linear polarisation on being vectorially combined in the film. The film is then scanned with an AFM over an area of 10 μm×10 μm. A remarkable surface undulation can be seen. This is all the more surprising as the intensity across the film during exposure is constant, while there is only a polarisation modulation. This points to a polarisation dependent strain induced in the film.

In another aspect of the invention the structural properties of DNO compounds may also be modified and intimately fine-tuned by selectively incorporating thioamide or selenoamide moieties into the backbone or the side chains. Thus, e.g., DNO-6-n can be modified as exemplified in FIG. 36. The thioamide group C(S)NH resembles the normal amide group C(O)NH in several ways; e.g., it is planar, too, and normally provides a trans configuration [Toniolo, C. *Biopolymers* 28, 245–257 (1989)]. The thioamide bond differs, however, in several ways from the normal amide bond; in particular, rotation around the C—N bond is more hindered due to the higher energy barrier [Hollosi et al. *Tetrahedron* 44, 195–202 (1988)] and, thus, incorporation of thioamide groups in replacement for a normal amide group offers the possibility to increase stiffniess in particular positions in a highly fine-regulated way. Furthermore, the thioamide group can participate in hydrogen bonds with other patterns and properties than those of normal amide hydrogen bonds; thus, for example, the so-called mixed intramolecular hydrogen bond NHC=O - - - HNC=S is stronger than the normal corresponding NHC=O - - - HNC=O due to the higher acidity of the thioamide group relative to the normal amide group [Toniolo, C. *Biopolymers* 28, 245–257 (1989)]. The thioamide modification is one of the most extensively studied synthetic modifications of peptides. In most cases, thioamide modifications are carried out using Lawesson's reagent or analogs thereof [Pederson, B. S. et al. *Bull. Soc. Chim. Belg.* 87, 223 (1978)].

The DNO oligomers are insoluble in most solvents, but are readily dissolved in trifluoroacetic acid or hexafluoroisopropanol. For preparation of a film of good optical quality, a DNO oligomer is dissolved in e.g. methylene chloride:trifluoroacetic acid:hexafluoroisopropanol (5:20:75 vol-%), filtered through a fine grade glass filter, cast onto a glass substrate and immediately dried in vacuo and at elevated temperature (cf. Example 26).

Figure 3:
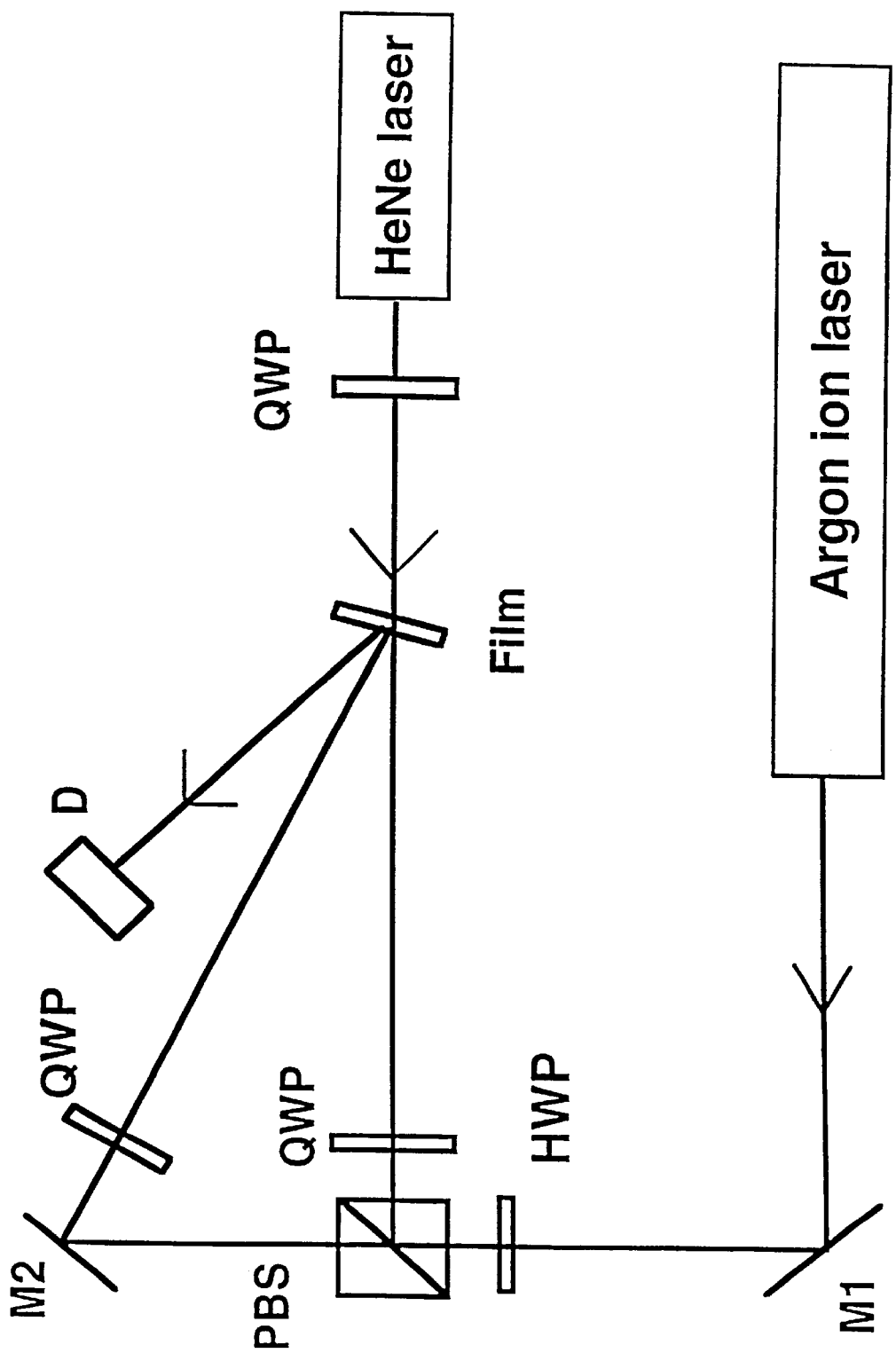
FIG. 3 Experimental polarisation holographic set-up to record diffraction gratings in DNO films. In the figure, HWP is a half-wave plate, QWP are quarter-wave plates, and M are mirrors. For the holographic experiments, the beam from the argon ion laser was split by means of a polarisation beam splitter (PBS), converted to orthogonally circularly polarised beams using appropriate quarter-wave plates; the argon laser was turned on manually with a delay of ca. 4 s. The beams were allowed to overlap on the film, giving a spatial resolution of about 510 lines/mm (a resolution of 3000 lines/mm can easily be achieved by changing the geometry of the set-up). The first order diffracted beam of a HeNe-laser was monitored by the detector D.

In order to test the use of DNO type oligomers for optical storage applications, holographic gratings have been recorded in the film. A polarisation holographic technique can be employed to record the gratings (FIG. 3). It is known that polarisation holographic recording in photoanisotropic materials gives rise to maximum diffraction efficiency (Nikolova, L. & Todorov, T. *Optica Acta* 31, 579–588 (1984); Huang, T. & Wagner, K. H. *J. Opt. Soc. Am.* A 10, 306–315 (1993)). It has been shown that by using two orthogonally circularly polarised beams to write a grating and a circularly polarised beam for the read-out, theoretically 100% efficiency can be obtained in one first-order diffracted beam, even for thin gratings (Nikolova, L. & Todorov, T. *Optica Acta* 31, 579–588 (1984)).

The examples below show that a suitably designed peptide oligomer with pendant azobenzene side chains is an outstanding medium for holographic optical recording. Thus, diffraction efficiencies near 100% in zero field have been obtained in DNO oligomers containing two or more residues which is larger (by far) than any measured to date for a thin (e.g. a film thickness of at the most 10 μm) photoanisotropic organic material. As mentioned previously, a high level of diffraction efficiency has been achieved with the photorefractive polymer composite reported last year by Meerholz et al. (*Nature* 371 497–499 (1994)). Their material, however, requires the application of a large externally applied electric field. More importantly, the storage time has been limited to only a matter of hours, as recently reported in *Physics Today* (Jan. 17–19, 1995). In contrast, the holograms written in the DNO materials appear to be completely stable at room temperature and exceptionally stable to heat, as they are not erased even after exposure to 150° C. for weeks. If needed, however, they can be almost completely erased, simply by exposure to circularly polarised light.

It is believed that immediate fields of applications will be in optical storage, especially stable holographic storage of text and images. It is contemplated that due to the high resolution capability of the material and its high temperature stability, approximately 2000 pages of information can be stored in one square cm of the film. This should find wide applications in medical and biomedical storage, in satellite imagery, in storage of commercial deeds, insurance policies, and literature.

By suitable modifications of the structure, especially of the group L, chromophores responding to different wavelengths can be incorporated in the successive side chains. Thus, the compound can be made sensitive to polarised white light. The spatial resolution of the compound will thus be better than commercial high-definition display systems. This can be especially useful for colour holography.

Ever since the rediscovery of holography, the possibility of holographic movies, with three-dimensional reproduction of images has been luring. Since the current invention allows for the storage of thousands of pictures in a small area, it is realistic that a holographic movie can be produced based, for example, on the principles discussed by Leith et al. ("Holographic Cinematography", E. N. Leith, D. B. Brumm and S. Hsiao, *Appl. Opt.* 11, 2016–2023 (1972)).

Furthermore, fabrication of optical components for the near infrared region of the spectrum, covering the range from 0.7 $\mu$m to 2 $\mu$m, is a possibility. Especially, fabrication of polarising thin films for use in the infrared spectral range will be importance. Fabrication of interference filters in thick films of DNO incorporated into polymers, will also be possible.

It may also-be possible to store images directly in the film; as for example in photographic techniques. Another way of storing information, is through direct writing in the film using a laser or other light sources. For example, a computer generated pattern or hologram can be directly scribed in the film by means of laser modulation. This makes fabrication of computer generated holograhic elements with special functions a possibility.

One of the interesting findings is that on scanning an optical grating in DNO produced by polarisation holography, with an Atomic Force Microscope (AFM) a strong surface undulation is observed. This is surprising because of the fact that in polarisation holography, the total intensity across the film is a constant, and only a polarisation modulation takes place. The height of the undulation observed is on the order of 1 $\mu$m for a film thickness of 4 $\mu$m (FIG. 58). The fabrication of grooves or channels through irradiation with polarised light can have applications in capillary electrophoresis for the fingerprinting of genes in DNA analysis, or in sensor applications.

It is believed that the immediate uses as well as the generic nature of these oligomers, taken together with their ease of synthesis and the enormous flexibility in terms of incorporating other side chains, should allow relatively simple expansion into the construction of molecular materials with other tailor-made properties. In one example, the oligomers discussed above should themselves exhibit nonlinear optical properties because the azobenzene side chains, which have dipole character, presumably are aligned in a manner where the dipole moments have the same direction. Below, incorporation of other ligand functions, such as those found in electron-conducting organic materials (Bechgaard, K. et al. *J. Am. Chem. Soc.* 103, 2440–2442 (1981); Bryce, M. R. & Petty, M. C. *Nature* 374, 771–776 (1995)) and ion-conducting materials are described.

It is contemplated that the chemical structure described above can be useful in many other applications. In one aspect of the invention, it is contemplated that by replacing the azobenzene pendants with nonlinear optical chromophores, it might be possible to construct materials with very high nonlinear optical coefficients. Second order optical effect, also called Pockels effect, can be used for second harmonic generation, electro-optical switching and optical rectification. Third order effect results in third harmonic generation, intensity dependent refractive changes, phase conjugation, four wave mixing etc. Usually materials for second order optical effects and third order effects are different. In the context of the present invention, successive side chains can have large second and third order effect respectively. Thus the same compound can be used for both second and third order effects.

Other applications of the nonlinear chromophores include their application in 3-dimensional two-photon memories. In this system, two photons at a specific wavelength are absorbed by the chromophore which is transferred to an excited state. This results in a local change in absorption or refractive index. If the excited state has an infinite lifetime, this would result in a permanent memory. (see, for example, Dvornikov, A. S., Malkin. J. & Rentzepis, P. M., *J. Phys. Chem.* 98, 6746–6752 (1994). When the chromophores have a broad inhomogeneous absorption, but narrow homogeneous absorption, it may even be possible to induce spectral hole burning effects at room temperature. (Kachru, R., Bai, Y. S., & Shen. X., *Adu. Mater.* 6, 791–793 (1994), Renn, A. & Wild, U. P. *Appl. Opt.* 26, 4040–4042 (1987)). Thus, the present invention also relates to two-photon and spectral hole-burning memories comprising compounds of the invention.

Photonic band gap materials are interesting recent materials which can be useful in novel laser architectures. The macroscopic lattice structures in these materials are such that certain electromagnetic frequencies are forbidden to exist within the structure. As another aspect of this invention, it is proposed that because of the large changes in refractive index induced by polarised light in these compounds, it might be possible to construct an artifical lattice structure such that electromagnetic frequencies in a certain interval may be forbidden to propagate in these compounds.

With respect to instrumentation and techniques for the determination of electrical-magnetic properties, e.g., magnetization and magnetic susceptibilities, which can, for example, be determined by the nonuniform field (the Faraday) method or the uniform field (the Gouy) method, standard technology can be used (see, e.g., "Physical Methods of Cheniistry Part V: Determination of Mass, Transport, and Electrical-Magnetic Properties", Weissberger and Rossiter, eds., John Wiley & Sons, Inc., New York, 1972 and "Molecular Magnetism" by O. Kahn, VCH Publishers, lnc., New York, 1993, and references herein); the magnetic susceptibilities can be either diamagnetic or paramagnetic. Likewise, other magnetic measurements as well as transport measurements, e.g., the previously mentioned electron-conductivity, Seebeck coefficients, and Hall coefficients, can be determined by standard methodologies (see, e.g., "Solid State Chemistry Techniques", Cheetham and Day, eds., Oxford Science Publications, Oxford, 1987, and references herein). DNO-based magnets may be used in future generations of electronic, magnetic and/or photonic devices ranging from information storage and magnetic imaging to static and low frequency magnetic shielding. It is contemplated that the DNO primary, secondary and tertiary structures are crucial for achieving the desired cooperative magnetic properties of such a molecular species based magnet. Additionally, in such DNO-magnets it is contemplated that both the donor and the acceptor, if present, must be radicals. The construction of DNO-based magnets, i.e., DNO compounds in which a magnetic long-range ordering is obtained, is envisaged to be done in a manner analogous to those illustrated for the construction of electron or ion-conducting DNO compounds. Thus, to obtain, e.g., a ferromagnetic interaction between the nearest-neighbor molecules, DNO compounds should be constructed in which the physical functionality L is a suitable derivative of, e.g., the organometallic donor-acceptor salt decamethylferrocenium tetracyanoethenide [Fe(Me$_5$C$_5$)$_2$]$^+$[TCNE] [Miller, J. S. et al. *J. Am. Chemn. Soc.* 109, 769 (1987). Miller, J. S. & Epstein, A. J. *J. Am. Chem. Soc.* 109, 3850 (1987); Miller, J. S., Epstein, A. J. & Reiff, W. M. *Science* 240, 40 (1988)], either alone or in combination with a photoresponsive functionality L, e.g., an azobenzene derivative, to enable optical control in a manner analogous to those outlined in FIGS. 37 and 38 for electron-conducting DNO compounds.

The decamethylferrocenium tetracyanoethenide [Fe(Me$_5$C$_5$)$_2$]$^+$[TCNE] electron transfer salt may be prepared by reaction between decamethylferrocene Fe(Me$_5$C$_5$)$_2$ (electron donor) and tetracyanoethylene (TCNE) (electron acceptor) (cf. FIG. 28). Thus, suitable derivatives of, e.g., Fe(Me$_5$C$_5$)$_2$ and TCNE may be incorporated as alternating side chains in DNO compounds. Either of TCNE or Fe(Me$_5$C$_5$)$_2$ may also be incorporated alone if the resulting DNO material is doped with the other one. Similarly, other electron donors, e.g. the metalloporphyrins, mangan-meso-tetraphenylporphinato (MnTPP, cf. FIG. 29) or manganoctadecylporphine (MnOEP), may be attached to DNO. Electron transfer complexes of MnTPP or MnOEP and TNCE or 7,7,8,8-tetracyano-p-quinodimethanide TNCQ, cf. FIG. 29) are contemplated to form ferromagnetic materials.

Of particular interest within the context of the present invention, the construction of DNO-based materials with photoconducting properties is envisaged to be performed in a manner analogous to those illustrated for the construction of electron or ion-conducting DNO compounds; photoconductivity is usually defined as the enhanced electrical conductivity of matter due to the motion of charge templates created by absorbed radiation. Thus, DNO compounds should be prepared in which the physically functional group L comprises a suitable derivative of, e.g., the disk-like thiotriphenylenes, which can exhibit very high mobilities for photoinduced charge templates, of the order of 0.1 cm$^2$ V$^{-1}$s$_{-1}$ (Adam, D. et al. *Nature* 371, 141–143 (1994)]. L should be incorporated into the DNO compounds either alone or in combination with a photoresponsive functionality L, e.g., an azobenzene derivative, to enable optical control as described in FIG. 37 and FIG. 38 for electron-conducting DNO compounds. Photoconductivity can be measured by standard technologies (see, e.g., "Physical Methods of Chemistry Part VIII: Determination of Electronic and Optical Properties", Rossiter and Baetzold, eds., John Wiley & Sons, Inc., New York, 1993, and references herein).

As mentioned previously, the construction of electron-conducting DNO compounds includes physical functionalities chosen from a wide variety of organic or organometallic donor and acceptor moieties, some of which are known to exhibit superconducting behavior. For the moieties in question and with regard to the relevant techniques for the determination of superconductivity, see also, e.g., "Organic Superconductors" by T. Ishiguro and K. Yamaji, Springer-Veriag, New York, 1990, and references herein, "Organic Superconductors: Synthesis, Structure, Properties and Theory" by J. M. Williams et al., Prentice-Hall, Inc., New Jersey, 1992, and references herein, and "One-Dimensional Conductors" by S. Kagoshima, H. Nagasawa and T. Sambongi, Springer-Verlag, New York, 1982, and references herein.

In another aspect of the invention, it is contemplated that because of the ease with which chirality can be incorporated in the DNO oligomers, insertion of proper side groups may make the system ferroelectric. The first report of ferroelectricity in (poly(vinylidene fluoride)) was made by Bergman et al. (J. B. Bergman Jr., J. H. McFee and G. R. Crane, *Appl. Phys. Lett.* 18, 203 (1971)) and by Nakamura and Wada (K. Nakamura and Y. Wada, *J. Polym. Sci.* A-2, 161 (1971)). The dielectric polarisation in these films were obtained by stretching and poling the film. Chiral oxirane rings have typically been employed in the polymers so far. (G. Scherowsky, *Makromol. Chem., Macromol. Symp.* 69, 87–98 (1993)). In the present invention, it is expected that no poling will be necessary and a chiral smectic C* may result if the side groups stack properly. Another possibility is that the ferroelectricity be potentially induced by photochromic or chromophore groups which have a chiral substituent next to the moiety which can undergo trans-cis isomerization. Ferroelectric modes have been obtained by incorporating chiral substituents in the side chains of polyesters (Vallerien, S. U, Zentel, R., Kremer, F., Kapitza, H. & Fisher, E. W. *Makromol. Chem., Rapid Commun.* 10, 333–338 (1989), polysiloxanes (Dumon, M., Nguyen, H. T., Mauzac, M., Destrade, C., Achard, M. F. & Gasparoux, H. *Macromolecules* 23, 355–357 (1990); Shenouda, I. G. & Chien, L. C. *Macromolecules* 26, 5020–5023 (1993) and Cooray, N. F., Kakimoto, M., Imai, Y. & Suzuki, Y. *Macromolecules* 27, 1592–1596(1994)) and polyacrylates (Giesselman, F., Zugenmaier, P., Scherowsky, G., Këhnpast, K. & Springer, J. *Makromol. Chem., Rapid Commun.* 13, 489–497 (1992) and Kühnpast, K, Springer, J., Davidson, P. & Scherowsky, G. *Makromol. Chem.* 193, 3097–3115 (1992)). Such ferroelectric oligomers may produce very fast switching between the different states of the molecules, when an alternating field is applied. These systems will find applications in the area of electrooptics. Theoretical work has demonstrated that chiral structures in this respect are predicted to be superior to the so-called "poled" polymer structures in which the oriented phases are thermodynamically unstable.

The incorporation of photoresponsive azobenzene moieties in structures of polypeptides has been shown to result in light-induced conformational changes of the helicity (B. L. Feringa, W. F. Jager and B. de Lange, *Tetrahedron* 490, 8267 (1993)). In a copolymer consisting of β-benzyl-L-aspartate and β-(m-benzylazo)benzyl Iaspartate, helicity was shown to reverse for irradiation with light below or above 400 nm. This helicity reversal has been followed through changes in optical rotation. Thus, the present invention also relates to the incorporation of suitable chiral amino-acids in DNO oligomers which provides another possibility of non-destructive recording and read-out based on the above principle.

In another aspect of this invention, it is contemplated that DNO bligomers with a nonlinear side group, incorporated into electron transporting polymers might exhibit photorefractivity. Photorefractivity is characterized by the fact that it exhibits spatial nonlocality. This arises because photogenerated charges migrate over the distance of a few $\mu$m in a photorefractive material. This charge transport gives rise to a charge distribution that is in phase with the intensity of light, when two interfering light beams are used to generate the charges. When the material is electro-optic, the application of an electric field changes the refractive index of the medium, producing a phase-shift between the light intensity pattern and the charge distribution pattern. The result of this phenomenon gives rise to two-beam coupling effects, in which energy from one of the illuminating beams can be transferred to the other beam. Again a nonisotropic system is required for the observation of this effect. In DNO oligomers, an anisotropy can be created through irradiation with light, when suitable chromophores -are incorporated in the system.

The synthesis of such diamino acid N$^\alpha$-substituted oligopeptides, also referred to as DNO oligomers (FIG. 1), involves three levels of protection employing tert-butyloxycarbonyl (Boc) (Carpino, L. A. *J. Am. Chem. Soc.* 79, 4427–4431 (1957)) as a weak acid-labile δ-amino protecting group, 9-fluorenylmethyloxycarbonyl (Famoc) (Carpino, L. A. & Han, G. Y. *J. Org. Chem* 37, 3404–3409 (1972)) as a weak base-labile α-amino protecting group, and 4-methylbenzhydrylamine (MBHA) (Pietta, P. G. & Marshall, G. R. *J. Chem. Soc.* D 650–651 (1970)) as a strong acid-labile anchoring linkage to the solid support. Each cycle of the solid-phase assembly consists of two individual coupling steps. The first step introduces the backbone unit and the second step incorporates the side-chain unit.

The principle of anchoring molecules onto a solid matrix, which helps in "keeping track" of the intermediate products during chemical transformations, is known as Solid-Phase Synthesis or Merrifield Synthesis [see Merrifield, R. B., *J. Am. Chem. Soc.* 85, 2149 (1963) and *Science* 232, 341 (1986)]. Established methods for the stepwise or fragment-wise solid-phase assembly of amino acids into peptides normally employ a beaded matrix of slightly cross-linked styrene-divinylbenzene copolymer, the cross-linked copolymer having been formed by the pearl polymerization of styrene monomer to which has been added a mixture of divinylbenzenes. A level of 1–2% cross-linking is usually employed. Such a matrix also applies to solid-phase DNO synthesis in the context of the present invention.

Concerning the initial functionalization of the solid phase, more than fifty methods have been described in connection with traditional solid-phase peptide synthesis [see Barany & Merrifield in "The Peptides" Vol. 2, Academic Press, New York, 1979, pp. 1–284, and Stewart & Young, "Solid Phase Peptide Synthesis", 2nd Ed., Pierce Chemical Company, Illinois, 1984], of which reactions for the introduction of chloromethyl (Merrifield resin; via a chloromethyl methyl ether SnCl$_4$ reaction), aminomethyl (via a N-hydroxymethylphthalimide reaction [see Mitchell et al., *Tetrahedron Lett.* 3795 (1976)] and benzhydrylamino [Pietta & Marshall, *J. Chem. Soc.* 650 (1970)] are the most widely applied. Regardless of its nature, the purpose of the functionality is normally to form an anchoring linkage between the copolymer solid support and the C-terminal of the first amino acid which it is desired to couple to the solid support. It is generally convenient to express the "concentration" of a functional group in terms of mmol/g. Other reactive functionalities which have been initially introduced include 4-methylbenzhydrylamino and 4-methoxybenzhydrylamino. All of these established methods are in principle useful within the context of the present invention. Preferred embodiments of DNO synthesis methods within the context of the present invention employ aminomethyl as the initial functionality, in that aminomethyl is particularly advantageous with respect to the incorporation of "spacer" or "handles" groups owing to the reactivity of the amino group of the aminomethyl functionality with respect to the essentially quantitative formation of amide bonds to a carboxylic acid group at one end of the spacer-forming reagent. A vast number of relevant spacer- or handle-forming bifunctional reagents have been described [see Barany et al. *Int. J. Peptide Protein Res.* 30, 705 (1987)], especially reagents which are reactive towards amino groups, such as the amino group in the aminomethyl function, including a 4-(haloalkyl)aryl-lower alkanoic acid such as 4-(bromomethyl)phenylacetic acid, a Boc-aminoacyl-4-(oxymethyl)aryl-lower alkanoic acid such as Boc-aminoacyl-4-(oxymethyl)phenylacetic acid, N-Boc-p-acylbenzhydrylamine such as N-Boc-p-glutaroylbenzhydrylamine, N-Boc-4'-lower alkyl-p-acylbenzhydrylamine such as N-Boc-4'-methyl-p-glutaroylbenzhydryamine, N-Boc-4'-lower alkoxy-p-acylbenzhydrylamine such as N-Boc-4'-methoxy-p-glutaroyl-benzhydrylamine and 4-hydroxymethylphenoxyacetic acid. One type of spacer group relevant within the context of the present invention is the phenylacetamidomethyl (Pam) handle [Mitchell & Merrifield, *J. Org. Chem.* 41, 2015 (1976)], which, deriving from the electron withdrawing effect of the 4-phenylacetamidomethyl group, is ca. 100 times more stable than the classic benzyl ester linkage towards the Boc-amino deprotection reagent trifluoroacetic acid (TFA).

Certain functionalities of particular relevance within the context of the present invention are those based on benzhydrylamino and derivatives thereof, including 4-methylbenzhydrylamino and 4-methoxybenzhydrylamino, which may be incorporated for the purpose of cleavage of a synthesized DNO chain from the solid support such that the C-terminal of the DNO chain is in amide form.

An alternative strategy concerning the introduction of spacer or handle groups is the so-called "preformed handle" strategy [see Tam et al. *Synthesis* 955–57 (1979)], which offers complete control over coupling of the first amino acid, and excludes the possibility of complications arising from the presence of undesired functional groups not related to the peptide or DNO synthesis. Other useful anchoring schemes include the "multidetachable" resins [Tam et al., *Tetrahedron Lett.* 4935 (1979) and *J. Am. Chem. Soc.* 102, 6117 (1980); Tam, *J. Org. Chem.* 60, 5291 (1985)], which provide more than one mode of release and thereby allow more flexibility in synthetic design.

Suitable choices for N-protection of the δ-amino group (or any other backbone amino group through which the oligomerization takes place) are the tert-butyloxycarbonyl (Boc) group [Carpino, *J. Am. Chem. Soc.* 79, 4427 (1957); McKay & Albertson, *J. Am. Chem. Soc.* 79, 4686 (1957); Anderson & McGregor, *J. Am. Chem. Soc.* 79, 6180 (1957)], normally in combination the 9-fluorenylmethyloxycarbonyl (Fmoc) group [Carpino & Han, *J. Am. Chem. Soc.* 92, 5748 (1970) and *J. Org. Chem.* 37, 3404 (1972)] for N-protection of the α-aminogroup (or any other pendant or backbone amino group through which the side chain is to be attached), or vice versa, although a number of other possibilities exist which are well known in conventional solid-phase peptide synthesis, such as protection combinations further including tert-butyl- or beniyl-based groups. Thus, a wide range of other useful amino protecting groups exist, some of which are Adoc [Hass et al., *J. Am. Chem. Soc.* 88, 1988 (1966)], Bpoc [Sieber & Iselin, *Helv. Chem. Acta.* 51, 614 (1968)], Mcb [Brady et al., *J. Org. Chem.* 42, 143 (1977)], Bic [Kemp & Hoyng, Tetrahedron 4624 (1975)], the o-nitrophenylsulfenyl (Nps) [Zervas et al., *J. Am. Chem. Soc.* 85, 3660 (1963)], and the dithiasuccinoyl (Dts) [Barany & Merrifield, *J. Am. Chem. Soc.* 99, 7363 (1977)]. In addition to these amino protecting groups and in particular those based on the widely used urethane functionality which successfully prohibits racemization (mediated by tautomerization of the readily formed oxazolinone (azlactone) intermediates [Goodman & Levine, *J. Am. Chem. Soc.* 86, 2918 (1964]) during the coupling of most ca-amino acids, clearly a whole range of nonurethane-type of amino protecting groups are applicable when assembling DNO molecules. Finally, whether the overall strategy for chemically assembling DNO molecules relies on for example differential acid stability of amino and side-chain protecting or employs an orthogonal, ie. chemoselective, protection scheme, the choice of side-chain protecting groups, in general, depends on the choice of the amino protecting group, since the protection of side-chain functionalities must withstand the conditions of the repeated amino deprotection cycles.

Based on the recognition that most operations are identical in the synthetic cycles of solid-phase peptide synthesis (as is also the case for solid-phase DNO synthesis), a new matrix, long-chain polystyrene-grafted polyethylene film (PEPS), has been reported [Berg et al., *J. Am. Chem. Soc.* 111, 8024 (1989)] aiming at facilitating and speeding up the preparation of large numbers of peptides. It is reasoned that the PEPS film support, comprising linker or spacer groups adapted to the particular chemistry in question, should be valuable in the synthesis of multiple DNO molecules. Two other methods proposed for the simultaneous synthesis of large numbers of peptides should apply as well to the preparation of multiple DNO molecules: The first of these methods [Geysen et al., *Proc. Natl. Acad. Sci. USA* 81, 3998 (1984)] utilizes acrylic acid-grafted polyethylene-rod-and-96-microtiter wells to immobilize the growing peptide chains and to perform the compartmentalized synthesis, and the second method [Houghten, *Proc. Natl. Acad. Sci. USA* 82, 5131 (1985)] utilizes a "tea bag" containing the traditionally used polymer beads to compartmentaize the synthesis. Other relevant proposals for multiple peptide or DNO synthesis in the context of the present invention include the simultaneous use of two different supports with different densities [Tregear, in "Chemistry and Biology of Peptides", J. Meienhofer, ed., Ann Arbor Sci. Publ., Ann Arbor, pp. 175–178 (1972)], combining of reaction vessels via a manifold [Gorman, *Anal. Biochem.* 136, 397 (1984)], multicolumn solid-phase synthesis (e.g. Krchnak et al., *Int. J. Peptide Protein Res.* 33, 209 (1989), and Holm & Meldal, in "Proceedings of the 20th European Peptide Symposium", G. Jung and E. Bayer, eds., Walter de Gruyter & Co., Berlin, pp. 208–210 (1989)], the use of cellulose paper [Eichler et al., *Collect. Czech. Chem. Commun.* 54, 1746 (1989)], the "portion-mixing" and library methods [Furka et al., *Int. J. Peptide Protein Res.*, 37, 487–493 (1991); Lam, K. S. et al., *Nature,* 354, 82–84. (1991) and *Nature,* 860, 768 (1992)]. Also, another library method can be used, namely, the recently reported "light-directed, spatially addressable, parallel chemical synthesis" technology [Fodor et al., *Science* 251, 767 (1991)], a technique that combines solid-phase chemistry and photolithography to produce thousands of highly diverse, but identifiable, permanently immobilized compounds (such as peptides) in a substantially simultaneous way.

While the conventional cross-linked styrene/divinylbenzene copolymer and other polystyrene-based matrices are the presently preferred in the context of solid-phase DNO synthesis, a non-limiting list of examples of solid supports, fashioned and compartmentalized in any suitable form, which may be of relevance are: (1) Particles based upon copolymers of dimethylacrylamide cross-linked with N,N'-bisacryloylethylenediamine, including a known amount of N-tert-butoxy-carbonyl-β-alanyl-N'-acryloylhexamethylenediamine. Several spacer molecules are typically added via the β-alanyl group, followed thereafter by the amino acid residue subunits. Also, the β-alanyl-containing monomer can be replaced with an acryloyl sarcosine monomer during polymerization to form resin beads. The polymerization is followed by reaction of the beads with ethylenediamine to form resin particles that contain primary amines as the covalently linked functionality.

Of relevance within the context of the present invention is also the so-called PEGA resin consisting of a beaded polyethyleneglycol polyacrylamide co-polymer [Meldal, M. *Tetrahedron Lett.,* 33, 3077–3080 (1992)]. The polyacrylamide-based supports are relatively more hydrophilic than are the polystyrene-based supports and are usually used with polar aprotic solvents including dimethylformamide, dimethylacetamide, N-methylpyrrolidone and the like [see Atherton et al., *J. Am. Chem. Soc.* 97, 6584 (1975), *Bioorg. Chem.* 8, 351 (1979), and *J. C. S. Perkin I* 538 (1981)]: (2) a second group of solid supports is based on silica-containing particles such as porous glass beads and silica gel. One example is the reaction product of trichloro-[3-(4-chloromethylphenyl)]-propylsilane and porous glass beads [see Parr & Grohmann, *Angew. Chem. Internal. Ed.* 11, 314 (1972)] sold under the trademark PORASIL E by Waters Associates, Framingham, Mass. Similarly, a mono ester of 1,4-dihydroxymethylbenzene and silica (sold under the trademark BIOPAK by Waters Associates) has been reported to be useful [see Bayer & Jung, *Tetrahedron Lett.* 4503 (1970)]; (3) a third general type of useful solid support may be termed composites in that they are constituted by two major ingredients, a resin and another material that is also substantially inert to the organic synthesis reaction conditions employee One exemplary composite [see Scott et al. *J. Chrom. Sci.* 9, 577 (1971)] utilized glass particles coated with hydrophobic, polymerized, cross-linked styrene containing reactive chloro methyl groups and was supplied by Northgate Laboratories, Inc., Hamden, Conn. Another exemplary composite contains a core of fluorinated ethylene polymer onto which is grafted polystyrene [see Kent & Merrifield, *Israel J. Chem.* 17, 243 (1978) and van Rietschoten in "Peptides 1974", Y. Wolman, Ed., Wiley and Sons, New York, 1975, pp. 113–116. Finally, (4) contiguous solid supports other than PEPS, such as cotton sheets [Lebl & Eichler, *Peptide Res.* 2, 232 (1989)] and hydroxypropylacrylate coated polypropylene membranes [Daniels et al., *Tetrahedron Lett.* 4345 (1989)], are suited for DNO synthesis as well.

Whether manually or automatically operated, solid-phase DNO synthesis in the context of the present invention is normally performed batchwise. However, most of the syntheses are equally well carried out in the continuous-flow mode, where the support is packed into columns [Bayer et al., *Tetrahedron Lett.* 4503 (1970) and Scott et al., *J. Chromatogr. Sci.* 9, 577 (1971)]. With respect to continuous-flow solid-phase synthesis the rigid poly(dimethylacrylamide)-Kieselguhr support [Atherton et al., *J. Chem. Soc., Chem. Commun.* 1151 (1981)] appears to be particularly successful, but another valuable configuration concerns the one worked out for the standard copoly (styrene-1%-divinylbenzene) support [Krchnak et al., *Tetrahedron Lett.* 4469 (1987)].

While the solid-phase technique is the presently preferred in the context of DNO synthesis, other methodologies or combinations thereof, for example in combination with the solid-phase technique, apply as well: (1) Clearly, the classical solution-phase methods for peptide synthesis [e.g. Bodanszky, "Principles of Peptide Synthesis", Springer-Verlag, Berlin-New York (1984)], either by stepwise assembly or by segment/fragment condensation, are of particular relevance when considering especially large scale productions (grams, kilograms, and even tons) of DNO compounds; (2) also, the so-called "liquid-phase" strategy, which utilizes soluble polymeric supports such as linear polystyrene [Shemyakin et al., *Tetrahedron Lett.* 2323

(1965)] and polyethylene glycol (PEG) [Mutter & Bayer, *Angew. Chem., Int. Ed. Engl.* 13, 88 (1974)], is useful; (3) random polymerization [this topic has been covered in the general texts and reviews of polymer chemistry, e.g., in Odian, "Principles of Polymerization", McGraw-Hill, New York (1970)] yielding mixtures of many molecular weights ("polydisperse") peptide or DNO molecules could be relevant for purposes preparation of thicker films; (4) a technique based on the use of polymer-supported amino acid active esters [Fridkin et al., *J. Am. Chem. Soc.* 87, 4646 (1965)], some times referred to as "inverse Merrfield synthesis" or "polymeric reagent synthesis", offers the advantage of isolation and purification of intermediate products, and may thus provide a particularly suitable method for the synthesis of medium-sized, optionally protected, DNO molecules, that can subsequently be used for fragment condensation into larger DNO molecules; (5) it is envisaged that DNO molecules may be assembled enzymatically by enzymes such as proteases or derivatives thereof with novel specificities (obtained for example by artificial means such as protein engineering). Also, one can envision the development of "DNO ligases" (much effort is currently directed towards the development of "peptide ligases") for the condensation of a number of DNO fragments into very large DNO molecules; (6) since antibodies can be generated to virtually any molecule of interest, the recently developed catalytic antibodies (abzymes), discovered simultaneously by the groups of Lerner [Tramantano et al., *Science* 234, 1566 (1986)] and of Schultz [Pollack et al., *Science* 234, 1570 (1986)], should also be considered as potential candidates for assembling DNO molecules. Thus, there has been considerable success in producing so-called abzymes catalysing acyl-transfer reactions [see for example Shokat et al., *Nature* 338, 269 (1989) and references therein]. Finally, completely artificial enzymes, recently pioneered by Stewart's group [Hahn et al., *Science* 248, 1544 (1990)], may be developed to suit DNO synthesis. In conclusion, no single strategy may be wholly suitable for the synthesis of a specific DNO molecule, and therefore, sometimes a combination of methods may work best.

Oligomers containing two or more residues were synthesized without difficulties. Glycine was used instead of LIornithine as the N-terminal backbone unit. A DNO dipeptide (designated DNO-6, FIG. 5) was synthesized from the readily available "submonomers", with greater than 99.5 percent overall coupling yield.

The holographic properties such as level of diffraction efficiency and writing time do not seem to be related to particular macroscopic phases of the material in DNO films. They correlate, however, intimately with the chemical structure of the oligomer. It is thus clear that these macroscopic properties largely reflect the properties of the individual oligomers and not macroscopic ensembles or aggregates of oligomers. For volume holographic applications it is therefore possible to dilute DNO oligomers into a thicker "host" medium consisting of, e.g., a polymer or a polymer composite. To obtain as efficient materials as possible it is important to minimize potential phase separation and it is important that the host contains as little crystallites or imperfections as possible in order to minimize scattering of light. Examples of such "hosts" include a number of polymers, e.g., polymethylmethacrylates and polystyrene-based polymers. Other "host" examples include DNO oligomers containing exclusively non-absorbing and non-photoisomerisable side chains. Also, glasses and other inorganic, or organic, compounds or composites may be used. One way of fabricating a homogeneous mixture without phase separation is to immobilize the DNO oligomers covalently to the host, such as immobilizing in a polyethylene-polystyrene graft (PEPS). Thick films of DNO oligomers, inmobilized within the bulk of a 65 $\mu$m thick PEPS film, have been fabricated resulting in diffraction efficiencies of 20%.

Thus, the present invention also relates to a solid material comprising a compound as described herein in admixture with a polymeric component, such as polystyrene-based polymers, poly(meth)acrylate-based polymers, etc.

EXAMPLES

Example 1

Preparation of 2-[4-(4Cyanophenylazo)phenoxy]-ethanoic acid (Azo1)

(a) 4-(4-Cyanophenylazo)phenol 47.20 g (0.4 mol) of 4-aminobenzonitrile Fluka, purum) was first dissolved in 400 mL of ethanol in a 1 L one-necked round bottom flask then 200 mL of 6 N HCl was added causing immediately a precipitate. The ethanol was then carefully removed by rotary evaporation under reduced pressure at maximum 35° C. After cooling to 0° C. 27.60 g (0.4 mol) of $NaNO_2$ dissolved in 150 mL of water was added during 20 min. constantly keeping the temperature below 5° C. The cold diazonium salt was coupled with 37.61 g (0.4 mol) of phenol (Merck, zur Analyse) in a solution of 48.0 g (1.2 mol) of NaOH in 400 mL of water by stirring 1 h without heating. The precipitate was washed with water, dissolved in 800 mL 50% aqueous ethanol then precipitated with 12 N HCl. 4-(4-cyanophenylazo)phenol was recovered by filtration and air-dried in a 91% yield.

The melting point of 4-(4-cyanophenylazo)phenol was 190.3° C. as determined on 5.24 mg by differential scanning calorimetry (DSC) of the second heating trace at a rate of 5° C./min. An UV-visible spectrum of 4-(4-cyanophenylazo) phenol as a 2.7 mg/L tetrahydrofuran solution reveals a $\lambda_{max}$ at 367 nm with $\epsilon_{max}$ 30,400 L/mol cm. A $^{13}C$ Nuclear Magnetic Resonance (NMR) spectrum recorded at 62.90 MHz of 55 mg of 4-(4cyanophenylazo)phenol in 0.5 mL of methyl sulfoxide-$d_6$ (DMSO-$d_6$) at 30° C. revealed the following chemical shifts (ppm): 112.15; 116.10; 118.42; 122.64; 125.48; 133.41; 145.34; 154.31; 162.08.

(b) Ethyl 2-[4-(4-cyarwphenylazo)phenoxy]-ethanoate 7.7 g (0.034 mol) of 4-(4-cyanophenylazo)phenol, 8.52 g (0.051 mol) ethyl bromoacetate (Fluka, pract.) and 5.66 g (0.041 mol) of dried $K_2CO_3$ were mixed in a 250 mL one-neck round flask fitted with a magnetic stirring bar. 100 mL of dry acetone was added, the flask was closed with a reflux condenser protected on the top with a $CaCl_2$-drying tube and the stirred solution was refluxed on an oil bath at 60° C. for 72 h After cooling the flask was transferred to a Rotavapor and the acetone is removed by rotary evaporation. The resulting solid mixture was added 100 mL of 30° C. water and filtered. The filtercake was mixed with 50 mL of cold ethanol. After filtration and vacuum drying 9.19 g (yield 87%) of ethyl 2-[4-(4-cyanophenylazo)-phenoxy]-ethanoate was recovered.

The melting point was determined on 5.00 mg of ethyl 2-[4-(4-cyanophenylazo)phenoxy]-ethanoate by DSC to 144.7° C. (second heating a 5° C./min). An UV-visible spectrum of ethyl 2-[4-(4-cyanophenylazo)phenoxy]-ethanoate on a 6.2 mg/L tetrahydrofuran solution reveals a $\lambda_{max}$ at 357 nm with $\epsilon_{max}$ 22,700 L/mol cm. A 62.90 MHz $^{13}C$ NMR spectrum of 50 mg of ethyl 2-[4-(4-cyanophenylazo)phenoxy]-ethanoate in 0.8 mL of DMSO-$d_6$ at 70° C. revealed the following chemical shifts (ppm):

13.78; 60.70; 65.23; 112.60; 115.38; 118.19; 122.72; 124.87; 133.42; 146.76; 154.27;.162.08; 168.01.

(c) 2-[4-(4-Cyanophenylozophenoxy]-ethanoic acid 1.95 g (0.006 mol) of ethyl 2-[4(4-cyanophenylazo)phenoxy]-ethanoate was dissolved in a mixture of 100 mL of dimethylformamide and 20 mL of water in a 250 mL one-neck round flask fitted with a magnetic stirring bar and a reflux condenser by heating to 90° C. while stirring on an oil bath. 1.3 g (0.033 mol) of NaOH was added. Stirring and heating were continued for ½ h. After cooling on an ice-water bath 6 mL of 6 N HCl was added. The precipitated crude product was recovered by filtration. The precipitate was suspended in a mixture of 10 mL of ethanol and 3 mL of water for 15 min. and filtered. The filtercake was washed with 10 mL of cold ethanol. After drying under vacuum overnight 1.17 g (yield 69%) of 2-[4-(4-cyanophenylazo)phenoxy]-ethanoic acid was obtained 2-[4-(4-Cyanophenylazo)phenoxy]-ethanoic acid shows no melting peak by DSC but starts to decompose at 340° C. heating rate 5° C./min). An UV-visible spectrum of 2-[4-(4cyanophenylazo)phenoxyl-ethanoic acid on a 4.7 mg/L methanol solution reveals a $\lambda_{max}$ at 363 nm with $\epsilon_{max}$ 23,100 L/mol cm. A 62.90 MHz $^{13}$C NMR spectrum of 4.4 mg of 2-[4-(4-cyanophenylazo)phenoxy]-ethanoic acid in 0.7 mL of DMSO-d$_6$ at 80° C. revealed the following chemical shifts (ppm, letters and numbers refer to the structure in FIG. 30.a): a 117.93; b 111.89; c 133.08; d 122.31; e 154.32; f 145.47; g 124.26; h 115.10; i 163.30; 1 168.36; 2 68.63.

Example 2

Preparation of 4-[4-(4-Cyanophenylazo)phenoxy]-butanoic acid (Azo10)

(a) Ethyl 4-[4-(4-cyanophenylazo)phenoxy]-butyrate 4.93 g (0.022 mol) of 4-(4-cyanophenylazo)phenol, 6.45 g (0.033 mol) of ethyl 4-bromobutyrate (Fluka, purum; >97%) and 3.95 g (0.029 mol) of oven dried K$_2$CO$_3$ were mixed in a 250 mL one-neck round flask fitted with a magnetic stirring bar. 80 mL of dry acetone was added, the flask was closed with a reflux condenser protected with a CaCl$_2$-drying tube and the stirred solution was refluxed on an oil bath at 60° C. for 72 h. After cooling the flask was transferred to a Rotavapor and the acetone was removed by rotary evaporation. The resulting solid mixture was added 50 mL of hot water and stirred. The aqueous mixture was allowed to cool and then filtered by suction from a water aspirator. The undried filtercake was transferred to a 150 mL beaker and dissolved in 50 mL of 96% ethanol after heating to boiling. A further recrystallization from 35 mL of 99% ethanol was performed. The solution was poured onto 250 mL of ice and filtered. After vacuum drying at 50° C. for 24 h a final yield of 6.41 g (86%) of ethyl 4-[4-(4-cyanophenylazo)phenoxy]-butyrate was obtained The melting point of ethyl 4-[4-(4-cyanophenylazo)phenoxy]-butyrate was 118.9° C. as determined on 5.60 mg by DSC of the second heating trace at a rate of 5° C./min. An UV-visible spectrum of ethyl 4-[4-(4-cyanophenylazo)phenoxy]-butyrate as a 5.8 mg/L tetrahydrofuran solution reveals a $\lambda_{max}$ at 365 nm with $\epsilon_{max}$ 23,700 L/mol cm. A 62.90 MHz $^{13}$C NMR spectrum of 22 mg of ethyl 4-[4-(4-cyanophenylazo)phenoxy]-butyrate in 0.6 mL of DMSO-d$_6$ at 30° C. revealed the following chemical shifts (ppm): 14.13; 24.15; 30.12; 59.93; 67.25; 112.58; 114.45; 118.52; 122.92; 125.31; 133.75; 146.19; 154.21; 162.22; 172.48.

(b) 4-[4-(4-Cyanophenylazo)phenoxy]-butanoic acid 6.30 g (0.019 mol) of ethyl 4-[4-(4-cyanophenylazo)phenoxy]-butyrate was dissolved in a mixture of 150 mL of dimethylformamide and 40 mL of water in a 500 mL one-neck round flask fitted with a magnetic stirring bar and a reflux condenser by heating to 90° C. while stirring on an oil bath. 3.8 g (0.095 mol) of NaOH was added through the condenser. Stirring and heating were continued for 1 h after which the reaction mixture was left for cooling to room temperature. The reaction mixture was then poured onto 200 of ice and acidified with 8N HCl until pH 2. The precipitated crude product was recovered by filtration. The precipitate was washed with 100 mL of hot ethanol and left overnight. After filtration and vacuum drying at 50° C. for 22 h. 5.49 g (yield 93%) of 4-[4-(4-cyanophenylazo)phenoxy]-butanoic acid was obtained 4-[4-(4-cyanophenylazo)phenoxy]-butanoic acid shows no melting below 200° C. by DSC when 6.50 mg was heated at 5° C./min. An UV-visible spectrum of 4-[4-(4-cyanophenylazo)phenoxy]-butanoic acid on a 2.5 mg/250 mL tetrahydrofuran solution reveals a $\lambda_{max}$ at 363 nm with $\epsilon_{max}$ 31,300 L/mol cm. A 62.90 MHz $^{13}$C NMR spectrum of 25 mg of 4-[4-(4-cyanophenylazo)phenoxy]-butanoic acid in 0.6 mL of DMSO-d$_6$ at 30° C. revealed the following chemical shifts (ppm); 24.19; 30.10; 67.36; 112.58; 115.27; 118.54; 122.92; 125.32; 133.75; 146.18; 154.22; 162.29; 174.04.

Example 3

Preparation of 5-[4-(4Cyanophenylazo)phenoxy]-pentanoic acid (Azo9)

(a) Ethyl 5-4-(4-cyanophenylazo)phenox]-pentanoate 4.93 g (0.022 mol) of 4-(4-cyanophenylazo)phenol, 6.53 g (0.031 mol) of ethyl 5-bromovalerate (Fluka, purum; >98%) and 3.95 g (0.029 mol) of oven dried K$_2$CO$_3$ were mixed in a 100 mL one-neck round flask fitted with a magnetic stirring bar. 50 mL of dry acetone was added, the flask was closed with a reflux condenser protected with a CaCl$_2$-drying tube and the stirred solution was refluxed on an oil bath at 60° C. for 72 h. After cooling the flask was transferred to a Rotavapor and the acetone was removed by rotary evaporation. The resulting solid mixture was added 50 mL of hot water and stirred. The aqueous mixture was allowed to cool and then filtered by suction from a water aspirator. The undried filtercake was dissolved in 160 mL of 99% ethanol after heating to boiling. A further recrystaization from 130 mL of 99% ethanol was performed The solution was cooled on an of ice-bath and filtered. After vacuum drying at 50° C. for 20 h a final yield of 6.84 g (84%) of ethyl 5-[4-(4-cyanophenylazo)phenoxy]-pentanoate was obtained.

The melting point of ethyl 5-[4(4-cyanophenylazo)phenoxy]-pentanoate was 112.5° C. as determined on 6.40 mg by DSC of the second heating trace at a rate of 5° C./min. An UV-visible spectrum of ethyl 5-[4-(4-cyanophenylazo)phenoxy]-pentanoate as a 2.55 mg/250 mL tetrahydrofuran solution reveals a $\lambda_{max}$ at 365 nm with $\epsilon_{max}$ 26,900 L/mol cm. A 62.90 MHz $^{13}$C NMR spectrum of 28 mg of ethyl 5-[4-(4-cyanophenylazo)phenoxy]-pentanoate in 0.6 mL of DMSO-d$_6$ at 30° C. revealed the following chemical shifts (ppm): 13.72; 20.84; 27.69; 32.97; 59.29; 67.66; 112.30; 115.03; 117.99; 122.48; 124.81; 133.23; 146.10; 154.17; 162.10; 172.23.

(b) 5-[4-(4-Cyanophenylazo)phenoxy]-pentanoic acid 6.47 g (0.018 mol) of ethyl 5-[4-(4-cyanophenylazo)phenoxy]-pentanoate was dissolved in a mixture of 130 mL of dimethylformamide and 41 mL of water in a 500 mL one-neck round flask fitted with a magnetic stirring bar and a reflux condenser by heating to 90° C. while stirring on an oil bath. 3.9 g (0.098 mol) of NaOH was added through the condenser. Stirring and heating were continued for 1 h after which the reaction mixture was left for cooling to room temperature. The reaction mixture was then diluted with 200 mL of water and acidified with 5.5 N HCl until pH 1.5. The precipitated crude orange product was isolated by filtration. The precipitate was dissolved in 90 mL of hot ethanol and left overnight. After filtration and vacuum drying for 22 h at 50° C. 4.61 g (yield 7.9%) of 5-[4-(4-cyanophenylazo) phenoxy]-pentanoic acid was obtained.

The melting point of 4-[4-(4cyanophenylazo)phenoxy]-pentanoic acid was 165.6° C. determined on 9.40 mg by DSC (second heating at 5° C./min). An UV-visible spectrum of 4-[4-(4-cyanophenylazo)phenoxy]-pentanoic acid on a 2.48 mg/250 mL tetrahydrofuran solution reveals a $\lambda_{max}$ at 365 nm with $\epsilon_{max}$ 27,700 L/mol cm. A 62.90 MHz $^{13}$C NMR spectrum of 26 mg of 5-[4-(4-cyanophenylazo)phenoxy]-pentanoic acid in 0.6 mL of DMSO-$d_6$ at 30° C. revealed the following chemical shifts (ppm); 21.20; 28.05; 33.34; 67.92; 112.56; 115.29; 118.55; 122.93; 125.33; 133.78; 146.14; 154.25; 162.44; 174.04.

Example 4

Preparation of 6-[4-(4-Cyanophenylazo)phenoxy]-hexanoic acid (Azo2)

(a) Ethyl 6-[4-(4-cyanophenylazo)phenoxy]-hexanoate 15.06 g (0.067 mol) of 4-(4-cyanophenylazo)phenol, 14.99 g (0.067 mol) of ethyl 6-bromo-hexanoate (Aldrich, 99%) and 11.76 g (0.085 mol) of oven dried $K_2CO_3$ were mixed in a 250 mL one-neck round flask fitted with a magnetic stirring bar. 160 mL of dry acetone was added, the flask was closed with a reflux condenser protected on the top with a $CaCl_2$-drying tube and the stirred solution was refluxed on an oil bath at 60° C. for 72 h. After cooling the flask was transferred to a Rotavapor and the acetone was removed by rotary evaporation. The resulting solid mixture was added 200 mL of hot water and stirred. The aqueous mixture was allowed to cool and then filtered by suction from a water aspirator. The undried filtercake was transferred to a 500 mL Erlenmeyer flask, 300 mL of ethanol was added and the content of the flask brought to boiling. After cooling 20.46 g (yield 83%) of ethyl 6-[4-(4-cyanophenyl-azo)phenoxy]-hexanoate was filtered off. The crude ethyl 6-[4-(4cyanophenylazo)phenoxy]-hexanoate was recrystallized from 750 mL of ethanol and then repeatedly from 650 mL of ethanoL After vacuum drying at 50° C. for 20 h a final yield of 17.21 g (70%) was obtained.

The melting point of ethyl 6-[4-(4-cyanophenylazo) phenoxy]-hexanoate was 132.3° C. as determined on 5.17 mg by DSC of the second heating trace at a rate of 5° C./min. An UV-visible spectrum of ethyl 6-[4-(4-cyanophenylazo) phenoxy]-hexanoate as a 7.8 mg/L tetrahydrofuran solution reveals a $\lambda_{max}$ at 365 nm with $\epsilon_{max}$ 25,200 L/mol cm. A 62.90 MHz $^{13}$C NMR spectrum of 25 mg of ethyl 6-[4-(4-cyanophenylazo)phenoxy]-hexanoate in 0.5 mL of DMSO-$d_6$ at 80° C. revealed the following chemical shifts (ppm): 13.60; 23.76; 24.57; 27.81; 33.18; 59.08; 67.85; 112.22; 114.95; 117.84; 122.35; 124.68; 133.08; 146.05; 154.14; 162.08; 172.16.

(b) 6-[4-(4-Cyanphenylazo)phenoxy]-hexanoic acid 6.92 g (0.019 mol) of ethyl 6-[4-(4-cyanophenylazo) phenoxy]-hexanoate was dissolved in 250 mL of dimethyl-formamide in a 500 mL one-neck round flask fitted with a magnetic stirring bar and a reflux condenser by heating to 90° C. while stirring on an oil bath. 7.48 g (0.187 mol) of NaOH in 80 mL of water was added through the condenser: Stirring and heating were continued for 4 h. After cooling on an ice-water bath 40 mL of 8N HCl was added. The precipitated crude product was recovered by filtration. The precipitate was washed with 200 mL of hot ethanol. After vacuum drying at 50° C. for 20 h. 4.67 g (yield 72%) of 6-[4-(4-cyanophenylazo)phenoxy]-hexanoic acid was obtained.

The melting point of 6-[4-(4-cyanophenylazo)phenoxy]-hexanoic acid was 194.4° C. determined on 4.68 mg-by DSC (second heating at 5° C./min). An UV-visible spectrum of 6-[4-(4-cyanophenylazo)phenoxy]-hexanoic acid on a 5.1 mg/L tetrahydrofuran solution reveals a $\lambda_{max}$ at 364 nm with $\epsilon_{max}$ 24,000 L/mol cm. A 62.90 MHz $^{13}$C NMR spectrum of 60 mg of ethyl 6-[4-(4-cyanophenylazo)phenoxy]-hexanoic acid in 1.0 mL of DMSO-$d_6$ at 80° C. revealed the following chemical shifts (ppm, letters and numbers refer to the structure in FIG. 30.b): a 118.29; b 112.22; c 133.48; d 122.72; e 154.31; f 146.19; g 125.09; h 115.20; i 162.37; 1 174.14; 2 33.58; 3 24.97; 4 28.17; 5 24.14; 6 68.10.

Example 5

Preparation of 2-[4-4-Cyanophenylazo)-2,3,5,6-tetradeutero-phenoxy]-ethanoic acid (Azo15)

(a) 4-(4-Cyanophenylazo)-2,3,5,6-tetradeutero-phenol 6.26 g (0.053 mol) of 4-aminobenzonitrile (Fluka, purum) was first dissolved in 55 mL of ethanol in a 250 mL one-necked round bottom flask then 15.66 g of 37% HCl in 15 mL of water was added causing immediately a precipitate. The ethanol was then slowly removed by cautious rotary evaporation under reduced pressure at maximum 35° C. After cooling to 0° C. an externally cooled solution of 3.72 g (0.053 mol) of $NaNO_2$ in 20 mL of water was added drop by drop constantly keeping the temperature below 5° C. The cold diazonium salt was added 5.00 g (0.050 mol) of phenol-$d_6$ (Aldrich, 98+ atom % D) in a solution of 6.37 g (0.159 mol) of NaOH in 75 mL of water drop by drop during 30 min. Stirring without heating was continued for 2 h. The reaction mixture was filtered and the precipitate washed with water, dissolved in 110 mL 50% aqueous ethanol and finally precipitated with 12 N HCl. 10.54 g (92% yield) of 4-(4-cyanophenylazo)-2,3,5,6-tetradeutero-phenol was recovered by filtration and air-dried.

The melting point of 4-(4-cyanophenylazo)-2,3,5,6-tetradeutero-phenol was 196.2° C. as determined on 9.10 mg by DSC of the second heating trace at a rate of 5° C./min. An UV-visible spectrum of 4-(4-cyanophenylazo)-2,3,5,6-tetradeutero-phenol as a 2.7 mg/L tetrahydrofuran solution reveals a $\lambda_{max}$ at 355 nm with $\epsilon_{max}$ 30,400 L/mol cm. A $^{13}$C Nuclear Magnetic Resonance (NMR) spectrum recorded at 62.90 MHz of 30 mg of 4-(4-cyanophenylazo)-2,3,5,6-tetradeuterophenol in 0.5 mL of DMSO-$d_6$ at 50° C. revealed the following chemical shifts (ppm): 112.07; 115.66 (center of triplet); 118.30; 122.55; 124.96 (center of triplet); 133:41; 145.17; 154.32; 161.87.

(b) Ethyl 2-[4-(4-cyanophenylazo)-2,3,5,6-tetradeutero-phenoxy]-ethanoate 6.00 g (0.026 mol) of 4-(4-cyanophenylazo)-2,3,5,6-tetradeutero-phenol, 6.51 g (0.039 mol) ethyl bromoacetate (Fluka, pract.) and 4.70 g (0.034 mol) of dried $K_2CO_3$ were mixed in a 250 mL one-neck round flask fitted with a magnetic stirring bar. 70 mL of dry acetone was added, the flask was closed with a reflux condenser protected on the top with a $CaCl_2$-drying tube and the stirred solution was refluxed on an oil bath at 60° C. for 70 h. After cooling the flask was transferred to a Rotavapor and the acetone was removed by rotary evaporation. The resulting solid mixture was added 80 mL of 30° C. water and filtered. The filtercake was dissolved in 50 mL of ethanol by boiling After cooling and filtration a further recrystallization in 300 mL of ethanol was performed The final filtration and vacuum drying furnish 5.78 g (yield 71%) of ethyl 2-[4-(4-cyanophenylazo)-2,3,5,6-tetradeutero-phenoxy]-ethanoate.

The melting point was determined on 8.60 mg of ethyl 2-[4-(4-cyanophenylazo)-2,3,5,6-tetradeutero-phenoxy]-ethanoate by DSC to 150.1° C. (the second heating trace at a rate of 5° C./min). An UV-visible spectrum of ethyl 2-[4-(4-cyanophenylazo)-2,3,5,6-tetradeutero-phenoxy]-ethanoate on a 2.5 mg/250 mL tetrahydrofin solution reveals a $\lambda_{max}$ at 360 nm with $\epsilon_{max}$ 30,600 L/mol cm. A 62.90 MHz $^{13}C$ NMR spectrum of 33 mg of ethyl 2-[4-(4-cyanophenylazo)-2,3,5,6-tetradeutero-phenoxy]-ethanoate in 0.6 mL of DMSO-$d_6$ at 50° C. revealed the following chemical shifts (ppm): 13.85; 60.64; 65.02; 112.57; 114.94 (center of small triplet); 118.24; 122.75; 124.53 (center of small triplet); 133.51; 146.64; 154.12; 161.03; 168.02.

(c) 2-[4-(4-Cyanophenylazo)-2,3,5,6-tetradeutero-phenoxy] ethanoic acid 5.57 g (0.018 mol) of ethyl 2-[4-(4-cyanophenylazo)-2,3,5,6-tetradutero-phenoxy]-ethanoate was dissolved in a mixture of 190 mL of dimethylformamide and 45 mL of water in a 500 mL one-neck round flask fitted with a magnetic stirring bar and a reflux condenser by heating to 90° C. while stirring on an oil bath. 3.71 g (0.093 mol) of NaOH was added in one portion. Stirring and heating were continued for 1 h. After cooling on an ice-water bath 26 mL of 6 N HCl was added. The precipitated crude product was recovered by filtration. The precipitate was suspended in a mixture of 10 mL of ethanol and 3 mL of water for 15 min. and filtered. The filtercake was dissolved in 40 mL of hot ethanol. After filtration when cold and drying under vacuum overnight 4.40 g (yield 87%) of 2-[4-(4-cyanophenylazo)-2,3,5,6-tetradeuterophenoxy]-ethanoic acid was obtained.

2-[4-(4-Cyanophenylazo)-2,3,5,6-tetradeutpro-phenoxy]-ethanoic acid shows no melting peak by DSC when heated to 200° C. at 5° C./min. An UV-visible spectrum of 2-[4-(4-cyanophenylazo)-2,3,5,6-tetradeutero-phenoxy]-ethanoic acid on a 2.5 mg/250 mL tertahydrofuran solution reveals a $\lambda_{max}$ at 357 nm with $\epsilon_{max}$ 40,800 L/mol cm. A 62.90 MHz $^{13}C$ NMR spectrum of 14 mg of 2-[4-(4-cyanophenylazo)-2,3,5,6-tetradeutero-phenoxy]-ethanoic acid in 0.5 mL of DMSO-$d_6$ at 70° C. revealed the following chemical shifts (ppm, letters and numbers refer to above structure): 64.98; 112.41; ~115.7 (center of small triplet); 118.00; 122.54; ~125 (center of small triplet); 133.27; 146.36; 154.15; 161.16; 169.04.

Example 6

Preparation of 2-[4-(4-Nitrophenylazo)phenoxy] ethanoic acid (Azo3)

(a) 4-(4-Nitrophenylazo)phenol 4-(4-Nitrophenylazo)phenol was prepared analogous with 4-(4-cyanophenylazo)phenol starting from 4-nitroaniline.

4-(4-Nitrophenylazo)phenol starts to decompose during melting at 205° C. as determined on 2.67 mg by DSC at a heating rate of 5° C./min. An UV-visible spectrum of 4-(4-nitrophenylazo)phenol as a 4.8 mg/L tetrahydrofran solution reveals a $\lambda_{max}$ at 380 nm with $\epsilon_{max}$ 27,500 L/mol cm. A $^{13}C$ NMR spectrum recorded at 62.90 MHz of 50 mg of 4-(4-nitrophenylazo)phenol in 0.5 mL of DMSO-$d_6$ at 70° C. revealed the following chemical shifts (ppm): 115.92; 122.52; 124.43; 125.27; 145.38; 147.61; 155.51; 162.00.

(b) Ethyl 2-[4-(4-nitrophenylazo)phenoxy]-ethanoate

Ethyl 2-[4-(4-nitrophenylazo)phenoxy]-ethanoate was prepared in a manner similar to ethyl 2-[4-(4-cyanophenylazo)phenoxy]-ethanoate starting from 4-(4-nitrophenylazo)phenol and ethyl bromoacetate.

The melting point was determined on 5.67 mg of ethyl 2-[4-(4-nitrophenylazo)phenoxy]-ethanoate by DSC to 145.0° C. (second heating at 5° C./min). An UV-visible spectrum of ethyl 2-[4-(4-nitrophenylazo)phenoxy] ethanoate on a 5.7 mg/L tetrahydrofuran solution reveals a $\lambda_{max}$ at 368 nm with $\epsilon_{max}$ 22,400 L/mol cm. A 62.90 MHz $^{13}C$ NMR spectrum of 25 mg of ethyl 2-[4-(4-nitrophenylazo)phenoxy]-ethanoate in 0.5 mL of DMSO-$d_6$ at 60° C. revealed the following chemical shifts (ppm): 13.72; 60.53; 65.04; 115.29; 122.86; 124.63; 124.92; 146.65; 147.98; 155.29; 161.20; 167.85.

(c) 2-[4-(4-Nitrophenylazo)phenoxy]-ethanoic acid

2-[4-(4-Nitrophenylazo)phenoxy]-ethanoic acid was prepared by hydrolysis of ethyl 2-[4-(4-nitrophenylazo) phenoxy]-ethanoate analogous with the preparation of 2-[4-(4-cyanophenyl-azo)phenoxy]-ethanoic acid.

2-[4-(4-Nitrophenylazo)phenoxy]-ethanoic acid shows a broad melting peak at 240° C. by DSC (heating rate 5° C./min). An UV-visible spectrum of 2-[4-(4-nitrophenylazo) phenoxy]-ethanoic acid on a 5.2 mg/L tetrahydrofuran solution reveals a $\lambda_{max}$ at 368 nm with $\epsilon_{max}$ 20,200 L/mol cm. A 62.90 MHz $^{13}C$ NMR spectrum of 12.7 mg of 2-[4-(4-nitrophenylazo)phenoxy]-ethanoic acid in 0.5 mL of DMSO-$d_6$ at 70° C. revealed the following chemical shifts (ppm, letters and numbers refer to the structure in FIG. 30.c): b 147.95; c 124.82; d 122.75; e 155.34; f 146.55; g 124.53; h 115.21; i 161.38; 1 169.00; 2 64.96.

Example 7

Preparation of 2-[4-(phenylazo)phenoxy]ethanoic acid (Azo4)

(a) Ethyl 2-[4-(phenylazo)phenoxy]-ethanote 10.89 g (0.055 mol) of 4-(phenylazo)phenol (Aldrich, 98%) and 9.88 g (0.072 mol) of oven dried $K_2CO_3$ were mixed in a 250 mL one-neck round flask fitted with a magnetic stirring bar and 100 mL of dry acetone was added 13.88 g (0.083 mol) of ethyl bromoacetate (Fluka, pract.) was then added, the flask was closed with a reflux condenser protected with a $CaCl_2$-drying tube, and the stirred solution was refluxed on an oil bath at 60° C. for 72 h. After cooling the flask was transferred to a Rotavapor and the acetone was removed by rotary evaporation. The resulting solid mixture was added 100 mL of hot water and stirred The aqueous mixture was allowed to cool and then filtered by suction from a water aspirator. The undried filtercake was transferred to a 250 mL beaker and dissolved in 75 mL of 96% ethanol and 12 mL of water after heating to boiling. After cooling the precipitate was recovered and recrystallized once more with 150 mL of 96% ethanol and 25 mL of water. After filtration and vacuum drying at 50° C. for 24 h a final yield of 11.69 g (75%) of ethyl 2-[4-(phenylazo)phenoxy]-ethanoate was obtained.

The melting point of ethyl 2-[4-(phenylazo)phenoxy]-ethanoate was 77.7° C. as determined on 5.90 mg by DSC of the second heating trace at a rate of 5° C./min. An UV-visible spectrum of ethyl 2-[4-(phenylazo)phenoxy]-ethanoate as a 250 mg/250 mL tetrahydrofuran solution reveals a $\lambda_{max}$ at 340 nm with $\epsilon_{max}$ 35,000 L/mol cm. A 62.90 MHz $^{13}C$ NMR spectrum of 47 mg of ethyl 2-[4-(phenylazo)phenoxy]-ethanoate in 1.2 mL of DMSO-$d_6$ at 57° C. revealed the following chemical shifts (ppm): 13.69; 60.45; 65.04; 115.09; 118.52; 121.92; 124.06; 128.98; 146.64; 152.01; 160.12; 167.95.

(b) 2-[4-(phenylazo)phenox]-ethanoic acid 3.66 g (0.013 mol) of ethyl 2-[4-(phenylazo)phenoxy]-ethanoate was dissolved in a mixture of 160 mL of dimethylformamide and 40 mL of water in a 250 mL one-neck round flask fitted with a magnetic stirring bar and a reflux condenser by heating to 90° C. while stirring on an oil bath.

3.6 g (0.090 mol) of NaOH was added in once through the condenser. Stirring and heating were continued for 1.5 h after which the reaction mixture was left for cooling finally on an ice-bath. The reaction mixture was then added 38 mL of 5.5 N HCl. A yellow precipitate was recovered and 40 mL of water was added. After filtration and vacuum drying 14 h at 50° C. 2.70 g (yield 82%) of 2-[4-(phenylazo)phenoxy]-ethanoic acid was obtained.

The melting point of 2-[4-(phenylazo)phenoxy]-ethanoic acid was 196.0° C. determined on 5.10 mg by DSC on the first heating trace at 5° C./min. An UV-visible spectrum of 2-[4-(phenylazo)phenoxy]-ethanoic acid on a 6.3 mg/L tetrahydrofuran solution reveals a $\lambda_{max}$ at 344 nm with $\epsilon_{max}$ 25,400 L/mol cm. A 62.90 MHz $^{13}$C NMR spectrum of 40 mg of 2-[4-(phenylazo)phenoxy]-ethanoic acid in 0.5 mL of DMSO-$d_6$ at 30° C. revealed the following chemical shifts ppm); 64.86; 115.22; 122.33; 124.51; 129.41; 130.91; 146.56; 152.09; 160.55; 169.84.

Example 8

Preparation of [4-(phenylazo)phenyl]-methanoic acid (Azo6)

9.18 g (0.067 mol) of 4-aminobenzoic acid (Merck, purum) was placed in a 250 mL one-necked round flask with a magnetic stirring bar and 100 mL of glacial acetic acid was added causing a light yellow solution. After 20 minutes 7.21 g (0.067 mol) of nitrosobenzene (Fluka, purum) was added in one portion immediately forming a green solution with particles. Stirring at room temperature was continued for 16 h. The formed metal shining precipitate was filtered off and washed once with 50 mL of cold glacial acetic acid and twice with 100 mL of cold water. The orange precipitate was dissolve in a hot mixture of 200 mL of ethanol and 20 mL of water. After cooling, filtration and 15 h drying under vacuum at 60° C. 10.96 g (72% yield) of [4-(phenylazo) phenyl]-methanoic acid was obtained.

[4-(phenylazo)phenyl]-methanoic acid shows no melting below 200° C. when 9.60 mg was heated by DSC at 5° C./min. An UV-visible spectrum of [4-(phenylazo)phenyl]-methanoic acid on a 2.5 mg/250 mL tetrahydrofuran solution reveals a $\lambda_{max}$ at 323 nm with $\epsilon_{max}$ 21,600 L/mol cm. A 62.90 MHz $^{13}$C NMR spectrum of 58 mg of [4-(phenylazo) phenyl]-methanoic acid in 0.6 mL of DMSO-$d_6$ at 30° C. revealed the following chemical shifts (ppm); 122.58 122.88; 129.56; 130.66; 132.17; 132.95; 152.00; 154.34; 166.76.

Example 9

Preparation of 2-[4-(phenylazo)phenyl]-ethanoic acid (Azo5)

10.13 g (0.067 mol) of 4-aminophenylacetic acid Merck, pro analysis) was placed in a 250 mL one-necked round flask with a magnetic stirring bar and 100 mL of glacial acetic acid was added; during 15 minutes a light yellow suspension was formed. 7.22 g (0.067 mol) of nitrosobenzene (Fluka, purum) was added rapidly resulting in a green suspension. Stirring at room temperature was continued for 18 h. The resulting metallic shining needles in a brown solution was vacuum filtered and washed once with 50 mL of cold glacial acetic acid and five times with 50 mL portions of cold water. The orange precipitate was dissolved by heating to boiling in a mixture of 160 mL of ethanol and 40 mL of water. After unforced cooling to room temperature the mixture was cooled on an ice/water bath and vacuum filtered. The filtercake was washed six times with 25 mL of externally cooled ethanoL After drying 16 h at 50° C. under vacuum 7.23 g (yield 45%) of 2-[4(phenylazo)phenyl]-ethanoic acid was obtained.

The melting point of 2-[4-(phenylazo)phenyl]-ethanoic acid was 197.4° C.; at slightly higher temperatures the acid decomposes as determined by DSC on heating 9.10 mg at 5° C./min. An UV-visible spectrum of 2-[4-(phenylazo) phenyl]-ethanoic acid on a 2.5 mg/250 mL tetrahydrofuran solution reveals a $\lambda_{max}$ at 321 nm with $\epsilon_{max}$ 40,100 L/mol cm. A 62.90 MHz $^{13}$C NMR spectrum of 52 mg of 2-[4-(phenylazo)phenyl]-ethanoic acid in 0.6 mL of DMSO-$d_6$ at 30° C. revealed the following chemical shifts (ppm); 40.54; 122.55; 129.47; 130.56; 131.44; 138.89; 150.82; 152.04; 172.30.

Example 10

Preparation of [(4-(4-Acetamide)phenylazo)phenyl]-methanoic acid (Azo8-acetyl)

(a) [(4-(4-Amino)phenylazo)phenyl]-methanoic acid 9.68 g (0.071 mol) of 4-aminobenzoic acid (Merck, p.a.) was weighed into a 250 mL one-neck round flask fitted with a magnetic stirring bar. 41 mL of 5.5 M HCl was added and the suspension cooled externally on an ice-bath. An ice-cold solution of 5.51 g (0.080 mol) of NaNO$_2$ in 15 mL of water was added drop by drop while stirring and keeping the solution below 5° C. After ½ h the mixture was added drop by drop over 15 minutes while vigorously mechanically stirring an ice-cold solution of 18.80 g (0.090 mol) of sodium(anilinomethylene)sulfonate, prepared as described by Morishima et al., *Macromolecules*, 26 (1993), pp. 3299–3305, in 250 mL of 0.86 M sodium acetate in a 500 mL 3-necked round flask, The reaction mixture was kept 18 h below 5° C. while stirring. The reaction mixture was then filtered and dissolved in 150 mL of 1 M NaOH by heating 2 h at 90° C. After 60 h at 5° C. orange crystals were formed. The crystalline product was collected by filtration, dissolved in 50 mL of boiling water, cooled to room temperature and acidified with 10 mL of 6 M HCl. After a final adjustment to pH~1, the precipitate was washed once more with 50 mL of water at 60° C. After cooling, filtration and drying under vacuum for 15 h at 50° C. 7.13 g (42% yield) of [(4-(4-amino)phenylazo)phenyl]-methanoic acid was obtained.

[(4-(4-Amino)phenylazo)phenyl]-methanoic acid shows no melting peak by DSC when heated to 200° C. at 5° C./min. An UV-visible spectrum of 2-[4-(phenylazo) phenyl]-ethanoic acid on a 2.5 mg/250 mL tetrahydrofuran solution reveals a $\lambda_{max}$ at 411 nm with $\epsilon_{max}$ 29,500 L/mol cm. A 62.90 NMHz $^{13}$C NMR spectrum of 55 mg of [(4-(4-amino)phenylazo)phenyl]-methanoic acid in 0.5 mL of DMSO-$d_6$ at 30° C. revealed the following chemical shifts (ppm): 114.38; 121.73; 125.91; 130.59; 130.95; 143.55; 152.67; 155.05; 167.00.

(b) [(4-(4-Acetamide)phenlylazo)phenyl]-methanoic acid 1.98 g (8.3 mmol) of [(4-(4-amino)phenylazo)phenyl]-methanoic acid was weighed into a 3-necked round flask fitted with a magnetic stirring bar. 90 mL of dimethylformamide and 4 mL (39 mmol) of anhydrous pyridine were added and stirring continued until a clear solution was obtained. After externally cooling on an ice-bath 0.81 g (10.4 mmol) of cold acetyl chloride (Aldrich, 98%) was added while stirring drop by drop at a rate keeping the temperature of the reaction mixture below 6° C. The mixture was allowed to beat to room temperature and 10 mL of 4 M HCl was added. After 70 h a red-brown precipitate was isolated and recrystallized in a boiling mixture of 200 mL of ethanol, 30 mL of water and 25 mL of dimethylformamide. After hot filtration, cooling and addition of 100 mL of water orange crystals precipitate; a final adjustment to pH~2 was performed The orange crystals were collected, washed with 50 mL of ethanol and vacuum dried 15 h to furnish 1.29 g (yield 54%) of [(4-(4-acetamide)phenylazo)phenyl]-methanoic acid.

[(4-(4-Acetamide)phenylazo)phenyl]-methanoic acid shows no melting peak by DSC when heated to 200° C. at 5° C./min. An UV-visible spectrum of 2-[4-(phenylazo) phenyl]-ethanoic acid on a 2.5 mg/250 mL tetrahydrofuran solution reveals a $\lambda_{max}$ at 368 nm with $\epsilon_{max}$ 23,200 L/mol cm. A 62.90 MHz $^{13}$C NMR spectrum of 48 mg of [(4-(4-acetamide)phenylazo)phenyl]-methanoic acid in 0.6 mL of DMSO-$d_6$ at 30° C. revealed the following chemical shifts (ppm). 24.25; 119.20; 122.34; 124.14; 130.63; 132.37; 143.12; 147.52; 154.56; 166.81; 168.95.

Example 11

Preparation of DNO6

(a) Solid-phase Synthesis Procedure for the Preparation of DNO-6

Oligomer DNO-6 was synthesized by a modified stepwise Merrifield method using two monomer subunits. The first one was the commercially available protected backbone monomer $N^\alpha$ Fmoc-L-Orn($N^\delta$-Boc)-OH (Bachem-Switzerland). The second one was the side-chain monomer CN—$C_6H_4$—N=N—$C_6H_4$—O—$CH_2$—COOH (Azo1) prepared as described in Example 1. Furthermore, Boc-Gly-OH (Bachem-Switzerland) was used to incorporate Gly as the N-terminal backbone unit. To obtain a C-terminal amide, the oligomer was assembled on a MBHA resin (Peninsula, England) initially loaded with 0.45 mmol of $N^\alpha$-Fmoc-L-Orn($N^\delta$-Boc) per gram resin. 2-(1H-benzotriazol-1-yl)-1,1,3,3-tetramethyluronium hexafluorophosphate (HBTU) (Richelieu, Canada) activation in combination with in situ neutralization allowed efficient incorporation of both backbone residues when the couplings were performed in 50% (v/v) pyridine in N,N-dimethylformamide with a monomer concentration of 0.10 M. The side-chain units were incorporated by in situ diisopropylcarbodiimide activation of the tetra-butylammonium salt of the Azo1 monomer (prepared as decribed below in (b)) in 50% (v/v) methylene chloride in N,N-dimethylformamide with a monomer concentration of 0.10 M in the presence of the weak acid 3,4-dihydro-3-hydroxy-4-oxo-1,2,3-benzotriazine (DHBt-OH) (Peninsula, England) (5 equivalents). The alternating deprotections of $N^\alpha$-Fmoc and $N^\delta$-Boc groups were accomplished with 20% (v/v) piperidine in N,N-dimethylformamide and 5%(v/v) m-cresol in trifluoroacetic acid in methylene chloride, respectively. A detailed synthetic protocol is described below in (c). The progress of the DNO synthesis was monitored throughout by the quantitative ninhydrin reaction [Sarin, V. K, Kent, S. B. H., Tam, J. P. & Merrifield, R. B. Anal. Biochem. 117, 147–157 (1981)], which indicated that the double coupling (2×30 min) of each backbone residue and the single coupling (1×30 min) of each side-chain residue proceeded with an efficiency of >99.9%, i.e., an overall coupling yield of >99.5%. Cleavage of the free DNO-6 oligomer, Gly-($N^\alpha$-Azo1)-L-Orn($N^\alpha$-Azo1)-$NH_2$, from the resin was accomplished with neat anhydrous HF at 0° C. for 1 h. The oligomer was extracted from the resin with 50% (v/v) trifluoroacetic acid in methylene chloride and was obtained as a reddish powder after evaporation of the solvents 0.5 gram of starting resin gave approximately 125 mg of the DNO-6 product (cleavage yield>80%). The DNO-6 oligomer was shown to have the expected molecular weight by fast atom bombardment mass spectrometry ($MH^+$; found (calcd.), 715.53 (715.34), (M–$Na^+$, 737.53) (cf. FIG. 32).

Differential scanning calorimetry (DSC) measurements of DNO-6 showed no thermal transitions in the temperature range from 25 to 210° C. DNO-6 decomposes at approximately 210° C.

(b) Preparation of tetrabutylammonium 2-[4(4-cyanophenylazo)phenoxy]-ethanoate 1.06 g (0.004 mol) of 2-[4-(4-cyanopbenylazo)phenoxy]-ethanoic acid was transferred to a 50 mL one-neck round flask fitted with a magnetic stirring bar and 10.4 mL of a 20% aqueous solution of tetrabutylammonium hydroxide (Merck, zur Synthese) was added and the mixture heated while stirring on an oilbath until a solution was formed The solution was cooled to approx. 30° C., 3.5 mL of methylene chloride was added and vigorously stirred. The liquids were transferred to a separating funnel with a pipette and allowed to separate. The dark red, lower methylene chloride solution was drained into a 25 mL beaker. The remaining aqueous phase was washed with additional 1.5 mL of methylene chloride which was also added the beaker. The combined methylene chloride solutions of tetrabutylammonium 2-[4-(4-cyanophenylazo)phenoxy]-ethanoate were dried with $Na_2SO_4$ for ½ h and filtered. The filtercake was further washed with 1 mL of methylene chloride and the combined tetrabutylammonium 2-[4-(4-cyanophenyl-azo)phenoxy]-ethanoate solution was diluted to 8 mL corresponding to an 0.5 M solution.

(c) General Synthetic Protocols

Synthesis was performed manually in a standard solid-phase peptide synthesis reaction vessel (Merrifield, R. B. et al., Biochemistry, vol. 21, pp 5020–5031 (1982)).The following coupling protocol was used to incorporate the protected amino acid in question: A solution of 0.2 M protected amino acid and 0.4 M diisopropylethylamine in pyridine was mixed with the same volume of 0.16 M HBTU in N,N-dimethylformamide (DMF), and left for 2 min before it, in the coupling step in question, was added to the resin. Coupling time was one hour or more. After coupling of the amino acid, the resin was washed with pyridine (2×2 min) and DMF (1×2 min). The following protocol was used to deprotect the Fmoc group: 20% piperidine in DMF (1×30 min), DMF (1×2 min), methylene chloride (1×2 min), 5% diisopropylethylamine in methylene chloride (1×2 min), methylene chloride (1×2 min), and 50% methylene chloride in DMF (1×2 min).

The following protocol was used to incorporate the Azo1 side chain: A methylene chloride solution of 0.2 M tetrabutylammonium salt of Azo1 monomer and 1.0 M diisopropylcarbodiimide was mixed with the same volume of 1.0 M DHBt-OH in DMF, and added to the resin. Coupling time was one hour or more. After coupling the resin was washed sequentially with N,N-di-methylformamide (DMF) (2×2 min), methylene chloride (2×1 min), 5% diisopropylethylamine in methylene chloride (1×2 min), and methylene chloride (2×2 min). The following protocol is used to deprotect the Boc group: 5% m-cresol in trifluoroacetic acid (2×2 min), 50% methylene chloride in DMF (3×2 min), and pyridine (2×2 min).

Example 12

Preparation of DNO-9, DNO-10, DNO-46, DNO49 and DNO-138

Figure 48:
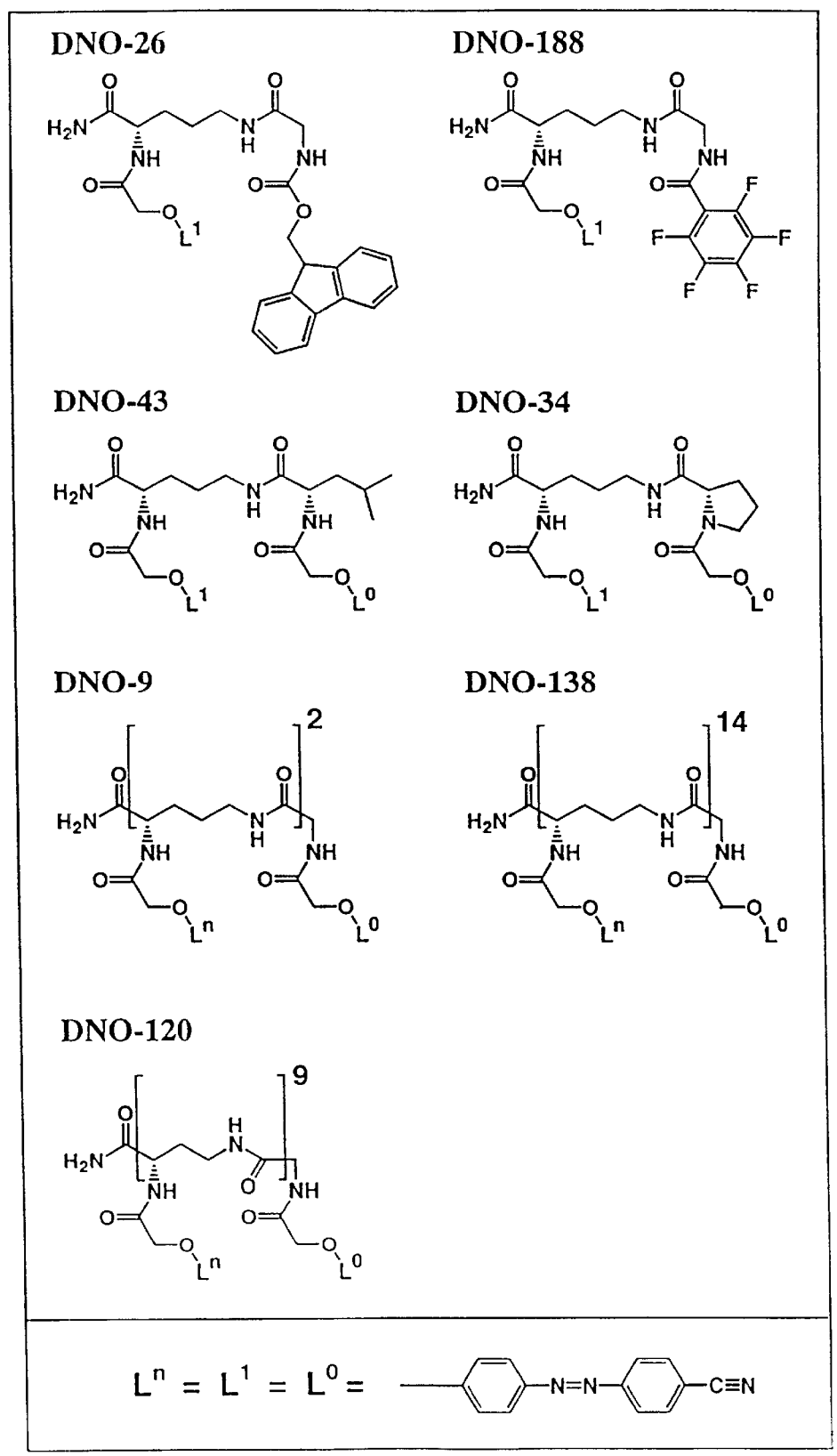
FIG. 48) before irradiation.

Oligomer DNO-138 (cf. FIG. 48 was prepared in a manner analogous to that of DNO-6 (cf. Example 11), except that the solid-phase synthesis was extended by thirteen additional cycles to incorporate thirteen additional backbone units and thirteen additional side-chain units. Resin-bound DNO-138 was assembled with an overall coupling yield of 79% as indicated by the ninhydrin analysis. 3.0 g of starting MBHA resin (substitution=0.4 milliequivalent/g) was employed. After the first additional cycle, a portion of the resin was taken out and coupled with Boc-Gly-OH and Azo1 as described for the synthesis of DNO-6 (cf. Example 11) to give the resin-bound DNO-9 product. After the second additional cycle, another portion of the resin was taken out and treated analogously with the first portion to give the resin-bound DNO-10 product. After the fifth additional cycle, a third portion of the resin was taken to and treated analogously with the first portion to give resion bound DNO-46 product. After the eighth additional cycle, a fourth portion of the resin was taken out and treated analogously with the first portion to give resin-bound DNO-49 product. Final cleavages (cf. Example 11) of resin-bound DNO-9 (290 mg), resin-bound DNO-10(229 mg), resin-bound DNO-46 (526 mg), resin-bound DNO-49 (449 mg) and resin-bound DNO-138 (105 mg), respectively, gave approximately 89 mg of the DNO-9 product, 132 mg of the DNO-10 product, 171 mg of the DNO-46 product, 227 m of the DNO-49 product and 12 mg of the DNO-138 product, respectively. Molecular weights: 1092.1 (DNO-9); 1469.5 (DNO-10); 2601.8 (DNO-46); 3734.0 (DNO-49).

Example 18

Preparation of DNO-12 and DNO-13

Oligomers (dimers) DNO-12 and DNO-13 (cf. FIG. 8) were prepared in a manner analogous to that of DNO-6 (cf. Example 11), except that for incorporation of the N-terminal backbone unit, i.e., L-Ala and D-Ala, respectively, Boc-L-Ala-OH (Bachem-Switzerland) and Boc-D-Ala-OH (Bachem-Switzerland), respectively, were used instead of Boc-Gly-OH. For the preparation of DNO-12 and DNO-13, 0.5 g and 0.25 g, respectively, of starting resin, were used. Each backbone unit and each sidehain unit was incorporated with an efficiency of >99% as indicated by the ninhydrin analysis. Final cleavage of resin-bound DNO-12 (396 mg) and resin-bound DNO-13 (160 mg) gave approximately 135 mg of the DNO-12 product and 48 mg of the DNO-13 product, respectively. Molecular weights: 728.7 (DNO-12); 728.7 (DNO-13).

Example 14

Preparation of DNO-14, DNO-18 and DNO-19

Dimers DNO-14, DNO-18 and DNO-19 (cf. FIG. 9) were prepared in a manner analogous to that of DNO-6 (cf. Example 11), except that for incorporation of the C-terminal backbone unit in DNO-14, i.e., L-Lys, $N^\alpha$-Fmoc-L-Lys($N^\epsilon$-Boc)-OH (Bachem-Switzerland) was used instead of $N^\alpha$-Fmoc-L-Orn($N^\delta$-Boc)-OH, and for incorporation of the C-terminal unit in DNO-18 and DNO-19, respectively, $N^\alpha$-Fmoc-$N^\gamma$-Boc-diamino-butyric acid (Bachem-Switzerland) and $N^\alpha$-Fmoc-$N^\beta$-Boc-L-diamino-propionic acid (Bachem-Switzerland), respectively, were used. For each preparation, 0.5 g of starting resin was used Each backbone unit and each side-chain unit was incorporated with an efficiency of >99% as indicated by the ninhydrin analysis. Final cleavage of resin-bound DNO-14 (120 mg) gave approximately 45 mg of the DNO-14 product. Cleavage of resin-bound DNO-18 gave approximately 137 mg of the DNO-18 product, and cleavage of resin-bound DNO-19 gave approximately 26 mg of the DNO-19 product. Molecular weights: 728.7 (DNO-14); 700.7 (DNO-18); 686.7 (DNO-19).

Example 15

Preparation of Azo1-IV and Azo1-V

Compounds Azo1-IV and Azo1-V (cf. FIG. 11), i.e., shortened fragments of DNO-6, were prepared in a manner analogous to that of DNO-6 (cf. Example 11), except that the syntheses were completed at earlier stages by acetylation of the glycine amino group in the case of Azo1-V and by acetylation of the delta group of ornithine in the case of Azo1-IV. 0.5 g of starting resin was used. Each backbone unit and each sidechain unit was incorporated with an efficiency of >99% as indicated by the ninhydrin analysis. Final cleavage of resin-bound Azo1-V (165 mg) and resin-bound Azo1-IV (140 mg) gave approximately 45 mg of the Azo1-V product and 32 mg of the Azo1-IV product, respectively.

Example 16

Preparation of Azo1-III

Compound Azo1-III (cf. FIG. 11), i.e., a shortened fragment or analogs of DNO-6, was prepared in a manner analogous to that of DNO-6 (cf. Example 11), except that the synthesis only consisted of a single cycle, namely that of coupling the side-chain monomer Azo1 to MBHA resin loaded with an alanine residue 0.5 g of starting resin was used for the synthesis and a substitution of ca. 0.5 mmol per gram was employed. The side-chain unit was incorporated with an efficiency of >99% as indicated by the ninhydrin analysis. Final cleavages of the resin-bound compound gave about 70 mg of the product.

Example 17

Preparation of DNO-22

Compound DNO-22 (cf. FIG. 16) was prepared in a manner analogous to that of DNO-6 (cf. Example 11), except that the synthesis only consisted of a single cycle, namely that of coupling the side-chain monomer Azo1 to MBHA resin loaded with a (2-aminoethyl)glycine residue (obtained from coupling with N-2-Boc-aminoethyl-$N^\alpha$-Boc-glycine-OH (Egholm, M. et al.) (ca. 0.9 mmol per gram). 0.5 g of starting resin was used. The side-chain units were incorporated quantitatively as indicated by the ninhydrin analysis and a picric acid test (uncoupled secondary groups cannot be determined by ninhydrin analysis). Final cleavage of the resin-bound compound gave about 360 mg of the DNO-22 product. Molecular weight: 643.7.

Example 18

Preparation of DNO-23 and DNO-24

Compounds DNO-23 and DNO-24 (cf. FIG. 18) were prepared in manners analogous with those of DNO-6 (cf. Example 11) and DNO-9 (cf. Example 12), respectively, except that for incorporation of the backbone units, ie., (2-aminoethyl)glycine (instead of L-ornithine) and glycine, N-2-Boc-aminoethyl-$N^\alpha$-benzyloxycarbonylglycine-OH (Egholm, M. et al.) was used instead of $N^\alpha$-Fmoc-L-Orn ($N^\delta$-Boc)-OH. Furthermore, prior to the coupling of the side-chain monomer Azo1, the benzyloxycarbonyl protecting groups were deprotected by the standard "low" trifluoromethanesulfonic acid-dimethyl sulfide-trifluoroacetic acid procedure (Tam, J. P. et al. *J. Am. Chem. Soc.* (1986)). The side-chain units were incorporated quantitatively as indicated by the ninhydrin analysis and a picric acid test. Final cleavages of the resin-bound compounds gave about 10 and 27 mg of the DNO-23 and DNO-24 products. Molecular weight: 700.7 (DNO-23).

Example 19

Preparation of DNO-2, DNO-20 and DNO-21

Dimers DNO-2, DNO-20 and DNO-21 (cf. FIG. 7) were prepared in a manner analogoous to that of dimer DNO-6 (cf. Example 11) except that the side chain monomers used were Azo2, Azo9 and Azo10 respectively, and that Azo2 was coupled directly in the form of its free acid (was not converted to the ammonium salt described in Example 11) by in situ diisopropylcarbodiimide activation (0.5 M9 in 50 vol % ethylene chloride in dimethylformamide. Each backbone unit and each side-chain unit was incorporated with an efficiency of >99% as indicated by the ninhydrin analysis. Final cleavage of resin-bound compounds gave 24 mg of DNO-2, 185 mg of DNO-20 and 139 mg of DNO-21, Molecular weights: 827.0 (dNO-2); 798.9 (DNO-20); 770.9 (DNO-21).

Example 20

Preparation of DNO-109, DNO-112, DNO-115 and DNO-120

Oligomers DNO-109, DNO-112 and DNO-115 (cf. FIG. 10) were prepared in a manner analogous to that of DNO-10, DNO-46, and DNO-49, respectively (cf. Example 12) except that $N^\alpha$-Fmoc-$N^\gamma$-Boc-L-diamino-butyric acid was used instead of $N^\alpha$-Fmoc-L-Orn($N^\delta$-Boc)-OH for incorporation of all backbone units except the N-terminal one (glycine). Final cleavages of small portions of resin-bound oligomer, gave 33 mg of the DNO-109 product, 46 mg of the DNO-112 product and 72 mg of the DNO-115 product, respectively.

Decamer DNO-120 (cf. FIGS. 48 and 43–45) was prepared by taking out a portion of the resin before coupling the N-terminal glycine unit of DNO-115 and coupling that portion with an L-alanine unit. Cleavage of resin-bound DNO-120 gave 88 mg of DNO-120 product.

Example 21

Preparation of DNO-34 and DNO-43

Dimers DNO-34 and DNO-43 (cf. FIG. 49) were prepared in a manner analogous to that of DNO-6 (cf. Example 11), except that for incorporation of the N-terminal backbone unit, i.e., L-Pro and L-Leu, respectively, Boc-L-Pro-OH (Bachem, Switzerland) and Boc-Leu-OH (Bachem, Switzerland), respectively, were used instead of Boc-Gly-OH. For the preparation of each compound, 0.5 g resin was used. All units were incorporated with an efficiency of >99% as indicated by ninhydrin analysis. Final cleavage of resin-bound DNO-34 and DNO-43, respectively, gave 142 mg of DNO-34 product and 178 mg of DNO-43 product, respectively. Molecular Weights: 754.8 (DNO-34); 770.9 (DNO-43).

Example 22

Preparation of DNO-26 and DNO-188

Dimers DNO-26 and DNO-188 (cf. FIG. 48) were prepared in a manner analogous to that of DNO-6 (cf. Example 11), except that an Fmoc group and a pentafluorophenyl carboxy group, respectively, were chosen as the N-terminal side chain of DNO-26 and DNO-188, respectively, instead of Azo1. In the case of DNO-26, the N-terminal backbone unit (Gly) and the N-terminal side-chain unit (Fmoc) were incorporated in a single step by coupling Fmoc-Gly-OH to $H_2$N-Orn(Azo1)-MBHA-resin. In the case of DNO-188, the N-terminal side chain was incorporated by coupling pentafluorobenzoic acid to $H_2$N-Gly-Orn(Azo1)-MBHA-resin. Ninhydrin analysis indicated that all couplings were complete. Final cleavages of the resin-bound oligomers gave approximately 169 mg of DNO-26 product and 97 mg of DNO-188 product. Molecular weights: 673, 7 (DNO-26); 465,5 (DNO-188).

Example 23

Preparation of DNO-127 and DNO-214

Dimers DNO-127 and DNO-214 (cf. FIG. 47) were prepared in a manner analogous to that of DNO-6 (cf. Example 11) and DNO-9 (cf. Example 12), respectively, except that $H_2$N-Gly-Orn($\alpha$-$NH_2$)-MBHA-resin was used instead of $H_2$N-MBHA-resin, in order to obtain the bisdimeric resin-bound compound DNO-127 and the bistrimeric resin-bound compound DNO-214. Ninhydrin analysis indicated that all couplings were complete. Final cleavages of the resin-bound oligomers gave approximately 331 mg of DNO-127 product and 244 mg of DNO-214 product. Molecular weight: 1583.7 (DNO-127).

Example 24

Preparation of DNO-206

The cyclic compound DNO-206 (cf. FIG. 46), designated cyclo{Dap(Azo1)-Dap(Azo1)-Dap(Azo1)-Asp}-$\beta$-$NH_2$, was prepared according to the synthetic steps described in (a), (b) and (c).
(a) Preparation of Fmoc-Dap(Boc)-Dap(Boc)-Dap(Boc)-Asp($\alpha$-OAll)-MBHA-resin N-$\alpha$-Fmoc-L-aspartic acid $\alpha$-allyl ester (Fmoc-Asp($\alpha$-Oall)-OH) (263 mg, 0.67 mmol) was attached to MBHA-resin (500 mg, 0.30 mmol equivalents/g) with HBTU (200 mg, 0.53 mmol) and diisopropylethylamine (200 µl, 1.15 mmol) in pyridine/N,N-dimethylformamide (DMF) (1:1, 5 mL) at 20° C. for 2 h in a solid-phase peptide synthesis reaction vessel. Then the vessel was drained and the resin was washed with DMF (2×2 min) and methylene chloride (2×2 min).The Fmoc-group was then removed with 20 vol % piperidine in DMF for 30 min., and the resin was washed with DMF (2×2 min), methylene chloride (2×2 min) and pyridine (2×2 min). A mixture of N-$\alpha$-Boc-N-$\beta$-Fmoc-L-diaminopropionic acid (Boc-Dap(Fmoc)) (213 mg, 0.5 mmol), HBTU (152 mg, 0.40 mmol) and diisopropylethylamine (174 µl, 1.0 mmol) was added to the peptidyl resin in pyridine/DMF (1:1, 5 mL). After shaking for 2 h at 20° C., ninhydrin analysis indicated that the coupling reaction was complete. The resin was washed with DMF (2×2 min) and methylene chloride (2×2 min). The deprotection and the coupling with Boc-Dap(Fmoc) was repeated twice to give Fmoc-Dap(Boc)-Dap(Boc)-Dap(Boc)-Asp($\alpha$-OAll)-MBHA-resin.
(b) Preparation of cyclo{Dap(Boc)-Dap(Boc)-Dap(Boc)-Asp}-MBHA-resin The Asp allyl ester protecting group was cleaved with Pd(0) using the following procedure: $(PPh_3)_4$Pd (520 mg, 0.45 mmol) was added to a mixture of $CHCl_3$: acetic acid: NMM (37:2:1 v/v/v, 5 mL) under argon. The solution was stirred for 20 min to dissolve the $(PPh_3)_4Pd$ The clear solution was added to the peptidyl resin and flushed with argon. After shaking in dark for 2 h at 20° C. the vessel was drained and the resin was washed with tetraydrofuran (3×2 min), DMF (3×2 min), methylene chloride (3×2 min), 5% diisopropylethylamine in methylene chloride (3×2 min), sodium diethyldithiocarbamate in DMF (5 mL, 0.02M, 3×15 min), DMF (5×2 min), methylene chloride (3×2 min) and DMF (2×2 min). The Fmoc-group was removed with piperidine as described above. The cyclization reaction was carried out by shaking the peptidyl resin in the presence of BOP (150 mg, 0.34 mmol), HOBt (50 mg, 0.36 mmol) and diisopropylethylamine (120 µl, 0.69 mmol) in DMF (5 mL) at 20° C. for 18 h. The resin was washed with DMF (2×2 min) and methylene chloride (2×2 min). Ninhydrin analysis indicated that the cyclization reaction was complete.

(c) Preparation of cyclo{Dap(Azo1)-Dap(Azo1)-Dap(Azo1)-Asp}-β-$NH_2$

The Boc-groups of the cyclo{Dap(Boc)-Dap(Boc)-Dap(Boc)-Asp}-MBHA-resin were removed with 5% m-cresol in trifluoroacetic acid (2×2 min, 5 mL) and the resin was washed with DMF (2×2 min), 5% diisopropylethylamine in methylene chloride (2×2 min), methylene chloride (2×2 min) and pyridine (2×2 min). A mixture of the tetrabutyl ammonium salt of 2-[4-(4-cyanophenylazo)phenoxy]-ethanoic acid (Azo1) (1.0 mmol), diisopropyl carbodiimide (740 µl, 4.78 mmol) and DHBT-OH (800 mg, 4.90 mmol) was added to the peptidyl resin in DCM/DMF (1:1, 5 mL). After shaking for 2 h at 20° C., the resin was washed with DMF (2×2 min) and methylene chloride (2×2 min). Ninhydrin analysis indicated that the coupling reactions were complete. Final HF cleavage of resin-bound DNO-206 was accomplished in a manner analogous to that described in Example 11 and gave approximately 128.5 mg of the DNO-206 product. Molecular weight: 1162.2.

Example 25

FTIR Polarisation Spectra of DNO-120 After Ar-ion Laser Irradiation a) FTIR Spectrum of DNO-120 Before Irradiation A hexafluoroisopropanol solution of a 10-mer based on diaminobutyric acid DNO-120 (cf. FIG. 48) was cast onto a KBr window. The resulting wet film was allowed to dry. A Fourier-Transform infrared (FTIR) spectrum was then recorded on a Perkin-Elmer 1760X FTIR spectrometer equipped with a Perkin-Elmer IR Data Manager collecting and analysis system as 32 scans with a resolution of 4 $cm^{-1}$. The following characteristic vibrations and the associated absorbances (A) were identified in the spectrum (cf. FIG. 44): $\nu$(N—H), 3326 $cm^{-1}$; $\nu_s(CH_2)+\nu_{as}(CH_2)$, 2947 $cm^{-1}$; $\nu$(C≡N), 2229 $cm^{-1}$; $\nu$(C=O)$_{amid\ I}$, 1667 $cm^{-1}$; $\nu$(C—N)+$\delta$(C—NH)$_{amid\ II}$, 1602 $cm^{-1}$; $\nu$(C=C)$_{arom\ ring}$, 1500 $cm^{-1}$; $\nu$(Ar—O—C)$_{aryl-alkyl-ether}$, 1250 $cm^{-1}$; $\nu$(C—H)$_{out\ of\ plane.arom.}$, 847 $cm^{-1}$.

b) FTIR Polarisation Spectra of DNO-120 After Ar Laser Irradiation

The film of DNO-120 on the KBr window was irradiated with linearly polarised 488 nm argon light at 400 mW for 600 s. New FTIR spectra were then recorded with the IR light polarised parallel (∥) and perpendicular (⊥) to the laser light polarisation by use of a ZnSe polariser; otherwise the conditions were as in a) above. The FTIR polarisation spectra shown in FIG. 45 demonstrate that the cyanoazobenzene chromophore (represented by the $\nu$(C≡N), 2229 $cm^{-1}$; $\nu$(C=C)$_{arom.\ ring}$, 1500 $cm^{-1}$; $\nu$(Ar—O—C)$_{aryl-alkyl-ether}$, 1250 $cm^{-1}$ vibrations) orient preferably perpendicular (⊥) to the laser light polarisation.

Example 26

Preparation of Glass Substrate Coated with a Film of DNO-6

2 mg of DNO-6 was dissolved in 5 vol % methylene chloride, 20 vol % trifluoroacetic acid and 75 vol % hexafluoroisopropanol and cast on a 20 mm diameter glass substrate kept in a desiccator. Vacuum was applied immediately after drying for about an hour, the film was transferred to an oven at 90° C. overnight. The thickness of the film was measured with a Dektak profiler to be 4 µm thick. When examining the film in a polarisation microscope at room temperature, the film exhibits no birefringence.

Example 27

Holographic Recording

In FIG. 3 a typical set-up for two-beam holography is shown. An argon ion laser (Innova 90-4) was used as the source. The argon-ion laser beam was divided into two by means of a polarisation beam splitter (PBS), after being deflected by a mirror M1. The ratio of the intensities of the two beams can be adjusted by rotating the half-wave plate HWP. One of the beams was directed to the film denoted DNO. The other beam, after being reflected by mirror M2 also falls on DNO. The two beams overlap on the film, DNO after passing through suitable quarter wave plates (QWP) to convert the overlapping beams to have orthogonal circular polarisation. A HeNe laser with a power of 4.2 mW measured with the detector D was used for the read-out of the grating. A quarter wave plate was used to convert the linearly polarised light to circularly polarised light. It has been shown by Nikolova and Todorov (Nikolova, L. & Todorov, T., *Optica Acta*, 31, 579–588, (1984)) that the highest diffraction efficiency is achieved in a set-up similar to the one described here. The intensity of the diffracted beam in the first order was measured by the detector D.

In the present case, the 488 nm light from an argon ion laser at a total intensity of 2 $W/cm^2$ was used as the writing beam and a 4.2 mW circularly polarised beam at 633 nm from a He—Ne laser was used for read-out. The He—Ne power transmitted through the film prior to holographic recording was 3.6 mW. Absorption losses in the film and reflection losses from the glass responsible for this attenuation limit the maximum achievable diffraction efficiency. The beam from the argon ion laser was split by means of a polarisation beam splitter, converted to orthogonally circularly polarised beams using appropriate quarter-wave plates. The beams were allowed to overlap on the film, giving a spatial frequency of about 510 lines/mm. The growth of the grating was monitored for a period of 300 s while the argon beam was on and for further 300 s with the argon beam turned off. The results are shown in FIG. 5. It can be seen that the diffracted power in the first order increases in about 300 s to 3.2 mW representing an absolute first-order diffraction efficiency of 76% corresponding to 89% of the maximum achievable. Diffracted power in higher orders accounted for additional 0.4 mW. This can be attributed to imperfect optical components and alignment. The diffraction efficiency remains stable after the argon laser was switched off. After a period of 300 s, one of the circularly polarised beams was switched on; the diffracted power decreased rapidly and reached a level of 0.05 mW after 300 s, resulting in erasure of about 98% of the grating. Holograms written in DNO-6 appear to be completely stable at room temperature and exceptionally stable to heat, as they were not erased after exposure to 150° C. for extended periods. A resolution of 3000 lines/mm can easily be achieved in DNO-6. The maximum diffraction efficiencies obtained with these and other oligomers together with the exposures for maximum diffracted power are listed in Table 1.

TABLE 1

Diffraction efficiencies obtained from DNO oligomers

| Name | argon laser | | 1st order diffraction | |
|---|---|---|---|---|
| | power (mW) | exposure(s) | max. (mW) | efficiency (%) |
| DNO-2 | 180 | 300 | 0.14 | 3 |
| DNO-6 | 180 | 300 | 3.2 | 76 |
| DNO-9 | 180 | 100 | 3.07 | 73 |
| DNO-10 | 250 | 12 | 0.7 | 17 |
| DNO-12 | 180 | 180 | 3.35 | 80 |
| DNO-13 | 200 | 100 | 0.9 | 21 |
| DNO-14 | 180 | 150 | 2.75 | 65 |
| DNO-18 | 200 | 12 | 1.9 | 45 |
| DNO-19 | 200 | 200 | 2.1 | 50 |
| DNO-20 | 250 | 300 | 0.27 | 6.5 |
| DNO-21 | 200 | 300 | 1.3 | 31 |
| DNO-26 | 200 | 2 | 1.8 | 43 |
| DNO-34 | 150 | 3 | 1.95 | 46 |
| DNO-43 | 200 | 2 | 1.3 | 31 |
| DNO-46 | 200 | 12 | 1.4 | 33 |
| DNO-49 | 200 | 12 | 2.2 | 52 |
| DNO-109 | 200 | 10 | 3 | 71 |
| DNO-112 | 200 | 15 | 3.2 | 76 |
| DNO-115 | 200 | 20 | 3 | 71 |
| DNO-127 | 200 | 25 | 2.3 | 55 |
| DNO-138 | 250 | 20 | 2.4 | 57 |
| DNO-188 | 250 | 4 | 1.1 | 26 |
| DNO-206 | 250 | 12 | 2.8 | 67 |
| DNO-214 | 250 | 2 | 2.8 | 67 |
| Azo1-III | 180 | 300 | 0.55 | 13 |
| Azo1-IV | 180 | 300 | 0.56 | 13 |
| Azo1-V | 180 | 300 | 0.52 | 12 |

Figure 6:
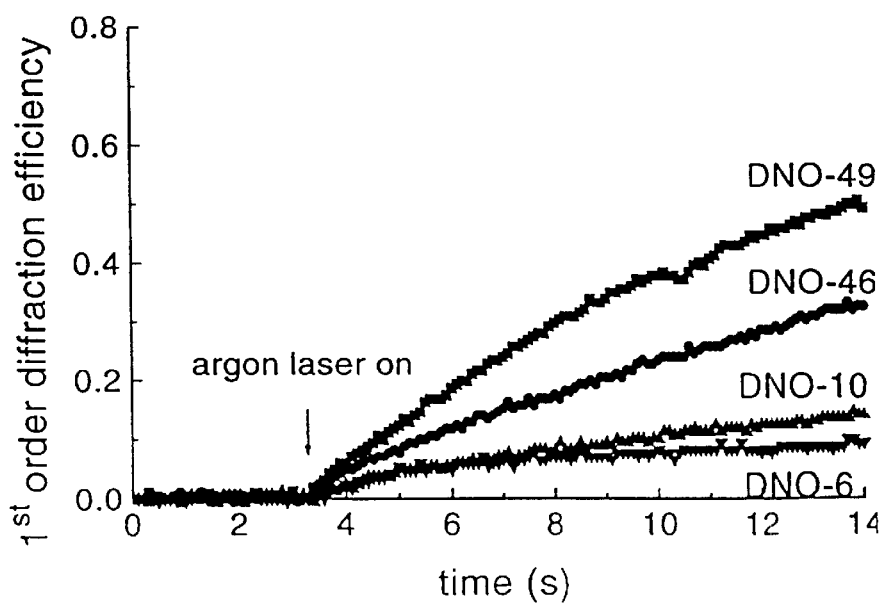
Figure 7:
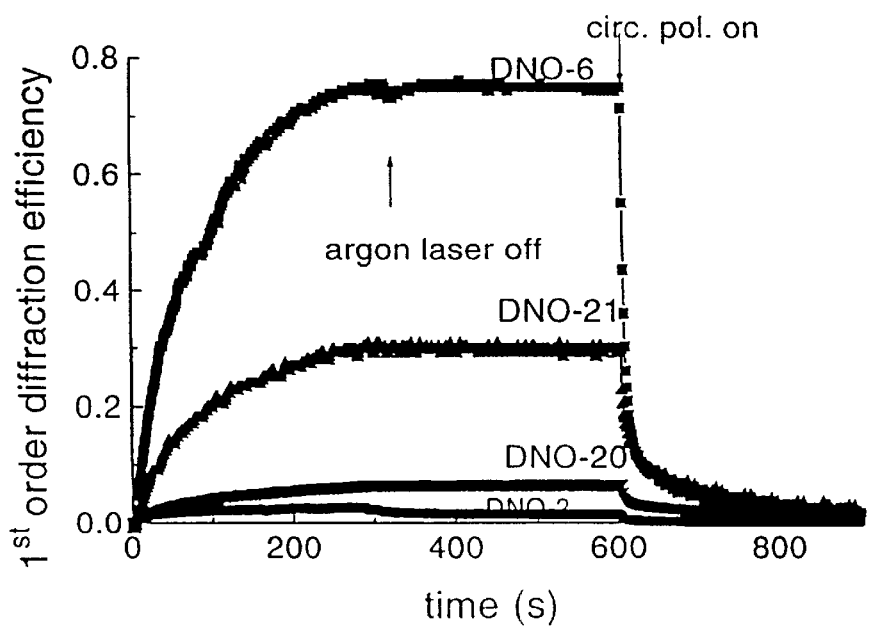
Figure 8:
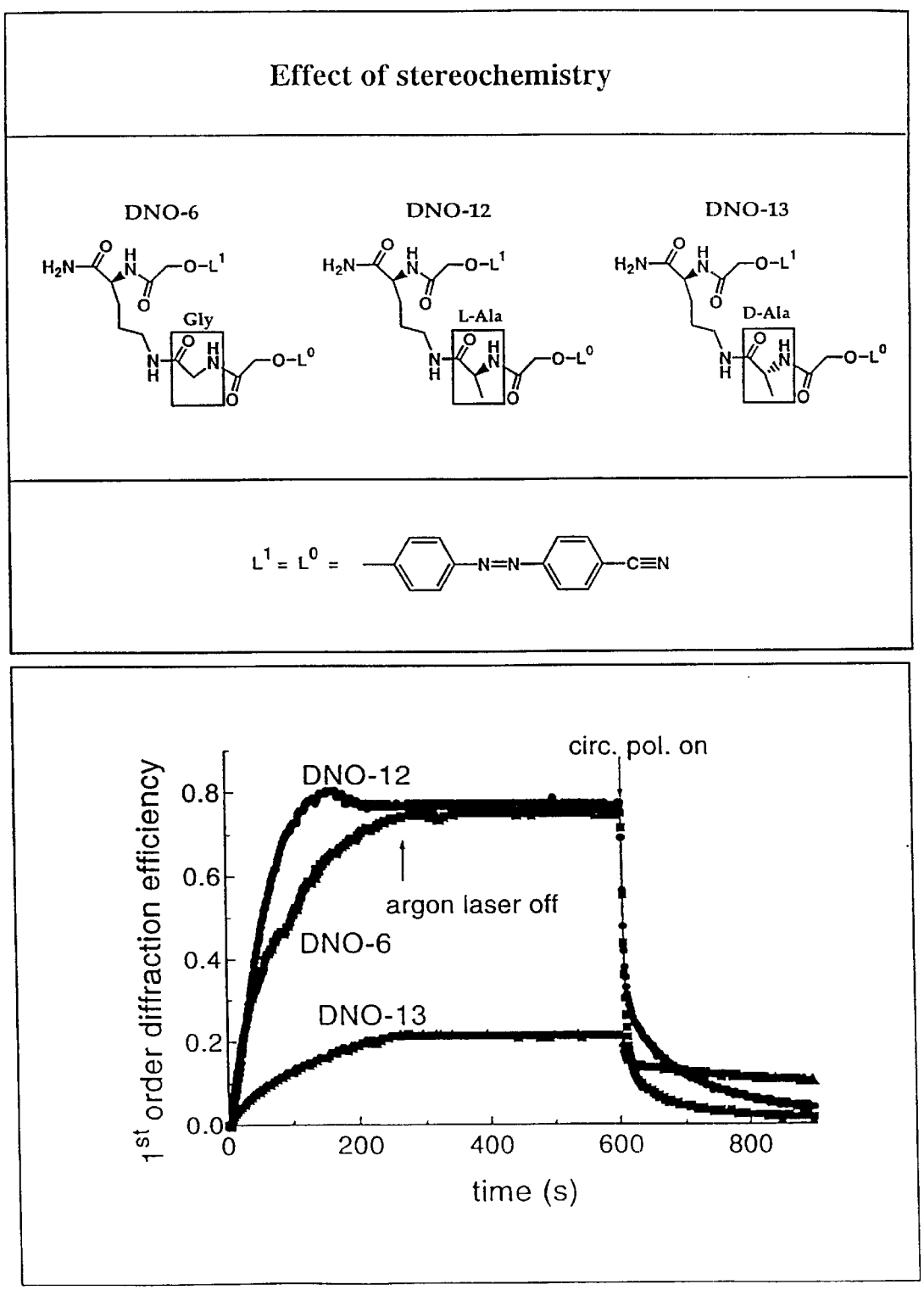

FIG. 5 shows that a much lower diffraction efficiency (15%) was obtained with the monomer Azo1-III which contains only a single azobenzene side chain. In FIG. 6 the effect of oligomer size is examined. It is seen that the writing time, i.e., the rate of formation of holographic gratings, accelerates with increasing ohgomer size, implying the existence of co-operative dynamic effects between neighbouring azobenzenes. Preliminary experiments indicate that about ten residues may be an optimal size. In order to examine the effects of structurally modifying the side chains of DNO-6, analogues were prepared in which the linker from the backbone to the azobenzene ligand is extended by two, three, and four methylene groups, respectively. FIG. 7 shows that the diffraction efficiency is lowered gradually upon increasing the number of methylene groups. For the most extended analogue, DNO-2, a maximum value of only 3% was obtained. These results indicate that increasing the flexibility of the linker between the backbone and the azobenzene ligand is deleterious to the ability of the backbone to impose stacking of the azobenzenes. Modifications of the backbone were undertaken to examine further the variability of the DNO structure. Substituting the achiral glycine unit of DNO-6 with an L-alanine unit (DNO-12, FIG. 8) was found to substantially shorten the writing time. Taken together with the inability of a D-alanine substituted analogue (DNO-13, FIG. 8) to reach more than 25% diffraction efficiency, these results indicate that a proper stacking is favoured when the azobenzenes were linked to backbone units with the same directionality. In FIG. 9 the effect of varying the number of bonds in the backbone is examined. It is seen that the writing time was accelerated markedly for the shorter diaminopropionic acid (4 bonds) and diaminobutyric acid (5 bonds) based dimers when compared with the longer ornithine (6 bonds) and lysine (7 bonds) based dimers. Apparently the molecular geometry of also the shorter backbones allows neighbouring azobenzenes to stack in a proper manner, and with stronger stacking interactions owing to their closer proximity. In FIG. 10 the effect of oligomer size is examined for diaminobutyric acid based oligomers. Again, it is seen that the writing time accelerates with increasing oligomer size. With a decamer, DNO-115, a first-order diffraction efficiency of 78% was reached in about 10 s. In the following it is shown that short DNO oligomers can be linked together in manners that enable writing times shortened considerably in comparison with those achieved in this study. In FIG. 47 a so-called bis-trimer, DNO-214, consisting of two ornithine-based DNO trimers which are linked to each other in a dendritic manner, is shown. DNO-214 represents an example of analogues which were designed to have increased rotational symmetry relative to Ê in their stationary orientation. DNO-214, which reaches ~85% of the maximum achievable diffraction efficiency within 2 s, was not only much faster than a linear ornithine-based hexamer, it was also considerably faster than the diaminobutyric acid based decamer DNO-115. Likewise, an ornithine-based bis-dimer, DNO-127 (cf. FIG. 47), was much faster than a linear ornithine-based tetramer (DNO-10).

Example 28

Environmental Stability of Holograms

Holograms written in DNO oligomers are completely stable at room temperature. So far, lifetimes close to one year have been achieved. The holograms are also exceptionally stable to heat and were not erased after exposure to 1800° C. for one month, and the films can be reused. This extraordinary stability may be reflected in the thermal behaviour of the materials as no thermal transitions were detected, by differential scanning calorimetry, in the temperature range from 25° C. to the decomposition temperature. The materials examined in this study decomposed between 210° C. and 230° C. as seen in FIG. 31. Nonetheless, holograms written prior to heating were still present after exposure to 250° C. for one month.

Example 29

Erasure of Holograms

The hologram stored in the film DNO may be erased by simply blocking one of the writing beams. As shown in FIG. 5, one of the circularly polarised beam was turned for a period of 300 s. As can be seen from the figure, 98% of the anisotropy was erased on irradiation with circularly polarised light It must be noted that the wavelength of the light was the same for recording and for erasing.

Another way of erasure is shown in FIG. 57. Here the anisotropy was induced with the 488 nm light from an argon laser for a period of about 300 ms. The anisotropy was read at the HeNe laser wavelength of 633 nm. A krypton laser at a wavelength of 351 nm was switched on as indicated in the figure. The UV light from the laser was seen to erase the anisotropy completely. A total number of 560 write-read-erase cycles have been performed in a film of DNO-6.

Example 30

Electrical Conductivity Measurements

The DNO film can be spin-coated to the four electrodes in a four-point measuring system. The film is then irradiated with polarised light from a laser in order to induce an ordering. A current is then applied between electrodes 1 and 4 and the voltage between electrodes 2 and 3 is measured. As an example, consider a case where a current of 100 nA is measured between electrodes 1 and 4 when a voltage of 1 V is applied between electrodes 2 and 3, the resulting resistance is calculated to be 1 V/100 nA=$10^7$ ohms. More properly, the resistance can be expressed as the specific resistance, s, which is a characteristic property of the material in question. s is calculated in relation to the volume of the material examined, and is calculated by the formula, s=R*a/t, where t is the thickness of the material and a is the area of cross-section. In the above example, if t=$10^{-5}$ cm and a=1 cm$^2$, then s=$10^{12}$ ohm cm. This can be expressed also as the specific conductivity W=$10^{-12}$ ohm$^{-1}$ cm$^{-1}$. In this case, the material has very poor conductivity. To be a good room temperature electron conductor, W must be about 1000 ohm$^{-1}$ cm$^{-1}$. For copper, W is about $10^6$ ohm$^{-1}$ cm$^{-1}$.

Example 31

Nonlinear Optics

The use of these compounds for nonlinear optics can be tested easily through observation of second and third harmonic generation. The compound, for example in the form of powder is irradiated with a Nd:YAG laser at 1064 nm. The laser is preferably Q-switched, such that short pulses on the order of 10–100 ns were generated. The laser light is focussed on the powder sample by means of lenses. The spectral composition of light emanating from the sample can be examined by means of a monochromator. One looks for light at half the wavelength, at 532 nm or at one-third the wavelength, at 352 nm. The sample can also be in the form of a film which enables the molecules to be oriented in a given direction, through irradiation with polarised light at 488 nm, for example. The nonlinear optical properties can also be investigated through electro-optical effects (electric field induced changes in refractive index) or through Kerr effects (light induced changes refractive index). These can be examined by incorporating the sample in one arm of an optical interferometer, such as Michelson's interferometer and observing the shift of the fringes as an electrical or optical field is applied.

Example 32

Preparation of Double-stranded DNO Compounds

As an example, a dimer-version of DNO-500-n (cf. FIG. 50) may be synthesized in the following manner:

1) N$^\alpha$-Fmoc(N$^\delta$-Boc)-OH is coupled to MBHA resin, e.g., as described in Example 11.
2) The Boc group is deprotected with trifluoroacetic acid; after neutralization and washing steps, the free δ-amino groups were coupled to Boc-Gly-OH to give Boc-Gly-Orn(N$^\alpha$-Fmoc)-MBHA resin.
3) The Boc group is deprotected, and after washing and neutralization steps, the free amino group is coupled with the 4,4'-divalent azobenzene derivative HOOC—CH$_2$—O—C$_6$H$_4$—N=N—C$_6$H$_4$—O—CH$_2$—C(O)—O—C(CH$_3$)$_3$ (I) to give (CH$_3$)$_3$C—O—C(O)—CH$_2$—O—C$_6$H$_4$—N=N—C$_6$H$_4$—O—CH$_2$—C(O)—NH-Gly-Orn(N$^\alpha$-Fmoc)-MBHA resin; the tert-butyl group is then removed with trifluoroacetic acid and after washing steps the free carboxylic acid group is further coupled to α-amino group of Orn(N$^\delta$-Boc)-CONH$_2$.
4) The Boc group in the compound prepared in (3) above is deprotected, and the free amino group is coupled with Boc-Gly.
5) The Boc group in the compound prepared in (4) is deprotected, and the free amino group is coupled with (I) to give (CH$_3$)$_3$C—O—C(O)—CH$_2$—O—C$_6$H$_4$—N=N—C$_6$H$_4$—O—CH$_2$—C(O)—NH-Gly-Orn(N$^\alpha$-(—C(O)—CH$_2$—O—C$_6$H$_4$—N=N—C$_6$H$_4$—O—CH$_2$—C(O)—NH-Gly-Orn(N$^\alpha$-Fmoc)-MBHA resin.
6) The tert-butyl group is deprotected with trifluoroacetic acid to give a free carboxylic acid group and the Fmoc group is deprotected as described in Example 11 to a free amino group.
7) The free amino group and the free carwboylic group are reacted with each other using, e.g., carbodiimide, to form an amide bond. The final dimer version of DNO-500-n is obtained by HF cleavage from the resin.

What is claimed is:

1. A compound having a physical functionality which may be influenced by external stimulation, said compound comprising at least one domain comprising 2–25 segments of the following formula G

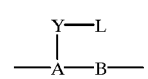

wherein

L is an azobenzene which is optionally substituted with one or more substituent(s) each independently selected from deuterium, hydroxy, fluorine, chlorine, bromine, and iodine, linear or branched optionally substituted $C_{1-6}$-alkyl, optionally substituted $C_{1-6}$-alkoxy, cyano, nitro, amino, mono- or di(optionally substituted $C_{1-6}$-alkyl)amino, mono- or di(optionally substituted $C_{1-6}$-alkyl)amino-$C_{1-6}$-alkyl, (optionally substituted $C_{1-6}$-alkyl)carbonylamino, (optionally substituted $C_{1-6}$-alkyl)carbonylamino-$C_{1-6}$-alkyl, aminocarbonyl, aminocarbonyl-$C_{1-6}$-alkyl, mono- or di(optionally substituted $C_{1-6}$-alkyl)aminocarbonyl, mono- or di(optionaily substituted $C_{1-6}$-alkyl)aminocarbonyl-$C_{1-6}$-alkyl, optionally substituted $C_{1-6}$-acyl, optionally substituted $C_{1-6}$-acyloxy, carboxy, —COSH, (optionally substituted $C_{1-6}$-alkoxy)carbonyl, thiolo, $C_{1-6}$-alkylthio, optionally substituted $C_{1-6}$-alkylthio-$C_{1-6}$-alkyl, guanidino, isocyano, isothiocyano, and thiocyano;

Y is a linking group selected from —O—(CH$_2$)$_p$—C(=O)—NH—, —O—(CH$_2$)$_p$—NH—C(=O)—, —O—(CH$_2$)$_p$—C(=O)—, —O—(CH$_2$)$_p$—NH—, —(CH$_2$)$_p$—C(=O)—NH—, —(CH$_2$)$_p$—NH—C(=O)—, —(CH$_2$)$_p$—C(=O)—, —(CH$_2$)$_p$—NH—, —OOC—(CH$_2$)$_p$—C(=O)—NH—, —OOC—(CH$_2$)$_p$—NH—C(=O)—, —OOC—(CH$_2$)$_p$—C(=O)—, —OOC—(CH$_2$)$_p$—NH—, —NH—(CH$_2$)$_p$—C(=O)—NH—, —N(C$_{1-6}$-alkyl)-(CH$_2$)$_p$—C(=O)—NH—, —NH—(CH$_2$)$_p$—NH—C(=O)—, —N(C$_{1-6}$alkyl)-(CH$_2$)$_p$—NH—C(=O)—, —NH—(CH$_2$)$_p$—C(=O)—, —N(C$_{1-6}$-alkyl)-(CH$_2$)$_p$—C(=O)—, —NH—(CH$_2$)$_p$—NH—, —N(C$_{1-6}$-alkyl)-(CH$_2$)$_p$—NH—, —NH—C(=O)—(CH$_2$)$_p$—C(=O)—NH—, —N(C$_{1-6}$-alkyl)-C(=O)—(CH$_2$)$_p$—C(=O)—NH—, —NH—C(=O)—(CH$_2$)$_p$—NH—C(=O)—, —N(C$_{1-6}$-alkyl)-C(=O)—(CH$_2$)$_p$—NH—C(=O)—, —NH—C(=O)—(CH$_2$)$_p$—C(=O)—, —N(C$_{1-6}$-alkyl)-C(=O)—(CH$_2$)$_p$—C(=O)—, —NH—C(=O)—(CH$_2$)$_p$—NH—, and —N(C$_{1-6}$-alkyl)-C(=O)—(CH$_2$)$_p$—NH—, wherein p is 0–5;

A is selected from a nitrogen atom and a group C—R in which R is selected from hydrogen and optionally substituted $C_{1-4}$-alkyl; and B is a chain consisting of groups selected from CHR² and C=O, wherein R² is selected from side chains of α-amino acids; $C_{1-6}$-alkyl; hydroxy; optionally substituted $C_{1-6}$-alkoxy; halogen; cyano; amino; mono- or di(optionally substituted $C_{1-6}$-alkyl)amino; mono- or di(optionally substituted $C_{1-6}$-alkyl)amino-$C_{1-6}$-alkyl; (optionally substituted $C_{1-6}$-alkyl)carbonylamino; (optionally substituted $C_{1-4}$-alkyl)carbonylamino-$C_{1-6}$-alkyl; aminocarbonyl; aminocarbonyl-$C_{1-6}$-alkyl; mono- or di(optionally substituted $C_{1-6}$-alkyl)aminocarbonyl; mono- or di(optionally substituted $C_{1-6}$-alkyl)aminocarbonyl-$C_{1-6}$-alkyl; optionally substituted $C_{1-6}$-acyl; optionally substituted $C_{1-6}$-acyloxy; carboxy; and (optionally substituted $C_{1-6}$-alkoxy)carbonyl; said chain B optionally being interrupted, initiated, or terminated by one or more groups selected from —O—, and —NR₂, wherein R³ is selected from hydrogen; $C_{1-6}$-alkyl; mono- or di(optionally substituted $C_{1-4}$-alkyl)amino-$C_{1-6}$-alkyl; (optionally substituted $C_{1-6}$-alkyl)carbonylamino-$C_{1-6}$-alkyl; aminocarbonyl-$C_{1-6}$-alkyl; mono- or di(optionally substituted $C_{1-6}$-alkyl)aminocarbonyl; mono- or di(optionally substituted $C_{1-6}$-alkyl)aminocarbonyl-$C_{1-6}$-alkyl; (optionally substituted aryl)-$C_{1-6}$-alkoxycarbonyl; optionally substituted $C_{1-6}$-acyl; and optionally substituted $C_{1-6}$-alkoxycarbonyl;

and wherein
1) the backbone chain —A—B— has a total of 4–7 consecutive covalent bonds between the radical positions and:
   (i) contains an amide function, or
   (ii) contains a part of an amide function, the remainder of which is contained in the corresponding linking group Y or in adjacent group(s) from any neighbouring segment; and
2) when the liking group Y has a total of at least 3 consecutive covalent bonds,
   (i) the linking group Y contains an amide function bound directly to the corresponding moiety A; or
   (ii) A constitutes the nitrogen atom of an amide function.

2. A compound according to claim 1, wherein A is selected from a nitrogen atom and a group C—H; and B is a chain consisting of groups selected from CHR² and C=O, wherein R² is selected from hydrogen and side chains of α-amino acids; said chain B optionally being interrupted, initiated, or terminated by one or more groups selected from —O—, and —NR³-, wherein R³ is selected from hydrogen, $C_{1-6}$-akyl, $C_{1-6}$acyl, and amino protecting groups.

3. A compound according to claim 1, wherein the backbone moiety —A—B— together with at least a part of the linking group Y is derived from one or more amino acid(s).

4. A compound according to claim 1, comprising a successive chain of 2 to 20 segments of the formula G.

5. A compound according to claim 4, having the formula $G^h$

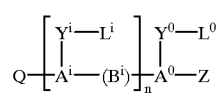

wherein n is a positive integer; i is a positive integer, assuming values 1 to n for the first to the nth bracketed unit, respectively; each of $Y^0, \ldots, Y^n$ independently is a linking group as defined for Y in claim 1; each of $L^0, \ldots, L^n$ independently is an optionally substituted azobenzene as defined for L in claim 1; each of $A^0, \ldots, A^n$ independently is a group as defined for A in claim 1; each of $B^1, \ldots, B^n$ independently is a chain as defined for B in claim 1; where $Y^i, A^i, B^i$ and $L^i$ are the choices of Y, A, B and L for the ith bracketed unit; and $Y^0, A^0, B^0$ and $L^0$, for the terminal unit, and Q and Z are terminating groups.

6. A compound according to claim 5, wherein
m is a positive integer, where $1 \leq m < n$,
1) each of the chains from $A^m—B^m—A^{m-1}$ has a total of at least 4 consecutive covalent bonds; and
2)
   a) when the biradical $Y^m$ has a total of at least 3 consecutive covalent bonds, each of the moieties $Y^0—L^0, \ldots, Y^n—L^n$ independently
      (i) contains an amide function bound directly to the corresponding moiety A, or
      (ii) contains a part of an amide function, the remainder of which is contained in the corresponding moiety A, or
      (iii) is bound directly to the nitrogen atom of an amide function which comprises the A moiety corresponding to the Y—L moiety; or
   b) each of the moieties $B^1—A^0—Z, \ldots, B^{m+1}—A^m—B^m, \ldots, B^n—A^n—Q$ includes a carbocyclic or heterocyclic ring;
and, where, when one or more of $A^0, \ldots, A^n$ is/are C—R, the group(s) C—R may form a carbocyclic or heterocyclic ring involving one or two of the adjacent groups B and Y; and $1 \leq m \leq n$.

7. A compound according to claim 5, wherein the groups Q and Z each independently are selected from side chains of α-amino acids; hydrogen, $C_{1-6}$-alkyl; hydroxy; optionally substituted $C_{1-6}$-alkoxy; halogen; cyano; amino; mono- or di(optionally substituted $C_{1-6}$-alkyl)amiiin; mono- or di(optionally substituted $C_{1-6}$-alkyl)amino-$C_{1-6}$-alkyl; (optionally substituted $C_{1-6}$-alkyl)carbonylamino; (optionally substituted $C_{1-6}$-alkyl)carbonylamino-$C_{1-6}$-alkyl; aminocarbonyl; aminocarbonyl-$C_{1-6}$-alkyl; mono- or di(optionally substituted $C_{1-6}$-alkyl)aminocarbonyl; mono- or di(optionally substituted $C_{1-6}$-alkyl)aminocarbonyl-$C_{1-6}$-alkyl; optionally substituted $C_{1-6}$-acyl; (optionally substituted aryl)-$C_{1-6}$-alkoxycarbonyl; optionally substituted $C_{1-6}$-acyloxy; carboxy; and (optionally substituted $C_{1-6}$-alkoxy)carbonyl; optionally substituted with a chain consisting of 1 to 5 amino acids, or extended by a chain B consisting of groups selected from CHR² and C=O, wherein R² is selected from side chains of α-amino acids; $C_{1-6}$-alkyl; hydroxy; optionally substituted $C_{1-6}$-alkoxy; halogen; cyano; amino; mono- or di(optionally substituted $C_{1-6}$-alkyl)amino; mono- or di(optionally substituted $C_{1-6}$-alkyl)amino-$CH_{1-6}$-alkyl; (optionally substituted $C_{1-6}$-alkyl)carbonylamino; (optionally substituted $C_{1-6}$-alkyl)carbonylamino-$CH_{1-6}$-alkyl; aminocarbonyl; aminocarbonyl-$C_{1-6}$-alkyl; mono- or di(optionally substituted $C_{1-6}$-alkyl)aminocarbonyl; mono- or di(optionally substituted $C_{1-6}$-alkyl)aminocarbonyl-$C_{1-6}$-alkyl; optionally substituted $C_{1-6}$-acyl; optionally substituted $C_{1-6}$-acyloxy; carboxy; and (optionally substituted $C_{1-6}$-alkoxy)carbonyl; and, when one or both of the group(s) Q and Z are part of a carbocyclic or heterocyclic ring or a macrocycle, Q and/or Z is/are selected from the biradicals of the before-mentioned groups and a single bond.

8. A compound according to claim 7, wherein, when A is C—R, the group Z is selected from amino, carboxy, C-(a chain of 1–5 amino acid(s))-amino, N-(a chain of 1–5 amino acid(s))-carbonyl, side chains of α-amino acids, hydrogen, deuterium, methyl, cyanomethyl, ethyl, 1-propyl, 2-propyl, 2-methyl-1-propyl, 2-hydroxy-2-methyl-1-propyl, 1-butyl, 2-butyl, methylthioethyl, benzyl, p-aminobenzyl, p-iodobenzyl, p-fluoro-benzyl, p-bromo-benzyl, p-chloro-benzyl, p-nitrobenzyl, 3-pyridylmethyl, 3,5-diiodo-4-hydroxybenzyl, 3,5-dibromo-4-hydroxybenzyl, 3,5-dichloro-4-hydroxy-benzyl, 3,5-difluoro-4-hydroxy-benzyl, 4-methoxybenzyl, 2-naphtylmethyl, 1-naphtylmethyl, 3-indolylmethyl, hydroxymethyl, 1-hydroxyethyl, mercaptomethyl, 2-mercapto-2-propyl, 4-hydroxybenzyl, aminocarbonylmethyl, 2-aminocarbonylethyl, carboxymethyl, 2-carboxyethyl, aminomethyl, 2-aminoethyl, 3-amino-propyl, 4-amino-1-butyl, 3-guanidino-1-propyl, and 4-imidazolylmethyl, and 1,3-propylene, 2-hydroxy-1,3-propylene, or 1,4-butylene forming a pyrrolidine ring, a 3-hydroxy-pyrrolidine ring, or a piperidine ring, respectively, involving A and a nitrogen atom of Y adjacent to A, and, when A is N, the group Z is selected from $C_{1-4}$-alkyl, $C_{1-4}$-acyl, $C_{1-4}$alkyl-carbonylamino-$C_{1-4}$-alkyl, and a chain of 1–5 amino acid(s).

9. A compound according to claim 7, wherein the group Q is selected from hydrogen, carboxy, aminocarbonyl, mono- or di($C_{1-6}$-alkyl)aminocarbonyl, N-(a chain of 1–3 amino acid(s))-carboxy, carboxy-$C_{1-3}$-alkyl, aminocarbonyl-$C_{1-3}$-alkyl, mono- di($C_{1-6}$-alkyl) aminocarbonyl-$C_{1-3}$-alkyl, and (N-a chain of 1–3 amino acid(s))-carbonyl-$C_{1-3}$-alkyl, where any methylene unit(s) of the alkyl group(s) is/are optionally substituted with groups selected from side chains of α-amino acids.

10. A compound according to claim 5, wherein the segments of the general formula $G^h$ are identical throughout the chain of segments.

11. A compound according to claim 5, wherein the segments in the general formula $G^h$ are derived from identical amino acids.

12. A compound according to claim 5, wherein the groups in each set $3A^0, \ldots, A^n$; $B^1, \ldots, B^n$; $Y^0, \ldots, Y^n$; and $L^0, \ldots, L^n$, respectively, are the same.

13. A compound according to claim 5, wherein the groups in each set $A^0, \ldots, A^n$; $B^1, \ldots, B^n$; respectively, are the same, and the groups in the set $Y^0$—$L^0, \ldots, Y^n$—$L^n$ comprises at least two structurally different types of groups.

14. A compound according to claim 5, said compound having the formula

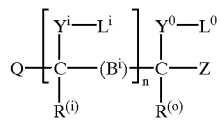

wherein each of $Y^0, \ldots, Y^n$ independently is selected from —O—$(CH_2)_p$—C(=O)—NH—, —$(CH_2)_p$—C(=O)—NH—, —O—$(CH_2)_p$—NH—C(=O)—, —$(CH_2)_p$—NH—C(=O)—, —$(CH_2)_p$—, where p is 0–5; each of $B^1, \ldots, B^n$ independently is selected from —$(CH_2)_q$—NH—C(=O)—$(CH_2)_r$, —$(CH_2)_q$—C(=O)—NH—$(CH_2)_r$—, where q and r each independently are 0–6, and the sum q+r is 0–6; each of $R^{(o)}, \ldots, R^{(n)}$ independently is selected from hydrogen and optionally substituted $C_{1-4}$-alkyl; $R^{(i)}$ are the choices of R for the ith bracketed unit and $R^0$ for the terminal unit; Q is selected from hydrogen, carboxy, aminocarbonyl, mono- or di($C_{1-6}$-alkyl)aminocarbonyl, and (a chain of 1–3 amino acids)-carbonyl; and Z is selected from side chains of the α-amino acids.

15. A compound according to claim 14, wherein q and r each independently are 0–4 and the sum r+q is 2–4.

16. A compound according to claim 14, said compound being of the formula

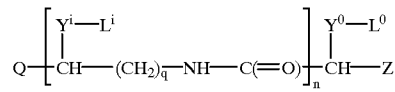

wherein q is 1–4 and n is 1–9.

17. A compound according to claim 16, wherein Q is selected from hydrogen and aminocarbonyl ($H_2N$—C(=O)—); $Y^0, \ldots, Y^n$ are selected from —O—$CH_2$—C(=O)—NH— and —$CH_2$—C(=O)—NH—; Z is selected from hydrogen and methyl; and n is 1–4.

18. A compound according to claim 17, wherein Q is aminocarbonyl ($H_2N$—C(=O)); $Y^0, \ldots, Y^n$ are —O—$CH_2$—C(=O)—NH—; Z is selected from hydrogen and methyl.

19. A compound according to claim 16, wherein n is 1; Q is aminocarbonyl ($H_2N$—C(=O)); $Y^0$ is —O—$CH_2$—C(=O)—N<; $Y^1$ is —O—$CH_2$—C(=O)—NH—; Z is 1,3-propylene forming a pyrrolidine ring involving the adjacent carbon atom ($A^0$) and the nitrogen atom of $Y^0$.

20. A compound according to claim 1, said compound having the formula

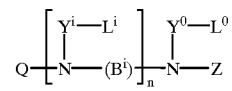

wherein n is a positive integer, i is a positive integer, assuming values 1 to n for the first to nth bracketed unit, respectively; each of $Y^0, \ldots, Y^n$ independently is selected from —O—$(CH_2)_p$—C(=O)—, —$(CH_2)_p$—C(=O)—, —$(CH_2)_p$—NH—C(=O)—, and —O—$(CH_2)_p$—NH—C(=O)—, where p is 0–5; each of $B^1$–$B^n$ independently is selected from —$(CH_2)_q$—NH—C(=O)—$(CH_2)_r$—, —$(CH_2)_q$—C(=O)—NH—$(CH_2)_r$—, where q and r are 0–4, and the sum q+r is 2–4, and where one of the hydrogen atoms of one or more of the methylene groups is/are optionally substituted with a group selected from side chains of α-amino acids; Q is selected from hydrogen, carboxy-$C_{1-3}$-alkyl, aminocarbonyl-$C_{1-3}$-alkyl, mono- or di($C_{1-6}$-alkyl)aminocarbonyl-$C_{1-3}$-alkyl; and Z is selected from hydrogen, $C_{1-4}$-alkylcarbonylamino-$C_{1-4}$-alkyl; and where $Y^i$, $B^i$ and $L^i$ are the choices of Y, B and L for the ith bracketed unit, and $Y^0$, $B^0$ and $L^0$, for the terminal unit.

21. A compound according to claim 20, said compound being of the formula

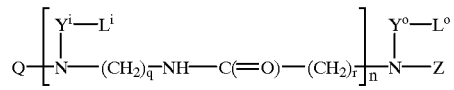

wherein q and r each are 1–3, and the sum q+r is 2–4.

22. A compound according to claim 1, said compound having the formula

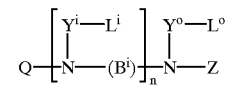

wherein n is a positive integer, i is a positve integer, assuming values 1 to n for the first to nth bracketed unit, each of $Y^0$–$Y^n$ independently is selected from —O—($CH_2$)$_p$—C(=O)—, —($CH_2$)$_p$—C(=O)—, —($CH_2$)$_p$—NH—C(=O)—, —O—($CH_2$)$_p$—NH—C(=O)—, where p is 0–5; each of $B^1$–$B^n$ independently is selected from —C(=O)—($CH_2$)$_q$—NH—C(=O)—($CH_2$)$_r$—, —C(=O)—($CH_2$)$_q$—C(=O)—NH—($CH_2$)$_r$—, —($CH_2$)$_s$—, where q and r each are 0–3, and the sum q+r is 1–3, s is 2–6, and where one of the hydrogens of one or more of the methylene groups is/are optionally substituted with a group selected from side chains of α-amino acids; Q is selected from hydrogen, carboxy-$C_{1-3}$-alkyl, aminocarbonyl-$C_{1-3}$-alkyl, mono- or di($C_{1-6}$-alkyl)aminocarbonyl-$C_{1-3}$-alkyl, and Z is selected from hydrogen, $C_{1-4}$-alkyl, $C_{1-4}$-alkyl-carbonylamino-$C_{1-4}$-alkyl; and where $Y^i$, $B^i$ and $L^i$ are the choices of Y, B and L for the ith bracketed unit, and $Y^0$, $B^0$ and $L^0$, for the terminal unit.

23. A compound according to claim 22, said compound being of the formula

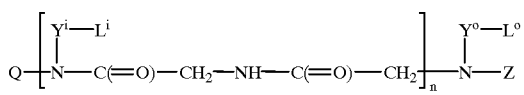

24. A organic compound according to claim 22, said compound being of the formula

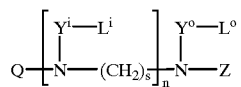

wherein s is 1–4.

25. A compound according to claim 1, wherein the compound further comprises one or more segments of the following formula G'

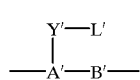

wherein the groups A', B', and Y' have the same meaning as defined for the groups A, B, and Y, respectively, and where the group L' designates a physically non-functional group comprising one or more physically non-functional ligand(s) selected from benzenes, thiophenes, imidazoles, pyrans, furans, pyrroles, pyrimidines, napthalenes, indenes, indoles, purines, quinolines, pentalines, azulenes, heptalenes, flourenes, carbazoles, xanthenes, acridines, pyrenes, anthracenes, anthraquinones, phenanthrenes, phenalenes, benzo[e]perimidines, and steroids.

26. A compound according to claim 1, comprising at least two domains each independently composed of b segment(s) of the general formula G and c segment(s) of the general formula G'

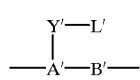

wherein the groups A', B', and Y' have the same meaning as defined for the groups A, B, and Y. respectively, and where the group L' designates a physically non-functional group comprising one or more physically non-functional ligand(s) selected from benzenes, thiophenes, imidazoles, pyrans, furans, pyrroles, pyrimidines, napthalenes, indenes, indoles, purines, quinolines, pentalines, azulenes, heptalenes, flourenes, carbazoles, xanthenes, acridines, pyrenes, anthracenes, anthraquinones, phenanthrenes, phenalenes, benzo[e]perimidines, and steroids, where b>0 and the sum b+c is at least 2.

27. A compound according to claim 26, wherein the individual domains are separated by spacer groups SP which have the same chemical structure as defined for the linking group Y.

28. A compound according to claim 27, wherein the spacer group -SP- has at least 3 consecutive covalent bonds.

29. A compound according to claim 1, wherein the chain of segments of the general formula G, and, optionally, segments of the general formula G' and any spacer groups, forms a macrocyclic structure.

30. A compound according to claim 1, wherein domains comprising segment(s) G and, optionally, segment(s) G' and spacer group(s) SP, are attached covalently to a template.

31. A compound according to claim 30, wherein the template is a dendritic structure having the domains attached to substantially all of the branches.

32. A compound according to claim 30, wherein the template is a cyclic structure having the domains attached to the rim thereof.

33. A novel organic compound according to claim 30, wherein the template is the polymeric matrix structure used for synthesizing the domains.

34. A compound according to claim 1, said compound comprising one or more segments of the formula G as defined in claim 1; and one or more segments of the formula G'

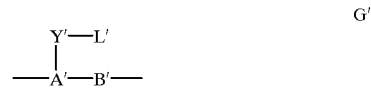

wherein the groups A', B', and Y' have the same meaning as defined for the groups A, B, and Y, respectively, and where the group L' designates a physically non-functional group comprising one or more physically non-functional ligand(s) selected from benzenes, thiophenes, inidazoles, pyrans, furans, pyrroles, pyrimidines, napthalenes, indenes, indoles, purines, quinolines, pentalines, azulenes, heptalenes, fluorenes, carbazoles, xanthenes, acridines, pyrenes, anthracenes, anthraquinones, phenanthrenes, phenalenes, benzo[e]perimidines, and steroids, and/or one or more spacer groups SP which have the same chemical structure as defined for the linking group Y.

35. A compound having a physical functionality which may be influenced by external stimulation, said compound having the general formula $G^0$

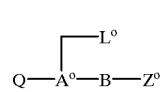

wherein B is a chain consisting of groups selected from $CHR^2$ and C=O, wherein $R^2$ is selected from side chains of α-amino acids; $C_{1-6}$-alkyl; hydroxy; optionally substituted $C_{1-6}$-alkoxy; halogen; cyano; amino; mono- or di(optionally substituted $C_{1-6}$-alkyl)amino; mono- or di(optionally substituted $C_{1-6}$-alkyl)amino-$C_{1-6}$-alkyl; (optionally substituted $C_{1-6}$-alkyl)carbonylamino; (optionally substituted $C_{1-6}$-alkyl)-carbonylamino-$C_{1-6}$-alkyl; aminocarbonyl; aminocarbonyl-$C_{1-6}$-alkyl; mono- or di-(optionally substituted $C_{1-6}$-alkyl)aminocarbonyl; mono- or di(optionally substituted $C_{1-6}$-alkyl)aminocarbonyl-$C_{1-6}$-alkyl; optionally substituted $C_{1-6}$-acyl; optionally substituted $C_{1-6}$-acyloxy; carboxy; and (optionally substituted $C_{1-6}$-alkoxy)carbonyl; said chain B optionally being interrupted, initiated, or terminated by one or more groups selected from —O—, and —$NR^3$—, wherein $R^3$ is selected from hydrogen; $C_{1-6}$-alkyl; mono- or di(optionally substituted $C_{1-6}$-alkyl)anino-$C_{1-6}$-alkyl; (optionally substituted $C_{1-6}$-alkyl)carbonylamino-$C_{1-6}$-alkyl; aminocarbonyl-$C_{1-6}$-alkyl; mono- or di(optionally substituted $C_{1-6}$-alkyl)aminocarbonyl; mono- or di(optionally substituted $C_{1-6}$alkyl)aminocarbonyl-$C_{1-6}$-alkyl; (optionally substituted aryl)-$C_{1-6}$-alkoxycarbonyl; optionally substituted $C_{1-6}$-acyl; and optionally substituted $C_{1-6}$-alkoxycarbonyl;
and wherein
1) the backbone chain —A—B— has a total of 4–7 consecutive covalent bonds between the radical positions and:
   (i) contains an amide function, or
   (ii) contains a part of an amide function, the remainder of which is contained in the corresponding linking group Y or in adjacent group(s) from any neighbouring segment; and
2) when the linking group Y has a total of at least 3 consecutive covalent bonds,
   (i) the linking group Y contains an amide function bound directly to the corresponding moiety A; or
   (ii) A constitutes the nitrogen atom of an amide function, $Y^0$ is a linking group selected from —O—$(CH_2)_p$—C(=O)—NH—, —O—$(CH_2)_p$—NH—C(=O)—, —O—$(CH_2)_p$—C(=O)—, —O—$(CH_2)_p$—NH—, —$(CH_2)_p$—C(=O)—NH—, —$(CH_2)_p$—NH—C(=O)—, —$(CH_2)_p$—C(=O)—, —$(CH_2)_p$—NH—, —OOC—$(CH_2)_p$—C(=O)—NH—, —OOC—$(CH_2)_p$—NH—C(=O)—, —OOC—$(CH_2)_p$—C(=O)—, —OOC—$(CH_2)_p$—NH—, —NH—$(CH_2)_p$—C(=O)—NH—, —N($C_{1-6}$-alkyl)-$(CH_2)_p$—C(=O)—NH—, —NH—$(CH_2)_p$—NH—C(=O)—, —N($C_{1-6}$-alkyl)-$(CH_2)_p$—NH—C(=O)—, —NH—$(CH_2)_p$—C(=O)—, —N($C_{1-6}$-alkyl)-$(CH_2)_p$—C(=O)—, —NH—$(CH_2)_p$—NH—, —N($C_{1-6}$-alkyl)-$(CH_2)_p$—NH—, —NH—C(=O)—$(CH_2)_p$—C(=O)—NH—, —N($C_{1-6}$-alkyl)-C(=O)—$(CH_2)_p$—C(=O)—NH—, —NH—C(=O)—$(CH_2)_p$—NH—C(=O)—, —N($C_{1-6}$-alkyl)-C(=O)—$(CH_2)_p$—NH—C(=O)—, —NH—C(=O)—$(CH_2)_p$—C(=O)—, —N($C_{1-6}$-alkyl)-C(=O)—$(CH_2)_p$—C(=O)—, —NH—C(=O)—$(CH_2)_p$—NH—, and —N($C_{1-6}$-alkyl)-C(=O)—$(CH_2)_p$—NH—, wherein p is 0–5;

wherein $L^0$ is an azobenzene which is optionally substituted with one or more substituent(s) each independently selected from deuterium, hydroxy, fluorine, chlorine, bromine, and iodine, linear or branched optionally substituted $C_{1-6}$-alkyl, optionally substituted $C_{1-6}$-alkoxy, cyano, nitro, amino, mono- or di(optionally substituted $C_{1-6}$-alkyl)amino, mono- or di(optionally substituted $C_{1-6}$-alkyl)amino-$C_{1-6}$-alkyl, (optionally substituted $C_{1-6}$-alkyl)carbonylamino, (optionally substituted $C_{1-6}$alkyl)carbonylamino-$C_{1-6}$-alkyl, aminocarbonyl, aminocarbonyl-$C_{1-6}$-alkyl, mono- or di(optionally substituted $C_{1-6}$-alkyl) aminocarbonyl, mono- or di(optionally substituted $C_{1-6}$-alkyl)aminocarbonyl-$C_{1-6}$-alkyl, optionally substituted $C_{1-6}$-acyl, optionally substituted $C_{1-6}$-acyloxy, carboxy, —COSH, (optionally substituted $C_{1-6}$-alkoxy) carbonyl, thiolo, $C_{1-6}$-alkylthio, optionally substituted $C_{1-6}$-alkylthio-$C_{1-6}$-alkyl, guanidino, isocyano, isothiocyano, and thiocyano;

wherein the group Q is selected from hydrogen, carboxy, aminocarbonyl, mono- or di($C_{1-6}$-alkyl)aminocarbonyl, N-(a chain of 1–3 amino acid(s))-carboxy, carboxy-$C_{1-3}$-alkyl, aminocarbonyl-$C_{1-3}$-alkyl, mono- di($C_{1-6}$-alkyl) aminocarbonyl-$C_{1-3}$-alkyl, and (N-a chain of 1–3 amino acid(s))-carbonyl-$C_{1-3}$-alkyl, where any methylene unit(s) of the alkyl group(s) is/are optionally substituted with groups selected from side chains of α-amino acids;

when $A^0$ is C—R, the group $Z^0$ is selected from amino, carboxy, C-(a chain of 1–5 amino acid(s))-amino, N-(a chain of 1–5 amino acid(s))-carbonyl, side chains of α-amino acids, hydrogen, deuterium, methyl, cyanomethyl, ethyl, 1-propyl, 2-propyl, 2-methyl-1-propyl, 2-hydroxy-2-methyl-1-propyl, 1-butyl, 2-butyl, methylthioethyl, benzyl, p-amino-benzyl, p-iodo-benzyl, p-fluoro-benzyl, p-bromo-benzyl, p-chloro-benzyl, p-nitro-benzyl, 3-pyridylmethyl, 3,5-diiodo-4hydroxy-benzyl, 3,5-dibromo-4-hydroxy-benzyl, 3,5-dichloro-4-hydroxy-benzyl, 3,5-difluoro-4-hydroxy-benzyl, 4-methoxy-benzyl, 2-naphtylmethyl, 1-naphtylmethyl, 3-indolylmethyl, hydroxymethyl, 1-hydroxyethyl, mercaptomethyl, 2-mercapto-2-propyl, 4-hydroxybenzyl, aminocarbonylmethyl, 2-aminocarbonylethyl, carboxymethyl, 2-carboxyethyl, aminomethyl, 2-aminoethyl, 3-amino-propyl, 4-amino-1-butyl, 3-guanidino-1-propyl, and 4-imidazolylmethyl, and 1,3-propylene, 2-hydroxy-1,3-propylene, or 1,4-butylene forming a pyrrolidine ring, a 3-hydroxy-pyrrolidine ring, or a piperidine ring, respectively, involving A and a nitrogen atom of Y adjacent to A; and, when A is N, the group Z is selected from $C_{1-4}$-alkyl, $C_{1-4}$-acyl, $C_{1-4}$-alkyl-carbonylamino-$C_{1-4}$-alkyl, and a chain of 1–5 amino acid.

36. A material which allows for introduction of optical anisotropy, said material comprising an organic compound, said compound comprising at least one domain comprising 2–25 segments of the following formula G

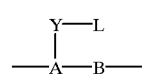

G wherein the backbone moiety —A—B— together with at least a part of the linking group Y is derived from one or more amino acid(s); and L is an azobenzene which is optionally substituted with one or more substituent(s) each independently selected from deuterium, hydroxy, halogen linear or branched optionally substituted $C_{1-6}$-alkyl, optionally substituted $C_{1-6}$-alkoxy, cyano, nitro, amino, mono- or di(optionally substituted $C_{1-6}$-alkyl)amino, mono- or di(optionally substituted $C_{1-6}$-alkyl)amino-$C_{1-6}$-alkyl, (optionally substituted $C_{1-6}$-alkyl)carbonylamino, (optionally substituted $C_{1-6}$alkyl)carbonylamino-$C_{1-6}$alkyl, aminocarbonyl, aminocarbonyl-$C_{1-6}$-alkyl, mono- or di(optionally substituted $C_{1-6}$-alkyl) aminocarbonyl, mono- or di(optionally substituted $C_{1-6}$-alkyl)aminocarbonyl-$C_{1-6}$-alkyl, optionally substituted $C_{1-6}$-acyl, optionally substituted $C_{1-6}$-acyloxy, carboxy, —COSH, (optionally substituted $C_{1-6}$-alkoxy) carbonyl, thiolo, $C_{1-6}$-alkylthio, optionally substituted $C_{1-6}$-alkythio-$C_{1-6}$-alkyl, guanidino, isocyano, isothiocyano, and thiocyano;

wherein Y is a linking group selected from —O—$(CH_2)_p$—C(=O)—NH—, —O—$(CH_2)_p$—NH—C(=O)—, —O—(CH$_2$)$_p$—C(=O)—, —O—(CH$_2$)$_p$—NH—, —(CH$_2$)$_p$—C(=O)—NH—, —(CH$_2$)$_p$—NH—C(=O)—, —(CH$_2$)$_p$—C(=O)—, —(CH$_2$)$_p$—NH—, —OOC—(CH$_2$)$_p$—C(=O)—NH—, —OOC—(CH$_2$)$_p$—NH—C(=O)—, —OOC—(CH$_2$)$_p$—C(=O)—, —OOC—(CH$_2$)$_p$—NH—, —NH—(CH$_2$)$_p$—C(=O)—NH—, —N(C$_{1-6}$-alkyl)-(CH$_2$)$_p$—C(=O)—NH—, —NH—(CH$_2$)$_p$—NH—C(=O)—, —N(C$_{1-6}$-alkyl)-(CH$_2$)$_p$—NH—C(=O)—, —NH—(CH$_2$)$_p$—C(=O)—, —N(C$_{1-6}$-alkyl)-(CH$_2$)$_p$—C(=O)—, —NH—(CH$_2$)$_p$—NH—, —N(C$_{1-6}$-alkyl)-(CH$_2$)$_p$—NH—, —NH—C(=O)—(CH$_2$)$_p$—C(=O)—NH—, —N(C$_{1-6}$-alkyl)-C(=O)—(CH$_2$)$_p$—C(=O)—NH—, —NH—C(=O)—(CH$_2$)$_p$—NH—C(=O)—, —N(C$_{1-6}$-alkyl)-C(=O)—(CH$_2$)$_p$—NH—C(=O)—, —NH—C(=O)—(CH$_2$)$_p$—C(=O)—, —N(C$_{1-6}$-alkyl)-C(=O)—(CH$_2$)$_p$—C(=O)—, —NH—C(=O)—(CH$_2$)$_p$—NH—, and —N(C$_{1-6}$-alkyl)-C(=O)—(CH$_2$)$_p$—NH—, wherein p is 0–5;

A is selected from a nitrogen atom and a group C—H; and

B is a chain consisting of groups selected from CHR$^2$ and C=O, wherein R$^2$ is selected from hydrogen and side chains of α-amino acids; said chain B optionally being interrupted, initiated, or terminated by one or more groups selected from O and —NR$^3$, wherein R$^3$ is selected from hydrogen, C$_{1-6}$-alkyl, C$_{1-6}$-acyl, and amino protecting groups;

and wherein 1) the backbone chain —A—B— has a total of 4–7 consecutive covalent bonds between the radical positions and:
   (i) contains an amide function, or
   (ii) contains a part of an amide function, the remainder of which is contained in the corresponding linking group Y or in adjacent group(s) from any neighbouring segment; and 2) when the linking group Y has a total of at least 3 consecutive covalent bonds,
   (i) the linking group Y contains an amide function bound directly to the corresponding moiety A; or
   (ii) A constitutes the nitrogen atom of an amide function.

37. A material according to claim 36, comprising a successive chain of segments of the formula G.

38. A material according to claim 36, having the formula G$^h$

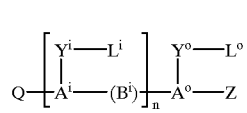

wherein n is a positive integer; i is a positive integer, assuming value 1 to n for the first to the nth bracketed unit, respectively; each of Y$^0$, ..., Y$^n$ independently is a linking group as defined for Y in claim 36; each of L$^0$, ..., L$^n$ independently is an optionally substituted azobenzene as defined for L in claim 36; each of A$^0$, ..., A$^n$ independently is a group as defined for A in claim 36; each of B$^1$, ..., B$^n$ independently is a chain as defined for B in claim 36; and where Y$^i$, A$^i$, B$^i$ and L$^i$ are the choices of Y, A, B and L for the ith bracketed unit and Y$^0$, A$^0$, B$^0$ and L$^0$ for the terminal unit, and Q and Z are terminating groups.

39. A material according to claim 38, said compound having the formula

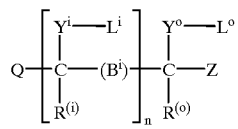

where i is a positive integer, assuming value 1 to n for the first to the nth bracketed unit, respectively; wherein each of Y$^0$, ..., Y$^n$ independently is selected from —O—(CH$_2$)$_p$—C(=O)—NH—, —(CH$_2$)$_p$—C(=O)—NH—, —O—(CH$_2$)$_p$—NH—C(=O)—, —(CH$_2$)$_p$—NH—C(=O)—, and —(CH$_2$)$_p$—, where p is 0–5; each of B$^1$, ..., B$^n$ independently is selected from —(CH$_2$)$_q$—NH—C(=O)—(CH$_2$)$_r$—, —(CH$_2$)$_q$—C(=O)—NH—(CH$_2$)$_r$—, where q and r each independently are 0–6, and the sum q+r is 0–6; each of R$^{(0)}$, ..., R$^{(n)}$ are independently selected from hydrogen and optionally substituted C$_{1-4}$-alkyl; where Y$^i$, B$^i$, L$^i$ and R$^i$ are the choices of Y, B, L and R for the ith bracketed unit, and Y$^0$, B$^0$, L$^0$ and R$^0$ for the terminal unit; Q is selected from hydrogen, carboxy, aminocarbonyl, mono- or di(C$_{1-6}$-alkyl)aminocarbonyl, and (a chain of 1–3 amino acids)-carbonyl; and Z is selected from side chains of the α-amino acids.

40. A material according to claim 39, said compound being of the formula

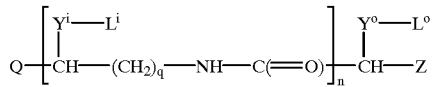

wherein q is 1–4 and n is 1–9.

41. A material according to claim 38, wherein the groups Q and Z each independently are selected from the same groups as defined for R$^2$ and R$^3$ above, optionally substituted with a chain consisting of 1 to 5 amino acids, or extended by a chain as defined for B above; and, when one or both of the group(s) Q and Z are part of a carbocyclic or heterocyclic ring or a macrocycle, Q and/or Z is/are selected from the biradicals of the before-mentioned groups and a single bond.

42. A material according to claim 41, wherein, when A is C—R, the group Z is selected from amino, carboxy, C-(a chain of 1–5 amino acid(s))-amino, N-(a chain of 1–5 amino acid(s))-carbonyl, side chains of α-amino acids, hydrogen, deuterium, methyl, cyanomethyl, ethyl, 1-propyl, 2-propyl, 2methyl-1-propyl, 2-hydroxy-2-methyl-1-propyl, 1-butyl, 2-butyl, methylthioethyl, benzyl, p-amino-benzyl, p-iodo-benzyl, p-fluoro-benzyl, p-bromo-benzyl, p-cbloro-benzyl, p-nitro-benzyl, 3-pyridylmethyl, 3,5-diiodo-4-hydroxy-benzyl, 3,5-dibromo-4-hydroxy-benzyl, 3,5-dichloro-4-hydroxy-benzyl, 3,5-difluoro-4-hydroxy-benzyl, 4-methoxy-benzyl, 2-naphtylmethyl, 1-naphtylmethyl, 3-indolylmethyl, hydroxymethyl, 1-hydroxyethyl, mercaptomethyl, 2-mercapto-2-propyl, 4-hydroxybenzyl, aminocarbonylmethyl, 2-aminocarbonylethyl, carboxymethyl, 2-carboxyethyl, aminomethyl, 2-aminoethyl, 3-amino-propyl, 4-amino-1-butyl, 3-guanidino-1-propyl, and 4-imidazolylmethyl, and 1,3-propylene, 2-hydroxy-1,3-propylene, or 1,4-butylene forming a pyrrolidine ring, a 3-hydroxy-pyrrolidine ring, or a piperidine ring, respectively, involving A and a nitrogen atom of Y adjacent to A; and, when A is N, the group Z is selected from C$_{1-4}$-alkyl, C$_{1-4}$-acyl, C$_{1-4}$-alkyl-carbonylamino-C$_{1-4}$-alkyl, and a chain of 1–5 amino acid(s).

43. A material according to claim 41, wherein the group Q is selected from hydrogen, carboxy, aminocarbonyl, mono- or di($C_{1-6}$-alkyl)aminocarbonyl, N-(a chain of 1–3 amino acid(s))-carboxy, carboxy-$C_{1-3}$-alkyl, aminocarbonyl-$C_{1-3}$-alkyl, mono- di($C_{1-6}$-alkyl) aminocarbonyl-$C_{1-3}$-alkyl, and (N-a chain of 1–3 amino acid(s))-carbonyl-$C_{1-3}$-alkyl, where any methylene unit(s) of the alkyl group(s) is/are optionally substituted with groups selected from side chains of α-amino acids.

44. A material according to claim 38, wherein the segments of the general formula $G^h$ are identical throughout the chain of segments.

45. A material according to claim 38, wherein the segments in the general formula $G^h$ are derived from identical amino aidds.

46. A material according to claim 38, wherein the groups in each set $A^0, \ldots, A^n$; $B^1, \ldots, B^n$; $\ldots, Y^0, \ldots, Y^n$; and $L^0, \ldots, L^n$, respectively, are the same.

47. A material according to claim 38, wherein the groups in each set $A^0, \ldots, A^n$; $B^1, \ldots, B^n$; respectively, are the same, and the groups in the set $Y^0—L^0, \ldots, Y^n—L^n$ comprises at least two structurally different types of groups.

48. A material according to claim 39, wherein q and r each independently are 0–4 and the sum r+q is 2–4.

49. A material according to claim 40, wherein Q is selected from hydrogen and aminocarbonyl ($H_2N$—C(=O)—); $Y^0, \ldots, Y^n$ are selected from —O—$CH_2$—C(=O)—NH— and —$CH_2$—C(=O)—NH—; Z is selected from hydrogen and methyl; and n is 1–4.

50. A material according to claim 49, wherein Q is aminocarbonyl ($H_2N$—C(=O)); $Y^0, \ldots, Y^n$ are —O—$CH_2$—C(=O)—NH—; Z is selected from hydrogen and methyl.

51. A material which allows for introduction of optically anisotropy, said material comprising peptide oligomers which contain optionally substituted azobenzenes.

52. A material according to claim 51, wherein the peptide oligomer is derived from an amino acid selected from ornithine, lysine, diaminobutyric acid, and diaminopropionic acid.

53. A material according to claim 51, wherein the optionally substituted azobenzenes are selected from azobenzenes which are optionally substituted with one or more substituent(s) each independently selected from deuterium, hydroxy, halogen such as fluorine, chlorine, bromine, and iodine, linear or branched optionally substituted $C_{1-6}$-alkyl, optionally substituted $C_{1-6}$-alkoxy, cyano, nitro, amino, mono- or di(optionally substituted $C_{1-6}$-alkyl)amino, mono- or di(optionally substituted $C_{1-6}$-alkyl)amino-$C_{1-6}$-alkyl, (optionally substituted $C_{1-6}$-alkyl)carbonylamino, (optionally substituted $C_{1-6}$-alkyl)carbonylamino-$C_{1-6}$-alkyl, aminocarbonyl, aminocarbonyl-$C_{1-6}$-alkyl, mono- or di(optionally substituted $C_{1-6}$-alkyl)aminocarbonyl, mono- or di(optionally substituted $C_{1-6}$-alkyl)aminocarbonyl-$C_{1-6}$-alkyl, optionally substituted $C_{1-6}$-acyl, optionally substituted $C_{1-6}$-acyloxy, carboxy, —COSH, (optionally substituted $C_{1-6}$-alkoxy)carbonyl, thiolo, $C_{1-6}$-alkylthio, optionally substituted $C_{1-6}$-alkylthio-$C_{1-6}$-alkyl, guanidino, isocyano, isothiocyano, and thiocyano.

54. A material according to claim 36, wherein the organic compound is monodisperse.

55. A material according to claim 36, wherein the organic compound is polydisperse.

56. A material according to claims 36, further comprising a polymeric component.

57. A material according to claim 36, wherein the diffraction efficiency is at least 70% for a film of said material having a thickness of at the most 10 μm.

58. A material according to claim 36, wherein stored holographic information is not erased when stored at 150° C. for one month.

59. In a process for storing information in an optical storage medium, the improvement comprising using, as the storage medium, a material according to claim 36.

60. A process according to claim 59, wherein the information is stored in the form of a hologram.

61. A process according to claim 59, wherein the material is monodisperse.

62. A process according to claim 59, for optically storing information comprising irradiation of an optically isotropic area of said material with polarised light, thereby forming an optically anisotropic phase in the irradiated area of the material.

63. A process according to claim 62, wherein the irradiation is carried out with polarized light of a single wavelength in the range of 100–1600 nm.

64. A process according to claim 63, wherein the irradiation is carried out with linearly or circularly polarized coherent light of a single wavelength in the range of 300–700 nm.

65. A process according to claim 62, wherein the said compound is irradiated with polarized light of a first wavelength in the range of 100–1600 nm, and said compound is simultaneously or subsequently irradiated with polarized light of a second wavelength, said second wavelength being in the range of 100–1600 nm.

66. A process according to claim 65, wherein the irradiation with the first and second wavelength is carried out with linearly or circularly polarized coherent light, said wavelengths being in the range of 300–700 nm.

67. A process according to claim 65, wherein the first and second wavelengths are different.

68. A process according to claim 62, wherein the stored information is erased by means of light, selected from linearly polarised light between 100 and 1600 nm, circularly polarised light between 100 and 1600 nm, and unpolarised light between 100 and 1600 nm.

69. A process according to claim 62, wherein the stored information is read out at a wavelength between 100 and 1600 nm.

70. A process according to claim 62, wherein the information is stored as bits by means of a focussed laser beam, optionally by means of a near-field microscope.

71. A process according to claim 62, wherein the information stored is erased by means selected from an electric field, a magnetic field; and heat.

72. In a process for storing information in an optical storage medium, using, as the storage medium, a material according to claim 51.

73. A process according to claim 51, wherein the information is stored in the form of a hologram.

74. A process according to claim 51, wherein the material is monodisperse.

75. A process according to claim 51 for optically storing information comprising irradiation of an optically isotropic area of said material with polarised light, thereby forming an optically anisotropic phase in the irradiated area of the material.

76. A process according to claim 75, wherein the irradiation is carried out with polarized light of a single wavelength in the range of 100–1600 nm.

77. A process according to claim 76, wherein the irradiation is carried out with linearly or circularly polarized coherent light of a single wavelength in the range of 300–700 nm.

78. A process according to claim 75, wherein the said compound is irradiated with polarized light of a first wavelength in the range of 100–1600 nm, and said compound is simultaneously or subsequently irradiated with polarized light of a second wavelength, said second wavelength being in the range of 100–1600 nm.

79. A process according to claim 78, wherein the irradiation with the first and second wavelength is carried out with linearly or circularly polarized coherent light, said wavelengths being in the range of 300–700 nm.

80. A process according to claim 78, wherein the first and second wavelengths are different.

81. A process according to claim 75, wherein the stored information is erased by means of light, selected from the group consisting of linearly polarised light between 100 and 1600 nm, circularly polarised light between 100 and 1600 nm, and unpolarised light between 100 and 1600 nm.

82. A process according to claim 75, wherein the stored information is read out at a wavelength between 100 and 1600 nm.

83. A process according to claim 75, wherein the information is stored as bits by means of a focused laser beam, optionally by means of a near-field microscope.

84. A process according to claim 75, wherein the information stored is erased by means selected from the group consisting of an electric field, a magnetic field, and heat.

* * * * *